US010494641B2

(12) United States Patent
Ohto et al.

(10) Patent No.: US 10,494,641 B2
(45) Date of Patent: Dec. 3, 2019

(54) TRANSFORMED PLANT AND METHOD FOR PRODUCING EXUDATE CONTAINING SUGAR USING TRANSFORMED PLANT

(71) Applicants: Chikara Ohto, Toyota (JP); Madoka Yonekura, Nagoya (JP); Naohiro Aoki, Tokyo (JP); Ryu Ohsugi, Tokyo (JP); Tatsuro Hirose, Joetsu (JP)

(72) Inventors: Chikara Ohto, Toyota (JP); Madoka Yonekura, Nagoya (JP); Naohiro Aoki, Tokyo (JP); Ryu Ohsugi, Tokyo (JP); Tatsuro Hirose, Joetsu (JP)

(73) Assignees: TOYOTA JIDOSHA KABUSHIKI KAISHA, Toyota-shi, Aichi-ken (JP); THE UNIVERSITY OF TOKYO, Bunkyo-ku, Tokyo (JP); National Agriculture and Food Research Organization, Tsukuba-shi, Ibaraki (JP)

(*) Notice: Subject to any disclaimer, the term of this patent is extended or adjusted under 35 U.S.C. 154(b) by 0 days.

(21) Appl. No.: 15/107,998

(22) PCT Filed: Dec. 25, 2014

(86) PCT No.: PCT/JP2014/084316
§ 371 (c)(1),
(2) Date: Jun. 24, 2016

(87) PCT Pub. No.: WO2015/099042
PCT Pub. Date: Jul. 2, 2015

(65) Prior Publication Data
US 2016/0319293 A1   Nov. 3, 2016

(30) Foreign Application Priority Data
Dec. 27, 2013   (JP) .................................. 2013-273128

(51) Int. Cl.
*C12N 15/82* (2006.01)
*C07K 14/415* (2006.01)

(52) U.S. Cl.
CPC ........ *C12N 15/8245* (2013.01); *C07K 14/415* (2013.01)

(58) Field of Classification Search
None
See application file for complete search history.

(56) References Cited

U.S. PATENT DOCUMENTS

| 9,115,366 | B2 | 8/2015 | Tissier et al. | |
| 2003/0236208 | A1* | 12/2003 | Kmiec | C12N 15/102 514/44 R |
| 2004/0168214 | A1 | 8/2004 | Kwart et al. | |
| 2011/0209248 | A1* | 8/2011 | Frommer | C07K 14/415 800/279 |

FOREIGN PATENT DOCUMENTS

| CA | 2760876 A1 | 11/2010 |
| CA | 2905873 A1 | 10/2014 |
| JP | 2001-512685 A | 8/2001 |
| JP | 2002-501755 A | 1/2002 |
| JP | 2008-528016 A | 7/2008 |
| JP | 2012-55208 A | 3/2012 |
| JP | 2012-525845 A | 10/2012 |
| WO | 99/38990 A1 | 8/1999 |
| WO | 2010/129540 A2 | 11/2010 |
| WO | 2013/086494 A1 | 6/2013 |
| WO | WO 2013/086494 A1 * | 6/2013 |
| WO | 2014159845 A1 | 10/2014 |

OTHER PUBLICATIONS

Jia et al., 2017, Frontiers in Plant Science 8:2178. doi: 10.3389/fpls.2017.02178.*
Chen et al., 2012, Science 335: 207-211.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Oryza sativa SWEET13 protein, NCBI/GenBank accession No. XP_015618459.1, published Mar. 1, 2016.*
Li-Qing Chen et al., "Sugar transporters for intercellular exchange and nutrition of pathogens", Nature, pp. 527-532, Nov. 25, 2010, vol. 468.
Hitomi Takanaga et al., "Facilitative plasma membrane transporters function during ER transit", The FASEB Journal, Aug. 2010, pp. 2849-2858, vol. 24.
Nicholas J. Talbot, "Raiding the sweet shop", Nature, Nov. 25, 2010, pp. 510-511, vol. 468.
Guillaume Pilot et al., "Overexpression of Glutamine DUMPER1 Leads to Hypersecretion of Glutamine from Hydathodes of *Arabidopsis* Leaves", The Plant Cell, Jul. 2004, pp. 1827-1840, vol. 16.
Héctor Candela et al., "Venation Pattern Formation in *Arabidopsis thaliana* Vegetative Leaves", Developmental Biology, 1999, pp. 205-216, vol. 205.
Eizo Maeda, "Structure and Function of Leaf Hydathodes in Rice and Wheat Plants", Rep. Tokal Br. Crop Sci. Soc. Japan, 1987, pp. 19-20, vol. 103.
Li-Qing Chen et al., "Sucrose Efflux Mediated by SWEET Proteins as a Key Step for Phloem Transport", Science, Jan. 13, 2012, pp. 207-211, vol. 335.
S. S. Ivanoff, "Guttation Injuries of Plants", The Botanical Review, 1963, pp. 202-229.
Fabien Chardon et al., "Leaf Fructose Content Is Controlled by the Vacuolar Transporter SWEET17 in *Arabidopsis*", Current Biology, Apr. 22, 2013, pp. 697-702, vol. 23.
Y.-X. Ge et al., "Partial silencing of the NEC1 gene results in early opening of anthers in *Petunia hybrida*", Mol Genet Genomics, 2001, pp. 414-423, vol. 265.

(Continued)

*Primary Examiner* — Bratislav Stankovic
(74) *Attorney, Agent, or Firm* — Sughrue Mion, PLLC

(57) ABSTRACT

The production of exudate containing sugar from a plant at a high concentration is provided. A nucleic acid encoding a transporter involved in sugar transportation having a certain consensus sequence derived from the amino acid sequences of the SWEET proteins classified in the clade III is introduced and/or expression of the protein is enhanced.

9 Claims, 28 Drawing Sheets
Specification includes a Sequence Listing.

(56) References Cited

OTHER PUBLICATIONS

Meng Yuan et al., "Rice MtN3/Saliva/SWEET Family Genes and Their Homologs in Cellular Organisms", Molecular Plant, May 2013, pp. 665-674, vol. 6, No. 3.

Julian I. Schroeder et al., "Using membrane transporters to improve crops for sustainable food production", Nature, May 2, 2013, pp. 60-66, vol. 497.

Jana Streubel et al., "Five phylogenetically close rice SWEET genes confer TAL effector-mediated susceptibility to *Xanthomonas oryzae* pv. *otyzae*", New-Phytologist, 2013, pp. 808-819, vol. 200.

Ingo Grunwald et al., "Identification of guttation fluid proteins: the presence of pathogenesis-related proteins in non-infected barley plants", Physiologia Plantarum, 2003, pp. 192-202, vol. 119.

Yue-Feng Guan et al., "Ruptured Pollen Grain1, a Member of the MtN3/saliva Gene Family, Is Crucial for Exine Pattern Forrnation and Cell Integrity of Microspores in *Arabidopsis*", Plant Physiology, Jun. 2008, pp. 852-863, vol. 147.

Patrick A.W. Klemens et al., "Overexpression of the Vacuolar Sugar Carrier AtSWEET16 Modifies Germination, Growth, and Stress Tolerance in *Arabidopsis*", Plant Physiology, Nov. 2013, pp. 1338-1352, vol. 163.

Bing Yang et al., "Os8N3 is a host disease-susceptibility gene for bacterial blight of rice", PNAS, Jul. 5, 2006, pp. 10503-10508, vol. 103, No. 27.

Yuan Hu Xuan et al., "Functional role of oligomerization for bacterial and plant SWEET sugar transporter family", PNAS, Sep. 11, 2013, pp. E3685-E3694.

Joan Doidy et al., "Sugar transporters in plants and in their interactions with fungi", Trends in Plant Science, Jul. 2012, pp. 413-422, vol. 17, No. 7.

Y. Doi et al., "The Guttatior from Rice Seedling Leaves as influenced by Root Activity", Bull. Fac. Agr., Yamaguchi Univ., 1953, pp. 133-162.

Yoshinori Fujii et al., "Intensity of Guttation in Rice Seedlings in Relation to Earliness or Lateness of the Variety", Japanese Journal of Crop Science, 1957, pp. 131-132, vol. 25, No. 3.

* cited by examiner

Fig. 2-1

```
XP 004235326 Solanum     --MAVDPG--HYAFAFGVLGNIISFIVFLSPI---PTFYSIYKKKSTEGYQ 44
XP 004235334 Solanum     -----MVFN--HWAFAFGVLGNIVSFIVFLSPI---PTFYNIYKKKSTEGYQ 42
ACV71016 Capsicum        --MTGISG--HWAFAFGVLGNIISFIVFLSPI---PTFYTIYKKKTAEGYQ 44
XP 004235333 Solanum     --MAFSAD--HWAFVFGVLGNIVSFIVFLSPL---PTFYTIYKKKTAEGYQ 44
XP 004235342 Solanum     --MAGISG--HWAPAFGVLGNIVSFIVFLSPL---PTFYKIYKKKSTDGYQ 44
XP 004235339 Solanum     ----MAIAG--HWAPVFGVLGNIISFIVFLSPI---PTFNKIYKKKSTEGYQ 43
XP 004241452 Solanum     --MAGFSD--HWTFAFGVLGNISFFVFLSPL---PTFYNIYKKKSTEGYQ 44
XP 004235340 Solanum     --------MTT---HLAFVFGLLGNIVSFMVYLAPV---PTFYKIYKKKSTEGFQ 41
AFK35161 Medicago        -----MAMTR-ESWAFVFGIIGNIISFAVFLSPL---PTFYVIFKKKSAEGPQ 44
CAC44123 Medicago        -----MAMTR-ESWAFVFGIIGNIISPAVFLSPL---PTFYVIFKKKSAEGPQ 44
XP 004503778 Cicer       -----MAMTR-ESWAFVFGLLGNIISFAVFLSPL---PTFYLIFKKKSTEGFQ 44
AFK48645 Lotus           -----MAMTR-ESWAFVFGLMGNVISFMVFLAPL---PTFYQIYKKKTAEGFQ 44
NP 001241307 Glycine     -----MTMHR-ESWAFVFGVMGNIISFGVFLAPL---PTFYQIYKKKSTEGFQ 44
NP 001242732 Glycine     -----MAINH-ETWAFIFGLLGNVISFMVFLASL---PTLYQIYKKKSTDGPQ 44
XP 003523161 Glycine     -----MAISH-ETWAFIFGLLGNVISPMVFLAPL---PTFYQIYKKKSSEGFQ 44
NP 001237418 Glycine     -----MAINH-ETWAFVFGLLGNVISFMVFLAPL---PTFYQIYKKKSTEEFQ 44
XP 003602780 Medicago    -----MALFYSEYWAFVFGVIGNVISCMTFLAPL---PTFYRIYKKKSTEGFQ 45
XP 004138032 Cucumis     -----MAISP-QTLAFVFGLLGNIISPMVFLAPL---PTFYKIYKKKSAEGYQ 44
EMJ10621 Prunus          -----MAIQH--PLTLSFGLLGNIISFLVFLAPV---PTFYTIYKRKTAEGFQ 43
XP 004297512 Fragaria    -----MAIHH--PLTLAFGLLGNIISPMVFLAPM---PTFYKIYKKKTTEGFQ 43
XP 002284244 Vitis       MALFPIHH--PLVFIFGILGNLISFMVYLAPL---PTFYQIYKRKSTEGFQ 46
EOA14646 Capsella        -----MAISQAVLATVFGILGNVISFFVCLAPI---PTFIRIYKRKSSEGYQ 44
NP 199892 AtSW10         -----MAISQAVLATVFGILGNIISPFVCLAPI---PTFVRIYKRKSSEGYQ 44
XP 002321731 Populus     -----MAL-HLTWMLAFGLLGNLISCLVCLAPL---PTFYQIYKKKTSEGPQ 43
XP 002322281 Populus     -----MAL-HLTWVFGFGLLGNFISCLVCLAPL---PTFYRICKKKTSQGFH 43
XP 002321730 Populus     -----MAL-HFTWVFGFGLLGNIISCLVCLAPL---PTFYQICKKKTSQGFQ 43
XP 002511127 Ricinus     -----MAY-HLSLEFLFGVLANIISSMVCLAPL---PTFYQICKKKTSEGFQ 43
XP 002511128 Ricinus     -----MAF-HLTLAFAFGLLGNIISPLVCLAPM---PTFYQICKKKTSEGFQ 43
CBI32263 Vitis           -----MAMLTVPHMAFAFGILGNIVSFLVYLSPL---PTFYRIYKRKSTEGPQ 45
EMJ01437 Prunus          -----MAAPDAFLLASVFGILGNIVAPMVYLAPL---PTFRIFKKKSTEGFQ 45
XP 002520679 Ricinus     -----MALNDPRFILAPGILGNIVSPLVYLAPL---PTFWRIVKKKSTEGFQ 44
XP 004247459 Solanum     -----MPLPTTLQLAFAFGILGNGVSFLVYLSPL---PTFYRIFKRKSTEGFQ 45
EOA28959 Capsella        -----MVFIKVHQLAFFPGLMGNIVSFGVFLSPV---PTFYGIYKKKSSKGFQ 45
NP 181439 AtSW09         -----MFLKVHEIAFLFGLLGNIVSFGVFLSPV---PTFYGIYKKKSSKGFQ 44
XP 002333315 Populus     -----MGFLSNDQLTFLFGLLGNIVAAGMFLAPV---PTFYTIFKRKSSEGFQ 45
NEC1 PETHY Petunia       -----MAQLRADDLSFIFGLLGNIVSPMVFLAPV---PTFYKIYKRKSSEGYQ 45
XP 002267792 Vitis       -----MAVVTVKQLAFIFGLLGNLVSFMVYLSPV---PTFFKIYKRKTSEGYQ 45
XP 004138978 Cucumis     -----MNGLSVHQLQFIFGLLGNIISFLVFLAPM---PTFWTIYKKKTSEGFQ 45
XP 004138979 Cucumis     -----MKGLSVHQLQFIFGLLGNIISFLVFLAPL---PTFWTVYKKKTSEGFQ 45
XP 003518628 Glycine     -----MVSISDHELVLIFGLLGNIVSFMVFLAPL---PTFYTIYKKKSSEGFQ 45
XP 004489106 Cicer       MSKMFTFSDHEMVLIFGLLGNIVSPLVFLAPL---PTFYSICKKKTSEGFQ 48
XP 003617528 Medicago    ----MFPFSNLKMVLLFGPLG-IVTFMSFLAPL---PTFYSIYKKKSSEGPH 44
XP 004302124 Fragaria    -----MAYSTTEQLAFSFGLLGNIVSPMVFLAPM---PTFYRIYKKKSSEGFQ 45
NOD3 MEDTR Medicago      -----MAISHNTLAFTFGMLGNVISFLVFLAPI---STFYRIYKKKSTEGFQ 44
NP 001239695 Glycine     -----MAISHSTLAFAFGMLGNVISFLVFLAPI---TTFYRIFKKKSTEGFQ 44
AFK39311 Lotus           -----MALSHNTLAFTFGMLGNVISFMVFLAPI---ATFYRIYKKKSTEGFQ 44
XP 003620983 Medicago    -----MAISHNTLAFAFGMLGNVISFMVFLAPM---TTFYRIYKKKSTEGFQ 44
XP 003530901 Glycine     -----MVITHHTLAFTFGMLGNVISFLVFLAPV---PTFYRIYKKKSTESFQ 44
XP 003524088 Glycine     -----MAIFNGHNHLALGFGMLGNVISFMVYLAPL---PTFYRIYKKKSTEGFQ 46
XP 003615405 Medicago    -----MDPHD-HDRLAFIFGILGNIISSMVYLAPL---PTFYRIWKKKSTEGPQ 45
XP 003547573 Glycine     -----MPTHHASAAIFGIIGNMISVMVYLAPV---PTFYQIYKKKCTDGFH 43
```

Fig. 2-2

```
XP 003593107 Medicago        -MAMISMNHHFLVIAFGLLGNIISCMVYLAPL---PTFIQIYKKKSTEGFQ 47
EOA22072 Capsella            --MGVVMNHHLLTIIPGILGNAVSFLVLVAPL---PTFYRIYKKKSTESFQ 46
NP 196821 AtSW15             --MGVMINHHFLAFIFGILGNVISFLVFLAPV---PTFYRIYKRKSTESFQ 46
EMJ23678 Prunus              -MGALADSHHPWAFTFGILGNVISFLVYLAPV---PTFYGIYKKKSTQGFQ 47
XP 004301046 Fragaria        --MSMYNSQHHLAFIFVVIGDVISFMVYLAPV---PTFYRIYKKKTTEGPQ 46
XP 002299333 Populus         ------------------MTGNIISFMVYLAPV---PTFIRILRKKSTEDFQ 31
XP 002514863 Ricinus         --MAIISTHPPLAFAFGILGNIISILVYLAPV---PTFYRIYRKKSTEGFQ 46
XP 004140547 Cucumis         --MTIFHSPHLLVFTFGLLGNIISFFVYLAPL---PTFYRIWQKKSTEGFH 46
XP 002264875 Vitis           -MAMAMANHHTLGLIFGILGNIISFLVYFAPA---PTFYRIYKRKSAEGFH 47
NP 199893 AtSW13             ------MALTNNLWAFVFGILGNIISFVVFLAPV---PTFVRICKKKSTEGFQ 44
XP 002862913 Arabiopsis      ------MALTHNVWAFVFGMLGNIISFVVFLAPV---PTFVRICKKKSTEGFQ 44
EOA14916 Capsella            ------MALTHNVWAFVFGIMGNIISFVVFLAPV---PTFIRICKKKSTEGFQ 44
EOA17919 Capsella            ------MVLAHNVLAVTFGVMGNIISFIVFLAPV---PTFVRICKKKSTEGFE 44
NP 194231 AtSW14             ------MVLTHNVLAVTFGVLGNIISFIVFLAPV---PTFVRICKKKSIEGFE 44
EOA21276 Capsella            --MALFDTHNTWAFVFGLLGNLISFAVFLSPV---PTFYRICKKKTTEGFQ 46
NP 197755 AtSW12             --MALFDTHNTWAFVFGLLGNLISFAVFLSPV---PTFYRICKKKTTEGFQ 46
EOA24501 Capsella            --MTLFNTENTWAFVFGLLGNVISFAVFLSPV---PTFYRIWKKKTTEGFQ 46
NP 190443 AtSW11             --MSLFNTENTWAFVFGLLGNLISFAVFLSPV---PTFYRIWKKKTTEGFQ 46
XP 002511126 Ricinus         --MAIFNTHNPSVFVFGLLGNIVSFVVFLAPV---PTFLRVCKKKSTEGFQ 46
XP 004297511 Fragaria        ----MTSSHSPLAFAFGILGNIVSFIVFLAPV---PTFYRVYKKKSTEGFQ 44
XP 004153501 Cucumis         -MALSFNTHNPAAFTFGLLGNIISFIVFLAPV---PTFMRIYKKKSTEGFQ 47
XP 004161952 Cucumis         -MALSFNTHNPAAFTFGLLGNIISFIVFLAPV---PTFMRIYKKKSTEGFQ 47
XP 004145146 Cucumis         -MAL-FDTHHPGVFAFGLLGNIISFIVFLAPV---PTFMRIYKKKSTEGFQ 46
XP 004138250 Cucumis         -MALSFMNHNPWIFAFGLLGNIFSFIVFLAPV---PTFIRVCRKKSTEGFQ 47
XP 004235470 Solanum         --MTSVSHTHPLVYTFGILGNLVSFMVFIAPV---PTFYRIVKKKSSEGFH 46
CBI15715 Vitis               -MAMFTVGHHPWVFASGILGNLMSFLVYLAPI---PTFTRVIKKKSTEGFQ 47
AFW71563 Zea                 -MAFLNMEQQTWAFTFGILGNIISLMVFLSPL---PTFYRVYRKKSTEGFQ 47
NP 001149028 Zea             -MAFLNMEQQTWAFTFGILGNIVSLMVFLSPL---PTFYRVYRNKSTEGFQ 47
XP 002453892 Sorghum         -MAFLNMEQQTWAFTFGILGNIISLMVFLSPL---PTFYRVYRKKSTEGFQ 47
EMT09236 Aegilops            -MAFLNMEQHTWAFTFGILGNIISLMVFLSPL---PTFYRVYRKKSTEGVQ 47
XP 003575028 Brachypodium    -MAFLNMEQHTWAFTFGILGNIISLMVFLSPL---PTFYRVYRKKSTEGFQ 47
NP 001046944 OsSW15          -MAFMSMERSTWAFTFGILGNLISLMVFLSPL---PTFYRVYRKKSTEGFQ 47
EMS46194 Triticum            -MAFLNMEQHTWAFTFGILGNIISLMVFLSPL---PTFYRVYRKKSTEGFQ 47
AFW88409 Zea                 -----MITVGHPVAFAVGILGNILSFLVILAPV---PTFYRVYAKKSTESFQ 44
XP 002465280 Sorghum         -----MITVGHPVVFAVGILGNILSFLVTLAPV---PTFYRVYKKKSTESFQ 44
BAJ99068 Hordeum             -----MAAVGSPLIFAVGILGNLSFLVILAPV---PTFYRVYKRKSTESFQ 44
EMT31030 Aegilops            -----MGAVGSPLVFAVGILGNLSFLVILAPV---PTFYRVYKRKSTESFQ 44
XP 003561640 Brachypodium    -----MAAIGNPWVFAVGILGNLSFLVILAPV---PTFHRVYKRKSTESFQ 44
NP 001050099 OsSW12          ---------MVQALVFAVGIVGNILSFLVILAPV---PTFYRVYKKKSTESFQ 41
BAK07340 Hordeum             MAGGLFSMAHPWASAFGILGNIISFLVFLAPT---PTFLRVYRKKSTEGFS 48
EMS45810 Triticum            MAEGLFSMAHPWASAFGILGNIISFLVFLAPT---PTFLRVYRKKSTEGFS 48
XP 003578398 Brachypodium    MAGALFSMAHPWASAFGILGNIISFLVFLAPT---PTFLRVYRKKSTEGFS 48
XP 002462642 Sorghum         MAGGLFSMEHPWVSAFGILGNIISFLVFLAPV---PTFLRVYRKKSTEGFS 48
EAZ09693 Oryza               ---------MDHLWASVFGILGNIVSFLVFLAPM---PTFLRVYRKKSTEGFS 41
NP 001148964 Zea             MAGGLFSMAHPAVTLSGIAGNIISFLVFLAPV---ATFLQVYRKKSTGGFS 48
XP 002444688 Sorghum         MAGGLFSMAHPAITLSGIAGNIISFLVFLAPV---ATFLQVYRKKSTGGFS 48
XP 003572455 Brachypodium    MAAGFLSMAHPAITLSGVAGNVISFLVFLAPV---TTFVQVVRKKTTGGFS 48
NP 001062354 OsSW11          MAGGFLSMANPAVTLSGVAGNISFLVFLAPV---ATFLQVYRKKSTGGYS 48
EMT31640 Aegilops            MAGGLFDMSHPASALAGIAGNIVSFFVFLAPM---ATFLQIYRKKTTGGFS 48
EMS51422 Triticum            --MGGLSMEHPWAFAFGLLGNVISFSSLLAPI---PTFYRIFKSKSTEGFQ 46
EMT20808 Aegilops            --MGGLSMEHPWAFAFGLLGNVISFSSLLAPI---PTFYRIFKSKSTEGFQ 46
```

Fig. 2-3

```
BAJ85621 Hordeum            ---MAGLSMEHPWAFAFGLLGNIISFTSLLAPI--PTFYRIFKSKSTEGFQ 46
EMT11081 Aegilops           ---MAGLSLEHPWAFAFGLLGNIISFTSLLAPI--PTFYRIFKSKSTEGFQ 46
XP 002442119 Sorghum        ---MAGLSLQHPWAFAFGLLGNVISFLTFLAPI--PTFYRIYKSKSTEGFQ 46
XP 002443167 Sorghum        ---MAGLSLQHPWAFAFGLLGNLISFLTFLAPI--PTFYRIYKTKSTEGFQ 46
NP 001141654 Zea            ---MAGLSLEHPWAFAFGLLGNVISFMTFLAPI--PTFYRIYKSKSTEGFQ 46
NP 001141106 Zea            ---MAGLSLQHPWAFTFGLLGNVISFMTFLAPI--PTFYRIYKSKSTEGFQ 46
SWT13 ORYSJ OsSW13 Oryza    ---MAGLSLQHPWAFAFGLLGNLISFTTYLAPI--PTFYRIYKSKSTEGFQ 46
XP 003576225 Brachypodium   ---MAGLSLEHPWAFAFGLLGNVISFMSYLAPI--PTFIRIYKSKSTEGFQ 46
BAJ94651 Hordeum            ---MGGLSAQHPWAFTFGLLGNVISFMTYLAPL--PTFYRIYKNKSTQGFQ 46
XP 003576036 Brachypodium   ---MAGLSLQHPWAFAFGLLGNVISFMTYLAPL--STFYRIYKNKSTQGFQ 46
EMT20480 Aegilops           ---MGGLSLQHPWAFAFGLLGNVISFMTYLAPL--PTFYRIYRSKSTQGFQ 46
EMT20481 Aegilops           ---MGGLSLEHPWAFAFGLLGNIISFMTYLAPL--PTFYRIYRSKSTQGFQ 46
NP 001132836 Zea            ---MAGLSLQHPMAFAFGLLGNIISFMTYLAPL--PTFCRIYRNKSTEGFQ 46
XP 002450786 Sorghum        ---MAGLSLQHPMAFAFGLLGNIISFMTYLAPLYRPTFYRIYKSKSTQGFQ 48
NP 001067955 OsSW14         ---MAGMSLQHPWAFAFGLLGNIISFMTYLAPL--PTFYRIYKSKSTQGFQ 46
                               . . .:  .:.  .*: : *
                            L-G--IS----LAP----PTF---I----K-----
                            I A  LT    ISS    S L V
                            V    VA    V      T
                            M    M     F      A
                            F    F
```

Fig. 2-4

```
XP 004235326 Solanum      SIPYVVALFSSMLWIYYALLK------SNMPLLIT-INSFGMPIETIYVGF 88
XP 004235334 Solanum      SIPYVVALFSSMLWIYYALLK------SNMPLLIT-INSFGMFIETIYVGL 86
ACV71016 Capsicum         SIPYVIALFSSMLWIYYAFLK------TNVTLLIT-INSFGIPIETIYVGL 88
XP 004235333 Solanum      SIPYVVALFSSMLWIYYAFLK------TNTTLLIT-INTFGVFVETIYVVF 88
XP 004235342 Solanum      SIPYVVALFSSMLWIYYAFLK------TNTTLLIT-INSFGVPIETIYVGF 88
XP 004235339 Solanum      SIPYVIALPSCMLWIYYAFLK------TNTTLLIT-INSFGMLIETIYVSL 87
XP 004241452 Solanum      SIPYVVALFSAMLWIYYAFLK------TNTTLLVT-INTFGCFIETLYVGF 88
XP 004235340 Solanum      SVPYVVGLFSAMLWIYYAFLK------PDTTLLIT-INSVGCFIQTFYICF 85
AFK35161 Medicago         ALPYVVALFSAMLWIYYAFVK------RESALLLIT-INTFGIVVESAYIIM 89
CAC44123 Medicago         ALPYVVALFSAMLWIYYAFVK------RESALLLIT-INTFGIVVESAYIIM 89
XP 004503778 Cicer        SLPYVVALFSAMLWIYYAFVK------REAALLLIT-INTFGIVVESCYLIV 89
AFK48645 Lotus            ALPYVVALFSAMLWIYYAFVK------RESALLLIT-INTFGIVVESIYIAF 89
NP 001241307 Glycine      SLPYVVALFSAMLWIYYAFVK------REAALLLIT-INTFGIVVESIYLAI 89
NP 001242732 Glycine      SLPYIVALFSSMLWIYYALVK------KDASLLLIT-INSFGCVIETIYLAI 89
XP 003523161 Glycine      SLPYVVALFSSMLWIYYALVK------KDASLLLIT-INSFGCVIETIYLAI 89
NP 001237418 Glycine      SLPYVVALFSSMLWIYYALVK------KDASLLLIT-INSFGCVIETIYLAI 89
XP 003602780 Medicago     SVPYVTALLSAMLWIYYAHVK------NKATLLLLT-INIYGFGIEAIYIII 90
XP 004138032 Cucumis      SVPYVVALFSAMLWIYYALLK------TN-ATFLIT-INSFGCVIESLYILL 88
EMJ10621 Prunus           ALPYVIALLSSMLYIYYALLKEE-FKEDATFLIT-INSFGCVVETLYISL 91
XP 004297512 Fragaria     ALPYAVALFSCMLWIYYALL---------KQDATFLIT-INSVGCVIETVYLAI 87
XP 002284244 Vitis        SVPYVVALFSAMLWIYYAFLN------TDASLLIT-INSVGCVIETSYIVM 90
EOA14646 Capsella         SVPYVISLFSAMLWLYYAMIK------KDAVMLIT-INSPAFVIQIVYISL 88
NP 199892 AtSW10          SIPYVISLFSAMLWMYYAMIK------KDAMMLIT-INSFAFVVQIVYISL 88
XP 002321731 Populus      SIPYVIALFSAMLWLPYAIFS------EDAILLIT-INTPAPFMEFGYITV 87
XP 002322281 Populus      SIPYVIALFSAMLWLFYALFK------EDALLLIT-INSFTFPMEIGYIFM 87
XP 002321730 Populus      SIPYVIALFSAMLWLPYASFS------ENAMLLIT-INSPAPFMEIGYIAV 87
XP 002511127 Ricinus      SVPYVIALFSAMLWLFYATFD------DNATLLIT-INSFTFPMEVGYLSV 87
XP 002511128 Ricinus      SIPYVIALFSATLWLFYAIFA------NDATLLIT-INSFAPFMETAYIAI 87
CBI32263 Vitis            SIPYSVALFSAMLLLYYAFLKTDN-----QIMLIT-INSVGTCIEATYLLV 90
EMJ01437 Prunus           SIPYSVALFSAMLMLYYAFLKTN------AFMLIT-INSVGCIIETSYLVM 89
XP 002520679 Ricinus      SIPYSVALFSAMLTLYYATLKEN------AILLIT-INSIGCLIEGIYLTI 88
XP 004247459 Solanum      SIPYSVSLFSAMLYLYYAYLKKN------EILLIT-INSFGTGIQLYLTI 89
EOA28959 Capsella         SIPYICALASATLLLYYGIMKTH------AYLIIS-INTFGCFIEITYLFL 89
NP 181439 AtSW09          SIPYICALASATLLLYYGIMKTH------AYLIIS-INTFGCFIEISYLFL 88
XP 002333315 Populus      SIPYSVALMSASLLLYYGLLKTN------AYLLIS-INSIGCAFEVTYLII 89
NEC1 PETHY Petunia        AIPYMVALFSAGLLLYYAYLRKN------AYLIVS-INGFGCAIELTYISL 89
XP 002267792 Vitis        ALPYSVGLLCASLFLYYALLQSG------KFLILS-INTIGSTIQATYLVL 89
XP 004138978 Cucumis      SIPYVVALMSAMLLLYYAALKTN------AYLLVS-INSFGCVIEVIYIAL 89
XP 004138979 Cucumis      CIPYVVALMSAMLLLYYAVLKTN------AYLLIS-INSFGCVIELIYIAL 89
XP 003518628 Glycine      SIPYAVALLSALLLLYYGFIKTN------ATLIIT-INCIGCVIEVSYLTM 89
XP 004489106 Cicer        SIPYVVALLSAMLLLYYGLLKTN------AILIIT-INCIGCVIEVLYLII 92
XP 003617528 Medicago     SIPYVVTLLSTLLFVYYGFLKTN------AIFLIT-INSIGCMEVAYLIM 88
XP 004302124 Fragaria     SIPYVVALLSAMLLLYYGVIKTN------AILIIS-INAFGIVIEVAYLIF 89
NOD3 MEDTR Medicago       SLPYLVALFSSMLWYYALLK------KDAFLLIT-INSFGCVVETIYIIL 88
NP 001239695 Glycine      SLPYLVALFSSMLWLYYALLK------KDAMLLLT-INSFGCVIEVIYIIL 88
AFK39311 Lotus            SLPYLVALFSSMLWLYYAMVK------KDAFLLIT-INSFGCVIEIIYIIL 88
XP 003620983 Medicago     SLPYLVALFSSMLWLYYAFLK------KDEFLLIT-INSFGCVVELIYIIL 88
XP 003530901 Glycine      SLPYLVALFSSMLWLYYALLK------RDAVLLIT-INSFGCVIEIIYIVL 88
XP 003524088 Glycine      SLPYLVALFSSMLWLYYASLKP------ADATLLIT-INSLGCVIEIVYIIM 91
XP 003615405 Medicago     SLPYLVALFSSMLWLYYGFVK------KHAFLLIT-INSAGCVIETIYIVT 89
XP 003547573 Glycine      SLPYLLSLMSSMLWLYYAFLKI-----HDGVVPLITINSIGCVIELIYILT 89
```

Fig. 2-5

| | | |
|---|---|---|
| XP 003593107 Medicago | SLPYLVALFSSMLWLYYG----I------QTNAIPIVSINAFGCVIEIIYCIM | 90 |
| E0A22072 Capsella | SLPYQVSLFSCMLWLYYALIK-------KNAFLLIT-INSFGCVVQTIYIAM | 90 |
| NP 196821 AtSWI5 | SLPYQVSLFSCMLWLYYALIK-------KDAFLLIT-INSFGCVVETLYIAM | 90 |
| EMJ23678 Prunus | SVPYLVALFSGMLWFYYALLK-------KNAMLLIT-INSFGTVIETTYIVM | 91 |
| XP 004301046 Fragaria | SLPYLVALFGSTLWLYYGIVK-------QNMVLLIT-INTPGSVMETLYIAM | 90 |
| XP 002299333 Populus | SLPYLVALFSSMLWLYYAMLK-------NDEILLVT-INSFGCVIETIYIAI | 75 |
| XP 002514863 Ricinus | SLPYLVALFSSMLWLYYAMLK-------KDVFLLVT-INAFGCVIETIYIIM | 90 |
| XP 004140547 Cucumis | ALPYLVALPSSALWLCYAFLK-------TNTFLLIT-INSFGCVIEPLYPIV | 90 |
| XP 002264875 Vitis | SLPYIVALFSAMLWLYYALLK-------KDAFLLIT-INSFGCAIESPYILL | 91 |
| NP 199893 AtSW13 | SLPYVSALFSAMLWIYYAMQKDG-----TAFLLIT-INAPGCVIETIYIVL | 89 |
| XP 002862913 Arabiopsis | SLPYVSALFSAMLWIYYAMQKDG-----SGFLLIT-INAVGCVIETIYIVL | 89 |
| E0A14916 Capsella | SLPYLSAIFSAMLWIYYAMQKDG-----SGFLLIT-INAVGCVIETIYIVL | 89 |
| E0A17919 Capsella | SLPYVSALFSAMLWIYYAMQKDG-----AGFLLIT-INAVGCFIETIYIIL | 89 |
| NP 194231 AtSW14 | SLPYVSALFSAMLWIYYALQKDG-----AGFLLIT-INAVGCFIETIYIIL | 89 |
| E0A21276 Capsella | SIPYVVALFSAMLWLYYATQKK------DVFLLVT-INSFGCFIETIYISI | 90 |
| NP 197755 AtSW12 | SIPYVVALFSAMLWLYYATQKK------DVFLLVT-INSFGCFIETIYISI | 90 |
| E0A24501 Capsella | SIPYVVALFSATLWLYYATQKK------DVFLLVT-INAFGCFIETIYISM | 90 |
| NP 190443 AtSW11 | SIPYVVALFSATLWLYYATQKK------DVFLLVT-INAFGCFIETIYISM | 90 |
| XP 002511126 Ricinus | SPPYVVSLFSAMLWLYYASLKS------DAFLLIT-INSVGCLIETIYITL | 90 |
| XP 004297511 Fragaria | SIPYIFALFSATIWIYYASLKS------DEMLLIT-INGFGCVIETIYIAM | 88 |
| XP 004153501 Cucumis | SIPYVVALFSAMLWLYYASFNP------NETLLIT-INSVGCLIETIYLAI | 91 |
| XP 004161952 Cucumis | SIPYVVALFSAMLWLYYASFNP------NETLLIT-INSVGCLIETIYLAI | 91 |
| XP 004145146 Cucumis | SVPYVVALFSAMLWLYYASFNS------NETLLIT-INSVGCLIETLYIAI | 90 |
| XP 004138250 Cucumis | SIPYVVALFSALLLIYYSTLNA------DEFFLMT-INSVGCFIETIYIAL | 91 |
| XP 004235470 Solanum | SLPYVVGLFSAMLWIYYAMVKT------NVTLLIT-INSFGCIAETIYVAL | 90 |
| CBI15715 Vitis | SVPYVIALFSAMLWMYYGLVN-------TNASPLLS-VNGFGCFIEIIYISI | 91 |
| AFW71563 Zea | STPYVVTLFSCMLWIFYALLK-------SGAELLVT-INGVGCVIEAAYLAA | 91 |
| NP 001149028 Zea | STPYVVTLFSCMLWILYALLK-------PGAELLVT-INGVGCVVETVYLAM | 91 |
| XP 002453892 Sorghum | STPYVVTLFSCMLWIFYALLK-------SGAELLVT-INGVGCVIETVYLGM | 91 |
| EMT09236 Aegilops | PTPYLVTLFSCLLWMYAFLK--------SGSELLLT-INAVGCVIESLYIAM | 91 |
| XP 003575028 Brachypodium | STPYVVTLFSCLLWMYAFLK--------SGAELLLT-INGVGCGIETLYIAM | 91 |
| NP 001046944 OsSW15 | STPYVVTLFSCMLWMYYAFVK-------SGAELLVT-INGVGCVIETVYLAM | 91 |
| EMS46194 Triticum | STPYLVTLFSCLLWMYAFLK--------SGSELLLT-INAVGCVIESLYIAM | 91 |
| AFW88409 Zea | SVPYVVALLSATLWLYYALLS-------TD-LLLLS-INTVACVAESVYLAV | 87 |
| XP 002465280 Sorghum | SVPYVVALLSAMLWLYYALLS-------ID-VLLLS-INTIACVVESVYLAI | 87 |
| BAJ99068 Hordeum | SVPYAMALLSAMLWLYYALLT-------KD-LLLLT-INTVGCVVETAYLAI | 87 |
| EMT31030 Aegilops | SVPYAMALLSAMLWLYYALLT-------KD-LLLLT-INTVGCVVESAYLAI | 87 |
| XP 003561640 Brachypodium | SAPYAMALLSAMLWLYYALLT-------AD-LLLLS-INAVGCVVETAYLAV | 87 |
| NP 001050099 OsSW12 | SVPYAVALLSAMLWLYYALLT-------SD-LLLLS-INSIGCLVESLYLTV | 84 |
| BAK07340 Hordeum | SVPYVVALFSCTLWILYALVK-------TNSSPLLT-INAFGCVVEAFYIVL | 92 |
| EMS45810 Triticum | AVPYVVALFSCMLWIFYALVK-------TNSSPLLT-INAFGCVVESFYILL | 92 |
| XP 003578398 Brachypodium | SVPYVVALFSCTLWILYALVK-------TNSSPLLT-INAFGCVVEAAYIVL | 92 |
| XP 002462642 Sorghum | SVPYVVALFSCTLWILYAVVK-------TNSSPLLT-INAFGCVVEATYILL | 92 |
| EAZ09693 Oryza | SVPYVVALPSCTLWILYAMVK-------TNSSPLLT-INAFGCVVEAAYIAV | 85 |
| NP 001148964 Zea | SVPYVVALFSSVLWIFYALVK-------TNSRPLLT-INAFGCGVEAAYIVL | 92 |
| XP 002444688 Sorghum | SVPYVVALFSSVLWIFYALVK-------TNSRPLLT-INAFGCGVEAAYIVF | 92 |
| XP 003572455 Brachypodium | AVPYVVALFSSTLWILYALLK-------GNSRPLLT-INGFGCGVELAYVVA | 92 |
| NP 001062354 OsSW11 | SVPYVVALFSSVLWIFYALVK-------TNSRPLLT-INAFGCGVEAAYIVL | 92 |
| EMT31640 Aegilops | SVPYVVALFSCSLLIFYALLK-------TDSPLLLT-INSFGCCIETVYIVA | 92 |
| EMS51422 Triticum | SVPYVVALFSAMLWIFYALVK-------TGEGLLIS-INAAGCVIETVYIVM | 90 |
| EMT20808 Aegilops | SVPYVVALFSAMLWIFYALVK-------TGEGLLIS-INAAGCVIETVYIVM | 90 |

Fig. 2-6

```
BAJ85621 Hordeum          SVPYVVALFSAMLWIFYALVK--------TGEGLLIT-INAAGCVIETVYIIM 90
EMT11081 Aegilops         SVPYVVALFSAMLWIFYALVK--------TGEGLLIS-INAAGCVIETVYIVM 90
XP 002442119 Sorghum      SVPYVVALFSAMLWIFYALIK--------SNETFLIT-INAAGCVIETIYIVM 90
XP 002443167 Sorghum      SVPYVVALFSAMLWIFYALIK--------SNETFLIT-INAAGCVIETIYIVM 90
NP 001141654 Zea          SVPYVVALFSAMLWIFYALIK--------SNETFLIT-INAAGCVIETIYIVM 90
NP 001141106 Zea          SVPYVVALFSAMLWIFYALIK--------SNETFLIT-INAAGCVIETVYVVM 90
SWT13 ORYSJ OsSW13 Oryza  SVPYVVALFSAMLWIFYALIK--------SNEALLIT-INAAGCVIETIYIVM 90
XP 003576225 Brachypodium SVPYVVALPSAMLWIYYALVK--------SNESLLIT-INAAGCVIETIYVVM 90
BAJ94651 Hordeum          SVPYVVALFSAMLWIYYALLK--------SDEYLLIT-INTAGCVIETIYIVL 90
XP 003576036 Brachypodium SVPYVVALFSAMLWIYYALLK--------SDGCLLIT-INTAGCVIETIYIVV 90
EMT20480 Aegilops         SVPYVVALFSAMLWIYYALLK--------SDELLLIT-INSAGCIIETIYIVM 90
EMT20481 Aegilops         SVPYVVALFSAMLWIYYALLK--------SDELLLIT-INSAGCVIETIYIIM 90
NP 001132836 Zea          SVPYVVALFSAMLWIYYALLK--------SNEFLLIT-INSAGCVIETLYIAT 90
XP 002450786 Sorghum      SVPYVVALFSAMLWIYYALLK--------SNEFLLIT-INSAGCVIETLYIVM 92
NP 001067955 OsSW14       SVPYVVALFSAMLWIYYALLK--------SDECLLIT-INSAGCVIETIYIAV 90
                          **   :  : .*.               : :*     :       * 
                          ---PY----L------L-I-YA----(7-13aa)----I---IN---------E---Y---
                                   I    I L  S                  L   V         Q
                                        M G                      V
                                        V                        M
                                        F
```

Fig. 2-7

```
XP 004235326 Solanum    YLFYAPKKARVHT-IKMLMLSVVGGFGAIVLVTEPLFK-GVVRGQIVGWI 136
XP 004235334 Solanum    YLLYAPNKARVHT-IKMLMLSVVGGFGAIVLITEPLFK-GVVRGQIVGWI 134
ACV71016 Capsicum       YLFYAPKKARVHT-VKMLLLTVVGGFGAIVLVTQFLFK-GVVRGQIVGWI 136
XP 004235333 Solanum    YLIYAPKKSRVQT-IKMLSLPVVGGFGAIILVTQPLFK-GVIRGQVVGWI 136
XP 004235342 Solanum    YLFYAPKKDRVQT-IKMLMLSVVGGFGAIVLITEPLFK-GVVRGQIVGWI 136
XP 004235339 Solanum    FLYYAPKKARVNT-VKMLLLTVVGGFGAIILVTQPLFK-GVVRGQIVGWI 135
XP 004241452 Solanum    YLFYAPKKARVQT-IKLLLLLVVGGFGAIILITQPLFK-GAIRAQIVGWI 136
XP 004235340 Solanum    FLFYATKKAKMDT-MKLLLSMNVVGLGLIIPLTQFFAK-GSNRAQIVGWI 133
AFK35161 Medicago       FLIYAPKKQRLST-IKLLLLLNVPGFGAMLLSTLYLSK-GAKRLAIIGWI 137
CAC44123 Medicago       FLIYAPKKQRLST-IKLLLLLNVPGFGAMLLSTLYLSK-GAKRLAIIGWI 137
XP 004503778 Cicer      FLIYATKKSRLST-IKLLLLLNVPGFGAMLLSTLYLAK-GAKRLAIIGWI 137
AFK48645 Lotus          FLFYAPKKSRLST-IKLLLLLNVPGFGAMLLATLYLSK-GAKRLQIIGWI 137
NP 001241307 Glycine    FLLYAPRKPRLTT-IKLLLLLNVPGFGAMLLSTLYLSK-GAKRLAIIGWI 137
NP 001242732 Glycine    FLIYAPSKTRLWT-IKLLLMLNVPGFGAMLLSTLYLTT-GSKRLSVIGWI 137
XP 003523161 Glycine    FLVYAPSKTRLWT-IKLLLMLNVPGFGGMLLSTLYLTT-GSKRLSVIGWI 137
NP 001237418 Glycine    FLIYAPSKTRLWT-IKLLLMLNVPGFGAMLLSTLYLTT-GSKRLTVIGWI 137
XP 003602780 Medicago   FLLYASNKARLST-IKLLFLT-VCGYGTMVILTTYLTK-GSKRLSIIGWI 137
XP 004138032 Cucumis    FIIYAPTKLRFQT-AKVIFLLNVLGFGMLALTLVLAK-GEKRLKVLGWI 136
EMJ10621 Prunus         FLFYAPKKARIST-LTLVFLLNLFGFGLMMLLTHPLAT-GEMRLKIVGWI 139
XP 004297512 Fragaria   FLFYSPKKARIST-VKFLLLLNVLGYGLMLVLTLPLAK-GEIRLKVVGWI 135
XP 002284244 Vitis      FLVYAPKKARITT-VKLVFLMNICGPGSILLLTLLLAE-GANRVRILGWV 138
EOA14646 Capsella       FFFYAPKKDKILT-VKFVLFVDVPAFGLIFFSTYPPIH-GNKRVQVLGYI 136
NP 199892 AtSW10        FFFYAPKKEKTLT-VKFVLFVDVLGFGAIFVLTYPIIH-ANKRVQVLGYI 136
XP 002321731 Populus    YLLYATKKDKILT-FKLLLLFNSFGPGLICVLTLFLTQ-GQKRVQVLGWI 135
XP 002322281 Populus    YLLYATKKDKILT-FKLLLFPNVPGFGLICVLTRPLTQ-RQKRVQVLGWI 135
XP 002321730 Populus    YLFYATKKDKILT-FKLLLLFNIFGPGLICALSLLLTE-GTKRVHVLGWI 135
XP 002511127 Ricinus    YLFYGTRKDRMLT-TKLVLFFNVPGFGMIAILTLFLTH-GRKRVDVLGWI 135
XP 002511128 Ricinus    YLFYAVKKDRLFT-TKLVLSLNIFAFGSICVIAMPLTH-GQKRVQLLGWI 135
CBI32263 Vitis          YMIYAPRTAKIYT-AKLLLLFNTGVYGAIVLSTPFLSK-GHRRAKIVGWV 138
EMJ01437 Prunus         YMIYAPAKTRIYT-AKLLVLPNVGVYGIVILSTYLIPN-HPLRIKVVGWI 137
XP 002520679 Ricinus    YMIYATQTSRVQIHFKLLILFNLGTYLLIVMLASELTH-GTLRVQVVGWI 137
XP 004247459 Solanum    FMIYATKSAKIFA-TKLLIGFNLVAFGAIVGLTYVFANENDLRISIVGWI 138
EOA28959 Capsella       YIFYAPREARIFT-LKLIVICNIGGLGLLILLVNLLVP-KPHRVSTVGWV 137
NP 181439 AtSW09        YILYAPREAKIST-LKLIVICNIGGLGLLILLVNLLVP-KQHRVSTVGWV 136
XP 002333315 Populus    YLIYAPKQEKMHT-MKLLLIFNMGSFGVVLLLTMLLMK-GKPRLSVVGWI 137
NEC1 PETHY Petunia      FLFYAPRKSKIFT-G-WLMLLELGALGMVMPITYLLAE-GSHRVMIVGWI 136
XP 002267792 Vitis      FIIYSPRAGKVAT-LKMILILNVASLGLVLLLTTLFSK-GKTRIQVVGWI 137
XP 004138978 Cucumis    YLFYAPKKQKIFT-LKLFIIPNLGFSGVMVGGTMPFLH-GMKRTNAVGWI 137
XP 004138979 Cucumis    YFYYAPKKLKIFT-LKLLMILNLGSYGVMVGGTMLILH-GNKRTHAVGWI 137
XP 003518628 Glycine    YIIYAPRKQKIST-LVMILIADIGGPGLTMLITTFAVK-GINRVHAVGWI 137
XP 004489106 Cicer      YIIYAPRKLKIST-LALILVADLGGLGLTLIITNPIVK-SYYRVHAVGLI 140
XP 003617528 Medicago   YITYAPKKLKIST-LVLILIVDMGGFGLTMIITTFIVK-GSPHVQVVGMI 136
XP 004302124 Fragaria   YLTYAPKKQRIFT-LNLILLVNVA-FGLTLAATIFLLS-GTKRVAAVGWI 136
NOD3 MEDTR Medicago     YIIYAPRDARNLT-FKLLSAMNVGSFALILIVTNYAVHGP-LRVQVLGWV 136
NP 001239695 Glycine    YITYATRDARNLT-LKLFFAMNVGAPALILLVTHFAVHGS-LRVQVLGWI 136
AFK39311 Lotus          YMIYAPRDARNLT-LKLFTAMNVGSFALILLVTHPAVHGP-LRVQVLGWI 136
XP 003620983 Medicago   YIIYATKDARKLT-IKLLLAMNIGSFGLILLVTKYAVHGP-IRVQVLGWI 136
XP 003530901 Glycine    YITYATRDARNLT-IKLFSAMNMTSPAVILLVTHFGVHGP-LRVQVLGWI 136
XP 003524088 Glycine    FTIYATKDARNLT-VKLFMVMNVGSFALIFLVTYPAMHGS-LRVQVVGWV 139
XP 003615405 Medicago   YLIYATKDARILT-IKLFMAMNVACSVLIVLTTQLAMHGK-LRVHVLGWI 137
XP 003547573 Glycine    YIKYAHKDARNLT-YTLFAAMN-IAFLTLVLSSHFALHGS-HRVKVIGWI 136
```

Fig. 2-8

```
XP_003593107 Medicago        YIAYATKDARKLT-IKLCAALNVVSFVLIFLIIQFSIPEN-HRVQVLGWI 138
E0A22072 Capsella            FLAYATRDKRISA-MKLFIAINVFFSLILLVTHFVVKTPTLQVSVLGWI 139
NP_196821 AtSW15             FFAYATREKRISA-MKLFIAMNVAFFSLILMVTHFVVKTPPLQVSVLGWI 139
EMJ23678 Prunus              FIFYAPKDARKFT-LKLFGFMNVGLFCSILVLSHFAVRSE-YRVPVLGWI 139
XP_004301046 Fragaria        YIVYATNASRKLT-IKLFGFMNLGLPSLIVVCISYAVHSE-YRALVLGXI 138
XP_002299333 Populus         YIAYATRESKVST-IKLLLSMNMGLFSLIILLTHPLASGS-TRVKALGWL 123
XP_002514863 Ricinus         YIIYATKKNRVST-FKVLTSMNLGLPAFIILFSHFLVKSS-VRAQVLGWI 138
XP_004140547 Cucumis         FIVFAANSVRMLT-IRIFAMMNMGLFGLILVAIHPIPNPS-NRTDVMGWI 138
XP_002264875 Vitis           YFPYAPMQAKKQT-LKVVISLNVGVFSILVVLIQFLLKGS-NRINVFGWI 139
NP_199893 AtSW13             FVSYANKKTRIST-LKVLGLLNFLGAAIVLVCELLTK-GSTREKVLGGI 137
XP_002862913 Arabiopsis      FVTYANKKTRIST-LKVLGLLNFLGAAIVLVCELLTE-GSTREKVLGGI 137
E0A14916 Capsella            FVTYANKKTRIST-LKVLGLLNFLGFAAIVLVCELLTK-GSTRAKVLGGI 137
E0A17919 Capsella            FLTYANKKARIST-LKVLGLLNFLGFAAIILVCELLTK-GSNREKVLGGI 137
NP_194231 AtSW14             FITYANKKARIST-LKVLGLLNFLGPAAIILVCELLTK-GSNREKVLGGI 137
E0A21276 Capsella            FLAFATKNRAMLT-VKLLLLMNVGGFCAILLLCQFLAK-GATRAKIIGGI 138
NP_197755 AtSW12             FVAFASKKARMLT-VKLLLLMNFGGFCLILLLCQFLAK-GTTRAKIIGGI 138
E0A24501 Capsella            FLAYAPKPARMLT-VKILLLMNFGGFCLILLLCQLLLK-GATRAKIIGGI 138
NP_190443 AtSW11             FLAYAPKPARMLT-VKMLLLMNFGGFCAILLLCQFLVK-GATRAKIIGGI 138
XP_002511126 Ricinus         FITYAPKQARITT-LKILLLLNFGGFCLILLLSHPLAK-GSERATILGWV 138
XP_004297511 Fragaria        YITYAPKKARVNT-LRLLLLVNFGGFCLILLPLSHFLTQ-GPTRVKVLGWV 136
XP_004153501 Cucumis         FIVFAPKQIRVST-LRFVLLLNFGGFCIILLVTHFLVH-GSNRVKVVGWI 139
XP_004161952 Cucumis         FIVFAPKQIRVST-LRFVLLLNFGGFCIILLVTHFLVH-GSNRVKVVGWI 139
XP_004145146 Cucumis         FIVFAPKQIRVST-LRFVLLLNFGGFCIILLVTHFLVH-GSNQVKVVGWI 138
XP_004138250 Cucumis         YIAYAPKKARIFT-VRFVLLLDVVGFCSILVVTQPLVK-RAYRARVIGFI 139
XP_004235470 Solanum         YFTYATKKARMKT-LGLVLLLNFGVPGLILFLTQILCQ-GTKRAEVIGWI 138
CBI15715 Vitis               YLIPAPRRARILT-LRLLLLINLGAFCLILIVTNPMVK-RPHRVKAVGWV 139
AFW71563 Zea                 YLVYAPKAARALT-AKMLLGLNVGVP-GLAALATMVVSSAGLRVRVLGWI 139
NP_001149028 Zea             YLVYAPKAARVLA-AKMLLGLNVAVF-GLVALVTMLLSDAGLRVHVLGWI 139
XP_002453892 Sorghum         YLLYAPKAARVLT-AKMLLGLNVGVP-GLVALVTMVLSNGGLRVKVLGWI 139
EMT09236 Aegilops            YLVYAPKSARLLT-AKLFIGLDVGLF-GLIALVTMLASYGPLRVQVVGWI 139
XP_003575028 Brachypodium    YLIYAPKSARLLT-AKLFLGLDVGLF-GLIALVTMLVSAGTLRVQIVGWI 139
NP_001046944 OsSW15          YLAYAPKSARMLT-AKMLLGLNIGLF-GVIALVTLLLSRGELRVHVLGWI 139
EMS46194 Triticum            YLVYAPKSARLLT-AKLFIGLDVGLF-GLIALVTMLASHGPLRVQVVGWI 139
AFW88409 Zea                 YLAYAPGPAKAFT-LKLLCAINMGLFGAMVAFLQFYVVDTQRRVSIAGGV 136
XP_002465280 Sorghum         YLTYAPKPAMAFT-LKLLFTMNMGLFGAMVAFLQFY--VDGQRRVSIAGGV 135
BAJ99068 Hordeum             YLAYAPKQAKAFT-AKLVCIMNVALYGAMVCVLQLLVRDGESRVTIAGGI 136
EMT31030 Aegilops            YLAYAPKQARTFT-AKLVCIMNVALYGAMVCVLQLLVKDGESRVTIAGGI 136
XP_003561640 Brachypodium    YLAYAPKQARAFT-VKLVFVMNVALYGAMVAFLQLYVRDGDRRVAIAGGV 136
NP_001050099 OsSW12          YLLYAPRQAMAFT-LKLVCAMNLALFAAVVAALQLLVKATDRRVTLAGGI 133
BAK07340 Hordeum             YLVYAPRPARMRA-LAFFLLLNVAAF-SLIVAVTVFLVPQPSRVKVLGSV 140
EMS45810 Triticum            YVVYAPRNARHRA-LAFFLLLDVAAF-SLIVVVTVFLVPQPSRVKVLGSV 140
XP_003578398 Brachypodium    YLVYAPRPARLRT-LASFLLLNVAAF-SLIVAVTVFLVAPMHRVKVLGSI 140
XP_002462642 Sorghum         YLIYAPRAARLRA-LAFFFLLDVAAL-ALIVVVVVLVAEPHRVKVLGSI 140
EAZ09693 Oryza               YLVYAPRPARLRA-LASFLLLNVAAF-SLVVVVTVAAVVQPHRVRVLGSI 133
NP_001148964 Zea             YLAYAPRRARLRT-LAYFFLLDVAAF-ALVVAVTLFAVREPHRVKFLGSV 140
XP_002444688 Sorghum         YLAYAPRKARLRT-LAYFFLLDVAAF-ALVVVVTLFVVREPHRVKFLGSV 140
XP_003572455 Brachypodium    YLLYAPRKARLRA-LAYPLALDVAAP-AIVAAVALLGVAPEHRVKFLGSV 140
NP_001062354 OsSW11          YLVYAPRRARLRT-LAFFLLLDVAAF-ALIVVTTLYLVPKPHQVKFLGSV 140
EMT31640 Aegilops            YLVYAPPRARLRT-LAYFFVLDVAAP-GLVLVVTMYAFAPAHRVKFLGSV 140
EMS51422 Triticum            YLVYAPRKAKIFT-AKIVVLLNITGF-GLIFLLTLFAFHGETRVVSLGWI 138
EMT20808 Aegilops            YLVYADRKAKIFT-AKIVVLLNIAGF-GLIPLLTLFAFHGETRVVTLGWI 138
```

Fig. 2-9

```
BAJ85621 Hordeum          YLVYAPRKAKIFT-AKIVLLLNVACF-GLIFLLTLFAFHGETRVVSLGWI 138
EMT11081 Aegilops         YLVYAPRKAKIFT-AKIVVLLNVACF-GLILLLTLFAFHGETRVISLGWI 138
XP 002442119 Sorghum      YFVYAPKKAKLFT-AKIMLLLNVGVF-GVILLVTLLLPKGDKRVVMLGWI 138
XP 002443167 Sorghum      YFVYAPKKAKLFT-AKIMLLLNVGVF-GVILLVTLLLPKGDKRVVMLGWI 138
NP 001141654 Zea          YFVYAPKKAKLFT-AKIMALLNGGVF-GVILLLTLLLPKGSKRVVLLGWI 138
NP 001141106 Zea          YFVYATKKGRMFT-AKIMLLLNVGAF-GAILLLTLLLPKGDKRVVMLGWI 138
SWT13 ORYSJ OsSW13 Oryza  YLAYAPKKAKVFT-TKILLLLNVGVF-GVILLLTLLLSHGEQRVVSLGWV 138
XP 003576225 Brachypodium YFVYAPRKAKLFT-AKIMLLLNGGVF-GVILFCTLPLAHGEKRVSLGWI 138
BAJ94651 Hordeum          YLAYAPKQARLFT-AKILLLLNVGVF-GLILLLTLLLTAGERRVVMLGWV 138
XP 003576036 Brachypodium YLAYAPKQAKLFT-AKILLLLNVGVF-GMILLLTLLLSEGEKRVVMLGWV 138
EMT20480 Aegilops         YLAYAPKQAKIFT-AKILLLLNVGVF-GLILLLTLLLAGGEKRVVMLGWV 138
EMT20481 Aegilops         YLTYAPKQAKLFT-AKILLLLNVGVF-GLILLLTLLLAGGEKRVVMLGWV 138
NP 001132836 Zea          YLLYAPNKAKLFT-AKILLLLNVGVF-GLILLLTLLLSAGPHRVVVLGWV 138
XP 002450786 Sorghum      YLLYAPKKAKLFT-AKILLLLNVGVF-GLILLLTLLLSAGQHRVVVLGWV 140
NP 001067955 OsSW14       YLVYAPKKAKMFT-AKLLLLVNVGVF-GLILLLTLLLSAGDRRIVVLGWV 138
                          : :.                            : * :
                          Y---YA-------------(35-36aa)--------------R-----G-V
                          P  FG                                     Q     I
                             S                                       H     L
```

Fig. 2-10

```
XP 004235326 Solanum     CLIFSLCVFVAPLGIVR-------QVIKTKSVEYMPLLLSVFLTLSAVMWFF 181
XP 004235334 Solanum     CLIFSLCVFVAPLGIVR-------KVIKTKSVEYMPLLLSVFLTLSAVMWFF 179
ACV71016 Capsicum        CLIFALSVFVAPLGIVR-------QVIKTKSVEYMPLLLSVFLTLSAVMWFF 181
XP 004235333 Solanum     CLIFSLCVFVAPLGIVR-------KVIKTKSVEYMPLLLSVFLTLSAVMWFF 181
XP 004235342 Solanum     CLIFSLCVFVAPLGIVK-------QVIKTKSVEYMPLLLSIFLTLSAVVWFF 181
XP 004235339 Solanum     CLIFSLCVFVAPLGIVR-------QVIKTKSVEYMPILLSVFLTISAVMWFF 180
XP 004241452 Solanum     CLVFSLCVFVAPLCIVR-------QVIKTKSVEYMPFLLSVFLTLSAVMWFF 181
XP 004235340 Solanum     CLIFSFCVFVAPLGVLR-------QVIRTKSVEYMPFQLSFFLTLSAVMWFL 178
AFK35161 Medicago        CLVFNISVFATPLFVIS-------KVIRSRSVEYMPFFLSFFLTINAVMWFF 182
CAC44123 Medicago        CLVFNISVFAAPLFVIS-------KVIRSRSVEYMPFFLSFFLTINAVMWFF 182
XP 004503778 Cicer       CLVFNITVFAAPLFIIS-------RVIRTRSVEYMPFFLSFFLTINAVMWFF 182
AFK48645 Lotus           CLVFNISVFAAPLFIIS-------KVIRTRSVEYMPFFLSPSLTINAVMWFF 182
NP 001241307 Glycine     CLVFNISVPAAPLFIIR-------RVIKTRSVEYMPFTLSMFLTINAVMWFF 182
NP 001242732 Glycine     CLVLNISVFAAPLCIMK-------RVIKTKSVEFMPFSLSFFLTINAVMWFF 182
XP 003523161 Glycine     CLVFNISVFAAPLCIMK-------RVIKTRSVEFMPFSLSLSLTINAVMWFF 182
NP 001237418 Glycine     CLVFNISVFAAPLCIIK-------RVIKTKSVEFMPFSLSFFLTINAVMWFF 182
XP 003602780 Medicago    CMVFNICVFASPLFILK-------QVIKTKSVAFMPLNLSFFLTLNAIVWFF 182
XP 004138032 Cucumis     CLVPNLSVPAAPLFIMG-------KVIKTKSVEYMPFALSFFLTLNAVMWFF 181
EMJ10621 Prunus          CLVFSLSVFVAPLGVLR-------RVIRTKSVEFMPFPLSFFLTLGAVTWFF 184
XP 004297512 Fragaria    CLVPNLTVPAAPLCILK-------KVIRTKSVEFMPFPLSFFLTLGAVMWFF 180
XP 002284244 Vitis       CLVFSLSVFLAPLCIMR-------QVIRTKSVEYMPFLLSFFLTLSAVMWFF 183
EOA14646 Capsella        CMVFALSVFVAPLGIIR-------KVIKTKSAEFMPFGLSFFLTLSAVMWFF 181
NP 199892 AtSW10         CMVFALSVFVAPLGIIR-------KVIKTKSAEFMPFGLSFFLTLSAVMWFF 181
XP 002321731 Populus     CMIFSLCVFVAPLFIVR-------EVIKTKSVEFMPFSLSFFLTLSAVMWFF 180
XP 002322281 Populus     CMTFSLCVFVAPLFIVR-------KVIRTKSVEFMPFSLSFFLTLSAVMWFF 180
XP 002321730 Populus     CMVFALCVFVAPLGVVR-------KVIRTKSVEFMPFSLSFFLTLSAVMWFF 180
XP 002511127 Ricinus     CMIFALCVFVAPLGIMR-------KVIKTKSVEFMPFSLSFFLTLSAVMWFF 180
XP 002511128 Ricinus     CMVFALCVFVAPLAIVR-------KVIKTKSVEFMPFSLSFFLTLSAVMWFF 180
CBI32263 Vitis           CAAFSLCVFAAPLSIMR-------LVIRTKSVEYMPFPLSFFLTICAVMWFF 183
EMJ01437 Prunus          SVVFSVCVFAAPLSIMR-------LVIRTRSVEFMSFPLSFCLTLCAVMWFF 182
XP 002520679 Ricinus     CAVFSVCVFAAPLSIMR-------LVIKTKSVEYMPFSLSFFLTLCAISWLG 182
XP 004247459 Solanum     CAVFSVSVPAAPLSIMR-------RVIQTKSVEFMPFPLSFFLTICAVMWFF 183
EOA28959 Capsella        CAAYSLAVFASPLSVMR-------KVIKTKSVEYMPFLLSLSLTLNAVMWFF 182
NP 181439 AtSW09         CAAYSLAVFASPLSVMR-------KVIKTKSVEYMPFLLSLSLTLNAVMWFF 181
XP 002333315 Populus     CAVFSVAVCAAPLSIMR-------RVVRTKSVEYLPFTLSASITLNAVMWFF 182
NEC1 PETHY Petunia       CAAINVAVPAAPLSIMR-------QVIKTKSVEFMPFTLSLFLTLCATMWFF 181
XP 002267792 Vitis       SAGVNIGTFVAPLSIIK-------RVIETRSVEYMPFNLSFFLTICATMRFF 182
XP 004138978 Cucumis     CAAFNLSVFASPLSIMK-------RVITTKSVEYMPFSLSFFLTLSATMWFF 182
XP 004138979 Cucumis     CAAPNLAVFASPLAIMK-------RVITTKSVEYMPFSLSFFLTLSATMWFF 182
XP 003518628 Glycine     CAIFNIAVFAAPLSIMR-------RVIKTKSVEFMPFSLSLFLTLCATMWFF 182
XP 004489106 Cicer       CAIPNIAVFAAPLSIMR-------KVIKTRSVEYMPFFLSLFLTLCATMWFF 185
XP 003617528 Medicago    CTIFNIGMFAAPLSIMK-------KVIKTRSVEYMPFPLSLFLTICATMWFF 181
XP 004302124 Fragaria    CAVFNIAVPAAPLSIMR-------EVIRTKSVEFMPFGLSLFLTLCATTWFF 181
NOD3 MEDTR Medicago      CVSLSVSVFAAPLSIVA-------QVVRTKSVEFMPFNLSFTLTLSATMWFG 181
NP 001239695 Glycine     CVSLSISVFAAPLSIVA-------QVVRTKSVEFMPFNLSFTLTLSAIMWFG 181
AFK39311 Lotus           CVSIAVSVFAAPLSIVA-------QVVRTKSVEFMPFNLSFTLTLSATMWFG 181
XP 003620983 Medicago    CVSISVSVFAAPLTIVA-------QVVRTKSVEFMPFNLSFTLTLSAIMWFG 181
XP 003530901 Glycine     CVSISVSVPAAPLSIVA-------QVVRTKSVEFMPFNLSFTLTLSAIMWFG 181
XP 003524088 Glycine     CVSIAVGVFAAPLSIVA-------QVIRTKNVEFMPFNLSLFLTISAVMWFF 184
XP 003615405 Medicago    CTSFAICVFAAPLTIMA-------KVIRTKSVEFMPINLSFFLTLSAIVWFF 182
XP 003547573 Glycine     CDAVSLSVFASPLSIMA-------KVIRTKSVQFMPFYLSFFLTLNAITWFV 181
```

Fig. 2-11

```
XP 003593107 Medicago        CTSISISVFAAPLSIVV-------RVVKTKSVEFMPPNLSLFLTLSAVVWFL 183
EOA22072 Capsella            CVAISVAVFAAPLMIVA-------RVVKTKSVEYMPFTLSFFLTISAVMWFG 184
NP 196821 AtSW15             CVAISVSVFAAPLMIVA-------RVIKTKSVEYMPFTLSFFLTISAVMWFA 184
EMJ23678 Prunus              NVAISVIVFAAPLSIVA-------QVIRTRSVEFMPSLSFFLTLSAVMWFS 184
XP 004301046 Fragaria        NVAVTICASAAPLSIVA-------QVIRTGSVEFMPFTLSFFLTLSGVLWFS 183
XP 002299333 Populus         CVAFSVCVFAAPLNIVK-------QIIRTKSVEFMPFTLSFFLTLSAVIWFA 168
XP 002514863 Ricinus         CVAVSVCVFAAPLSIVA-------QVIKTRSVEFMPPNLSFFLTLSAIMWFA 183
XP 004140547 Cucumis         CVAVSVSVFAAPLSIIR-------QVMTTKSVEFMPFTLSFFLTLSAIMWFA 183
XP 002264875 Vitis           CASFSVAVFAAPLSIVA-------RVIRTKSVEFMPPSLSFFLTLSAIMWFA 184
NP 199893 AtSW13             CVGFSVSVFAAPLSIMR-------VVVRTRSVEFMPFSLSLFLTISAVTWLF 182
XP 002862913 Arabiopsis      CVGFSVSVFAAPLSIMR-------VVVRTRSVEFMPFSLSLFLTISAVTWLF 182
EOA14916 Capsella            CVGFSVSVFAAPLSIMR-------LVVRTRSVEFMPFSLSLFLTISAVTWLF 182
EOA17919 Capsella            CVGFSVCVFAAPLSIMR-------VVIRTKSVEFMPFSLSLFLTLSAITWLF 182
NP 194231 AtSW14             CVGFSVCVFAAPLSIMR-------VVIRTKSVEFMPFSLSLFLTISAITWLF 182
EOA21276 Capsella            CVGFSVCVFAAPLSIIR-------TVIKTKSVEYMPFSLSLTLTISAVIWLL 183
NP 197755 AtSW12             CVGFSVCVFAAPLSIIR-------TVIKTKSVEYMPFSLSLTLTISAVIWLL 183
EOA24501 Capsella            CVGFSVCVFAAPLSIIR-------TVIKTRSVEYMPFSLSLTLTISAIIWFL 183
NP 190443 AtSW11             CVGFSVCVFAAPLSIIR-------TVIKTRSVEYMPFSLSLTLTISAVIWLL 183
XP 002511126 Ricinus         CVIFSVSVFAAPLSVMR-------IVIRTKSVEFMPPYLSFFLTLSAIMWLF 183
XP 004297511 Fragaria        CVAFSVSVFAAPLSIMR-------LVIRTKSVEFMPFSLSFFLTLSAIMWLF 181
XP 004153501 Cucumis         CVAFSISVFAAPLTIIR-------LVIRTKSVEFMPPYLSFFLTLSATSWLL 184
XP 004161952 Cucumis         CVAFSISVFAAPLTIIR-------LVIRTKSVEFMPFYLSFFLTLSATSWLL 184
XP 004145146 Cucumis         CVAFSVSVFAAPLTIMR-------LVIRTKSVEFMPFSLSFFLTLSAITWLL 183
XP 004138250 Cucumis         CGGLSVSVFAAPLSIMK-------RVIRTRSVEYMPFSLSFFLTLSAVMWLC 184
XP 004235470 Solanum         CMAFSISVFVAPLSIMG-------RVIRTKSVEFMPPNLSLALTVSAVMWFL 183
CBI15715 Vitis               CLIFAVSVFAAPLSIMASILYRLVIRTKSVEFMPLPLSICLTLSAVGWFF 189
APW71563 Zea                 CVSVALSVFAAPLSIMR-------QVVRTKSVEFMPISLSFPLVLSAVIWFA 184
NP 001149028 Zea             CVSVSLSVFAAPLSIMR-------QVIRTKSVEFMPISLSFPLVLSAVVWFA 184
XP 002453892 Sorghum         CVSVALSVFAAPLSIMR-------QVIRTKSVEFMPISLSFPLVLSAVIWFA 184
EMT09236 Aegilops            CVAVALGVFAAPLSIIR-------LVIRTKSVEFMPFSLSFPLVLSAVIWFA 184
XP 003575028 Brachypodium    CVAVALGVFAAPLSIIR-------LVIRTKSVEFMPISLSFPLVLSAVIWFA 184
NP 001046944 OsSW15          CVAVSLSVFAAPLSIIR-------LVIRTKSVEFMPFSLSFPLVLSAVIWFL 184
EMS46194 Triticum            CVAVALGVFAAPLSIIR-------LVIRTKSVEFMPFSLSFPLVLSAVIWFA 184
AFW88409 Zea                 GAAFALAVFVAPLAIIR-------RVMRTKSVEFMPFWLSFPLTVSAVVWFF 181
XP 002465280 Sorghum         GAAFALAVFVAPLTIIR-------QVIRTKSVEYMPFWLSFPLTISAVVWFF 180
BAJ99068 Hordeum             GSAFALAVFVAPLAIIR-------QVIRTKSVEFLPFWLSFPLTISAVVWFF 181
EMT31030 Aegilops            GSAFALAVFVAPLAIIR-------QVIRTKSVEFLPFWLSFPLTISAVVWFF 181
XP 003561640 Brachypodium    GAAFAFAVFVAPLAIIR-------QVIRTKSVEFLPFWLSFPLTISAVVWFF 181
NP 001050099 OsSW12          GASFALAVFVAPLTIIR-------QVIRTKSVEFMPFWLSFPLTLSAVVWFP 178
BAK07340 Hordeum             CLAFSMAVFVAPLSVIF-------VVIKTKSAEYMPFSLSFFLTLSAVAWFF 185
EMS45810 Triticum            CLAFSMAVFVAPLSVIF-------VVIKTKSAEYMPFSLSFFLTLSAVAWFF 185
XP 003578398 Brachypodium    CLAFSMAVFVAPLSVIF-------VVIKTKSAEYMPFSLSFFLTLSAVAWFF 185
XP 002462642 Sorghum         CLAFSMAVFVAPLSVIF-------VVIRTKSAEFMPFTLSFFLTLSAVAWFL 185
EAZ09693 Oryza               CLAFSMAVFVAPMSVIM-------VVIKTKSAEFMPFSLSFFLTLSAVAWFF 178
NP 001148964 Zea             CLAFSMAVFVAPLSIIV-------KVVKTKSVEFLPISLSFCLTLSAVAWFC 185
XP 002444688 Sorghum         CLAFSMAVFVAPLSIIV-------KVVKTKSVEFLPISLSFCLTLSAVAWFC 185
XP 003572455 Brachypodium    CLAFSMAVFVAPLSIIF-------KVIKTKSVEFMPISLSFCLVLSAVAWFC 185
NP 001062354 OsSW11          CLAFSMAVFVAPLSIIF-------KVIKTKSVEFMPIGLSVCLTLSAVAWFC 185
EMT31640 Aegilops            CLAFSMAVFVAPLSIIV-------KVIKTKSVEFLPVGLSFCLVLSAVAWFC 185
EMS51422 Triticum            CVGFSVCVFVAPLSIIG-------RVIKTKSVEYMPFTLSLTLTLSAIVWFL 183
EMT20808 Aegilops            CVGFSVCVFVAPLSIIG-------RVIKTKSVEYMPFTLSLTLTLSAIVWFL 183
```

Fig. 2-12

```
BAJ85621 Hordeum              CVGFSVCVFVAPLSIIG-------RVIKTKSVEYMPFSLSLTLTLSAVVWFL 183
EMT11081 Aegilops             CVGFSVCVFVAPLSIIG-------RVIKTKSVEYMPFSLSLTLTLSAVVWFL 183
XP_002442119 Sorghum          CVGFSVSVFVAPLSIMR-------RVIQTKSVEYMPFSLSLSLTLSAVVWFL 183
XP_002443167 Sorghum          CVGFSVSVFVAPLSIMR-------RVIQTKSMEYMPFSLSLSLTLSAVVWFL 183
NP_001141654 Zea              CVGFSVSVFVAPLSIMR-------RVIQTKSVEYMPFSLSLSLTLSAVVWFL 183
NP_001141106 Zea              CVGFSVSVFVAPLSIMR-------RVIQTKSVEYMPFSLSLSLTLSAVVWFL 183
SWT13_ORYSJ OsSW13 Oryza      CVAFSYSVFVAPLSIIK-------RVIQSRSVEYMPFSLSLTLTLSAVVWFL 183
XP_003576225 Brachypodium     CVAFSVSVFVAPLSIIG-------RVIKTRSVEYMPFSLSLSLTLSAVVWFL 183
BAJ94651 Hordeum              CVGFSVCVFVAPLSVIR-------LVVRTRSVEFMPPSLSLSLTASAVVWFL 183
XP_003576036 Brachypodium     CVGFSVSVFVAPLSVIR-------LVVRTRSVEFMPPNLSLSLTLSAVVWFL 183
EMT20480 Aegilops             CVGFSVSVFVAPLSIIR-------LVVRTRSVEFMPPSLSLSLTVSAVVWFL 183
EMT20481 Aegilops             CVGFSVSVFVAPLSVIR-------LVVRTRSVEFMPPSLSLSLTVSAVVWFL 183
NP_001132836 Zea              CVAFSYSVFVAPLSIIR-------QVVRTRSVEFMPPSLSPSLTASAVVWFL 183
XP_002450786 Sorghum          CVAFSYSVFVAPLSIIR-------QVVRTRSVEFMPPSLSLSLTVSAVVWFL 185
NP_001067955 OsSW14           CVGFSVSVFVAPLSIIR-------LVVRTKSVEFMPPSLSPSLTISAVVWFL 183
                                  :*: ::          ::  .   ::., **   .  . *:
                              -----V-----APL-II(2-7aa)VV-T-S---FMPP-LS---LT--A---WP-
                                   M    S M VM          II S N   YLSI    IV G   L
                                   L    T   V           M              V
                                   I         L                         L
                                   F
```

Fig. 2-13

```
XP 004235326 Solanum    YGLLLKDINIAAPNVLGFIFGILQIILYAIYSKKEKSIIKEQKLPEIQKT 231
XP 004235334 Solanum    YGLLLKDINIAAPNVLGFIPGILQIVLYAIYSKKEKVILKEQKLPEIQTP 229
ACV71016 Capsicum       YGLLLKDINIAAPNVLGFIFGVLQIVLYAIYSKKEKVILKEQKLPEIQKP 231
XP 004235333 Solanum    YGLLLKDINIAAPNILGFIFGVLQMILYVIYSKKEKAILKEQKLPEIQKG 231
XP 004235342 Solanum    YGLLLKDINIAIPNVLGFILGILQMVLYVIYNKKEKAILKEQKLPEKLQN 231
XP 004235339 Solanum    YGLLLKDVNIAAPNILGFIFGILQMILYAMYRKKHKPIVNVN--VEVQNP 228
XP 004241452 Solanum    YGLLLKDFNIAIPNVLGFIPGILQMILYVMYNKKEKVVIKEQNLPELKDH 231
XP 004235340 Solanum    YGLRKDYNIAIPNVLGPSLGVIQMTLYLI-KNAKKVTKEVK----LEV 223
AFK35161 Medicago       YGLLLRDYYVALPNTLGFVFGIIQMVVYLIYR-------NATPV------- 219
CAC44123 Medicago       YGLLLRDYYVALPNTLGFVFGIIQMVVYLIYR-------NATPV------- 219
XP 004503778 Cicer      YGLLLKDYYVALPNTLGFVFGIIQMVMYLIYR-------NATPVP------ 220
AFK48645 Lotus          YGMLLRDYYVALPNTLGFVPGIIQMVVYLIYR-------NATPVV------ 220
NP 001241307 Glycine    YGLLLRDYYVALPNTLGFVFGIIQMGMYLMYR-------NATPVA------ 220
NP 001242732 Glycine    YGLLLKDYYIALPNTLGFLFGIIQMVLYLIYR-------NAKPQG------ 220
XP 003523161 Glycine    YGLLLKDYYIALPNTLGFLPGIIQMVLYLVYR-------NAKPQT------ 220
NP 001237418 Glycine    YGLLLKDYYVALPNTLGFFSIIQMVLYLIYR--------NAKTP------- 219
XP 003602780 Medicago   YGLLIDDFYIAIPNTLGFVPGIVQMVIYLIYK-------DAIPL------- 219
XP 004138032 Cucumis    YGLLLKDYYIALPNVVGFVPGIIQMILYVIVKHIGNKSRIPVK-------- 224
EMJ10621 Prunus         YGLLIKDYNIAFPNILGFLFGIAQMVLYIVYK-------NTKKV------- 221
XP 004297512 Fragaria   YGFLLKDYNIAPPNILGPMPGIAQMVLYIVYK-------NAKKVVL----- 219
XP 002284244 Vitis      YGLMLKDFYIAGPNILGFVFGIVQMVLYLIYR-------NRKKV------- 220
EOA14646 Capsella       YGLLLKDKNIALPNVLGFIPGVLQMLFVIYK--------KPGTK------- 218
NP 199892 AtSW10        YGLLLKDMNIALPNVLGFIPGVLQMILFLIYK-------KPGTK------- 218
XP 002321731 Populus    YGYLKKDQFVAVPNILGFLFGIIQMVLYVIYR-------NPMKI------- 217
XP 002322281 Populus    YGFLKKDQFVAVPNILGLLPGILQMVLYMIYG-------NSKKV------- 217
XP 002321730 Populus    YGYLKKDKFVAIPNILGFIFGILQMVLYLIYR-------NPKKN------- 217
XP 002511127 Ricinus    YGFLKKDIYVVIPNVLGFFFGIVQMILYLIYR-------NSKK-------- 216
XP 002511128 Ricinus    YGFLKKDLYAVPNILGPMPGVLQMILYLIYR--------NPKKT------- 217
CBI32263 Vitis          YGLLIRDFYIAFPNILGFAFGIAQMILYTIYK-------NAKKGVL----- 222
EMJ01437 Prunus         YGLLVRDLFIAAPNILGFAPGLAQMIMYLMFK-------NSKKSML----- 221
XP 002520679 Ricinus    YGLAVNDYFIASPNILGPLFGIVQMLYMIYK--------NKKNEIL----- 221
XP 004247459 Solanum    YGLLKKDMYIAMPNILGFSFGIAQMILYAIYR-------NRKQQVL----- 222
EOA28959 Capsella       YGLLIKDKFIAMPNILGPLPGVAQMILYMMYQ-------GSTKTDL----- 221
NP 181439 AtSW09        YGLLIKDKFIAMPNILGFLFGVAQMILYMMYQ-------GSTKTDL----- 220
XP 002333315 Populus    YGLLQHDYYIALPNVLGFLPGIAQMILYMVYK-------NLKKNVE----- 221
NEC1 PETHY Petunia      YGFFKKDFYIAFPNILGPLFGIVQMLLYFVYK-------DSKRID------ 219
XP 002267792 Vitis      YGIFVRDFFIAIPNVVGFVFGIAQMFLYIIYK-------YMMKSD------ 220
XP 004138978 Cucumis    YGFFIKDLFIALPNVVGFLLGMVQMIMYIY--------------------- 212
XP 004138979 Cucumis    YGFFIKDLFIALPNIVGFLLGMVQMIMYMIYK-------DRKGNSL----- 221
XP 003518628 Glycine    YGFFDKDDFIMFPNVLGFIPGISQMILYMIYK-------NS-KKNG----- 220
XP 004489106 Cicer      YGLFDKDNYIMLPNVLGPLFGISQMILYLIYK-------NA-KNKV----- 223
XP 003617528 Medicago   YGFFDKDKYIMLPNGLGFLLGVSQMILYLIYK-------NA-KNNV----- 219
XP 004302124 Fragaria   YGLFTKDYYIALPNVLGFLPGIAQMILYMVYR-------NSGKDHD----- 220
NOD3 MEDTR Medicago     YGFFLKDICIXLPNVLGXVLGLLQMLLYAIYR-------NGGEKAMK---- 221
NP 001239695 Glycine    YGLFLKDICIALPNVLGFALGLLQMLLYAIYR-------NGNKKVDKI--- 222
AFK39311 Lotus          YGLFLKDICIALPNILGPGLGLIQMVLYAIYR-------NGNEKGKK---- 221
XP 003620983 Medicago   YGLFLKDICIALPNVLGFALGLVQMILYCIYR-------NGDKKKAN---- 221
XP 003530901 Glycine    YGLPLKDICIALPNVLGFVLGLLQMLLYTIYR-------KGNKKTNT---- 221
XP 003524088 Glycine    YGLLLKDICIAIPNILGFTLGLLQMLYAIYR--------NGKTNNKEVV-- 226
XP 003615405 Medicago   YGLLLHDICIAIPNVLGFILGLLQMLLYAIYN-------KS---------- 216
XP 003547573 Glycine    YGLSIQDKCIYVPNVGGFGLGLVQMVLYGIY--------RNGGESEK---- 220
```

Fig. 2-14

```
XP 003593107 Medicago      YGFVKRDICIYLPNVVGFILGIIQMVLYGYYS------KYSVEKEK------ 223
EOA22072 Capsella          YGLFLNDICIAIPNVVGFVLGMLQMVLYCVYR------NASEKPEIE----- 225
NP 196821 AtSW15           YGLFLNDICIAIPNVVGFVLGLLQMVLYLVYR------NSNEKP-------- 222
EMJ23678 Prunus            YGLFLKDICIAIPNVLGFILGLLQMLLYAIYR------NRKPIEDDE----- 225
XP 004301046 Fragaria      YGMLLKDIFIALPNGLGFVLGLLQMLFYAIYR------NRKQVTVDQ----- 224
XP 002299333 Populus       YGLFIKDMCVALPNILGFVLGLLQMLLYGIYR------NAEK---------- 204
XP 002514863 Ricinus       YGLSTKDTCVALPNVLGFILGLLQMLYVIYR-------KAKKVIL------- 222
XP 004140547 Cucumis       YGLLLNDICIAIPNVVGFILGLLQMVVYAIYR------KRKIVIMEE----- 224
XP 002264875 Vitis         YGLLKNDPCVAIPNILGVILGLVQMVLYGFYR------NAGKEKMEK----- 225
NP 199893 AtSW13           YGLAIKDFYVALPNVLGAFLGAVQMILYIIFK------YYKTP--------- 219
XP 002862913 Arabiopsis    YGLAIKDFYVALPNVLGAFLGAVQMILYIIFK------YYKIP--------- 219
EOA14916 Capsella          YGLAIKDFYVALPNVLGAFLGAVQMILYIVFK------YYMTP--------- 219
EOA17919 Capsella          YGLAIKDFYVALPNIMGAFLGAVQMSLYVIFK------YYKSPV-------- 220
NP 194231 AtSW14           YGLAIKDFYVALPNILGAFLGAVQMILYVIFK------YYKTPL-------- 220
EOA21276 Capsella          YGLALKDIYVAFPNVIGFALGALQMILYVVYK------YCKTS--SD----- 222
NP 197755 AtSW12           YGLALKDIYVAFPNVIGFVLGALQMILYVVYK------YCKTP--SD----- 222
EOA24501 Capsella          YGLALKDIYVAFPNVLGFALGALQMILYVVYK------YCKTSPHPH----- 224
NP 190443 AtSW11           YGLALKDIYVAFPNVLGFALGALQMILYVVYK------YCKTS--PH----- 222
XP 002511126 Ricinus       YGLLLKDLYIAVPNILGLVFGVLQMILYVIYK------NVKTV--------- 220
XP 004297511 Fragaria      YGLLLKDLYVAAPNILGPSFGVVQMILYAAYR------NKKTV--------- 218
XP 004153501 Cucumis       YGVFLKDIYIAVPNIPGFMFGIAQMILYLIYK------KRE----------- 219
XP 004161952 Cucumis       YGVFLKDIYIAVPNIPGFMFGIAQMILYLIYK------KRE----------- 219
XP 004145146 Cucumis       YGVFLKDIYVALPNVLGFIFGVAQMILYLIYR------KYEIA--------- 220
XP 004138250 Cucumis       YGLFLKDLYVALPNTLGFTFGMAQMILYAIYR------NAKP---------- 220
XP 004235470 Solanum       YGLLLKDVYYAVPNIPGMILGVLQMILYGIYR------NSKSNN-------- 221
CBI15715 Vitis             YGILQMDLYIAMPNTLGFVFGLIQMILYAMYR------NSTPVT-------- 227
AFW71563 Zea               YGALKRDVFVAFPNVLGPVFGVAQIALYMAY-------RNKEPA-------- 221
NP 001149028 Zea           YGALKKDVFVAFPNVLGFVFGLAQMALYMAYS------RNRKPA-------- 222
XP 002453892 Sorghum       YGALKKDVFVAAPNVLGPVFGLAQMALYMAY-------RNKKPA-------- 221
EMT09236 Aegilops          YGALKKDIFVAMPNVLGLLFGVAQMALYMAY-------RNKKPAT------- 222
XP 003575028 Brachypodium  YGLLKKDVFVAVPNVLGFVFGVAQMALYMAY-------RNKSPA-------- 221
NP 001046944 OsSW15        YGLLKKDVFVALPNVLGFVFGVAQMALYMAY-------RSKKPLVASSS--- 226
EMS46194 Triticum          YGALKKDIFVAMPNVLGFLFGVAQMALYMAY-------RNKKPATVAVI--- 226
AFW88409 Zea               YGLLIKDFFVAMPNVLGLLFGLAQMVLFPVYR------NRNPKKN------- 220
XP 002465280 Sorghum       YGLLMKDFFVAMPNVLGLLFGLAQMALYFVYR------NRNPKQN------- 219
BAJ99068 Hordeum           YGLLMKDFFVATPNVLGLLFGLAQMALHLVYK------N---PKKK------ 218
EMT31030 Aegilops          YGLLMKDFFVATPNVLGLLFGLAQMSLHLVYK------N---PKKK------ 218
XP 003561640 Brachypodium  YGLLMKDFFVAMPNVLGLLFGLAQMALHLVYK------N---PKKKK----- 219
NP 001050099 OsSW12        YGLLMKDFFVATPNVLGLLFGLAQMVLYVVYK------N---PKKN------ 215
BAK07340 Hordeum           YGLFTKDIYVTLPNVGGFFFGVAQMTLYFCYR------KPDTSA-------- 223
EMS45810 Triticum          YGLFTKDIYVTLPNVGGFFFGVAQMTLYFCYR------KPDTSA-------- 223
XP 003578398 Brachypodium  YGLFTKDIYVTLPNVGGFFFGIAQMTLYFCYR------KPGTSA-------- 223
XP 002462642 Sorghum       YGIFTKDPYVTLPNVGGFFFGCIQMVLYCCYR------KP-SAS-------- 222
EAZ09693 Oryza             YGLFTNDLYVTLPNVGGFFFGCVQMALYFKYR------KPNTAAGG------ 218
NP 001148964 Zea           YGLFTKDPFVMYPNVGGFFFSCVQMGLYFWYR------KPRPAAKN------ 225
XP 002444688 Sorghum       YGLFTKDPFVMYPNVGGFFFSCVQMGLYFWYR------KPRP-AKN------ 224
XP 003572455 Brachypodium  YGYFTKDPYVMYPNVGGFFFSCVQMGLYFYYR------RPSN---------- 221
NP 001062354 OsSW11        YGLFTKDPYVMYPNVGGFFFSCVQMGLYFWYR------KPRN---------- 221
EMT31640 Aegilops          YGLFTKDPFVMYPNVGGFFFSCVQIGLYCWYR------KPSN---------- 221
EMS51422 Triticum          YGLLIKDKYVALPNILGFTFGVIQMVLYVFYM------NKTP---------- 219
EMT20808 Aegilops          YGLLIKDKYVALPNILGFTFGVIQMVLYVFYM------NKTP---------- 219
```

Fig. 2-15

```
BAJ85621 Hordeum          YGLLIKDKYVALPNTLGFTFGMIQMVLYMFYM------NATPV------ 220
EMT11081 Aegilops         YGLLIKDKYVALPNTLGFTFGMIQMVLYMFYM------NATP------- 219
XP 002442119 Sorghum      YGLLIKDKYVALPNTLGFTFGVVQMVLYVLYM------NKTPV------ 220
XP 002443167 Sorghum      YGLLIKDKYVALPNILGFTFGMVQMVLYVLYM------NKTPV------ 220
NP 001141654 Zea          YGLLIKDKYVALPNVLGFIPGVVQMVLYVFYM------NKTPV------ 220
NP 001141106 Zea          YGLLIKDKYVALPNILGFTPGVVQMVLYVVYM------NKTPL------ 220
SWT13 ORYSJ OsSW13 Oryza  YGLLIKDKYVALPNILGFTFGVVQMGLYVFYM------NATPV------ 220
XP 003576225 Brachypodium YGLLIKDKYVALPNILGFSFGVVQMALYMFYM------NKTPI------ 220
BAJ94651 Hordeum          YGLLIKDKYVALPNTLGFAFGVIQMGLYALYR------NATP------- 219
XP 003576036 Brachypodium YGLLIKDKYVALPNILGFAFGVTQMGLYALYR------NSTP------- 219
EMT20480 Aegilops         YGLLIKDKYVALPNILGFAFGVIQMGLYAIYC------NATP------- 219
EMT20481 Aegilops         YGLLIKDKYVALPNILGFAPGVIQMGLYALYC------NAMP------- 219
NP 001132836 Zea          YGLLIKDKYVALPNVLGFTPGVVQMGMYALYR------NATPR------ 220
XP 002450786 Sorghum      YGLLIKDKYVALPNVLGFSFGVVQMGLYALYR------NATPR------ 222
NP 001067955 OsSW14       YGLLIKDKYVALPNVLGFSFGVIQMGLYAMYR------NSTPK------ 220
                          **  *  :  ** * :. *:..
                          YG----D---V--PN--G--FG---QM-LY-------------------
                                 I          LS   I MH
                                                 IF
                                                 V
                                                 F
```

Fig. 3-1

```
AtSW09              ------MFLKVHEIAPLFGLLGNIVSPGVFLSPVPTFYGIYKKKSSKGFQSI 46
PhNEC1              ----MAQLRADDLSFIFGLLGNIVSPMVFLAPVPTFYKIYKRKSSEGYQAI 47
XP_003617528 Medicago  ------MFPFSNLKMVLLPGPLG-IVTFMSFLAPLPTFYSIYKKKSSEGFHSI 46
NOD3_MEDTR Medicago ------MAISHNTLAPTFGMLGNVISFLVFLAPISTFYRIYKKKSTEGFQSL 46
XP_003620983 Medicago  ------MAISHNTLAFAPGMLGNVISPMVFLAPMTTFYRIYKKKSTEGFQSL 46
AtSW15              ---MGVMINHHFLAFIFGILGNVISPLVFLAPVPTFYRIYKRKSTESFQSL 48
XP_003615405 Medicago  ----MDPHDHDRLAFIFGILGNIISSMVYLAPLPTFYRIWKKKSTEGFQSL 47
XP_003593107 Medicago  -MAMISMNHHFLVIAFGLLGNIISCMVYLAPLPTFIQIYKKKSTECFQSL 49
AtSW11              ---MSLPNTENTWAFVFGLLGNLISPAVFLSPVPTFYRIWKKKTTEGFQSI 48
AtSW12              ---MALFDTHNTWAFVFGLLGNLISFAVFLSPVPTFYRICKKKTTEGFQSI 48
AtSW13              ------MALTNNLWAFVFGILGNIISFVVFLAPVPTFVRICKKKSTEGFQSL 46
AtSW14              -----MVLTHNVLAVTFGVLGNIISFIVFLAPVPTFVRICKKKSIEGFESL 46
OsSW13              -MAGLSLQHP-WAFAFGLLGNLISPTTYLAPIPTFYRIYKSKSTEGFQSV 48
OsSW14              -MAGMSLQHP-WAFAFGLLGNIISPMTYLAPLPTFYRIYKSKSTQGFQSV 48
OsSW15              -MAFMSMERSTWAFTFGILGNLISLMVFLSPLPTFYRVYRKKSTEGFQST 49
AFK35161 Medicago   ----MAMTR-ESWAFVFGIIGNIISFAVFLSPLPTFYVIFKKKSAEGFQAL 46
CAC44123 Medicago   ----MAMTR-ESWAFVFGIIGNIISFAVFLSPLPTFYVIPKKKSAEGFQAL 46
XP_003602780 Medicago  ----MALFYSEYWAFVFGVIGNVISCMTFLAPLPTFYRIYKKKSTEGFQSV 47
AtSW10              ----MAISQ-AVLATVFGILGNIISFPVCLAPIPTFVRIYKRKSSEGYQSI 46
OsSW12              -----------MVQALVFAVGIVGNILSFLVILAPVPTFYRVYKKKSTESFQSV 43
OsSW11              MAGGFLSMANPAVTLSGVAGNIISPLVFLAPVATPLQVYKKKSTGGYSSV 50
                                          *. * ::: *:*:.** :: *:    ::

Consensus                            GL-G-IIS----LAPLPTF---I-K-KS----F-S-
                                    I VVT    S VS    V R   T  Y A
                                    V LL     IT                Y A
                                    M               MA
                                    F
```

```
AtSW09              PYICALASATLLLYYGIMKT-HAYLIISINTFGCPIEISYLFLYILYAPR 95
PhNEC1              PYMVALFSAGLLLYYAYLRK-NAYLIVSINGPGCAIELTYISLFLFYAPR 96
XP_003617528 Medicago  PYVVTLLSTLLFVYYGFLKT-NAIFLITINSIGCVMEVAYLIMYITYAPK 95
NOD3_MEDTR Medicago PYLVALFSSMLWLYYALLKK-DAFLLITINSFGCVVETIYIILYIIYAPR 95
XP_003620983 Medicago  PYLVALFSSMLWLYYAFLKK-DEFLLITINSFGCVVELIYIILYIIYATK 95
AtSW15              PYQVSLFSCMLWLYYALIKK-DAFLLITINSPGCVVETLYIAMFFAYATR 97
XP_003615405 Medicago  PYLVALFSSMLWLYYGFVKK-HAPLLITINSAGCVIETIYIVTYLIYATK 96
XP_003593107 Medicago  PYLVALFSSMLWLYYG-IQT-NAIFIVSINAFGCVIEIIYCIMYIAYATK 97
AtSW11              PYVVALFSATLWLYYATQKK-DVFLLVTINAFGCPIETIYISMFLAYAPK 97
AtSW12              PYVVALFSAMLWLYYATQKK-DVFLLVTINSPGCFIETIYISIFVAFASK 97
AtSW13              PYVSALFSAMLWIYYAMQKDGTAFLLITINAFGCVIETTYIVLFVSYANK 96
AtSW14              PYVSALFSAMLWIYYALQKDGAGFLLITINAVGCFIETIYIILFITYANK 96
OsSW13              PYVVALFSAMLWIFYALIKS-NEALLITINAAGCVIETIYIVMYLAYAPK 97
OsSW14              PYVVALFSAMLWIYYALLKS-DECLLITINSAGCVIETIYIAVYLVYAPK 97
OsSW15              PYVVTLFSCMLWMYYAFVKS-GAELLVTINGVGCVIETVYLAMYLAYAPK 98
AFK35161 Medicago   PYVVALFSAMLWIYYAFVKRESALLLITINTFGIVVESAYIIMFLIYAPK 96
CAC44123 Medicago   PYVVALFSAMLWIYYAFVKRESALLLITINTFGIVVESAYIIMFLIYAPK 96
XP_003602780 Medicago  PYVTALLSAMLWIYYAHVKNKATLLLLTINIYGPGIEAIYIIIPLLYASN 97
AtSW10              PYVISLFSAMLWMYYAMIK-KDAMMLITINSFAFVVQIVYISLFFFYAPK 95
OsSW12              PYAVALLSAMLWLYYALLTS--DLLLLSINSIGCLVESLYLTVYLLYAPR 91
OsSW11              PYVVALFSSVLWIFYALVKT-NSRPLLTINAFGCGVEAAYIVLYLVYAPR 99
                    ** :** * ::*,         ::**  , :: *  *, .*.

Consensus           PY--AL-S--L-LYYA---------LITIN--G--IE-Y----FL-YA-K
                       S        IF G           IVS   A  VQ        YI F R
                       T        M                 L   M         V  N
                                V                                  F
```

Fig. 3-2

```
AtSW09              EAKISTLKLIVICNIGGLGLLILLVNLLVPK-QHRVSTVGWVCAAYSLAV 144
PhNEC1              KSKIFTG-WLMLLELGALGMVMPITYLLAEG-SHRVMIVGWICAAINVAV 144
XP_003617528 Medicago  KLKISTLVLILIVDMGGFGLTMIITTFIVKG-SFHVQVVGMICTIFNIGM 144
NOD3_MEDTR Medicago    DARNLTFKLLSAMNVGSFALILIVTNYAVHG-PLRVQVLGWVCVSLSVSV 144
XP_003620983 Medicago  DARKLTIKLLLAMNIGSFGLILLVTKYAVHG-PIRVQVLGWICVSISVSV 144
AtSW15              EKRISAMKLFIAMNVAFFSLILMVTHFVVKTPPLQVSVLGWICVAISVSV 147
XP_003615405 Medicago  DARILTIKLFMAMNVACSVLIVLTTQLAMHG-KLRVHVLGWICTSPAICV 145
XP_003593107 Medicago  DARKLTIKLCAALNVVSFVLIFLIIQFSIPE-NHRVQVLGWICTSISISV 146
AtSW11              PARMLTVKMLLLMNFGGFCAILLLCQFLVKG-ATRAKIIGGICVGFSVCV 146
AtSW12              KARMLTVKLLLLMNFGGFCLILLLCQFLAKG-TTRAKIIGGICVGFSVCV 146
AtSW13              KTRISTLKVLGLLNFLGFAAIVLVCELLTKG-STREKVLGGICVGFSVSV 145
AtSW14              KARISTLKVLGLLNFLGFAAIILVCELLTKG-SNREKVLGGICVGFSVCV 145
OsSW13              KAKVFTTKILLLLNVGVFGVILLLTLLLSHG-EQRVVSLGWVCVAFSVSV 146
OsSW14              KAKMFTAKLLLLVNVGVFGLILLLTLLLSAG-DRRIVVLGWVCVGFSVSV 146
OsSW15              SARMLTAKMLGLNIGLFGVIALVTLLLSRG-ELRVHVLGWICVAVSLSV 147
AFK35161 Medicago   KQRLSTIKLLLLLNVFGFGAMLLSTLYLSKG-AKRLAIIGWICLVFNISV 145
CAC44123 Medicago   KQRLSTIKLLLLLNVFGFGAMLLSTLYLSKG-AKRLAIIGWICLVFNISV 145
XP_003602780 Medicago  KARLSTIKLLFLT--VCGYGTMVILTTYLTKG-SKRLSIIGWICMVFNICV 145
AtSW10              KEKTLTVKFVLFVDVLGFGAIFVLTYFIIHA-NKRVQVLGYICMVFALSV 144
OsSW12              QAMAFTLKLVCAMNLALFAAVVAALQLLVKATDRRVTLAGGIGASPALAV 141
OsSW11              RARLRTLAFFLLLDVAAFALIVVTTLYLVPK-PHQVKFLGSVCLAFSMAV 148
                           :          .            :  *:    : :
Consensus           -------T-------------V---------------R-----G-I------V-V
                           A           F                Q        V     I M
                                       L                H              L
                                       I                               M
                                       M
```

```
AtSW09              FASPLSVMRKVIKTKSVEYMPFLLSLSLTLNAVMWFFYGLLIKDKFIAMP 194
PhNEC1              FAAPLSIMRQVIKTKSVEFMPFTLSLFLTLCATMWFFYGFFKKDFYIAFP 194
XP_003617528 Medicago  FAAPLSIMKKVIKTRSVEYMPFPLSLFLTICATMWFFYGFFDKDYIMLP 194
NOD3_MEDTR Medicago    FAAPLSIVAQVVRTKSVEFMPFNLSFTLTLSATMWFGYGFFLKDICIXLP 194
XP_003620983 Medicago  FAAPLTIVAQVVRTKSVEFMPFNLSFTLTLSAIMWFGYGLFLKDICIALP 194
AtSW15              FAAPLMIVARVIKTKSVEYMPFTLSFFLTISAVMWFAYGLFLNDICIAIP 197
XP_003615405 Medicago  FAAPLTIMAKVIRTKSVEFMPINLSFFLTLSAIVWFFYGLLLHDICIAIP 195
XP_003593107 Medicago  FAAPLSIVVRVVKTKSVEFMPFNLSLFLTLSAVVWFLYGFVKRDICIYLP 196
AtSW11              FAAPLSIIRTVIKTRSVEYMPFSLSLTLTISAVIWLLYGLALKDIYVAFP 196
AtSW12              FAAPLSIIRTVIKTKSVEYMPFSLSLTLTISAVIWLLYGLALKDIYVAFP 196
AtSW13              FAAPLSIMRVVVRTRSVEFMPFSLSLFLTISAVTWLFYGLAIKDFYVALP 195
AtSW14              FAAPLSIMRVVIRTKSVEFMPFSLSLFLTISAITWLFYGLAIKDFYVALP 195
OsSW13              FVAPLSIIKRVIQSRSVEYMPFSLSLTLTLSAVVWFLYGLLIKDKYVALP 196
OsSW14              FVAPLSIIRLVVRTKSVEFMPFSLSFSLTISAVVWFLYGLLIKDKYVALP 196
OsSW15              FAAPLSIIRLVIRTKSVEFMPPSLSFFLVLSAVIWFLYGLLKKDVFVALP 197
AFK35161 Medicago   FATPLFVISKVIRSRSVEYMPFFLSFFLTINAVMWFFYGLLLRDYYVALP 195
CAC44123 Medicago   FAAPLFVISKVIRSRSVEYMPFPLSFFLTINAVMWFFYGLLLRDYYVALP 195
XP_003602780 Medicago  FASPLFILKQVIKTKSVAFMPLNLSFFLTLNAIVWFFYGLLIDDPFYIAIP 195
AtSW10              FVAPLGIIRKVIKTKSAEFMPFGLSFFLTLSAVMWFFYGLLLKDMNIALP 194
OsSW12              FVAPLTIIRQVIRTKSVEFMPFWLSFFLTLSAVVWFYGLLMKDFFVATP 191
OsSW11              FVAPLSIIFKVIKTKSVEFMPIGLSVCLTLSAVAWFCYGLFTKDPYVMYP 198
                    *.:**  :: *::::*,.:**:**.*,:* *:**:  * : *
Consensus           FAAPL--II---VIKTKSV-FMPF-LSL-LTL-A----WF-YGL------D---V----P
                          VS      VM    VRSR A   Y   I F   VI             L F          I
                          T       V     Q          L V
                          L
```

Fig. 3-3

```
AtSW09              NILGPLFGVAQMILYMMYQGSTK-TDLPTE------------NQLANKTDVN  233
PhNEC1              NILGPLFGIVQMLLYFVYKDSKR-IDDEKS------------DPVREATKSK  233
XP 003617528 Medicago  NGLGFLLGVSQMILYLIYKNAKNNVEASSST-----------NQLQEHGCDG  234
NOD3 MEDTR Medicago   NVLGXVLGLLQMLLYAIYRNGGEKAMKKEK------------KAPIEPPKSI  234
XP 003620983 Medicago NVLGFALGLVQMILYCIYRNGDKK---KANS-----------KAAL----KSV  229
AtSW15              NVVGFVLGLLQMVLYLVYRNSNEKPEKINS------------SEQQ--LKSI  235
XP 003615405 Medicago NVLGFILGLLQMLLYAIYNKSVKE--EYAL------------EPMT----NI  229
XP 003593107 Medicago NVVGFILGIIQMVLYGYYSKYSVE--KEKE------------QAVI----NI  230
AtSW11              NVLGFALGALQMILYVVVYKYCKTSPHLGEK-----------EVEAAKLPEV  236
AtSW12              NVIGFVLGALQMILYVVVYKYCKTPSDLVEK-----------ELEAAKLPEV  236
AtSW13              NVLGAFLGAVQMILYIIFKYYKTP--VAQK------------TDKSKDVSDH  233
AtSW14              NILGAFLGAVQMILYVIFKYYKTPL-VVDE------------TEKPKTVSDH  234
OsSW13              NILGFTFGVVQMGLYVFYMNATPVAGEGKE------------GKGKLAAAEELPV 239
OsSW14              NVLGFSFGVIQMGLYAMYRNSTPKAVLTKEVEAATATGDDDHSAAGVKEH  246
OsSW15              NVLGFVFGVAQMALYMAYRSKKPLVASSSS----AVVAAGLEIKLPEHVKE  244
AFK35161 Medicago   NTLGFVFGIIQMVVYLIYRN-ATPVVEAPM------------KGQELSGGHI  234
CAC44123 Medicago   NTLGFVFGIIQMVVYLIYRN-ATPVVEAPM------------KGQELSGGHI  234
XP 003602780 Medicago NTLGFVFGIVQMVIYLIYKD-AIPLESTKL------------QKPNDHVLNI  234
AtSW10              NVLGFIPGVLQMILPLIYKKPGTKVLEPPG------------IKLQDISEHV  234
OsSW12              NVLGLLFGLAQMVLYVVYKNPKKNSAVSEA------------AAAQQVEVKDQQ 233
OsSW11              NVGGFFFSCVQMGLYFWYRKPRNTAVLPTTSDSMSPISAAAAATQRVIEL  248
                    *  *  :  **  ::   :

Consensus           N---G---LG---QM-LY---Y
                         FS      VF  F
                                  I
```

Fig. 4-1

```
At5g50790.1 AtSW10    ------MAISQAVLATVFGILGNIISFFVCLAPIPTFVRIYKRKSSEGYQSIPYVISLFSAM 56
At5g13170.1 AtSW15    --MGVMINDHFLAFIFGILGNVISFLVFLAPVPTFYRIYKRKSTESFQSLPYQVSLFSCM 58
At3g48740.1 AtSW11    ---MSLPNTENTWAFVFGLLGNLISFAVFLSPVPTFYRIWKKKTTEGFQSIPYVVALFSAT 58
At5g23660.1 AtSW12    ---MALFDTHNTWAFVFGLLGNLISFAVFLSPVPTFYRICKKKTTEGFQSIPYVVALFSAM 58
At5g50800.1 AtSW13    ------MALTNNLWAPVFGILGNIISFVVFLAPVPTFVRICKKKSTEGFQSLPYVSALFSAM 56
At4g25010.1 AtSW14    ------MVLTHNVLAVTFGVLGNIISFIVFLAPVPTFVRICKKKSIEGFESLPYVSALFSAM 56
Os12g0476200 OsSW13   -MAGLSLQHP-WAFAFGLLGNLISFTTYLAPIPTFYRIYKSKSTEGFQSVPYVVALFSAM 58
Os11g0508600 OsSW14   -MAGMSLQHP-WAFAFGLLGNIISFMTYLAPLPTFYRIYKSKSTQGFQSVPYVVALFSAM 58
Os02g0513100 OsSW15   -MAFMSMERSTWAFTFGILGNLISLMVFLSPLPTFYRVYRKKSTEGFQSTPYVVTLFSCM 59
At2g39060.1 AtSW09    ------MPLKVHEIAFLFGLLGNIVSFPGVFLSPVPTFYGIYKKKSSKGFQSIPYICALASAT 56
Os03g0347500 OsSW12   ---------MVQALVPAVGIVGNILSFLVILAPVPTFYRVYKKKSTESFQSVPYAVALLSAM 53
Os08g0535200 OsSW11   MAGGFLSMANPAVTLSGVAGNIISFLVFLAPVATFLQVYKKKSTGGYSSVPYVVALFSSV 60
                           .  *:  **::*: . *:*:.**   :  :  *:  .:.*  ** :** *:
Consensus             A-----GI-GNIISF-V-LAPVPTF---I-K-KS---GFQS-PY--AL-SA-
                            V      L   LL L T S IA    V R  T SYS       S   C
                            V      VV       I                            E T S
```

```
At5g50790.1 AtSW10    LWMYYAMIKK-DAMMLITINSFAFVVQIVYISLFFPYAPKKEKTLTVKPVLFVDVLGPFGA 115
At5g13170.1 AtSW15    LWLYYALIKK-DAFLLITINSFGCVVETLYIAMPFFAYATREKRISAMKLFIAMNVAFFSL 117
At3g48740.1 AtSW11    LWLYYATQKK-DVFLLVTINAPGCFIETIYISMFLAYAPKPARMLTVKMLLLMNFGGFCA 117
At5g23660.1 AtSW12    LWLYYATQKK-DVFLLVTINSFGCFIETIYISIFVAFASKKARMLTVKLLLLMNFGGFCL 117
At5g50800.1 AtSW13    LWIYYAMQKDGTAPLLITINAFGCVIETIYIVLFVSYANKKTRISTLKVLGLLNPLGFAA 116
At4g25010.1 AtSW14    LWIYYALQKDGAGFLLITINAVGCFIETIYIILPFITYANKKARISTLKVLGLLNPLGFAA 116
Os12g0476200 OsSW13   LWIFYALIKS-NEALLITINAAGCVIETIYIVMYLAYAPKKAKVFTTKILLLLNVGVFGV 117
Os11g0508600 OsSW14   LWIYYALLKS-DECLLITINSAGCVIETIYIAVYLVYAPKKAKMFTAKLLLLVNVGVPGL 117
Os02g0513100 OsSW15   LWMYYAFVKS-GAELLVTINCVTVYLAMVLAYAPKSARMLTAKMLLGLNIGLFGV 117
At2g39060.1 AtSW09    LLLYYGIMKT-HAYLIISINTFGCFIEISYLFLYILYAPREAKISTLKLIVICNIGGGLGL 115
Os03g0347500 OsSW12   LWLYYALLTS--DLLLLSINSIGCLVESLYLTVYLLYAPRQAMAFTLKLVCAMNLALFAA 111
Os08g0535200 OsSW11   LWIFYALVKT-NSRPLLTINAFGCGVEAAYIVLYLVYAPRRARLRTLAPFLLLDVAAFAL 119
                      *  ::*.   ,  ::::**  ,   :: *:   :. :*  :        :  .. . :
Consensus             L-LYYA--K-----LLITIN--G---IE-YI-LFL-YA-K------T-LL---NF--F---
                         IF G  T        MILS    A  VQ   LMYI F  R       A  MF   DV  L
                         M          P V              V V           FV       I
                                                      I F                VI   L
                                                                            I
```

```
At5g50790.1 AtSW10    IFVLTYFIIHAN-KRVQVLGYICMVFALSVFVAPLGIIRKVIKTKSAEFMPFGLSFFLTL 174
At5g13170.1 AtSW15    ILMVTHFVVKTPPLQVSVLGWICVAISVSVFAAPLMIVARVIKTKSVEYMPFTLSFFLTI 177
At3g48740.1 AtSW11    ILLLCQFLVKGA-TRAKIIGGICVGFSVCVFAAPLSIIRTVIKTRSVEYMPFSLSLTLTI 176
At5g23660.1 AtSW12    ILLLCQFLAKGT-TRAKIIGGICVGFSVCVFAAPLSIIRTVIKTRSVEYMPFSLSLTLTI 176
At5g50800.1 AtSW13    IVLVCELLTKGS-TREKVLGGICVGFSVSVFAAPLSIMRVVVRTRSVEFMPFSLSLFLTI 175
At4g25010.1 AtSW14    IILVCELLTKGS-NREKVLGGICVGFSVCVFAAPLSIMRVVIRTKSVEFMPFSLSLFLTI 175
Os12g0476200 OsSW13   ILLLTLLLSHGE-QRVVSLGWVCVAFSVSVFVAPLSIIKRVIQSRSVEYMPFSLSLTLTL 176
Os11g0508600 OsSW14   ILLLTLLLSAGD-RRIVVLGWVCYGFSVSVFVAPLSIIRLVVRTKSVEFMPFSLSFSLTI 176
Os02g0513100 OsSW15   IALVTLLLSRGE-LRVHVLGWICVAVSLSVFAAPLSIIRLVIRTKSVEFMPFSLSFFLVL 177
At2g39060.1 AtSW09    LILLVNLLVPKQ-HRYSTVGWVCAAYSLAVFASPLSVMRKVIKTKSVEYMPFLSLSLTL 174
Os03g0347500 OsSW12   VVAALQLLVKATDRRVTLAGGIGASFALAVPVAPLTIIRQVIRTKSVEFMPFWLSPFLTL 171
Os08g0535200 OsSW11   IVVTTLYLVPKP-HQVKFLGSVCLAPFSMAVFVAPLSIIPKVIKTKSVEFMPIGLSVCLTL 178
                      :     :      :        *: :  ::.**..:**  ::  *::::.*:**: *:.*. ;
Consensus             I-------L-------R----G-I-----SVCVFAAPL-II--VIKTKSVEFMPF-LSL-LTL
                      L        I      Q    V           ALS VS   VM       VRSR AY I  F  VI
                      V        V                       MA     V         Q                   V
```

Fig. 4-2

```
At5g50790.1 AtSW10    SAVMWFFYGLLLKDMNIALPNVLGFIFGVLQMILPLIYKKPGTKVLEPPGIKLQDISEHV 224
At5g13170.1 AtSW15    SAVMWFAYGLFLNDICIALPNVVGPVLGLLQMVLYLVYRNSNEKPEKINSSEQQLKSIVV 227
At3g48740.1 AtSW11    SAVIWLLYGLALKDIYVAFPNVLGFALGALQMILYVVYKYCKTSPHLGEKEVEAAKLPEV 226
At5g23660.1 AtSW12    SAVIWLLYGLALKDIYVAFPNVIGFVLGALQMILYVVYKYCKTPSDLVEKELEAAKLPEV 226
At5g50300.1 AtSW13    SAVTWLFYGLAIKDFYVALPNVLGAFLGAVQMILYIIFKYYKTPVAQKTDKSKDVSDHSI 223
At4g25010.1 AtSW14    SAITWLFYGLAIKDFYVALPNILGAFLGAVQMILYVIFKYYKTPLVVDETEKPKTVSDHS 224
Os12g0476200 OsSW13   SAVVWFLYGLLIKDKYVALPNILGFTFGVVQMGLYVFYMNATPVAGEGKEGKGKLAAAEE 229
Os11g0508600 OsSW14   SAVVWFLYGLLIKDKYVALPNVLGFSFGVIQMGLYAMYRNSTPKAVLTKEVEAATATGDD 236
Os02g0513100 OsSW15   SAVIWFLYGLLKKDVFVALPNVLGFVPGVAQMALYMAYRSKKPLVASSSSAVVAAGLETK 234
At2g39060.1 AtSW09    NAVMWFFYGLLIKDKFIAMPNILGFLFGVAQMILYMMYQGSTKTDLPTENQLANKTDVNE 224
Os03g0347500 OsSW12   SAVVWFFYGLLMKDPFVATPNVLGLLFGLAQMVLYVVYKNPKKNSAVSEA-AAAQGVEVK 221
Os08g0535200 OsSW11   SAVAWFCYGLFTKDPYVMYPNVGGPFFSCVQMGLYFWYRKPRNTAVLPTTSDSMSPISAA 238
                      .*: *: ***  :*  : **: *   :.  **  *:   :

Consensus             SAV-WF-YGL--KD--V---PNV-G--PG--QM-LY---Y
                      N I  L       N  I     I    LS      F F
```

Fig. 5

```
At5g50790.1 AtSW10    ---MAISQAVLATVFGILGNIISFFVCLAPIPTFVRIYKRKSSEGYQSIPYVISLFSAMLW  58
At5g13170.1 AtSW15    MGVMINHHFLAFIFGILGNVISFLVFLAPVPTFYRIYKRKSTESFQSLPYQVSLFSCMLW  60
At3g48740.1 AtSW11    MSLFNTENTWAFVFGLLGNLISFAVFLSPVPTFYRIWKKKTTEGFQSIPYVVALFSATLW  60
At5g23660.1 AtSW12    MALFDTHNTWAFVFGLLGNLISFAVFLSPVPTFYRICKKKTTEGFQSIPYVVALFSAMLW  60
At5g50800.1 AtSW13    ---MALTNNLWAFVFGILGNIISPVVFLAPVPTFVRICKKKSTEGFQSLPYVSALFSAMLW  58
At4g25010.1 AtSW14    ---MVLTHNVLAVTFGVLGNIISFIVFLAPVPTFVRICKKKSIEGFESLPYVVSALFSAMLW  58
At2g39060.1 AtSW09    ---MFLKVHEIAFLFGLLGNIVSFGVFLSPVPTFYGIYKKKSSKGFQSIPYICALASATLL  58
                        :    *  **:***:!**  *   *:*:***   * *:*:  :.::!**   :*  *.  *
Consensus             M--T-----A--FGLLGNIISP-V-LSPVPTF--I-KKKS-EGFQSIPY--AL-SA-L-
                      L   K        I  LV        A I           R T KSYE L         S    C
                      V   N             V V
                          S At5g50790.1 AtSW10    MYYAMIKK-DAMMLITINSPAFVVQIVYISLFFPYAPKKEKTLTVKFVLFVDVLGFGAIF  117
At5g13170.1 AtSW15    LYYALIKK-DAFLLITINSFGCVVETLYIAMFFAYATREKRISAMKLFIAMNVAFFSLIL  119
At3g48740.1 AtSW11    LYYATQKK-DVFLLVTINAFGCFIETIYISMFLAYAPKPARMLTVKMLLLMNFGGFCAIL  119
At5g23660.1 AtSW12    LYYATQKK-DVFLLVTINSFGCFIETIYISIFVAFASKKARMLTVKLLLLMNFGGFCLIL  119
At5g50800.1 AtSW13    IYYAMQKDGTAFLLITINAFGCVIETIYIVLFVSYANKKTRISTLKVLGLLNFLGFAAIV  118
At4g25010.1 AtSW14    IYYALQKDGAGFLLITINAVGCFIETIYIILFITYANKKARISTLKVLGLLNFLGFAAII  118
At2g39060.1 AtSW09    LYYGIMKT-HAYLIISINTFGCFIEISYLFLYILYAPREAKISTLKLIVICNIGGLGLLI  117
                     :**. *   :::!**:. ..:: *:  :!. :*    :   !!*.     :.   : :.
Consensus             LYYA---K-------LLITINAFG-FIE---YI-LFF-YA-K---R---TLKVL-----NF-F---IL
                     I   G          MIVS   SVA VVQ    L MYV F  R  K   AV LI        DV  L   LI
                     M                    T           I I             M MV  I        V
                                                                          L                         FF              F At5g50790.1 AtSW10    VLTYFIIHAN-KRVQVLGYICMVFALSVFVAPLGIIRKVIKTKSAEFMPFGLSFFLTLSA  176
At5g13170.1 AtSW15    MVTHFVVKTPPLQVSVLGWICVAISVSVFAAPLMIVARVIKTKSVEYMPFTLSFPLTISA  179
At3g48740.1 AtSW11    LLCQFLVKGA-TRAKIIGGICVGFSVCVFAAPLSIIRTVIKTRSVEYMPFSLSLTLTISA  178
At5g23660.1 AtSW12    LLCQFLAKGT-TRAKIIGGICVGFSVCVFAAPLSIIRTVIKTKSVEYMPFSLSLTLTISA  178
At5g50800.1 AtSW13    LVCELLTKGS-TREKVLGGICVGFSVSVFAAPLSIMRVVVRTRSVEFMPPSLSLFLTISA  177
At4g25010.1 AtSW14    LVCELLTKGS-NREKVLGGICVGFSVCVFAAPLSIMRVVIRTKSVEFMPFSLSLFLTISA  177
At2g39060.1 AtSW09    LLVNLLVPKQ-HRVSTVGWVCAAYSLAVFASPLSVMRKVIKTKSVEYMPFLLSLSLTLNA  176
                     ::  ::         :  .:*  :*    ::.**.:**  ::   *:!:*:*.!*** **: **!,*
Consensus             LL---FL-------R-K-LG-IC---SVSVFAAPL-IM--VIKTKSVEYMPF-LSL-LTISA
                     MV    LI           Q S  I  V        ALC  VS    VI       VR R A F          F   LN
                     V    V           Q V                    A         V At5g50790.1 AtSW10    VMWFFYGLLLKDMNIALPNVLGFIFGVLQMILFLIYK-KPGTKV-LEPPGIKLQDISEHV  234
At5g13170.1 AtSW15    VMWFAYGLFLNDICIAIPNVVGFVLGLLQMVLYLVYR-NSNEKP-EKINSSEQQLKSIVV  237
At3g48740.1 AtSW11    VIWLLYGLALKDIYVAFPNVLGFALGALQMILYVVYK-YCKTSPHLGEKEVEAAKLPEYS  237
At5g23660.1 AtSW12    VIWLLYGLALKDIYVAFPNVIGFVLGALQMILYVVYK-YCKTPSDLVEKELEAAKLPEYS  237
At5g50800.1 AtSW13    VTWLFYGLAIKDFYVALPNVGAFLGAVQMILYIIFK-YYKTP---VAQKTDKSKDVSDHS  234
At4g25010.1 AtSW14    ITWLFYGLAIKDFYVALPNILGAFLGVAQMILYVIFK-YYKTPL-VVDETEKPKTVSDHS  235
At2g39060.1 AtSW09    VMWFFYGLLIKDKFIAMPNILGFLPGVAQMILYMMYQGSTKTDLPTENQLANKTDVNEVP  236
                     : *:  ***  ::*  :*!**:!:*   :*  **:*::::
Consensus             V-WL-YGL-LKD---VALPNVLG--LG--QMILYVVYK
                      I  F        IN   I F       II      F           V FLIFR
                                               I     V               F               IM Q
                                      M                                               M
```

Fig. 7
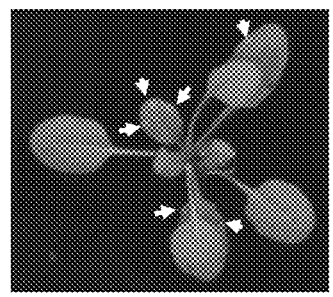 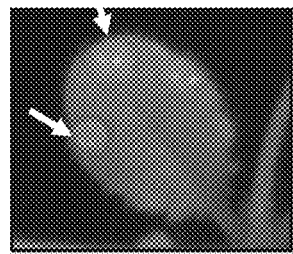
Enlargement

Fig. 9
 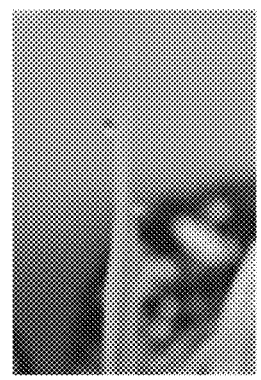
Enlargement

SEQUENCE LISTING

```
<160> NUMBER OF SEQ ID NOS: 175

<210> SEQ ID NO 1
<211> LENGTH: 13
<212> TYPE: PRT
<213> ORGANISM: Artificial Sequence
<220> FEATURE:
<223> OTHER INFORMATION: Synthetic consensus sequence 1
<220> FEATURE:
<221> NAME/KEY: misc_feature
<222> LOCATION: (1)..(1)
<223> OTHER INFORMATION: Xaa is L, I, V, M or F
<220> FEATURE:
```

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is G or A
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is I, L, V, M or F
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa is L, I, V or F
<220> FEATURE:
<221> NAME/KEY: misc_feature
<222> LOCATION: (12)..(12)
<223> OTHER INFORMATION: Xaa is A or S
<220> FEATURE:
<221> NAME/KEY: misc_feature
<222> LOCATION: (13)..(13)
<223> OTHER INFORMATION: Xaa is P or S

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 34
<212> TYPE: PRT
<213> ORGANISM: Artificial Sequence
<220> FEATURE:
<223> OTHER INFORMATION: Synthetic consensus sequence 1
<220> FEATURE:
<221> NAME/KEY: misc_feature
<222> LOCATION: (1)..(1)
<223> OTHER INFORMATION: Xaa is P, S, T or A
<220> FEATURE:
<221> NAME/KEY: misc_feature
<222> LOCATION: (3)..(3)
<223> OTHER INFORMATION: Xaa is F or L
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is I or V
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(18)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is L or I
<220> FEATURE:
<221> NAME/KEY: misc_feature
<222> LOCATION: (25)..(28)
```

```
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa is L or I
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa is I, L, M, V or F
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa is A, S or G

<400> SEQUENCE: 2

Xaa Thr Xaa Xaa Xaa Xaa Xaa Xaa Xaa Lys Xaa Xaa Xaa Xaa Xaa Xaa
 1               5                  10                  15

Xaa Xaa Pro Tyr Xaa Xaa Xaa Xaa Xaa Xaa Xaa Xaa Xaa Xaa Xaa Xaa
             20                  25                  30

Tyr Xaa

<210> SEQ ID NO 3
<211> LENGTH: 20
<212> TYPE: PRT
<213> ORGANISM: Artificial Sequence
<220> FEATURE:
<223> OTHER INFORMATION: Synthetic consensus sequence 1
<220> FEATURE:
<221> NAME/KEY: misc_feature
<222> LOCATION: (1)..(1)
<223> OTHER INFORMATION: Xaa is I or V
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is E or Q
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa is Y or F
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is Y or F
<220> FEATURE:
<221> NAME/KEY: misc_feature
<222> LOCATION: (20)..(20)
<223> OTHER INFORMATION: Xaa is A, G or S

<400> SEQUENCE: 3

Xaa Asn Xaa Xaa Xaa Xaa Xaa Xaa Xaa Xaa Xaa Tyr Xaa Xaa Xaa Xaa
```

```
                1               5                    10                   15

Xaa Xaa Xaa Xaa
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic consensus sequence 1
<220> FEATURE:
<221> NAME/KEY: misc_feature
<222> LOCATION: (1)..(1)
<223> OTHER INFORMATION: Xaa is R, Q or H
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is V, I or L
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is V, M, L, I or F
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is A, S or T
<220> FEATURE:
<221> NAME/KEY: misc_feature
<222> LOCATION: (21)..(21)
<223> OTHER INFORMATION: Xaa is L or M
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is I or V
<220> FEATURE:
<221> NAME/KEY: misc_feature
<222> LOCATION: (24)..(24)
<223> OTHER INFORMATION: Xaa is I, M, V or L

<400> SEQUENCE: 4

Xaa Xaa Xaa Xaa Xaa Gly Xaa Xaa Xaa Xaa Xaa Xaa Xaa Xaa Xaa Xaa
1               5                   10                  15

Xaa Xaa Xaa Pro Xaa Xaa Xaa Xaa
            20

<210> SEQ ID NO 5
<211> LENGTH: 55
<212> TYPE: PRT
<213> ORGANISM: Artificial Sequence
<220> FEATURE:
<223> OTHER INFORMATION: Synthetic consensus sequence 1
<220> FEATURE:
<221> NAME/KEY: misc_feature
<222> LOCATION: (1)..(1)
```

```
<223> OTHER INFORMATION: Xaa is V or I
<220> FEATURE:
<221> NAME/KEY: misc_feature
<222> LOCATION: (2)..(2)
<223> OTHER INFORMATION: Xaa is V, I or M
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is T or S
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is S or N
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is F or Y
<220> FEATURE:
<221> NAME/KEY: misc_feature
<222> LOCATION: (10)..(10)
<223> OTHER INFORMATION: Xaa is M or L
<220> FEATURE:
<221> NAME/KEY: misc_feature
<222> LOCATION: (11)..(11)
<223> OTHER INFORMATION: Xaa is P or S
<220> FEATURE:
<221> NAME/KEY: misc_feature
<222> LOCATION: (12)..(12)
<223> OTHER INFORMATION: Xaa is F, I, V or L
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa is L or I
<220> FEATURE:
<221> NAME/KEY: misc_feature
<222> LOCATION: (19)..(19)
<223> OTHER INFORMATION: Xaa is T or V
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa is A or G
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is F or L
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
```

```
<222> LOCATION: (30)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa is V or I
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa is F or L
<220> FEATURE:
<221> NAME/KEY: misc_feature
<222> LOCATION: (48)..(48)
<223> OTHER INFORMATION: Xaa is G or S
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa is M or I
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa is L, M, I, V or F
<220> FEATURE:
<221> NAME/KEY: misc_feature
<222> LOCATION: (55)..(55)
<223> OTHER INFORMATION: Xaa is Y, H or F

<400> SEQUENCE: 5

Xaa Xaa Xaa Xaa Xaa Xaa Xaa Xaa Xaa Xaa Xaa Xaa Xaa Leu Ser Xaa
1               5                   10                  15

Xaa Xaa Xaa Xaa Xaa Xaa Xaa Xaa Trp Xaa Xaa Tyr Gly Xaa Xaa Xaa
            20                  25                  30

Xaa Asp Xaa Xaa Xaa Xaa Xaa Pro Asn Xaa Xaa Gly Xaa Xaa Xaa Xaa
        35                  40                  45

Xaa Xaa Gln Xaa Xaa Xaa Xaa
    50                  55

<210> SEQ ID NO 6
<211> LENGTH: 50
<212> TYPE: PRT
<213> ORGANISM: Artificial Sequence
<220> FEATURE:
<223> OTHER INFORMATION: Synthetic consensus sequence 2
<220> FEATURE:
<221> NAME/KEY: misc_feature
<222> LOCATION: (2)..(2)
<223> OTHER INFORMATION: Xaa is L, I, V, F or M
<220> FEATURE:
<221> NAME/KEY: misc_feature
<222> LOCATION: (3)..(3)
```

```
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is I, V or L
<220> FEATURE:
<221> NAME/KEY: misc_feature
<222> LOCATION: (7)..(7)
<223> OTHER INFORMATION: Xaa is I, V or L
<220> FEATURE:
<221> NAME/KEY: misc_feature
<222> LOCATION: (8)..(8)
<223> OTHER INFORMATION: Xaa is S or T
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is A or S
<220> FEATURE:
<221> NAME/KEY: misc_feature
<222> LOCATION: (16)..(16)
<223> OTHER INFORMATION: Xaa is L, V, I or M
<220> FEATURE:
<221> NAME/KEY: misc_feature
<222> LOCATION: (17)..(17)
<223> OTHER INFORMATION: Xaa is P, S, T or A
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa is I or V
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is K or R
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa is S or T
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa is F or Y
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa is S or A
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
```

```
<222> LOCATION: (37)..(38)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa is A, S or T
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa is L, I, M or V
<220> FEATURE:
<221> NAME/KEY: misc_feature
<222> LOCATION: (48)..(48)
<223> OTHER INFORMATION: Xaa is Y or F
<220> FEATURE:
<221> NAME/KEY: misc_feature
<222> LOCATION: (50)..(50)
<223> OTHER INFORMATION: Xaa is A or G

<400> SEQUENCE: 6

Gly Xaa Xaa Gly Xaa Xaa Xaa Xaa Xaa Xaa Xaa Xaa Leu Xaa Pro Xaa
1               5                   10                  15

Xaa Thr Phe Xaa Xaa Xaa Xaa Xaa Xaa Lys Xaa Xaa Xaa Xaa Xaa Xaa
            20                  25                  30

Xaa Xaa Pro Tyr Xaa Xaa Xaa Leu Xaa Ser Xaa Xaa Leu Xaa Xaa Xaa
        35                  40                  45

Tyr Xaa
    50

<210> SEQ ID NO 7
<211> LENGTH: 31
<212> TYPE: PRT
<213> ORGANISM: Artificial Sequence
<220> FEATURE:
<223> OTHER INFORMATION: Synthetic consensus sequence 2
<220> FEATURE:
<221> NAME/KEY: misc_feature
<222> LOCATION: (1)..(1)
<223> OTHER INFORMATION: Xaa is L or I
<220> FEATURE:
<221> NAME/KEY: misc_feature
<222> LOCATION: (2)..(2)
<223> OTHER INFORMATION: Xaa is I, V or L
<220> FEATURE:
<221> NAME/KEY: misc_feature
<222> LOCATION: (3)..(3)
<223> OTHER INFORMATION: Xaa is T or S
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is G or A
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (11)..(11)
```

```
<223> OTHER INFORMATION: Xaa is I, V or M
<220> FEATURE:
<221> NAME/KEY: misc_feature
<222> LOCATION: (12)..(12)
<223> OTHER INFORMATION: Xaa is E or Q
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is F or Y
<220> FEATURE:
<221> NAME/KEY: misc_feature
<222> LOCATION: (20)..(20)
<223> OTHER INFORMATION: Xaa is L, I, V or F
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa is Y or F
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa is K, R or N
<220> FEATURE:
<221> NAME/KEY: misc_feature
<222> LOCATION: (26)..(30)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa is T or A

<400> SEQUENCE: 7

Xaa Xaa Xaa Ile Asn Xaa Xaa Xaa Xaa Xaa Xaa Xaa Xaa Xaa Tyr Xaa
1               5                   10                  15

Xaa Xaa Xaa Xaa Xaa Xaa Ala Xaa Xaa Xaa Xaa Xaa Xaa Xaa Xaa
            20                  25                  30

<210> SEQ ID NO 8
<211> LENGTH: 84
<212> TYPE: PRT
<213> ORGANISM: Artificial Sequence
<220> FEATURE:
<223> OTHER INFORMATION: Synthetic consensus sequence 2
<220> FEATURE:
<221> NAME/KEY: misc_feature
<222> LOCATION: (1)..(1)
<223> OTHER INFORMATION: Xaa is R, Q or H
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is I or V
<220> FEATURE:
<221> NAME/KEY: misc_feature
```

```
<222> LOCATION: (9)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is V, I, L or M
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa is V or M
<220> FEATURE:
<221> NAME/KEY: misc_feature
<222> LOCATION: (18)..(18)
<223> OTHER INFORMATION: Xaa is A or V
<220> FEATURE:
<221> NAME/KEY: misc_feature
<222> LOCATION: (19)..(19)
<223> OTHER INFORMATION: Xaa is A, S or T
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is I or V
<220> FEATURE:
<221> NAME/KEY: misc_feature
<222> LOCATION: (24)..(24)
<223> OTHER INFORMATION: Xaa is I, M, V or L
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is I or V
<220> FEATURE:
<221> NAME/KEY: misc_feature
<222> LOCATION: (29)..(29)
<223> OTHER INFORMATION: Xaa is K, R or Q
<220> FEATURE:
<221> NAME/KEY: misc_feature
<222> LOCATION: (30)..(30)
<223> OTHER INFORMATION: Xaa is T or S
<220> FEATURE:
<221> NAME/KEY: misc_feature
<222> LOCATION: (31)..(31)
<223> OTHER INFORMATION: Xaa is K or R
<220> FEATURE:
<221> NAME/KEY: misc_feature
<222> LOCATION: (33)..(33)
<223> OTHER INFORMATION: Xaa is V or A
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa is F or Y
<220> FEATURE:
<221> NAME/KEY: misc_feature
<222> LOCATION: (38)..(38)
<223> OTHER INFORMATION: Xaa is F, I or L
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa is L, F or V
<220> FEATURE:
```

```
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa is T or V
<220> FEATURE:
<221> NAME/KEY: misc_feature
<222> LOCATION: (46)..(46)
<223> OTHER INFORMATION: Xaa is L or I
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa is F or L
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa is L or F
<220> FEATURE:
<221> NAME/KEY: misc_feature
<222> LOCATION: (57)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa is V or I
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (68)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa is L or F
<220> FEATURE:
<221> NAME/KEY: misc_feature
<222> LOCATION: (74)..(74)
<223> OTHER INFORMATION: Xaa is G or S
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa is L, V or I
<220> FEATURE:
<221> NAME/KEY: misc_feature
<222> LOCATION: (81)..(81)
<223> OTHER INFORMATION: Xaa is Y or F
```

-continued

```
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa is Y or F

<400> SEQUENCE: 8

Xaa Xaa Xaa Xaa Xaa Gly Xaa Xaa Xaa Xaa Xaa Xaa Xaa Xaa Xaa Xaa
1               5                   10                  15

Phe Xaa Xaa Pro Leu Xaa Xaa Xaa Xaa Xaa Val Xaa Xaa Xaa Xaa Ser
            20                  25                  30

Xaa Xaa Xaa Met Pro Xaa Xaa Leu Ser Xaa Xaa Leu Xaa Xaa Xaa Ala
        35                  40                  45

Xaa Xaa Trp Xaa Xaa Tyr Gly Xaa Xaa Xaa Xaa Asp Xaa Xaa Xaa Xaa
    50                  55                  60

Xaa Pro Asn Xaa Xaa Gly Xaa Xaa Xaa Xaa Xaa Gln Met Xaa Xaa
65                  70                  75                  80

Xaa Xaa Xaa Xaa

<210> SEQ ID NO 9
<211> LENGTH: 57
<212> TYPE: PRT
<213> ORGANISM: Artificial Sequence
<220> FEATURE:
<223> OTHER INFORMATION: Synthetic consensus sequence 3
<220> FEATURE:
<221> NAME/KEY: misc_feature
<222> LOCATION: (1)..(1)
<223> OTHER INFORMATION: Xaa is A or V
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is I, L or V
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa is I, L or V
<220> FEATURE:
<221> NAME/KEY: misc_feature
<222> LOCATION: (11)..(11)
<223> OTHER INFORMATION: Xaa is I, L or V
<220> FEATURE:
<221> NAME/KEY: misc_feature
<222> LOCATION: (13)..(13)
<223> OTHER INFORMATION: Xaa is F or L
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa is V or T
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa is A or S
```

```
<220> FEATURE:
<221> NAME/KEY: misc_feature
<222> LOCATION: (20)..(20)
<223> OTHER INFORMATION: Xaa is V, L or I
<220> FEATURE:
<221> NAME/KEY: misc_feature
<222> LOCATION: (21)..(21)
<223> OTHER INFORMATION: Xaa is P or A
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is I or V
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is K or R
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa is S or T
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa is G or S
<220> FEATURE:
<221> NAME/KEY: misc_feature
<222> LOCATION: (35)..(35)
<223> OTHER INFORMATION: Xaa is F or Y
<220> FEATURE:
<221> NAME/KEY: misc_feature
<222> LOCATION: (36)..(36)
<223> OTHER INFORMATION: Xaa is Q, S or E
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa is A, S or T
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa is A, C or S
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
```

-continued

<223> OTHER INFORMATION: Xaa is L, I or M
<220> FEATURE:
<221> NAME/KEY: misc_feature
<222> LOCATION: (52)..(52)
<223> OTHER INFORMATION: Xaa is Y or F
<220> FEATURE:
<221> NAME/KEY: misc_feature
<222> LOCATION: (54)..(54)
<223> OTHER INFORMATION: Xaa is A or G
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa is K or T

<400> SEQUENCE: 9

Xaa Xaa Xaa Xaa Gly Xaa Xaa Gly Asn Xaa Xaa Ser Xaa Xaa Xaa Xaa
1               5                   10                  15

Leu Xaa Pro Xaa Xaa Thr Phe Xaa Xaa Xaa Xaa Xaa Xaa Lys Xaa Xaa
            20                  25                  30

Xaa Xaa Xaa Xaa Ser Xaa Pro Tyr Xaa Xaa Xaa Leu Xaa Ser Xaa Xaa
        35                  40                  45

Leu Xaa Xaa Xaa Tyr Xaa Xaa Xaa Xaa
    50                  55

<210> SEQ ID NO 10
<211> LENGTH: 54
<212> TYPE: PRT
<213> ORGANISM: Artificial Sequence
<220> FEATURE:
<223> OTHER INFORMATION: Synthetic consensus sequence 3
<220> FEATURE:
<221> NAME/KEY: misc_feature
<222> LOCATION: (1)..(1)
<223> OTHER INFORMATION: Xaa is L, M or P
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is I, L or V
<220> FEATURE:
<221> NAME/KEY: misc_feature
<222> LOCATION: (4)..(4)
<223> OTHER INFORMATION: Xaa is T or S
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is G or A
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa is I or V
<220> FEATURE:
<221> NAME/KEY: misc_feature
<222> LOCATION: (13)..(13)
<223> OTHER INFORMATION: Xaa is E or Q
<220> FEATURE:
<221> NAME/KEY: misc_feature
<222> LOCATION: (14)..(15)
<223> OTHER INFORMATION: Xaa can be any naturally occurring amino acid

```
<220> FEATURE:
<221> NAME/KEY: misc_feature
<222> LOCATION: (17)..(17)
<223> OTHER INFORMATION: Xaa is I or L
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is L, M, V or I
<220> FEATURE:
<221> NAME/KEY: misc_feature
<222> LOCATION: (20)..(20)
<223> OTHER INFORMATION: Xaa is F or Y
<220> FEATURE:
<221> NAME/KEY: misc_feature
<222> LOCATION: (21)..(21)
<223> OTHER INFORMATION: Xaa is L, I, V or F
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is Y or F
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is K or R
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa is T or A
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa is L, M, F, V or I
<220> FEATURE:
<221> NAME/KEY: misc_feature
<222> LOCATION: (36)..(36)
<223> OTHER INFORMATION: Xaa is L, F, V or I
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa is N or D
<220> FEATURE:
<221> NAME/KEY: misc_feature
<222> LOCATION: (41)..(41)
<223> OTHER INFORMATION: Xaa is F, V, I or L
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa is F or L
<220> FEATURE:
<221> NAME/KEY: misc_feature
<222> LOCATION: (45)..(46)
```

```
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa is I, L or V
<220> FEATURE:
<221> NAME/KEY: misc_feature
<222> LOCATION: (48)..(53)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa is L, I or V

<400> SEQUENCE: 10

Xaa Xaa Xaa Xaa Ile Asn Xaa Xaa Xaa Xaa Xaa Xaa Xaa Xaa Xaa Tyr
1               5                   10                  15

Xaa Xaa Xaa Xaa Xaa Xaa Xaa Ala Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa
    50

<210> SEQ ID NO 11
<211> LENGTH: 84
<212> TYPE: PRT
<213> ORGANISM: Artificial Sequence
<220> FEATURE:
<223> OTHER INFORMATION: Synthetic consensus sequence 3
<220> FEATURE:
<221> NAME/KEY: misc_feature
<222> LOCATION: (1)..(1)
<223> OTHER INFORMATION: Xaa is R or Q
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is I or V
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is S or A
<220> FEATURE:
<221> NAME/KEY: misc_feature
<222> LOCATION: (14)..(14)
<223> OTHER INFORMATION: Xaa is V, L or M
<220> FEATURE:
<221> NAME/KEY: misc_feature
<222> LOCATION: (15)..(15)
<223> OTHER INFORMATION: Xaa is C, S or A
<220> FEATURE:
<221> NAME/KEY: misc_feature
<222> LOCATION: (18)..(18)
<223> OTHER INFORMATION: Xaa is A or V
<220> FEATURE:
<221> NAME/KEY: misc_feature
<222> LOCATION: (19)..(19)
<223> OTHER INFORMATION: Xaa is A or S
<220> FEATURE:
<221> NAME/KEY: misc_feature
<222> LOCATION: (22)..(22)
<223> OTHER INFORMATION: Xaa can be any naturally occurring amino acid
```

```
<220> FEATURE:
<221> NAME/KEY: misc_feature
<222> LOCATION: (23)..(23)
<223> OTHER INFORMATION: Xaa is I or V
<220> FEATURE:
<221> NAME/KEY: misc_feature
<222> LOCATION: (24)..(24)
<223> OTHER INFORMATION: Xaa is I, M or V
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is I or V
<220> FEATURE:
<221> NAME/KEY: misc_feature
<222> LOCATION: (29)..(29)
<223> OTHER INFORMATION: Xaa is K, R or Q
<220> FEATURE:
<221> NAME/KEY: misc_feature
<222> LOCATION: (30)..(30)
<223> OTHER INFORMATION: Xaa is T or S
<220> FEATURE:
<221> NAME/KEY: misc_feature
<222> LOCATION: (31)..(31)
<223> OTHER INFORMATION: Xaa is K or R
<220> FEATURE:
<221> NAME/KEY: misc_feature
<222> LOCATION: (33)..(33)
<223> OTHER INFORMATION: Xaa is V or A
<220> FEATURE:
<221> NAME/KEY: misc_feature
<222> LOCATION: (35)..(35)
<223> OTHER INFORMATION: Xaa is F or Y
<220> FEATURE:
<221> NAME/KEY: misc_feature
<222> LOCATION: (38)..(38)
<223> OTHER INFORMATION: Xaa is F or I
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa is L, F or V
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa is T or V
<220> FEATURE:
<221> NAME/KEY: misc_feature
<222> LOCATION: (46)..(46)
<223> OTHER INFORMATION: Xaa is L or I
<220> FEATURE:
<221> NAME/KEY: misc_feature
<222> LOCATION: (47)..(47)
<223> OTHER INFORMATION: Xaa is S or N
<220> FEATURE:
<221> NAME/KEY: misc_feature
<222> LOCATION: (49)..(49)
<223> OTHER INFORMATION: Xaa is V or I
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa is F or L
<220> FEATURE:
<221> NAME/KEY: misc_feature
<222> LOCATION: (53)..(53)
```

```
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa is K or N
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa is V or I
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa is V or I
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa is F or L
<220> FEATURE:
<221> NAME/KEY: misc_feature
<222> LOCATION: (74)..(74)
<223> OTHER INFORMATION: Xaa is G or S
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa is Y or F
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa is Y or F

<400> SEQUENCE: 11

Xaa Xaa Xaa Xaa Xaa Gly Xaa Xaa Xaa Xaa Xaa Xaa Xaa Xaa Xaa Val
1               5                   10                  15

Phe Xaa Xaa Pro Leu Xaa Xaa Xaa Xaa Val Xaa Xaa Xaa Xaa Xaa Ser
            20                  25                  30

Xaa Glu Xaa Met Pro Xaa Xaa Leu Ser Xaa Xaa Leu Xaa Xaa Xaa Ala
        35                  40                  45

Xaa Xaa Trp Xaa Xaa Tyr Gly Leu Xaa Xaa Xaa Asp Xaa Xaa Xaa Xaa
    50                  55                  60

Xaa Pro Asn Xaa Xaa Gly Xaa Xaa Xaa Xaa Xaa Gln Met Xaa Leu
65                  70                  75                  80
```

Xaa Xaa Xaa Xaa

```
<210> SEQ ID NO 12
<211> LENGTH: 65
<212> TYPE: PRT
<213> ORGANISM: Artificial Sequence
<220> FEATURE:
<223> OTHER INFORMATION: Synthetic consensus sequence 4
<220> FEATURE:
<221> NAME/KEY: misc_feature
<222> LOCATION: (1)..(1)
<223> OTHER INFORMATION: Xaa is M, L or V
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is T, K, N or S
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is L, I or V
<220> FEATURE:
<221> NAME/KEY: misc_feature
<222> LOCATION: (18)..(18)
<223> OTHER INFORMATION: Xaa is I, L or V
<220> FEATURE:
<221> NAME/KEY: misc_feature
<222> LOCATION: (19)..(19)
<223> OTHER INFORMATION: Xaa is I or V
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is S or A
<220> FEATURE:
<221> NAME/KEY: misc_feature
<222> LOCATION: (28)..(28)
<223> OTHER INFORMATION: Xaa is V or I
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa is K or R
<220> FEATURE:
<221> NAME/KEY: misc_feature
<222> LOCATION: (39)..(39)
<223> OTHER INFORMATION: Xaa is S or T
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
```

```
<222> LOCATION: (41)..(41)
<223> OTHER INFORMATION: Xaa is E or K
<220> FEATURE:
<221> NAME/KEY: misc_feature
<222> LOCATION: (42)..(42)
<223> OTHER INFORMATION: Xaa is G or S
<220> FEATURE:
<221> NAME/KEY: misc_feature
<222> LOCATION: (43)..(43)
<223> OTHER INFORMATION: Xaa is F or Y
<220> FEATURE:
<221> NAME/KEY: misc_feature
<222> LOCATION: (44)..(44)
<223> OTHER INFORMATION: Xaa is Q or E
<220> FEATURE:
<221> NAME/KEY: misc_feature
<222> LOCATION: (46)..(46)
<223> OTHER INFORMATION: Xaa is I or L
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa is A or S
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa is A or C
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa is L, I or M
<220> FEATURE:
<221> NAME/KEY: misc_feature
<222> LOCATION: (62)..(62)
<223> OTHER INFORMATION: Xaa is A or G
<220> FEATURE:
<221> NAME/KEY: misc_feature
<222> LOCATION: (63)..(64)
<223> OTHER INFORMATION: Xaa can be any naturally occurring amino acid

<400> SEQUENCE: 12

Xaa Xaa Xaa Xaa Xaa Xaa Xaa Xaa Ala Xaa Xaa Phe Gly Xaa Leu Gly
1               5                   10                  15

Asn Xaa Xaa Ser Phe Xaa Val Xaa Leu Xaa Pro Xaa Pro Thr Phe Xaa
            20                  25                  30

Xaa Ile Xaa Lys Xaa Lys Xaa Xaa Xaa Xaa Xaa Xaa Ser Xaa Pro Tyr
        35                  40                  45

Xaa Xaa Xaa Leu Xaa Ser Xaa Xaa Leu Xaa Xaa Tyr Tyr Xaa Xaa Xaa
    50                  55                  60

Lys
65

<210> SEQ ID NO 13
<211> LENGTH: 54
<212> TYPE: PRT
<213> ORGANISM: Artificial Sequence
<220> FEATURE:
<223> OTHER INFORMATION: Synthetic consensus sequence 4
```

-continued

```
<220> FEATURE:
<221> NAME/KEY: misc_feature
<222> LOCATION: (1)..(1)
<223> OTHER INFORMATION: Xaa is L or M
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is I or V
<220> FEATURE:
<221> NAME/KEY: misc_feature
<222> LOCATION: (4)..(4)
<223> OTHER INFORMATION: Xaa is T or S
<220> FEATURE:
<221> NAME/KEY: misc_feature
<222> LOCATION: (7)..(7)
<223> OTHER INFORMATION: Xaa is A, S or T
<220> FEATURE:
<221> NAME/KEY: misc_feature
<222> LOCATION: (8)..(8)
<223> OTHER INFORMATION: Xaa is F or V
<220> FEATURE:
<221> NAME/KEY: misc_feature
<222> LOCATION: (9)..(9)
<223> OTHER INFORMATION: Xaa is G or A
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa is F or V
<220> FEATURE:
<221> NAME/KEY: misc_feature
<222> LOCATION: (12)..(12)
<223> OTHER INFORMATION: Xaa is I or V
<220> FEATURE:
<221> NAME/KEY: misc_feature
<222> LOCATION: (13)..(13)
<223> OTHER INFORMATION: Xaa is E or Q
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa is I or L
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is L, M or I
<220> FEATURE:
<221> NAME/KEY: misc_feature
<222> LOCATION: (20)..(20)
<223> OTHER INFORMATION: Xaa is F or Y
<220> FEATURE:
<221> NAME/KEY: misc_feature
<222> LOCATION: (21)..(21)
<223> OTHER INFORMATION: Xaa is F, V, I or L
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is Y or F
<220> FEATURE:
<221> NAME/KEY: misc_feature
<222> LOCATION: (25)..(25)
```

```
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is K or R
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa is R or K
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa is T or A
<220> FEATURE:
<221> NAME/KEY: misc_feature
<222> LOCATION: (33)..(33)
<223> OTHER INFORMATION: Xaa is L, V or M
<220> FEATURE:
<221> NAME/KEY: misc_feature
<222> LOCATION: (35)..(35)
<223> OTHER INFORMATION: Xaa is V, L, M or F
<220> FEATURE:
<221> NAME/KEY: misc_feature
<222> LOCATION: (36)..(36)
<223> OTHER INFORMATION: Xaa is L, I, V or F
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa is N or D
<220> FEATURE:
<221> NAME/KEY: misc_feature
<222> LOCATION: (41)..(41)
<223> OTHER INFORMATION: Xaa is F, V or I
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa is F or L
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa is I or L
<220> FEATURE:
<221> NAME/KEY: misc_feature
<222> LOCATION: (48)..(48)
<223> OTHER INFORMATION: Xaa is L, I, V or F
<220> FEATURE:
<221> NAME/KEY: misc_feature
<222> LOCATION: (49)..(49)
<223> OTHER INFORMATION: Xaa is L, M or V
<220> FEATURE:
<221> NAME/KEY: misc_feature
<222> LOCATION: (50)..(50)
<223> OTHER INFORMATION: Xaa is L or V
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
```

<222> LOCATION: (53)..(53)
<223> OTHER INFORMATION: Xaa is F or L
<220> FEATURE:
<221> NAME/KEY: misc_feature
<222> LOCATION: (54)..(54)
<223> OTHER INFORMATION: Xaa is L, I or V

<400> SEQUENCE: 13

Xaa Xaa Xaa Xaa Ile Asn Xaa Xaa Xaa Xaa Xaa Xaa Xaa Xaa Tyr
1               5                   10                  15

Xaa Xaa Xaa Xaa Xaa Xaa Xaa Ala Xaa Xaa Xaa Xaa Xaa Xaa Xaa
            20                  25                  30

Xaa Lys Xaa Xaa Xaa Xaa Xaa Xaa Xaa Xaa Xaa Xaa Xaa Xaa Xaa
        35                  40                  45

Xaa Xaa Xaa Xaa Xaa Xaa
    50

<210> SEQ ID NO 14
<211> LENGTH: 85
<212> TYPE: PRT
<213> ORGANISM: Artificial Sequence
<220> FEATURE:
<223> OTHER INFORMATION: Synthetic consensus sequence 4
<220> FEATURE:
<221> NAME/KEY: misc_feature
<222> LOCATION: (1)..(1)
<223> OTHER INFORMATION: Xaa is R or Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is K, S or Q
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is L, I or V
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is I or V
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is S or A
<220> FEATURE:
<221> NAME/KEY: misc_feature
<222> LOCATION: (14)..(14)
<223> OTHER INFORMATION: Xaa is V or L
<220> FEATURE:
<221> NAME/KEY: misc_feature
<222> LOCATION: (15)..(15)
<223> OTHER INFORMATION: Xaa is S, C or A
<220> FEATURE:
<221> NAME/KEY: misc_feature
<222> LOCATION: (18)..(18)
<223> OTHER INFORMATION: Xaa is A or V
<220> FEATURE:
<221> NAME/KEY: misc_feature
<222> LOCATION: (19)..(19)

```
<223> OTHER INFORMATION: Xaa is A or S
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is I or V
<220> FEATURE:
<221> NAME/KEY: misc_feature
<222> LOCATION: (24)..(24)
<223> OTHER INFORMATION: Xaa is M, I or V
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is I or V
<220> FEATURE:
<221> NAME/KEY: misc_feature
<222> LOCATION: (29)..(29)
<223> OTHER INFORMATION: Xaa is K or R
<220> FEATURE:
<221> NAME/KEY: misc_feature
<222> LOCATION: (31)..(31)
<223> OTHER INFORMATION: Xaa is K or R
<220> FEATURE:
<221> NAME/KEY: misc_feature
<222> LOCATION: (33)..(33)
<223> OTHER INFORMATION: Xaa is V or A
<220> FEATURE:
<221> NAME/KEY: misc_feature
<222> LOCATION: (35)..(35)
<223> OTHER INFORMATION: Xaa is Y or F
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa is L or F
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa is I or L
<220> FEATURE:
<221> NAME/KEY: misc_feature
<222> LOCATION: (47)..(47)
<223> OTHER INFORMATION: Xaa is S or N
<220> FEATURE:
<221> NAME/KEY: misc_feature
<222> LOCATION: (49)..(49)
<223> OTHER INFORMATION: Xaa is V or I
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa is L or F
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
```

```
<222> LOCATION: (58)..(58)
<223> OTHER INFORMATION: Xaa is L or I
<220> FEATURE:
<221> NAME/KEY: misc_feature
<222> LOCATION: (59)..(59)
<223> OTHER INFORMATION: Xaa is K or N
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa is V or I
<220> FEATURE:
<221> NAME/KEY: misc_feature
<222> LOCATION: (65)..(65)
<223> OTHER INFORMATION: Xaa is L, F, I or M
<220> FEATURE:
<221> NAME/KEY: misc_feature
<222> LOCATION: (68)..(68)
<223> OTHER INFORMATION: Xaa is V or I
<220> FEATURE:
<221> NAME/KEY: misc_feature
<222> LOCATION: (69)..(69)
<223> OTHER INFORMATION: Xaa is L, I or V
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa is L or F
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa is I or V
<220> FEATURE:
<221> NAME/KEY: misc_feature
<222> LOCATION: (81)..(81)
<223> OTHER INFORMATION: Xaa is Y or F
<220> FEATURE:
<221> NAME/KEY: misc_feature
<222> LOCATION: (82)..(82)
<223> OTHER INFORMATION: Xaa is V, L, I or M
<220> FEATURE:
<221> NAME/KEY: misc_feature
<222> LOCATION: (83)..(83)
<223> OTHER INFORMATION: Xaa is V, I or M
<220> FEATURE:
<221> NAME/KEY: misc_feature
<222> LOCATION: (84)..(84)
<223> OTHER INFORMATION: Xaa is Y or F
<220> FEATURE:
<221> NAME/KEY: misc_feature
<222> LOCATION: (85)..(85)
<223> OTHER INFORMATION: Xaa is K, R or Q

<400> SEQUENCE: 14

Xaa Xaa Xaa Xaa Xaa Gly Xaa Xaa Cys Xaa Xaa Xaa Xaa Xaa Val
1               5                   10                  15

Phe Xaa Xaa Pro Leu Xaa Xaa Xaa Xaa Val Xaa Xaa Thr Xaa Ser
            20                  25                  30

Xaa Glu Xaa Met Pro Phe Xaa Leu Ser Xaa Xaa Leu Thr Xaa Xaa Ala
        35                  40                  45

Xaa Xaa Trp Xaa Xaa Tyr Gly Leu Xaa Xaa Asp Xaa Xaa Xaa Ala
    50                  55                  60

Xaa Pro Asn Xaa Xaa Gly Xaa Xaa Xaa Gly Xaa Xaa Gln Met Xaa Leu
65                  70                  75                  80
```

-continued

```
Xaa Xaa Xaa Xaa Xaa
                85

<210> SEQ ID NO 15
<211> LENGTH: 258
<212> TYPE: PRT
<213> ORGANISM: Arabidopsis thaliana

<400> SEQUENCE: 15

Met Phe Leu Lys Val His Glu Ile Ala Phe Leu Phe Gly Leu Leu Gly
1               5                   10                  15

Asn Ile Val Ser Phe Gly Val Phe Leu Ser Pro Val Pro Thr Phe Tyr
            20                  25                  30

Gly Ile Tyr Lys Lys Lys Ser Ser Lys Gly Phe Gln Ser Ile Pro Tyr
        35                  40                  45

Ile Cys Ala Leu Ala Ser Ala Thr Leu Leu Tyr Tyr Gly Ile Met
    50                  55                  60

Lys Thr His Ala Tyr Leu Ile Ser Ile Asn Thr Phe Gly Cys Phe
65                  70                  75                  80

Ile Glu Ile Ser Tyr Leu Phe Leu Tyr Ile Leu Tyr Ala Pro Arg Glu
                85                  90                  95

Ala Lys Ile Ser Thr Leu Lys Leu Ile Val Ile Cys Asn Ile Gly Gly
            100                 105                 110

Leu Gly Leu Leu Ile Leu Leu Val Asn Leu Leu Val Pro Lys Gln His
        115                 120                 125

Arg Val Ser Thr Val Gly Trp Val Cys Ala Ala Tyr Ser Leu Ala Val
    130                 135                 140

Phe Ala Ser Pro Leu Ser Val Met Arg Lys Val Ile Lys Thr Lys Ser
145                 150                 155                 160

Val Glu Tyr Met Pro Phe Leu Leu Ser Leu Ser Leu Thr Leu Asn Ala
                165                 170                 175

Val Met Trp Phe Phe Tyr Gly Leu Leu Ile Lys Asp Lys Phe Ile Ala
            180                 185                 190

Met Pro Asn Ile Leu Gly Phe Leu Phe Gly Val Ala Gln Met Ile Leu
        195                 200                 205

Tyr Met Met Tyr Gln Gly Ser Thr Lys Thr Asp Leu Pro Thr Glu Asn
    210                 215                 220

Gln Leu Ala Asn Lys Thr Asp Val Asn Glu Val Pro Ile Val Ala Val
225                 230                 235                 240

Glu Leu Pro Asp Val Gly Ser Asp Asn Val Glu Gly Ser Val Arg Pro
                245                 250                 255

Met Lys

<210> SEQ ID NO 16
<211> LENGTH: 289
<212> TYPE: PRT
<213> ORGANISM: Arabidopsis thaliana

<400> SEQUENCE: 16

Met Ala Ile Ser Gln Ala Val Leu Ala Thr Val Phe Gly Ile Leu Gly
1               5                   10                  15

Asn Ile Ile Ser Phe Phe Val Cys Leu Ala Pro Ile Pro Thr Phe Val
            20                  25                  30

Arg Ile Tyr Lys Arg Lys Ser Ser Glu Gly Tyr Gln Ser Ile Pro Tyr
        35                  40                  45
```

Val Ile Ser Leu Phe Ser Ala Met Leu Trp Met Tyr Tyr Ala Met Ile
 50                  55                  60

Lys Lys Asp Ala Met Met Leu Ile Thr Ile Asn Ser Phe Ala Phe Val
 65                  70                  75                  80

Val Gln Ile Val Tyr Ile Ser Leu Phe Phe Phe Tyr Ala Pro Lys Lys
                 85                  90                  95

Glu Lys Thr Leu Thr Val Lys Phe Val Leu Phe Val Asp Val Leu Gly
            100                 105                 110

Phe Gly Ala Ile Phe Val Leu Thr Tyr Phe Ile Ile His Ala Asn Lys
            115                 120                 125

Arg Val Gln Val Leu Gly Tyr Ile Cys Met Val Phe Ala Leu Ser Val
130                 135                 140

Phe Val Ala Pro Leu Gly Ile Ile Arg Lys Val Ile Lys Thr Lys Ser
145                 150                 155                 160

Ala Glu Phe Met Pro Phe Gly Leu Ser Phe Phe Leu Thr Leu Ser Ala
                165                 170                 175

Val Met Trp Phe Phe Tyr Gly Leu Leu Leu Lys Asp Met Asn Ile Ala
                180                 185                 190

Leu Pro Asn Val Leu Gly Phe Ile Phe Gly Val Leu Gln Met Ile Leu
            195                 200                 205

Phe Leu Ile Tyr Lys Lys Pro Gly Thr Lys Val Leu Glu Pro Pro Gly
210                 215                 220

Ile Lys Leu Gln Asp Ile Ser Glu His Val Val Asp Val Val Arg Leu
225                 230                 235                 240

Ser Thr Met Val Cys Asn Ser Gln Met Arg Thr Leu Val Pro Gln Asp
                245                 250                 255

Ser Ala Asp Met Glu Ala Thr Ile Asp Ile Asp Glu Lys Ile Lys Gly
                260                 265                 270

Asp Ile Glu Lys Asn Lys Asp Glu Lys Glu Val Phe Leu Ile Ser Lys
            275                 280                 285

Asn

<210> SEQ ID NO 17
<211> LENGTH: 289
<212> TYPE: PRT
<213> ORGANISM: Arabidopsis thaliana

<400> SEQUENCE: 17

Met Ser Leu Phe Asn Thr Glu Asn Thr Trp Ala Phe Val Phe Gly Leu
 1               5                  10                  15

Leu Gly Asn Leu Ile Ser Phe Ala Val Phe Leu Ser Pro Val Pro Thr
                 20                  25                  30

Phe Tyr Arg Ile Trp Lys Lys Lys Thr Thr Glu Gly Phe Gln Ser Ile
             35                  40                  45

Pro Tyr Val Val Ala Leu Phe Ser Ala Thr Leu Trp Leu Tyr Tyr Ala
 50                  55                  60

Thr Gln Lys Lys Asp Val Phe Leu Leu Val Thr Ile Asn Ala Phe Gly
 65                  70                  75                  80

Cys Phe Ile Glu Thr Ile Tyr Ile Ser Met Phe Leu Ala Tyr Ala Pro
                 85                  90                  95

Lys Pro Ala Arg Met Leu Thr Val Lys Met Leu Leu Leu Met Asn Phe
            100                 105                 110

Gly Gly Phe Cys Ala Ile Leu Leu Leu Cys Gln Phe Leu Val Lys Gly
            115                 120                 125

```
Ala Thr Arg Ala Lys Ile Ile Gly Gly Ile Cys Val Gly Phe Ser Val
    130                 135                 140

Cys Val Phe Ala Ala Pro Leu Ser Ile Ile Arg Thr Val Ile Lys Thr
145                 150                 155                 160

Arg Ser Val Glu Tyr Met Pro Phe Ser Leu Ser Leu Thr Leu Thr Ile
                165                 170                 175

Ser Ala Val Ile Trp Leu Leu Tyr Gly Leu Ala Leu Lys Asp Ile Tyr
                180                 185                 190

Val Ala Phe Pro Asn Val Leu Gly Phe Ala Leu Gly Ala Leu Gln Met
                195                 200                 205

Ile Leu Tyr Val Val Tyr Lys Tyr Cys Lys Thr Ser Pro His Leu Gly
    210                 215                 220

Glu Lys Glu Val Glu Ala Ala Lys Leu Pro Glu Val Ser Leu Asp Met
225                 230                 235                 240

Leu Lys Leu Gly Thr Val Ser Ser Pro Glu Pro Ile Ser Val Val Arg
                245                 250                 255

Gln Ala Asn Lys Cys Thr Cys Gly Asn Asp Arg Arg Ala Glu Ile Glu
                260                 265                 270

Asp Gly Gln Thr Pro Lys His Gly Lys Gln Ser Ser Ser Ala Ala Ala
                275                 280                 285

Thr

<210> SEQ ID NO 18
<211> LENGTH: 285
<212> TYPE: PRT
<213> ORGANISM: Arabidopsis thaliana

<400> SEQUENCE: 18

Met Ala Leu Phe Asp Thr His Asn Thr Trp Ala Phe Val Phe Gly Leu
1               5                   10                  15

Leu Gly Asn Leu Ile Ser Phe Ala Val Phe Leu Ser Pro Val Pro Thr
                20                  25                  30

Phe Tyr Arg Ile Cys Lys Lys Thr Thr Glu Gly Phe Gln Ser Ile
                35                  40                  45

Pro Tyr Val Val Ala Leu Phe Ser Ala Met Leu Trp Leu Tyr Tyr Ala
    50                  55                  60

Thr Gln Lys Lys Asp Val Phe Leu Leu Val Thr Ile Asn Ser Phe Gly
65                  70                  75                  80

Cys Phe Ile Glu Thr Ile Tyr Ile Ser Ile Phe Val Ala Phe Ala Ser
                85                  90                  95

Lys Lys Ala Arg Met Leu Thr Val Lys Leu Leu Leu Met Asn Phe
                100                 105                 110

Gly Gly Phe Cys Leu Ile Leu Leu Leu Cys Gln Phe Leu Ala Lys Gly
                115                 120                 125

Thr Thr Arg Ala Lys Ile Ile Gly Gly Ile Cys Val Gly Phe Ser Val
    130                 135                 140

Cys Val Phe Ala Ala Pro Leu Ser Ile Ile Arg Thr Val Ile Lys Thr
145                 150                 155                 160

Lys Ser Val Glu Tyr Met Pro Phe Ser Leu Ser Leu Thr Leu Thr Ile
                165                 170                 175

Ser Ala Val Ile Trp Leu Leu Tyr Gly Leu Ala Leu Lys Asp Ile Tyr
                180                 185                 190

Val Ala Phe Pro Asn Val Ile Gly Phe Val Leu Gly Ala Leu Gln Met
                195                 200                 205
```

Ile Leu Tyr Val Val Tyr Lys Tyr Cys Lys Thr Pro Ser Asp Leu Val
210                 215                 220

Glu Lys Glu Leu Glu Ala Ala Lys Leu Pro Glu Val Ser Ile Asp Met
225                 230                 235                 240

Val Lys Leu Gly Thr Leu Thr Ser Pro Glu Pro Val Ala Ile Thr Val
            245                 250                 255

Val Arg Ser Val Asn Thr Cys Asn Cys Asn Asp Arg Asn Ala Glu Ile
            260                 265                 270

Glu Asn Gly Gln Gly Val Arg Asn Ser Ala Ala Thr Thr
            275                 280                 285

<210> SEQ ID NO 19
<211> LENGTH: 294
<212> TYPE: PRT
<213> ORGANISM: Arabidopsis thaliana

<400> SEQUENCE: 19

Met Ala Leu Thr Asn Asn Leu Trp Ala Phe Val Phe Gly Ile Leu Gly
1               5                   10                  15

Asn Ile Ile Ser Phe Val Val Phe Leu Ala Pro Val Pro Thr Phe Val
            20                  25                  30

Arg Ile Cys Lys Lys Lys Ser Thr Glu Gly Phe Gln Ser Leu Pro Tyr
            35                  40                  45

Val Ser Ala Leu Phe Ser Ala Met Leu Trp Ile Tyr Tyr Ala Met Gln
50                  55                  60

Lys Asp Gly Thr Ala Phe Leu Leu Ile Thr Ile Asn Ala Phe Gly Cys
65                  70                  75                  80

Val Ile Glu Thr Ile Tyr Ile Val Leu Phe Val Ser Tyr Ala Asn Lys
                85                  90                  95

Lys Thr Arg Ile Ser Thr Leu Lys Val Leu Gly Leu Leu Asn Phe Leu
            100                 105                 110

Gly Phe Ala Ala Ile Val Leu Val Cys Glu Leu Leu Thr Lys Gly Ser
            115                 120                 125

Thr Arg Glu Lys Val Leu Gly Gly Ile Cys Val Gly Phe Ser Val Ser
130                 135                 140

Val Phe Ala Ala Pro Leu Ser Ile Met Arg Val Val Arg Thr Arg
145                 150                 155                 160

Ser Val Glu Phe Met Pro Phe Ser Leu Ser Leu Phe Leu Thr Ile Ser
                165                 170                 175

Ala Val Thr Trp Leu Phe Tyr Gly Leu Ala Ile Lys Asp Phe Tyr Val
            180                 185                 190

Ala Leu Pro Asn Val Leu Gly Ala Phe Leu Gly Ala Val Gln Met Ile
            195                 200                 205

Leu Tyr Ile Ile Phe Lys Tyr Tyr Lys Thr Pro Val Ala Gln Lys Thr
210                 215                 220

Asp Lys Ser Lys Asp Val Ser Asp His Ser Ile Asp Ile Ala Lys Leu
225                 230                 235                 240

Thr Thr Val Ile Pro Gly Ala Val Leu Asp Ser Ala Val His Gln Pro
                245                 250                 255

Pro Ala Leu His Asn Val Pro Glu Thr Lys Ile Gln Leu Thr Glu Val
            260                 265                 270

Lys Ser Gln Asn Met Thr Asp Pro Lys Asp Gln Ile Asn Lys Asp Val
            275                 280                 285

Gln Lys Gln Ser Gln Val
            290

<210> SEQ ID NO 20
<211> LENGTH: 281
<212> TYPE: PRT
<213> ORGANISM: Arabidopsis thaliana

<400> SEQUENCE: 20

```
Met Val Leu Thr His Asn Val Leu Ala Val Thr Phe Gly Val Leu Gly
1               5                   10                  15

Asn Ile Ile Ser Phe Ile Val Phe Leu Ala Pro Val Pro Thr Phe Val
            20                  25                  30

Arg Ile Cys Lys Lys Lys Ser Ile Glu Gly Phe Glu Ser Leu Pro Tyr
        35                  40                  45

Val Ser Ala Leu Phe Ser Ala Met Leu Trp Ile Tyr Tyr Ala Leu Gln
    50                  55                  60

Lys Asp Gly Ala Gly Phe Leu Leu Ile Thr Ile Asn Ala Val Gly Cys
65                  70                  75                  80

Phe Ile Glu Thr Ile Tyr Ile Ile Leu Phe Ile Thr Tyr Ala Asn Lys
                85                  90                  95

Lys Ala Arg Ile Ser Thr Leu Lys Val Leu Gly Leu Leu Asn Phe Leu
            100                 105                 110

Gly Phe Ala Ala Ile Ile Leu Val Cys Glu Leu Leu Thr Lys Gly Ser
        115                 120                 125

Asn Arg Glu Lys Val Leu Gly Gly Ile Cys Val Gly Phe Ser Val Cys
    130                 135                 140

Val Phe Ala Ala Pro Leu Ser Ile Met Arg Val Val Ile Arg Thr Lys
145                 150                 155                 160

Ser Val Glu Phe Met Pro Phe Ser Leu Ser Leu Phe Leu Thr Ile Ser
                165                 170                 175

Ala Ile Thr Trp Leu Phe Tyr Gly Leu Ala Ile Lys Asp Phe Tyr Val
            180                 185                 190

Ala Leu Pro Asn Ile Leu Gly Ala Phe Leu Gly Ala Val Gln Met Ile
        195                 200                 205

Leu Tyr Val Ile Phe Lys Tyr Tyr Lys Thr Pro Leu Val Val Asp Glu
    210                 215                 220

Thr Glu Lys Pro Lys Thr Val Ser Asp His Ser Ile Asn Met Val Lys
225                 230                 235                 240

Leu Ser Ser Thr Pro Ala Ser Gly Asp Leu Thr Val Gln Pro Gln Thr
                245                 250                 255

Asn Pro Asp Val Ser His Pro Ile Lys Thr His Gly Asp Leu Glu
            260                 265                 270

Asp Gln Met Asp Lys Lys Met Pro Asn
        275                 280
```

<210> SEQ ID NO 21
<211> LENGTH: 292
<212> TYPE: PRT
<213> ORGANISM: Arabidopsis thaliana

<400> SEQUENCE: 21

```
Met Gly Val Met Ile Asn His Phe Leu Ala Phe Ile Phe Gly Ile
1               5                   10                  15

Leu Gly Asn Val Ile Ser Phe Leu Val Phe Leu Ala Pro Val Pro Thr
            20                  25                  30

Phe Tyr Arg Ile Tyr Lys Arg Lys Ser Thr Glu Ser Phe Gln Ser Leu
        35                  40                  45
```

Pro Tyr Gln Val Ser Leu Phe Ser Cys Met Leu Trp Leu Tyr Tyr Ala
    50                  55                  60

Leu Ile Lys Lys Asp Ala Phe Leu Leu Ile Thr Ile Asn Ser Phe Gly
65                  70                  75                  80

Cys Val Val Glu Thr Leu Tyr Ile Ala Met Phe Phe Ala Tyr Ala Thr
                    85                  90                  95

Arg Glu Lys Arg Ile Ser Ala Met Lys Leu Phe Ile Ala Met Asn Val
                100                 105                 110

Ala Phe Phe Ser Leu Ile Leu Met Val Thr His Phe Val Lys Thr
            115                 120                 125

Pro Pro Leu Gln Val Ser Val Leu Gly Trp Ile Cys Val Ala Ile Ser
    130                 135                 140

Val Ser Val Phe Ala Ala Pro Leu Met Ile Val Ala Arg Val Ile Lys
145                 150                 155                 160

Thr Lys Ser Val Glu Tyr Met Pro Phe Thr Leu Ser Phe Phe Leu Thr
                165                 170                 175

Ile Ser Ala Val Met Trp Phe Ala Tyr Gly Leu Phe Leu Asn Asp Ile
                180                 185                 190

Cys Ile Ala Ile Pro Asn Val Val Gly Phe Val Leu Gly Leu Leu Gln
            195                 200                 205

Met Val Leu Tyr Leu Val Tyr Arg Asn Ser Asn Glu Lys Pro Glu Lys
    210                 215                 220

Ile Asn Ser Ser Glu Gln Gln Leu Lys Ser Ile Val Val Met Ser Pro
225                 230                 235                 240

Leu Gly Val Ser Glu Val His Pro Val Val Thr Glu Ser Val Asp Pro
                245                 250                 255

Leu Ser Glu Ala Val His His Glu Asp Leu Ser Lys Val Thr Lys Val
            260                 265                 270

Glu Glu Pro Ser Ile Glu Asn Gly Lys Cys Tyr Val Glu Ala Thr Arg
    275                 280                 285

Pro Glu Thr Val
    290

<210> SEQ ID NO 22
<211> LENGTH: 307
<212> TYPE: PRT
<213> ORGANISM: Oryza sativa

<400> SEQUENCE: 22

Met Ala Gly Gly Phe Leu Ser Met Ala Asn Pro Ala Val Thr Leu Ser
1               5                   10                  15

Gly Val Ala Gly Asn Ile Ile Ser Phe Leu Val Phe Leu Ala Pro Val
                20                  25                  30

Ala Thr Phe Leu Gln Val Tyr Lys Lys Lys Ser Thr Gly Gly Tyr Ser
            35                  40                  45

Ser Val Pro Tyr Val Val Ala Leu Phe Ser Ser Val Leu Trp Ile Phe
    50                  55                  60

Tyr Ala Leu Val Lys Thr Asn Ser Arg Pro Leu Leu Thr Ile Asn Ala
65                  70                  75                  80

Phe Gly Cys Gly Val Glu Ala Ala Tyr Ile Val Leu Tyr Leu Val Tyr
                85                  90                  95

Ala Pro Arg Arg Ala Arg Leu Arg Thr Leu Ala Phe Phe Leu Leu Leu
                100                 105                 110

Asp Val Ala Ala Phe Ala Leu Ile Val Val Thr Thr Leu Tyr Leu Val

```
            115                 120                 125
Pro Lys Pro His Gln Val Lys Phe Leu Gly Ser Val Cys Leu Ala Phe
    130                 135                 140

Ser Met Ala Val Phe Val Ala Pro Leu Ser Ile Ile Phe Lys Val Ile
145                 150                 155                 160

Lys Thr Lys Ser Val Glu Phe Met Pro Ile Gly Leu Ser Val Cys Leu
                165                 170                 175

Thr Leu Ser Ala Val Ala Trp Phe Cys Tyr Gly Leu Phe Thr Lys Asp
            180                 185                 190

Pro Tyr Val Met Tyr Pro Asn Val Gly Gly Phe Phe Ser Cys Val
        195                 200                 205

Gln Met Gly Leu Tyr Phe Trp Tyr Arg Lys Pro Arg Asn Thr Ala Val
    210                 215                 220

Leu Pro Thr Thr Ser Asp Ser Met Ser Pro Ile Ser Ala Ala Ala Ala
225                 230                 235                 240

Ala Thr Gln Arg Val Ile Glu Leu Pro Ala Gly Thr His Ala Phe Thr
                245                 250                 255

Ile Leu Ser Val Ser Pro Ile Pro Ile Leu Gly Val His Lys Val Glu
            260                 265                 270

Val Val Ala Ala Glu Gln Ala Ala Asp Gly Val Ala Ala Ala Ala Ala
        275                 280                 285

Ala Asp Lys Glu Leu Leu Gln Asn Lys Pro Glu Val Ile Glu Ile Thr
290                 295                 300

Ala Ala Val
305

<210> SEQ ID NO 23
<211> LENGTH: 300
<212> TYPE: PRT
<213> ORGANISM: Oryza sativa

<400> SEQUENCE: 23

Met Val Gln Ala Leu Val Phe Ala Val Gly Ile Val Gly Asn Ile Leu
1               5                   10                  15

Ser Phe Leu Val Ile Leu Ala Pro Val Pro Thr Phe Tyr Arg Val Tyr
                20                  25                  30

Lys Lys Lys Ser Thr Glu Ser Phe Gln Ser Val Pro Tyr Ala Val Ala
            35                  40                  45

Leu Leu Ser Ala Met Leu Trp Leu Tyr Tyr Ala Leu Leu Thr Ser Asp
        50                  55                  60

Leu Leu Leu Leu Ser Ile Asn Ser Ile Gly Cys Leu Val Glu Ser Leu
65                  70                  75                  80

Tyr Leu Thr Val Tyr Leu Leu Tyr Ala Pro Arg Gln Ala Met Ala Phe
                85                  90                  95

Thr Leu Lys Leu Val Cys Ala Met Asn Leu Ala Leu Phe Ala Ala Val
            100                 105                 110

Val Ala Ala Leu Gln Leu Leu Val Lys Ala Thr Asp Arg Arg Val Thr
        115                 120                 125

Leu Ala Gly Gly Ile Gly Ala Ser Phe Ala Leu Ala Val Phe Val Ala
130                 135                 140

Pro Leu Thr Ile Ile Arg Gln Val Ile Arg Thr Lys Ser Val Glu Phe
145                 150                 155                 160

Met Pro Phe Trp Leu Ser Phe Phe Leu Thr Leu Ser Ala Val Val Trp
                165                 170                 175
```

```
Phe Phe Tyr Gly Leu Leu Met Lys Asp Phe Val Ala Thr Pro Asn
            180                 185                 190

Val Leu Gly Leu Leu Phe Gly Leu Ala Gln Met Val Leu Tyr Val Val
    195                 200                 205

Tyr Lys Asn Pro Lys Lys Asn Ser Ala Val Ser Glu Ala Ala Ala Ala
        210                 215                 220

Gln Gln Val Glu Val Lys Asp Gln Gln Gln Leu Gln Met Gln Leu Gln
225                 230                 235                 240

Ala Ser Pro Ala Val Ala Pro Leu Asp Val Asp Ala Asp Ala Asp Ala
                245                 250                 255

Asp Leu Glu Ala Ala Pro Ala Thr Pro Gln Arg Pro Ala Asp Asp
        260                 265                 270

Asp Ala Ile Asp His Arg Ser Val Val Asp Ile Pro Pro Pro
        275                 280                 285

Gln Pro Pro Ala Leu Pro Ala Val Glu Val Ala
        290                 295                 300
```

<210> SEQ ID NO 24
<211> LENGTH: 296
<212> TYPE: PRT
<213> ORGANISM: Oryza sativa

<400> SEQUENCE: 24

```
Met Ala Gly Leu Ser Leu Gln His Pro Trp Ala Phe Ala Phe Gly Leu
1               5                   10                  15

Leu Gly Asn Leu Ile Ser Phe Thr Thr Tyr Leu Ala Pro Ile Pro Thr
            20                  25                  30

Phe Tyr Arg Ile Tyr Lys Ser Lys Ser Thr Glu Gly Phe Gln Ser Val
        35                  40                  45

Pro Tyr Val Val Ala Leu Phe Ser Ala Met Leu Trp Ile Phe Tyr Ala
    50                  55                  60

Leu Ile Lys Ser Asn Glu Ala Leu Leu Ile Thr Ile Asn Ala Ala Gly
65                  70                  75                  80

Cys Val Ile Glu Thr Ile Tyr Ile Val Met Tyr Leu Ala Tyr Ala Pro
                85                  90                  95

Lys Lys Ala Lys Val Phe Thr Thr Lys Ile Leu Leu Leu Asn Val
        100                 105                 110

Gly Val Phe Gly Val Ile Leu Leu Thr Leu Leu Leu Ser His Gly
    115                 120                 125

Glu Gln Arg Val Val Ser Leu Gly Trp Val Cys Val Ala Phe Ser Val
130                 135                 140

Ser Val Phe Val Ala Pro Leu Ser Ile Ile Lys Arg Val Ile Gln Ser
145                 150                 155                 160

Arg Ser Val Glu Tyr Met Pro Phe Ser Leu Ser Leu Thr Leu Thr Leu
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Thr Phe Gly Val Val Gln Met
        195                 200                 205

Gly Leu Tyr Val Phe Tyr Met Asn Ala Thr Pro Val Ala Gly Glu Gly
    210                 215                 220

Lys Glu Gly Lys Gly Lys Leu Ala Ala Ala Glu Glu Leu Pro Val Val
225                 230                 235                 240

Val Asn Val Gly Lys Leu Ala Ala Ala Thr Pro Asp Arg Ser Thr Gly
                245                 250                 255
```

```
Ala Val His Val His Pro Val Pro Arg Ser Cys Ala Ala Glu Ala Ala
            260                 265                 270

Ala Ala Glu Pro Glu Val Leu Val Asp Ile Pro Pro Pro Pro Pro Pro
        275                 280                 285

Arg Ala Val Glu Val Ala Ala Val
    290                 295

<210> SEQ ID NO 25
<211> LENGTH: 303
<212> TYPE: PRT
<213> ORGANISM: Oryza sativa

<400> SEQUENCE: 25

Met Ala Gly Met Ser Leu Gln His Pro Trp Ala Phe Ala Phe Gly Leu
1               5                   10                  15

Leu Gly Asn Ile Ile Ser Phe Met Thr Tyr Leu Ala Pro Leu Pro Thr
            20                  25                  30

Phe Tyr Arg Ile Tyr Lys Ser Lys Ser Thr Gln Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asp Glu Cys Leu Leu Ile Thr Ile Asn Ser Ala Gly
65                  70                  75                  80

Cys Val Ile Glu Thr Ile Tyr Ile Ala Val Tyr Leu Val Tyr Ala Pro
                85                  90                  95

Lys Lys Ala Lys Met Phe Thr Ala Lys Leu Leu Leu Leu Val Asn Val
            100                 105                 110

Gly Val Phe Gly Leu Ile Leu Leu Thr Leu Leu Leu Ser Ala Gly
        115                 120                 125

Asp Arg Arg Ile Val Val Leu Gly Trp Val Cys Val Gly Phe Ser Val
    130                 135                 140

Ser Val Phe Val Ala Pro Leu Ser Ile Ile Arg Leu Val Val Arg Thr
145                 150                 155                 160

Lys Ser Val Glu Phe Met Pro Phe Ser Leu Ser Phe Ser Leu Thr Ile
                165                 170                 175

Ser Ala Val Val Trp Phe Leu Tyr Gly Leu Leu Ile Lys Asp Lys Tyr
            180                 185                 190

Val Ala Leu Pro Asn Val Leu Gly Phe Ser Phe Gly Val Ile Gln Met
        195                 200                 205

Gly Leu Tyr Ala Met Tyr Arg Asn Ser Thr Pro Lys Ala Val Leu Thr
    210                 215                 220

Lys Glu Val Glu Ala Ala Thr Ala Thr Gly Asp Asp His Ser Ala
225                 230                 235                 240

Ala Gly Val Lys Glu His Val Asn Ile Ala Lys Leu Ser Ala Ala
                245                 250                 255

Val Asp Val Val Lys Thr Arg Glu Val His Pro Val Ala Val Glu Ser
            260                 265                 270

Pro Pro Ala Glu Ala Pro Pro Glu Glu Asp Asp Lys Ala Ala Ala
        275                 280                 285

Thr Ala Ala Ala Val Ala Gly Ala Gly Glu Lys Lys Val Ala Ala
    290                 295                 300

<210> SEQ ID NO 26
<211> LENGTH: 319
<212> TYPE: PRT
```

<213> ORGANISM: Oryza sativa

<400> SEQUENCE: 26

```
Met Ala Phe Met Ser Met Glu Arg Ser Thr Trp Ala Phe Thr Phe Gly
1               5                   10                  15

Ile Leu Gly Asn Leu Ile Ser Leu Met Val Phe Leu Ser Pro Leu Pro
            20                  25                  30

Thr Phe Tyr Arg Val Tyr Arg Lys Lys Ser Thr Glu Gly Phe Gln Ser
        35                  40                  45

Thr Pro Tyr Val Val Thr Leu Phe Ser Cys Met Leu Trp Met Tyr Tyr
    50                  55                  60

Ala Phe Val Lys Ser Gly Ala Glu Leu Leu Val Thr Ile Asn Gly Val
65                  70                  75                  80

Gly Cys Val Ile Glu Thr Val Tyr Leu Ala Met Tyr Leu Ala Tyr Ala
                85                  90                  95

Pro Lys Ser Ala Arg Met Leu Thr Ala Lys Met Leu Leu Gly Leu Asn
            100                 105                 110

Ile Gly Leu Phe Gly Val Ile Ala Leu Val Thr Leu Leu Leu Ser Arg
        115                 120                 125

Gly Glu Leu Arg Val His Val Leu Gly Trp Ile Cys Val Ala Val Ser
    130                 135                 140

Leu Ser Val Phe Ala Ala Pro Leu Ser Ile Ile Arg Leu Val Ile Arg
145                 150                 155                 160

Thr Lys Ser Val Glu Phe Met Pro Phe Ser Leu Ser Phe Phe Leu Val
                165                 170                 175

Leu Ser Ala Val Ile Trp Phe Leu Tyr Gly Leu Leu Lys Lys Asp Val
            180                 185                 190

Phe Val Ala Leu Pro Asn Val Leu Gly Phe Val Phe Gly Val Ala Gln
        195                 200                 205

Met Ala Leu Tyr Met Ala Tyr Arg Ser Lys Lys Pro Leu Val Ala Ser
    210                 215                 220

Ser Ser Ser Ala Val Val Ala Ala Gly Leu Glu Ile Lys Leu Pro Glu
225                 230                 235                 240

His Val Lys Glu Val Gln Ala Val Ala Lys Gly Ala Val Ala Ala Ala
                245                 250                 255

Pro Glu Gly Arg Ile Ser Cys Gly Ala Glu Val His Pro Ile Asp Asp
            260                 265                 270

Val Met Pro Ser Glu Val Val Glu Val Lys Val Asp Asp Glu Glu Thr
        275                 280                 285

Asn Arg Thr Asp Glu Met Ala Gly Asp Gly Asp His Ala Met Val Arg
    290                 295                 300

Thr Glu Gln Ile Ile Lys Pro Asp Met Ala Ile Val Val Glu Val
305                 310                 315
```

<210> SEQ ID NO 27
<211> LENGTH: 252
<212> TYPE: PRT
<213> ORGANISM: Medicago truncatula

<400> SEQUENCE: 27

```
Met Phe Pro Phe Ser Asn Leu Lys Met Val Leu Leu Phe Gly Phe Leu
1               5                   10                  15

Gly Ile Val Thr Phe Met Ser Phe Leu Ala Pro Leu Pro Thr Phe Tyr
            20                  25                  30

Ser Ile Tyr Lys Lys Lys Ser Ser Glu Gly Phe His Ser Ile Pro Tyr
```

```
                35                  40                  45
Val Val Thr Leu Leu Ser Thr Leu Leu Phe Val Tyr Tyr Gly Phe Leu
 50                  55                  60

Lys Thr Asn Ala Ile Phe Leu Ile Thr Ile Asn Ser Ile Gly Cys Val
 65                  70                  75                  80

Met Glu Val Ala Tyr Leu Ile Met Tyr Ile Thr Tyr Ala Pro Lys Lys
                     85                  90                  95

Leu Lys Ile Ser Thr Leu Val Leu Ile Leu Ile Val Asp Met Gly Gly
                100                 105                 110

Phe Gly Leu Thr Met Ile Ile Thr Thr Phe Ile Val Lys Gly Ser Phe
                115                 120                 125

His Val Gln Val Val Gly Met Ile Cys Thr Ile Phe Asn Ile Gly Met
                130                 135                 140

Phe Ala Ala Pro Leu Ser Ile Met Lys Lys Val Ile Lys Thr Arg Ser
145                 150                 155                 160

Val Glu Tyr Met Pro Phe Pro Leu Ser Leu Phe Leu Thr Ile Cys Ala
                165                 170                 175

Thr Met Trp Phe Phe Tyr Gly Phe Phe Asp Lys Asp Lys Tyr Ile Met
                180                 185                 190

Leu Pro Asn Gly Leu Gly Phe Leu Gly Val Ser Gln Met Ile Leu
                195                 200                 205

Tyr Leu Ile Tyr Lys Asn Ala Lys Asn Val Glu Ala Ser Ser Thr
210                 215                 220

Asn Gln Leu Gln Glu His Gly Cys Asp Gly Gly Asn Asn Gln Ile Phe
225                 230                 235                 240

Pro Thr Val Val Glu Met Lys Glu Ile Asn Ile Val
                245                 250

<210> SEQ ID NO 28
<211> LENGTH: 270
<212> TYPE: PRT
<213> ORGANISM: Medicago truncatula

<400> SEQUENCE: 28

Met Ala Leu Phe Tyr Ser Glu Tyr Trp Ala Phe Val Phe Gly Val Ile
 1               5                  10                  15

Gly Asn Val Ile Ser Cys Met Thr Phe Leu Ala Pro Leu Pro Thr Phe
                20                  25                  30

Tyr Arg Ile Tyr Lys Lys Lys Ser Thr Glu Gly Phe Gln Ser Val Pro
                35                  40                  45

Tyr Val Thr Ala Leu Leu Ser Ala Met Leu Trp Ile Tyr Tyr Ala His
 50                  55                  60

Val Lys Asn Lys Ala Thr Leu Leu Leu Thr Ile Asn Ile Tyr Gly
 65                  70                  75                  80

Phe Gly Ile Glu Ala Ile Tyr Ile Ile Phe Leu Leu Tyr Ala Ser
                 85                  90                  95

Asn Lys Ala Arg Leu Ser Thr Ile Lys Leu Leu Phe Leu Thr Val Cys
                100                 105                 110

Gly Tyr Gly Thr Met Val Ile Leu Thr Thr Tyr Leu Thr Lys Gly Ser
                115                 120                 125

Lys Arg Leu Ser Ile Ile Gly Trp Ile Cys Met Val Phe Asn Ile Cys
                130                 135                 140

Val Phe Ala Ser Pro Leu Phe Ile Leu Lys Gln Val Ile Lys Thr Lys
145                 150                 155                 160
```

```
Ser Val Ala Phe Met Pro Leu Asn Leu Ser Phe Phe Leu Thr Leu Asn
                165                 170                 175
Ala Ile Val Trp Phe Phe Tyr Gly Leu Leu Ile Asp Asp Phe Tyr Ile
            180                 185                 190
Ala Ile Pro Asn Thr Leu Gly Phe Val Phe Gly Ile Val Gln Met Val
        195                 200                 205
Ile Tyr Leu Ile Tyr Lys Asp Ala Ile Pro Leu Glu Ser Thr Lys Leu
    210                 215                 220
Gln Lys Pro Asn Asp His Val Leu Asn Ile Cys Glu Asp Val Pro Asn
225                 230                 235                 240
Gly Ala Leu Gln Pro Asp Pro Asn Gln Val Val Lys Ser Gly Ala Pro
                245                 250                 255
Ala Val Ala Val Ile Gly Asp Glu Asp Pro Asn Asn Gly Lys
            260                 265                 270

<210> SEQ ID NO 29
<211> LENGTH: 255
<212> TYPE: PRT
<213> ORGANISM: Medicago truncatula

<400> SEQUENCE: 29

Met Ala Met Thr Arg Glu Ser Trp Ala Phe Val Phe Gly Ile Ile Gly
1               5                   10                  15
Asn Ile Ile Ser Phe Ala Val Phe Leu Ser Pro Leu Pro Thr Phe Tyr
                20                  25                  30
Val Ile Phe Lys Lys Lys Ser Ala Glu Gly Phe Gln Ala Leu Pro Tyr
            35                  40                  45
Val Val Ala Leu Phe Ser Ala Met Leu Trp Ile Tyr Tyr Ala Phe Val
        50                  55                  60
Lys Arg Glu Ser Ala Leu Leu Leu Ile Thr Ile Asn Thr Phe Gly Ile
65                  70                  75                  80
Val Val Glu Ser Ala Tyr Ile Ile Met Phe Leu Ile Tyr Ala Pro Lys
                85                  90                  95
Lys Gln Arg Leu Ser Thr Ile Lys Leu Leu Leu Leu Leu Asn Val Phe
                100                 105                 110
Gly Phe Gly Ala Met Leu Leu Ser Thr Leu Tyr Leu Ser Lys Gly Ala
            115                 120                 125
Lys Arg Leu Ala Ile Ile Gly Trp Ile Cys Leu Val Phe Asn Ile Ser
        130                 135                 140
Val Phe Ala Thr Pro Leu Phe Val Ile Ser Lys Val Ile Arg Ser Arg
145                 150                 155                 160
Ser Val Glu Tyr Met Pro Phe Phe Leu Ser Phe Phe Leu Thr Ile Asn
                165                 170                 175
Ala Val Met Trp Phe Phe Tyr Gly Leu Leu Leu Arg Asp Tyr Tyr Val
            180                 185                 190
Ala Leu Pro Asn Thr Leu Gly Phe Val Phe Gly Ile Ile Gln Met Val
        195                 200                 205
Val Tyr Leu Ile Tyr Arg Asn Ala Thr Pro Val Val Glu Ala Pro Met
    210                 215                 220
Lys Gly Gln Glu Leu Ser Gly Gly His Ile Ile Asp Val Val Lys Ile
225                 230                 235                 240
Gly Thr Asp Pro Asn Arg Ala Gly Gly Gly Ala Gly Ser Lys Val
                245                 250                 255

<210> SEQ ID NO 30
```

```
<211> LENGTH: 255
<212> TYPE: PRT
<213> ORGANISM: Medicago truncatula

<400> SEQUENCE: 30

Met Ala Met Thr Arg Glu Ser Trp Ala Phe Val Phe Gly Ile Ile Gly
1               5                   10                  15

Asn Ile Ile Ser Phe Ala Val Phe Leu Ser Pro Leu Pro Thr Phe Tyr
            20                  25                  30

Val Ile Phe Lys Lys Ser Ala Glu Gly Phe Gln Ala Leu Pro Tyr
        35                  40                  45

Val Val Ala Leu Phe Ser Ala Met Leu Trp Ile Tyr Tyr Ala Phe Val
50                  55                  60

Lys Arg Glu Ser Ala Leu Leu Leu Ile Thr Ile Asn Thr Phe Gly Ile
65                  70                  75                  80

Val Val Glu Ser Ala Tyr Ile Ile Met Phe Leu Ile Tyr Ala Pro Lys
                85                  90                  95

Lys Gln Arg Leu Ser Thr Ile Lys Leu Leu Leu Leu Asn Val Phe
            100                 105                 110

Gly Phe Gly Ala Met Leu Leu Ser Thr Leu Tyr Leu Ser Lys Gly Ala
        115                 120                 125

Lys Arg Leu Ala Ile Ile Gly Trp Ile Cys Leu Val Phe Asn Ile Ser
130                 135                 140

Val Phe Ala Ala Pro Leu Phe Val Ile Ser Lys Val Ile Arg Ser Arg
145                 150                 155                 160

Ser Val Glu Tyr Met Pro Phe Phe Leu Ser Phe Phe Leu Thr Ile Asn
                165                 170                 175

Ala Val Met Trp Phe Phe Tyr Gly Leu Leu Leu Arg Asp Tyr Tyr Val
            180                 185                 190

Ala Leu Pro Asn Thr Leu Gly Phe Val Phe Gly Ile Ile Gln Met Val
        195                 200                 205

Val Tyr Leu Ile Tyr Arg Asn Ala Thr Pro Val Val Glu Ala Pro Met
210                 215                 220

Lys Gly Gln Glu Leu Ser Gly Gly His Ile Ile Asp Val Val Lys Ile
225                 230                 235                 240

Gly Thr Asp Ser Asn Arg Ala Gly Gly Gly Ala Gly Ser Lys Val
                245                 250                 255

<210> SEQ ID NO 31
<211> LENGTH: 268
<212> TYPE: PRT
<213> ORGANISM: Medicago truncatula
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid

<400> SEQUENCE: 31

Met Ala Ile Ser His Asn Thr Leu Ala Phe Thr Phe Gly Met Leu Gly
1               5                   10                  15

Asn Val Ile Ser Phe Leu Val Phe Leu Ala Pro Ile Ser Thr Phe Tyr
            20                  25                  30

Arg Ile Tyr Lys Lys Ser Thr Glu Gly Phe Gln Ser Leu Pro Tyr
        35                  40                  45
```

```
Leu Val Ala Leu Phe Ser Ser Met Leu Trp Leu Tyr Tyr Ala Leu Leu
 50                  55                  60

Lys Lys Asp Ala Phe Leu Leu Ile Thr Ile Asn Ser Phe Gly Cys Val
 65                  70                  75                  80

Val Glu Thr Ile Tyr Ile Ile Leu Tyr Ile Ile Tyr Ala Pro Arg Asp
                 85                  90                  95

Ala Arg Asn Leu Thr Phe Lys Leu Leu Ser Ala Met Asn Val Gly Ser
            100                 105                 110

Phe Ala Leu Ile Leu Ile Val Thr Asn Tyr Ala Val His Gly Pro Leu
            115                 120                 125

Arg Val Gln Val Leu Gly Trp Val Cys Val Ser Leu Ser Val Ser Val
130                 135                 140

Phe Ala Ala Pro Leu Ser Ile Val Ala Gln Val Val Arg Thr Lys Ser
145                 150                 155                 160

Val Glu Phe Met Pro Phe Asn Leu Ser Phe Thr Leu Thr Leu Ser Ala
                165                 170                 175

Thr Met Trp Phe Gly Tyr Gly Phe Phe Leu Lys Asp Ile Cys Ile Xaa
            180                 185                 190

Leu Pro Asn Val Leu Gly Xaa Val Leu Gly Leu Leu Gln Met Leu Leu
            195                 200                 205

Tyr Ala Ile Tyr Arg Asn Gly Gly Glu Lys Ala Met Lys Lys Glu Lys
            210                 215                 220

Lys Ala Pro Ile Glu Pro Lys Ser Ile Val Ile Glu Thr Gln Leu
225                 230                 235                 240

Glu Lys Ile Glu Gln Glu Lys Asn Lys Asp Asp Asn Glu Glu
            245                 250                 255

Lys Asp Lys Ser Glu Glu Pro Ile Gly Cys Gly Val
            260                 265

<210> SEQ ID NO 32
<211> LENGTH: 268
<212> TYPE: PRT
<213> ORGANISM: Medicago truncatula

<400> SEQUENCE: 32

Met Ala Ile Ser His Asn Thr Leu Ala Phe Ala Phe Gly Met Leu Gly
 1               5                  10                  15

Asn Val Ile Ser Phe Met Val Phe Leu Ala Pro Met Thr Thr Phe Tyr
                 20                  25                  30

Arg Ile Tyr Lys Lys Lys Ser Thr Glu Gly Phe Gln Ser Leu Pro Tyr
             35                  40                  45

Leu Val Ala Leu Phe Ser Ser Met Leu Trp Leu Tyr Tyr Ala Phe Leu
 50                  55                  60

Lys Lys Asp Glu Phe Leu Leu Ile Thr Ile Asn Ser Phe Gly Cys Val
 65                  70                  75                  80

Val Glu Leu Ile Tyr Ile Ile Leu Tyr Ile Ile Tyr Ala Thr Lys Asp
                 85                  90                  95

Ala Arg Lys Leu Thr Ile Lys Leu Leu Leu Ala Met Asn Ile Gly Ser
            100                 105                 110

Phe Gly Leu Ile Leu Leu Val Thr Lys Tyr Ala Val His Gly Pro Ile
            115                 120                 125

Arg Val Gln Val Leu Gly Trp Ile Cys Val Ser Ile Ser Val Ser Val
130                 135                 140

Phe Ala Ala Pro Leu Thr Ile Val Ala Gln Val Val Arg Thr Lys Ser
145                 150                 155                 160
```

```
Val Glu Phe Met Pro Phe Asn Leu Ser Phe Thr Leu Thr Leu Ser Ala
            165                 170                 175

Ile Met Trp Phe Gly Tyr Gly Leu Phe Leu Lys Asp Ile Cys Ile Ala
        180                 185                 190

Leu Pro Asn Val Leu Gly Phe Ala Leu Gly Leu Val Gln Met Ile Leu
            195                 200                 205

Tyr Cys Ile Tyr Arg Asn Gly Asp Lys Lys Ala Asn Ser Lys Ala
        210                 215                 220

Ala Leu Lys Ser Val Val Ile Glu Ser Ser Leu Gly Gly Thr Gly Glu
225                 230                 235                 240

Val Phe Gln Val Glu Lys Asn Asp Gly Glu Glu Glu Glu Lys Lys
                245                 250                 255

Lys Thr Ile Glu Glu Thr Glu Tyr Asp Ser Lys Val
            260                 265
```

<210> SEQ ID NO 33
<211> LENGTH: 269
<212> TYPE: PRT
<213> ORGANISM: Medicago truncatula

<400> SEQUENCE: 33

```
Met Asp Pro His Asp His Asp Arg Leu Ala Phe Ile Phe Gly Ile Leu
1               5                   10                  15

Gly Asn Ile Ile Ser Ser Met Val Tyr Leu Ala Pro Leu Pro Thr Phe
            20                  25                  30

Tyr Arg Ile Trp Lys Lys Lys Ser Thr Glu Gly Phe Gln Ser Leu Pro
        35                  40                  45

Tyr Leu Val Ala Leu Phe Ser Ser Met Leu Trp Leu Tyr Tyr Gly Phe
    50                  55                  60

Val Lys Lys His Ala Phe Leu Leu Ile Thr Ile Asn Ser Ala Gly Cys
65                  70                  75                  80

Val Ile Glu Thr Ile Tyr Ile Val Thr Tyr Leu Ile Tyr Ala Thr Lys
                85                  90                  95

Asp Ala Arg Ile Leu Thr Ile Lys Leu Phe Met Ala Met Asn Val Ala
            100                 105                 110

Cys Ser Val Leu Ile Val Leu Thr Thr Gln Leu Ala Met His Gly Lys
        115                 120                 125

Leu Arg Val His Val Leu Gly Trp Ile Cys Thr Ser Phe Ala Ile Cys
    130                 135                 140

Val Phe Ala Ala Pro Leu Thr Ile Met Ala Lys Val Ile Arg Thr Lys
145                 150                 155                 160

Ser Val Glu Phe Met Pro Ile Asn Leu Ser Phe Phe Leu Thr Leu Ser
                165                 170                 175

Ala Ile Val Trp Phe Phe Tyr Gly Leu Leu Leu His Asp Ile Cys Ile
            180                 185                 190

Ala Ile Pro Asn Val Leu Gly Phe Ile Leu Gly Leu Leu Gln Met Leu
        195                 200                 205

Leu Tyr Ala Ile Tyr Asn Lys Ser Val Lys Glu Glu Tyr Ala Leu Glu
    210                 215                 220

Pro Met Thr Asn Ile Val Ile Val Asn Pro Leu Gly Ile Pro Cys Glu
225                 230                 235                 240

Val Phe Ser Leu Pro Val Ile Asp Asn Val Asn Lys Ile Glu Lys Glu
                245                 250                 255

Gly Ala Glu Glu Met Glu Lys Ser Val Glu Asn Leu Thr
```

<210> SEQ ID NO 34
<211> LENGTH: 288
<212> TYPE: PRT
<213> ORGANISM: Medicago truncatula

<400> SEQUENCE: 34

Met Ala Met Ile Ser Met Asn His His Phe Leu Val Ile Ala Phe Gly
1               5                   10                  15

Leu Leu Gly Asn Ile Ile Ser Cys Met Val Tyr Leu Ala Pro Leu Pro
            20                  25                  30

Thr Phe Ile Gln Ile Tyr Lys Lys Lys Ser Thr Glu Cys Phe Gln Ser
        35                  40                  45

Leu Pro Tyr Leu Val Ala Leu Phe Ser Ser Met Leu Trp Leu Tyr Tyr
    50                  55                  60

Gly Ile Gln Thr Asn Ala Ile Phe Ile Val Ser Ile Asn Ala Phe Gly
65                  70                  75                  80

Cys Val Ile Glu Ile Ile Tyr Cys Ile Met Tyr Ile Ala Tyr Ala Thr
                85                  90                  95

Lys Asp Ala Arg Lys Leu Thr Ile Lys Leu Cys Ala Ala Leu Asn Val
            100                 105                 110

Val Ser Phe Val Leu Ile Phe Leu Ile Gln Phe Ser Ile Pro Glu
        115                 120                 125

Asn His Arg Val Gln Val Leu Gly Trp Ile Cys Thr Ser Ile Ser Ile
130                 135                 140

Ser Val Phe Ala Ala Pro Leu Ser Ile Val Val Arg Val Val Lys Thr
145                 150                 155                 160

Lys Ser Val Glu Phe Met Pro Phe Asn Leu Ser Leu Phe Leu Thr Leu
                165                 170                 175

Ser Ala Val Val Trp Phe Leu Tyr Gly Phe Val Lys Arg Asp Ile Cys
            180                 185                 190

Ile Tyr Leu Pro Asn Val Val Gly Phe Ile Leu Gly Ile Ile Gln Met
        195                 200                 205

Val Leu Tyr Gly Tyr Tyr Ser Lys Tyr Ser Val Glu Lys Glu Lys Glu
    210                 215                 220

Gln Ala Val Ile Asn Ile Val Val Asn Pro Leu Gly Ser Ser Glu
225                 230                 235                 240

Val Phe Pro Ile Pro Leu Asp Glu Asn Lys Glu Ser Ile Glu Asp Val
                245                 250                 255

Ile Asn Gln Gln Phe Gln Val Lys Lys Val Gly Glu Glu Asp Ala Lys
            260                 265                 270

Glu Lys His Asp Asn Asn Val Glu Ala Ile Glu Phe Gln Cys Val Val
        275                 280                 285

<210> SEQ ID NO 35
<211> LENGTH: 265
<212> TYPE: PRT
<213> ORGANISM: Petunia hybrida

<400> SEQUENCE: 35

Met Ala Gln Leu Arg Ala Asp Asp Leu Ser Phe Ile Phe Gly Leu Leu
1               5                   10                  15

Gly Asn Ile Val Ser Phe Met Val Phe Leu Ala Pro Val Pro Thr Phe
            20                  25                  30

Tyr Lys Ile Tyr Lys Arg Lys Ser Ser Glu Gly Tyr Gln Ala Ile Pro

```
            35                  40                  45
Tyr Met Val Ala Leu Phe Ser Ala Gly Leu Leu Tyr Ala Tyr
 50                  55                  60

Leu Arg Lys Asn Ala Tyr Leu Ile Val Ser Ile Asn Gly Phe Gly Cys
 65                  70                  75                  80

Ala Ile Glu Leu Thr Tyr Ile Ser Leu Phe Leu Phe Tyr Ala Pro Arg
                 85                  90                  95

Lys Ser Lys Ile Phe Thr Gly Trp Leu Met Leu Glu Leu Gly Ala
                100                 105                 110

Leu Gly Met Val Met Pro Ile Thr Tyr Leu Leu Ala Glu Gly Ser His
            115                 120                 125

Arg Val Met Ile Val Gly Trp Ile Cys Ala Ala Ile Asn Val Ala Val
130                 135                 140

Phe Ala Ala Pro Leu Ser Ile Met Arg Gln Val Ile Lys Thr Lys Ser
145                 150                 155                 160

Val Glu Phe Met Pro Phe Thr Leu Ser Leu Phe Leu Thr Leu Cys Ala
                165                 170                 175

Thr Met Trp Phe Phe Tyr Gly Phe Phe Lys Lys Asp Phe Tyr Ile Ala
            180                 185                 190

Phe Pro Asn Ile Leu Gly Phe Leu Gly Ile Val Gln Met Leu Leu
        195                 200                 205

Tyr Phe Val Tyr Lys Asp Ser Lys Arg Ile Asp Glu Lys Ser Asp
210                 215                 220

Pro Val Arg Glu Ala Thr Lys Ser Lys Glu Gly Val Glu Ile Ile
225                 230                 235                 240

Asn Ile Glu Asp Asp Asn Ser Asp Asn Ala Leu Gln Ser Met Glu Lys
                245                 250                 255

Asp Phe Ser Arg Leu Arg Thr Ser Lys
            260                 265

<210> SEQ ID NO 36
<211> LENGTH: 301
<212> TYPE: PRT
<213> ORGANISM: Capsicum annuum

<400> SEQUENCE: 36

Met Thr Gly Ile Ser Gly His Trp Ala Phe Ala Phe Gly Val Leu Gly
 1               5                  10                  15

Asn Ile Ile Ser Phe Ile Val Phe Leu Ser Pro Ile Pro Thr Phe Tyr
                20                  25                  30

Thr Ile Tyr Lys Lys Lys Thr Ala Glu Gly Tyr Gln Ser Ile Pro Tyr
            35                  40                  45

Val Ile Ala Leu Phe Ser Ser Met Leu Trp Ile Tyr Tyr Ala Phe Leu
 50                  55                  60

Lys Thr Asn Val Thr Leu Leu Ile Thr Ile Asn Ser Phe Gly Ile Phe
 65                  70                  75                  80

Ile Glu Thr Ile Tyr Val Gly Leu Tyr Leu Phe Tyr Ala Pro Lys Lys
                 85                  90                  95

Ala Arg Val His Thr Val Lys Met Leu Leu Leu Thr Val Val Gly Gly
                100                 105                 110

Phe Gly Ala Ile Val Leu Val Thr Gln Phe Leu Phe Lys Gly Val Val
            115                 120                 125

Arg Gly Gln Ile Val Gly Trp Ile Cys Leu Ile Phe Ala Leu Ser Val
130                 135                 140
```

```
Phe Val Ala Pro Leu Gly Ile Val Arg Gln Val Ile Lys Thr Lys Ser
145                 150                 155                 160

Val Glu Tyr Met Pro Leu Leu Leu Ser Val Phe Leu Thr Leu Ser Ala
                165                 170                 175

Val Met Trp Phe Phe Tyr Gly Leu Leu Leu Lys Asp Ile Asn Ile Ala
            180                 185                 190

Ala Pro Asn Val Leu Gly Phe Ile Phe Gly Val Leu Gln Ile Val Leu
                195                 200                 205

Tyr Ala Ile Tyr Ser Lys Lys Glu Lys Val Ile Leu Lys Glu Gln Lys
                210                 215                 220

Leu Pro Glu Ile Gln Lys Pro Ala Val Ile Val Ala Asp Asp Asn Thr
225                 230                 235                 240

Asn Ala Asn Lys Lys Leu Pro Glu Leu Thr His Glu Gln Ile Ile Asp
                245                 250                 255

Ile Val Lys Leu Ala Gly Leu Leu Thr Cys Thr Glu Lys Ser His Val
                260                 265                 270

Ala Thr Cys Pro His Asp Val Asn Cys Gly Val Glu Ala Thr Asn Val
                275                 280                 285

Glu Asn Asn Ile Pro Lys Leu Gln Thr Val Glu Ala Thr
                290                 295                 300

<210> SEQ ID NO 37
<211> LENGTH: 260
<212> TYPE: PRT
<213> ORGANISM: Lotus japonicus

<400> SEQUENCE: 37

Met Ala Leu Ser His Asn Thr Leu Ala Phe Thr Phe Gly Met Leu Gly
1               5                   10                  15

Asn Val Ile Ser Phe Met Val Phe Leu Ala Pro Ile Ala Thr Phe Tyr
                20                  25                  30

Arg Ile Tyr Lys Lys Lys Ser Thr Glu Gly Phe Gln Ser Leu Pro Tyr
            35                  40                  45

Leu Val Ala Leu Phe Ser Ser Met Leu Trp Leu Tyr Tyr Ala Met Val
50                  55                  60

Lys Lys Asp Ala Phe Leu Leu Ile Thr Ile Asn Ser Phe Gly Cys Val
65                  70                  75                  80

Ile Glu Ile Ile Tyr Ile Ile Leu Tyr Met Ile Tyr Ala Pro Arg Asp
                85                  90                  95

Ala Arg Asn Leu Thr Leu Lys Leu Phe Thr Ala Met Asn Val Gly Ser
                100                 105                 110

Phe Ala Leu Ile Leu Leu Val Thr His Phe Ala Val His Gly Pro Leu
            115                 120                 125

Arg Val Gln Val Leu Gly Trp Ile Cys Val Ser Ile Ala Val Ser Val
                130                 135                 140

Phe Ala Ala Pro Leu Ser Ile Val Ala Gln Val Val Arg Thr Lys Ser
145                 150                 155                 160

Val Glu Phe Met Pro Phe Asn Leu Ser Phe Thr Leu Thr Leu Ser Ala
                165                 170                 175

Thr Met Trp Phe Gly Tyr Gly Leu Phe Leu Lys Asp Ile Cys Ile Ala
            180                 185                 190

Leu Pro Asn Ile Leu Gly Phe Gly Leu Gly Leu Ile Gln Met Val Leu
                195                 200                 205

Tyr Ala Ile Tyr Arg Asn Gly Asn Glu Lys Gly Lys Lys Pro Ala Ala
                210                 215                 220
```

Ala Leu Lys Ser Val Val Ile Glu Ile Pro Thr Ser Asn Val Ile Gly
225                 230                 235                 240

Glu Glu Val Gly Glu Lys Glu Lys Thr Glu Pro Pro Val Asn
            245                 250                 255

Ala Cys Ala Ala
        260

<210> SEQ ID NO 38
<211> LENGTH: 247
<212> TYPE: PRT
<213> ORGANISM: Lotus japonicus

<400> SEQUENCE: 38

Met Ala Met Thr Arg Glu Ser Trp Ala Phe Val Phe Gly Leu Met Gly
1               5                   10                  15

Asn Val Ile Ser Phe Met Val Phe Leu Ala Pro Leu Pro Thr Phe Tyr
                20                  25                  30

Gln Ile Tyr Lys Lys Lys Thr Ala Glu Gly Phe Gln Ala Leu Pro Tyr
            35                  40                  45

Val Val Ala Leu Phe Ser Ala Met Leu Trp Ile Tyr Tyr Ala Phe Val
50                  55                  60

Lys Arg Glu Ser Ala Leu Leu Leu Ile Thr Ile Asn Thr Phe Gly Ile
65                  70                  75                  80

Val Val Glu Ser Ile Tyr Ile Ala Phe Phe Leu Phe Tyr Ala Pro Lys
                85                  90                  95

Lys Ser Arg Leu Ser Thr Ile Lys Leu Leu Leu Leu Asn Val Phe
            100                 105                 110

Gly Phe Gly Ala Met Leu Leu Ala Thr Leu Tyr Leu Ser Lys Gly Ala
        115                 120                 125

Lys Arg Leu Gln Ile Ile Gly Trp Ile Cys Leu Val Phe Asn Ile Ser
130                 135                 140

Val Phe Ala Ala Pro Leu Phe Ile Ile Ser Lys Val Ile Arg Thr Arg
145                 150                 155                 160

Ser Val Glu Tyr Met Pro Phe Phe Leu Ser Phe Ser Leu Thr Ile Asn
                165                 170                 175

Ala Val Met Trp Phe Phe Tyr Gly Met Leu Leu Arg Asp Tyr Tyr Val
            180                 185                 190

Ala Leu Pro Asn Thr Leu Gly Phe Val Phe Gly Ile Ile Gln Met Val
        195                 200                 205

Val Tyr Leu Ile Tyr Arg Asn Ala Thr Pro Val Val Ile Glu Glu Lys
210                 215                 220

Val Lys Gly Gln Glu Met Ser Gly Asp His Ile Ile Asp Val Ala Lys
225                 230                 235                 240

Gly Gly Ala Val Ser Lys Val
                245

<210> SEQ ID NO 39
<211> LENGTH: 333
<212> TYPE: PRT
<213> ORGANISM: Zea mays

<400> SEQUENCE: 39

Met Ala Phe Leu Asn Met Glu Gln Gln Thr Trp Ala Phe Thr Phe Gly
1               5                   10                  15

Ile Leu Gly Asn Ile Ile Ser Leu Met Val Phe Leu Ser Pro Leu Pro
                20                  25                  30

-continued

```
Thr Phe Tyr Arg Val Tyr Arg Lys Ser Thr Glu Gly Phe Gln Ser
            35                  40                  45

Thr Pro Tyr Val Val Thr Leu Phe Ser Cys Met Leu Trp Ile Phe Tyr
 50                  55                  60

Ala Leu Leu Lys Ser Gly Ala Glu Leu Val Thr Ile Asn Gly Val
 65                  70                  75                  80

Gly Cys Val Ile Glu Ala Ala Tyr Leu Ala Tyr Leu Val Tyr Ala
                 85                  90                  95

Pro Lys Ala Ala Arg Ala Leu Thr Ala Lys Met Leu Leu Gly Leu Asn
                100                 105                 110

Val Gly Val Phe Gly Leu Ala Ala Leu Ala Thr Met Val Val Ser Ser
                115                 120                 125

Ala Gly Leu Arg Val Arg Val Leu Gly Trp Ile Cys Val Ser Val Ala
130                 135                 140

Leu Ser Val Phe Ala Ala Pro Leu Ser Ile Met Arg Gln Val Val Arg
145                 150                 155                 160

Thr Lys Ser Val Glu Phe Met Pro Ile Ser Leu Ser Phe Phe Leu Val
                165                 170                 175

Leu Ser Ala Val Ile Trp Phe Ala Tyr Gly Ala Leu Lys Arg Asp Val
                180                 185                 190

Phe Val Ala Phe Pro Asn Val Leu Gly Phe Val Phe Gly Val Ala Gln
                195                 200                 205

Ile Ala Leu Tyr Met Ala Tyr Arg Asn Lys Glu Pro Ala Ala Val Thr
210                 215                 220

Val Glu Glu Ala Lys Leu Pro Glu His Ala Lys Glu Val Val Val Ala
225                 230                 235                 240

Ala Ala Ala Ala Glu Ala Arg Ala Ser Cys Gly Ala Glu Val His Pro
                245                 250                 255

Ile Asp Ile Asp Ile Glu Ala Thr Pro Thr Pro Val Glu Glu Val His
                260                 265                 270

Glu Pro Gln Val Val Val Val Asp Val Asp Val Glu Pro Val Thr
                275                 280                 285

Cys Ala Gly Ala Ala Glu Ala Ala Gly Ala Gly Ala Asp Ala Ser
                290                 295                 300

Gly Val Ala Asp Gly Gly Val Pro Gly Pro Met Ala Pro Pro Glu Gln
305                 310                 315                 320

Leu Ala Ile Lys Pro Asp Met Ala Ile Ser Val Glu Ala
                325                 330
```

<210> SEQ ID NO 40
<211> LENGTH: 305
<212> TYPE: PRT
<213> ORGANISM: Zea mays

<400> SEQUENCE: 40

```
Met Ile Thr Val Gly His Pro Val Ala Phe Ala Val Gly Ile Leu Gly
 1               5                  10                  15

Asn Ile Leu Ser Phe Leu Val Ile Leu Ala Pro Val Pro Thr Phe Tyr
                 20                  25                  30

Arg Val Tyr Ala Lys Lys Ser Thr Glu Ser Phe Gln Ser Val Pro Tyr
            35                  40                  45

Val Val Ala Leu Leu Ser Ala Thr Leu Trp Leu Tyr Tyr Ala Leu Leu
 50                  55                  60

Ser Thr Asp Leu Leu Leu Leu Ser Ile Asn Thr Val Ala Cys Val Ala
```

65                  70                  75                  80
    Glu Ser Val Tyr Leu Ala Val Tyr Leu Ala Tyr Ala Pro Gly Pro Ala
                    85                  90                  95
    Lys Ala Phe Thr Leu Lys Leu Leu Cys Ala Ile Asn Met Gly Leu Phe
                100                 105                 110
    Gly Ala Met Val Ala Phe Leu Gln Phe Tyr Val Val Asp Thr Gln Arg
                115                 120                 125
    Arg Val Ser Ile Ala Gly Gly Val Gly Ala Ala Phe Ala Leu Ala Val
                130                 135                 140
    Phe Val Ala Pro Leu Ala Ile Ile Arg Arg Val Met Arg Thr Lys Ser
    145                 150                 155                 160
    Val Glu Phe Met Pro Phe Trp Leu Ser Phe Phe Leu Thr Val Ser Ala
                    165                 170                 175
    Val Val Trp Phe Phe Tyr Gly Leu Leu Ile Lys Asp Phe Phe Val Ala
                    180                 185                 190
    Met Pro Asn Val Leu Gly Leu Leu Phe Gly Leu Ala Gln Met Val Leu
                    195                 200                 205
    Phe Phe Val Tyr Arg Asn Arg Asn Pro Lys Lys Asn Gly Ala Val Ser
    210                 215                 220
    Glu Met Gln Gln Ala Ala Val Gln Ala Asp Ala Glu Lys Glu Arg Arg
    225                 230                 235                 240
    Ser His Ala Asn Ala Asp Gly Glu Ala Asp Val Arg Thr Val Ile Val
                    245                 250                 255
    Asp Ile Met Pro Pro Pro Ala Met Met Arg His Ala Asp Arg Glu
                    260                 265                 270
    Ala Arg Gly Gly Ala Gly Thr Gly Arg Arg Ala Ala Arg Glu Gln
            275                 280                 285
    Gly Gly Ala Arg Arg Arg Glu Asp Arg Glu Ala Leu Gly Gly Gly
        290                 295                 300
    Ile
    305

<210> SEQ ID NO 41
<211> LENGTH: 289
<212> TYPE: PRT
<213> ORGANISM: Hordeum vulgare

<400> SEQUENCE: 41

Met Ala Gly Leu Ser Met Glu His Pro Trp Ala Phe Ala Phe Gly Leu
    1               5                   10                  15
    Leu Gly Asn Ile Ile Ser Phe Thr Ser Leu Leu Ala Pro Ile Pro Thr
                    20                  25                  30
    Phe Tyr Arg Ile Phe Lys Ser Lys Ser Thr Glu Gly Phe Gln Ser Val
                35                  40                  45
    Pro Tyr Val Val Ala Leu Phe Ser Ala Met Leu Trp Ile Phe Tyr Ala
                50                  55                  60
    Leu Val Lys Thr Gly Glu Gly Leu Leu Ile Thr Ile Asn Ala Ala Gly
    65                  70                  75                  80
    Cys Val Ile Glu Thr Val Tyr Ile Ile Met Tyr Leu Val Tyr Ala Pro
                    85                  90                  95
    Arg Lys Ala Lys Ile Phe Thr Ala Lys Ile Val Leu Leu Leu Asn Val
                    100                 105                 110
    Ala Gly Phe Gly Leu Ile Phe Leu Leu Thr Leu Phe Ala Phe His Gly
                115                 120                 125

```
Glu Thr Arg Val Val Ser Leu Gly Trp Ile Cys Val Gly Phe Ser Val
            130                 135                 140

Cys Val Phe Val Ala Pro Leu Ser Ile Ile Gly Arg Val Ile Lys Thr
145                 150                 155                 160

Lys Ser Val Glu Tyr Met Pro Phe Ser Leu Ser Leu Thr Leu Thr Leu
                165                 170                 175

Ser Ala Val Val Trp Phe Leu Tyr Gly Leu Leu Ile Lys Asp Lys Tyr
                180                 185                 190

Val Ala Leu Pro Asn Ile Leu Gly Phe Thr Phe Gly Met Ile Gln Met
            195                 200                 205

Val Leu Tyr Met Phe Tyr Met Asn Ala Thr Pro Val Val Ala Ser Asp
            210                 215                 220

Ala Lys Glu Gly Lys Glu Ala Trp Lys Val Pro Ala Glu Asp His Val
225                 230                 235                 240

Val Val Ile Asn Val Gly Lys Ala Asp Lys Ser Ser Cys Ala Glu Val
                245                 250                 255

Arg Pro Val Ala Asp Val Pro Arg Cys Ala Ala Glu Ala Ala Ala
                260                 265                 270

Pro Gly Gln Gln Val Met Ala Val Asp Phe Ala Arg Ser Val Glu Val
            275                 280                 285

Val

<210> SEQ ID NO 42
<211> LENGTH: 292
<212> TYPE: PRT
<213> ORGANISM: Hordeum vulgare

<400> SEQUENCE: 42

Met Gly Gly Leu Ser Ala Gln His Pro Trp Ala Phe Thr Phe Gly Leu
1               5                   10                  15

Leu Gly Asn Val Ile Ser Phe Met Thr Tyr Leu Ala Pro Leu Pro Thr
            20                  25                  30

Phe Tyr Arg Ile Tyr Lys Asn Lys Ser Thr Gln Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asp Glu Tyr Leu Leu Ile Thr Ile Asn Thr Ala Gly
65                  70                  75                  80

Cys Val Ile Glu Thr Ile Tyr Ile Val Leu Tyr Leu Ala Tyr Ala Pro
                85                  90                  95

Lys Gln Ala Arg Leu Phe Thr Ala Lys Ile Leu Leu Leu Leu Asn Val
            100                 105                 110

Gly Val Phe Gly Leu Ile Leu Leu Leu Thr Leu Leu Leu Thr Ala Gly
        115                 120                 125

Glu Arg Arg Val Val Met Leu Gly Trp Val Cys Val Gly Phe Ser Val
    130                 135                 140

Cys Val Phe Val Ala Pro Leu Ser Val Ile Arg Leu Val Val Arg Thr
145                 150                 155                 160

Arg Ser Val Glu Phe Met Pro Phe Ser Leu Ser Leu Ser Leu Thr Ala
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Ala Phe Gly Val Ile Gln Met
        195                 200                 205
```

```
Gly Leu Tyr Ala Leu Tyr Arg Asn Ala Thr Pro Ile Pro Ala Pro Lys
    210                 215                 220

Glu Met Asp Ala Pro Glu Ser Glu Asp Gly Ala Val Lys Ala Pro Glu
225                 230                 235                 240

His Val Val Asn Ile Ala Lys Leu Gly Thr Ala Ala Ala Ile Glu
                245                 250                 255

Leu Asn Thr Asn His Pro Val Glu Pro Pro Pro Met Lys Glu Gly
            260                 265                 270

Thr Ala Lys Ala Cys Ala Thr Gly Glu Lys Leu Asp Lys Ala Thr His
        275                 280                 285

Val Glu Gln Val
    290

<210> SEQ ID NO 43
<211> LENGTH: 314
<212> TYPE: PRT
<213> ORGANISM: Hordeum vulgare

<400> SEQUENCE: 43

Met Ala Ala Val Gly Ser Pro Leu Ile Phe Ala Val Gly Ile Leu Gly
1               5                   10                  15

Asn Ile Leu Ser Phe Leu Val Ile Leu Ala Pro Val Pro Thr Phe Tyr
                20                  25                  30

Arg Val Tyr Lys Arg Lys Ser Thr Glu Ser Phe Gln Ser Val Pro Tyr
            35                  40                  45

Ala Met Ala Leu Leu Ser Ala Met Leu Trp Leu Tyr Tyr Ala Leu Leu
        50                  55                  60

Thr Lys Asp Leu Leu Leu Leu Thr Ile Asn Thr Val Gly Cys Val Val
65                  70                  75                  80

Glu Thr Ala Tyr Leu Ala Ile Tyr Leu Ala Tyr Ala Pro Lys Gln Ala
                85                  90                  95

Lys Ala Phe Thr Ala Lys Leu Val Cys Ile Met Asn Val Ala Leu Tyr
            100                 105                 110

Gly Ala Met Val Cys Val Leu Gln Leu Leu Val Arg Asp Gly Glu Ser
        115                 120                 125

Arg Val Thr Ile Ala Gly Gly Ile Gly Ser Ala Phe Ala Leu Ala Val
    130                 135                 140

Phe Val Ala Pro Leu Ala Ile Ile Arg Gln Val Ile Arg Thr Lys Ser
145                 150                 155                 160

Val Glu Phe Leu Pro Phe Trp Leu Ser Phe Phe Leu Thr Ile Ser Ala
                165                 170                 175

Val Val Trp Phe Phe Tyr Gly Leu Leu Met Lys Asp Phe Phe Val Ala
            180                 185                 190

Thr Pro Asn Val Leu Gly Leu Leu Phe Gly Leu Ala Gln Met Ala Leu
        195                 200                 205

His Leu Val Tyr Lys Asn Pro Lys Lys Lys Gly Asp Val Ser Glu Val
    210                 215                 220

Gln Leu Pro Asp Asp Asp Glu Lys Asn Gln Leu Pro Leu His His Gln
225                 230                 235                 240

Gln Gln Gln Gln Ala Gly Thr Thr Gly His Val Val Ala Pro Pro Ile
                245                 250                 255

Ile Asp Asp Gly Glu Gln Val Val Asn Gly Ser Glu Asp Asp Val Gly
            260                 265                 270

Gly Asn Lys Gln Gln Ser Val Ser Val Met Asp Ile Val Leu Pro Pro
        275                 280                 285
```

```
Pro Glu Glu His Pro Thr Leu Pro Pro Leu Asp His Pro Ala Pro Leu
        290                 295                 300

Pro Pro Met Arg Met Ala Val Glu Val Val
305                 310
```

<210> SEQ ID NO 44
<211> LENGTH: 287
<212> TYPE: PRT
<213> ORGANISM: Hordeum vulgare

<400> SEQUENCE: 44

```
Met Ala Gly Gly Leu Phe Ser Met Ala His Pro Trp Ala Ser Ala Phe
1               5                   10                  15

Gly Ile Leu Gly Asn Ile Ile Ser Phe Leu Val Phe Leu Ala Pro Thr
            20                  25                  30

Pro Thr Phe Leu Arg Val Tyr Arg Lys Ser Thr Glu Gly Phe Ser
        35                  40                  45

Ser Val Pro Tyr Val Val Ala Leu Phe Ser Cys Thr Leu Trp Ile Leu
    50                  55                  60

Tyr Ala Leu Val Lys Thr Asn Ser Ser Pro Leu Leu Thr Ile Asn Ala
65                  70                  75                  80

Phe Gly Cys Val Val Glu Ala Phe Tyr Ile Val Leu Tyr Leu Val Tyr
                85                  90                  95

Ala Pro Arg Pro Ala Arg Met Arg Ala Leu Ala Phe Phe Leu Leu Leu
            100                 105                 110

Asn Val Ala Ala Phe Ser Leu Ile Val Ala Val Thr Val Phe Leu Val
        115                 120                 125

Pro Gln Pro Ser Arg Val Lys Val Leu Gly Ser Val Cys Leu Ala Phe
    130                 135                 140

Ser Met Ala Val Phe Val Ala Pro Leu Ser Val Ile Phe Val Val Ile
145                 150                 155                 160

Lys Thr Lys Ser Ala Glu Tyr Met Pro Phe Ser Leu Ser Phe Phe Leu
                165                 170                 175

Thr Leu Ser Ala Val Ala Trp Phe Phe Tyr Gly Leu Phe Thr Lys Asp
            180                 185                 190

Ile Tyr Val Thr Leu Pro Asn Val Gly Gly Phe Phe Phe Gly Val Ala
        195                 200                 205

Gln Met Thr Leu Tyr Phe Cys Tyr Arg Lys Pro Asp Thr Ser Ala Leu
    210                 215                 220

Val Leu Pro Thr Gly Ile His Asp Val Ser Thr Glu Ala Ala Ala Gln
225                 230                 235                 240

Gln Glu Val Glu Leu Pro Glu Gly Thr His Pro Ala Val Ala Met Leu
                245                 250                 255

Thr Val Ser Thr Leu Pro Met Leu Ala Glu Leu Gln Lys Met Glu Gln
            260                 265                 270

Glu Ile Ser Ser Pro Thr Pro Arg Lys Gly Tyr Ile Lys Ala Phe
        275                 280                 285
```

<210> SEQ ID NO 45
<211> LENGTH: 288
<212> TYPE: PRT
<213> ORGANISM: Vitis vinifera

<400> SEQUENCE: 45

```
Met Ala Met Phe Thr Val Gly His His Pro Trp Val Phe Ala Ser Gly
1               5                   10                  15
```

```
Ile Leu Gly Asn Leu Met Ser Phe Leu Val Tyr Leu Ala Pro Ile Pro
         20                  25                  30

Thr Phe Thr Arg Val Ile Lys Lys Ser Thr Glu Gly Phe Gln Ser
         35                  40                  45

Val Pro Tyr Val Ile Ala Leu Phe Ser Ala Met Leu Trp Met Tyr Tyr
 50                  55                  60

Gly Leu Val Asn Thr Asn Ala Ser Phe Leu Leu Ser Val Asn Gly Phe
 65                  70                  75                  80

Gly Cys Phe Ile Glu Ile Ile Tyr Ile Ser Ile Tyr Leu Ile Phe Ala
                 85                  90                  95

Pro Arg Arg Ala Arg Ile Leu Thr Leu Arg Leu Leu Leu Ile Asn
             100                 105                 110

Leu Gly Ala Phe Cys Leu Ile Leu Ile Val Thr Asn Phe Met Val Lys
             115                 120                 125

Arg Pro His Arg Val Lys Ala Val Gly Trp Val Cys Leu Ile Phe Ala
 130                 135                 140

Val Ser Val Phe Ala Ala Pro Leu Ser Ile Met Ala Ser Ile Leu Tyr
145                 150                 155                 160

Arg Leu Val Ile Arg Thr Lys Ser Val Glu Phe Met Pro Leu Pro Leu
                 165                 170                 175

Ser Ile Cys Leu Thr Leu Ser Ala Val Gly Trp Phe Phe Tyr Gly Ile
             180                 185                 190

Leu Gln Met Asp Leu Tyr Ile Ala Met Pro Asn Thr Leu Gly Phe Val
             195                 200                 205

Phe Gly Leu Ile Gln Met Ile Leu Tyr Ala Met Tyr Arg Asn Ser Thr
 210                 215                 220

Pro Val Thr Lys Glu Pro Lys Leu Pro Glu Gln Val Ile Asp Ile Val
225                 230                 235                 240

Lys Leu Asn Thr Asn Ser Thr Pro Glu Val His Pro Val Ser Thr Leu
                 245                 250                 255

Gln Pro Asn Cys Val Glu Asn Glu Gly Gly Asn Gly Gln Asn Ala Arg
             260                 265                 270

Lys Glu Thr Glu His Ala Glu Glu Ser Met Gly Gly Ser Asn Arg Val
             275                 280                 285

<210> SEQ ID NO 46
<211> LENGTH: 341
<212> TYPE: PRT
<213> ORGANISM: Vitis vinifera

<400> SEQUENCE: 46

Met Ala Met Leu Thr Val Pro His Met Ala Phe Ala Phe Gly Ile Leu
 1               5                  10                  15

Gly Asn Ile Val Ser Phe Leu Val Tyr Leu Ser Pro Leu Pro Thr Phe
                 20                  25                  30

Tyr Arg Ile Tyr Lys Arg Lys Ser Thr Glu Gly Phe Gln Ser Ile Pro
             35                  40                  45

Tyr Ser Val Ala Leu Phe Ser Ala Met Leu Leu Leu Tyr Tyr Ala Phe
 50                  55                  60

Leu Lys Thr Asp Asn Gln Ile Met Leu Ile Thr Ile Asn Ser Val Gly
 65                  70                  75                  80

Thr Cys Ile Glu Ala Thr Tyr Leu Leu Val Tyr Met Ile Tyr Ala Pro
                 85                  90                  95

Arg Thr Ala Lys Ile Tyr Thr Ala Lys Leu Leu Leu Leu Phe Asn Thr
```

```
            100                 105                 110
Gly Val Tyr Gly Ala Ile Val Leu Ser Thr Phe Phe Leu Ser Lys Gly
            115                 120                 125

His Arg Arg Ala Lys Ile Val Gly Trp Val Cys Ala Ala Phe Ser Leu
130                 135                 140

Cys Val Phe Ala Ala Pro Leu Ser Ile Met Arg Leu Val Ile Arg Thr
145                 150                 155                 160

Lys Ser Val Glu Tyr Met Pro Phe Pro Leu Ser Phe Phe Leu Thr Ile
                165                 170                 175

Cys Ala Val Met Trp Phe Phe Tyr Gly Leu Leu Ile Arg Asp Phe Tyr
                180                 185                 190

Ile Ala Phe Pro Asn Ile Leu Gly Phe Ala Phe Gly Ile Ala Gln Met
            195                 200                 205

Ile Leu Tyr Thr Ile Tyr Lys Asn Ala Lys Lys Gly Val Leu Ala Glu
        210                 215                 220

Phe Lys Leu Gln Glu Leu Pro Asn Gly Leu Val Phe Pro Thr Leu Lys
225                 230                 235                 240

Lys Ala Glu Asn Thr Asp Thr Asn Pro Asn Asp Gln Pro Glu Asp Thr
                245                 250                 255

Ala Met Thr Glu Gly Gly Ala Arg Asp Lys Ala Val Glu Pro Ser Gly
            260                 265                 270

Glu Leu Lys His Asn Ser Ser Ser Leu Val Val Arg Phe Cys Leu Arg
        275                 280                 285

Ala Leu Arg Leu Ser Phe His His Val Ser Phe Ser Arg Ile Ile Ala
    290                 295                 300

Tyr Thr Asn Gln Arg Asn Thr Val Asn Thr Met Arg Val Tyr Leu Leu
305                 310                 315                 320

Tyr Ile Ala Met Tyr Glu Asn Lys Ser Ile Leu Val Phe Ile Thr Leu
                325                 330                 335

Phe Ser Gln Ile Leu
            340

<210> SEQ ID NO 47
<211> LENGTH: 293
<212> TYPE: PRT
<213> ORGANISM: Oryza sativa Indica

<400> SEQUENCE: 47

Met Asp His Leu Trp Ala Ser Val Phe Gly Ile Leu Gly Asn Ile Val
1               5                   10                  15

Ser Phe Leu Val Phe Leu Ala Pro Met Pro Thr Phe Leu Arg Val Tyr
                20                  25                  30

Arg Lys Lys Ser Thr Glu Gly Phe Ser Ser Val Pro Tyr Val Val Ala
            35                  40                  45

Leu Phe Ser Cys Thr Leu Trp Ile Leu Tyr Ala Met Val Lys Thr Asn
        50                  55                  60

Ser Ser Pro Leu Leu Thr Ile Asn Ala Phe Gly Cys Val Val Glu Ala
65                  70                  75                  80

Ala Tyr Ile Ala Val Tyr Leu Val Tyr Ala Pro Arg Pro Ala Arg Leu
                85                  90                  95

Arg Ala Leu Ala Ser Phe Leu Leu Leu Asn Val Ala Ala Phe Ser Leu
            100                 105                 110

Val Val Val Val Thr Val Ala Ala Val Val Gln Pro His Arg Val Arg
        115                 120                 125
```

```
Val Leu Gly Ser Ile Cys Leu Ala Phe Ser Met Ala Val Phe Val Ala
    130                 135                 140

Pro Met Ser Val Ile Met Val Val Ile Lys Thr Lys Ser Ala Glu Phe
145                 150                 155                 160

Met Pro Phe Ser Leu Ser Phe Phe Leu Thr Leu Ser Ala Val Ala Trp
                165                 170                 175

Phe Phe Tyr Gly Leu Phe Thr Asn Asp Leu Tyr Val Thr Leu Pro Asn
            180                 185                 190

Val Gly Gly Phe Phe Gly Cys Val Gln Met Ala Leu Tyr Phe Lys
        195                 200                 205

Tyr Arg Lys Pro Asn Thr Ala Ala Gly Gly Val Met Ile Leu Pro Thr
    210                 215                 220

Thr Ala Ala Ala Ala Val Asp Gly Ala Val Ala Glu Pro Ala Ala
225                 230                 235                 240

Ala Ala Gln Gln Leu Ala Glu Glu Leu Glu Met Glu Leu Ala Ala Ala
                245                 250                 255

Gly Ala His Ala Val Ala Val Leu Pro Ala Ser Ala Leu Pro Val Leu
            260                 265                 270

Ala Glu Leu His Lys Met Glu Gln Glu Ile Gly Thr Pro Arg Lys Gly
        275                 280                 285

Ala Thr Lys Thr Val
        290

<210> SEQ ID NO 48
<211> LENGTH: 284
<212> TYPE: PRT
<213> ORGANISM: Prunus persica

<400> SEQUENCE: 48

Met Ala Ala Pro Asp Ala Phe Leu Leu Ala Ser Val Phe Gly Ile Leu
1               5                   10                  15

Gly Asn Ile Val Ala Phe Met Val Tyr Leu Ala Pro Leu Pro Thr Phe
            20                  25                  30

Tyr Arg Ile Phe Lys Lys Lys Ser Thr Glu Gly Phe Gln Ser Ile Pro
        35                  40                  45

Tyr Ser Val Ala Leu Phe Ser Ala Met Leu Met Leu Tyr Tyr Ala Phe
    50                  55                  60

Leu Lys Thr Asn Ala Phe Met Leu Ile Thr Ile Asn Ser Val Gly Cys
65                  70                  75                  80

Ile Ile Glu Thr Ser Tyr Leu Val Met Tyr Met Ile Tyr Ala Pro Ala
                85                  90                  95

Lys Thr Arg Ile Tyr Thr Ala Lys Leu Leu Val Leu Phe Asn Val Gly
            100                 105                 110

Val Tyr Gly Val Ile Val Leu Ser Thr Tyr Leu Ile Pro Asn His Phe
        115                 120                 125

Leu Arg Ile Lys Val Val Gly Trp Ile Ser Val Phe Ser Val Cys
    130                 135                 140

Val Phe Ala Ala Pro Leu Ser Ile Met Arg Leu Val Ile Arg Thr Arg
145                 150                 155                 160

Ser Val Glu Phe Met Ser Phe Pro Leu Ser Phe Cys Leu Thr Leu Cys
                165                 170                 175

Ala Val Met Trp Phe Phe Tyr Gly Leu Leu Val Arg Asp Leu Phe Ile
            180                 185                 190

Ala Ala Pro Asn Ile Leu Gly Phe Ala Phe Gly Leu Ala Gln Met Ile
        195                 200                 205
```

```
Met Tyr Leu Met Phe Lys Asn Ser Lys Ser Met Leu Pro Glu Phe
    210                 215                 220

Ser Leu Asn Gln Ile Pro Asn Val Val Ala Val Asn Asp Ile Val Ala
225                 230                 235                 240

Ser Asp Ser Gln Leu Lys Thr Glu Asp Thr Lys Lys Ser Ser Glu Ala
                    245                 250                 255

Glu Glu Asn Gln Ser Thr Glu Ser Met Thr Asn Asp Arg Arg Ala Gly
                260                 265                 270

Asp Ala Ala Ala Glu Pro Asn Glu Ser Ile Val
                275                 280
```

<210> SEQ ID NO 49
<211> LENGTH: 293
<212> TYPE: PRT
<213> ORGANISM: Prunus persica

<400> SEQUENCE: 49

```
Met Ala Ile Gln His Pro Leu Thr Leu Ser Phe Gly Leu Leu Gly Asn
1               5                   10                  15

Ile Ile Ser Phe Leu Val Phe Leu Ala Pro Val Pro Thr Phe Tyr Thr
                20                  25                  30

Ile Tyr Lys Arg Lys Thr Ala Glu Gly Phe Gln Ala Leu Pro Tyr Val
                35                  40                  45

Ile Ala Leu Leu Ser Ser Met Leu Tyr Ile Tyr Tyr Ala Leu Leu Lys
            50                  55                  60

Glu Glu Phe Lys Glu Asp Ala Thr Phe Leu Ile Thr Ile Asn Ser Phe
65                  70                  75                  80

Gly Cys Val Val Glu Thr Leu Tyr Ile Ser Leu Phe Leu Phe Tyr Ala
                85                  90                  95

Pro Lys Lys Ala Arg Ile Ser Thr Leu Thr Leu Val Phe Leu Leu Asn
                100                 105                 110

Leu Phe Gly Phe Gly Leu Met Met Leu Leu Thr His Phe Leu Ala Thr
            115                 120                 125

Gly Glu Met Arg Leu Lys Ile Val Gly Trp Ile Cys Leu Val Phe Ser
130                 135                 140

Leu Ser Val Phe Val Ala Pro Leu Gly Val Leu Arg Arg Val Ile Arg
145                 150                 155                 160

Thr Lys Ser Val Glu Phe Met Pro Phe Pro Leu Ser Phe Pro Leu Thr
                165                 170                 175

Leu Gly Ala Val Thr Trp Phe Tyr Gly Leu Leu Ile Lys Asp Tyr
                180                 185                 190

Asn Ile Ala Phe Pro Asn Ile Leu Gly Phe Leu Phe Gly Ile Ala Gln
            195                 200                 205

Met Val Leu Tyr Ile Val Tyr Lys Asn Thr Lys Lys Val Leu Glu Glu
    210                 215                 220

Gln Pro Lys Val Gln Glu Leu Ser Glu His Ile Ile Asp Val Val Lys
225                 230                 235                 240

Ile Ser Ser Leu Val Cys Pro Glu Leu Asn Pro Val Val Leu Gln Pro
                245                 250                 255

Thr Leu Asp Ile Thr Asn Asp Met Ile Glu Ala Val Gln Asn Ile Ile
                260                 265                 270

Val Met Ala Glu Lys Thr Glu Glu Ala Lys Glu Ala Met Asp Ile Asp
                275                 280                 285

Ala Ser Thr Lys Val
```

<210> SEQ ID NO 50
<211> LENGTH: 277
<212> TYPE: PRT
<213> ORGANISM: Prunus persica

<400> SEQUENCE: 50

Met Gly Ala Leu Ala Asp Ser His His Pro Trp Ala Phe Thr Phe Gly
1               5                   10                  15

Ile Leu Gly Asn Val Ile Ser Phe Leu Val Tyr Leu Ala Pro Val Pro
                20                  25                  30

Thr Phe Tyr Gly Ile Tyr Lys Lys Lys Ser Thr Gln Gly Phe Gln Ser
            35                  40                  45

Val Pro Tyr Leu Val Ala Leu Phe Ser Gly Met Leu Trp Phe Tyr Tyr
        50                  55                  60

Ala Leu Leu Lys Lys Asn Ala Met Leu Leu Ile Thr Ile Asn Ser Phe
65                  70                  75                  80

Gly Thr Val Ile Glu Thr Ile Tyr Ile Val Met Phe Ile Phe Tyr Ala
                85                  90                  95

Pro Lys Asp Ala Arg Lys Phe Thr Leu Lys Leu Phe Gly Phe Met Asn
            100                 105                 110

Val Gly Leu Phe Cys Ser Ile Leu Val Leu Ser His Phe Ala Val Arg
        115                 120                 125

Ser Glu Tyr Arg Val Pro Val Leu Gly Trp Ile Asn Val Ala Ile Ser
    130                 135                 140

Val Ile Val Phe Ala Ala Pro Leu Ser Ile Val Ala Gln Val Ile Arg
145                 150                 155                 160

Thr Arg Ser Val Glu Phe Met Pro Phe Ser Leu Ser Phe Phe Leu Thr
                165                 170                 175

Leu Ser Ala Val Met Trp Phe Ser Tyr Gly Leu Phe Leu Lys Asp Ile
            180                 185                 190

Cys Ile Ala Ile Pro Asn Val Leu Gly Phe Ile Leu Gly Leu Leu Gln
        195                 200                 205

Met Leu Leu Tyr Ala Ile Tyr Arg Asn Arg Lys Pro Ile Glu Asp Asp
    210                 215                 220

Glu Lys Lys Ile Pro Ala Ala Asp Gln His Val Lys Asn Val Val Gly
225                 230                 235                 240

Leu Thr Thr Leu Ala Thr Ser Glu Val His Pro Val Asp Pro Pro Pro
                245                 250                 255

Arg Asp His Asp Lys Ser Val Glu Val Asp Ala Gly Ser His Thr Ala
            260                 265                 270

Ala Ala Ser Cys Ala
        275

<210> SEQ ID NO 51
<211> LENGTH: 287
<212> TYPE: PRT
<213> ORGANISM: Triticum urartu

<400> SEQUENCE: 51

Met Ala Glu Gly Leu Phe Ser Met Ala His Pro Trp Ala Ser Ala Phe
1               5                   10                  15

Gly Ile Leu Gly Asn Ile Ile Ser Phe Leu Val Phe Leu Ala Pro Thr
                20                  25                  30

Pro Thr Phe Leu Arg Val Tyr Arg Lys Lys Ser Thr Glu Gly Phe Ser

```
            35                  40                  45
Ala Val Pro Tyr Val Val Ala Leu Phe Ser Cys Met Leu Trp Ile Phe
 50                  55                  60

Tyr Ala Leu Val Lys Thr Asn Ser Ser Pro Leu Leu Thr Ile Asn Ala
 65                  70                  75                  80

Phe Gly Cys Val Val Glu Ser Phe Tyr Ile Leu Leu Tyr Val Val Tyr
                 85                  90                  95

Ala Pro Arg Asn Ala Arg His Arg Ala Leu Ala Phe Phe Leu Leu Leu
                100                 105                 110

Asp Val Ala Ala Phe Ser Leu Ile Val Val Thr Val Phe Leu Val
                115                 120                 125

Pro Gln Pro Ser Arg Val Lys Val Leu Gly Ser Val Cys Leu Ala Phe
                130                 135                 140

Ser Met Ala Val Phe Val Ala Pro Leu Ser Val Ile Phe Val Val Ile
145                 150                 155                 160

Lys Thr Lys Ser Ala Glu Tyr Met Pro Phe Ser Leu Ser Phe Phe Leu
                165                 170                 175

Thr Leu Ser Ala Val Ala Trp Phe Phe Tyr Gly Leu Phe Thr Lys Asp
                180                 185                 190

Ile Tyr Val Thr Leu Pro Asn Val Gly Gly Phe Phe Gly Val Ala
                195                 200                 205

Gln Met Thr Leu Tyr Phe Cys Tyr Arg Lys Pro Asp Thr Ser Ala Leu
210                 215                 220

Val Leu Pro Thr Gly Ile His Asp Val Ser Thr Glu Ala Ala Ala Gln
225                 230                 235                 240

Gln Glu Val Glu Leu Pro Gly Thr His Pro Ala Ala Ala Met Leu
                245                 250                 255

Thr Val Ser Thr Leu Pro Met Leu Ala Glu Leu Gln Lys Met Glu Gln
                260                 265                 270

Glu Ile Ser Ser Pro Thr Pro Arg Lys Gly Tyr Ile Lys Ala Phe
                275                 280                 285

<210> SEQ ID NO 52
<211> LENGTH: 345
<212> TYPE: PRT
<213> ORGANISM: Triticum urartu

<400> SEQUENCE: 52

Met Ala Phe Leu Asn Met Glu Gln His Thr Trp Ala Phe Thr Phe Gly
 1                   5                  10                  15

Ile Leu Gly Asn Ile Ile Ser Leu Met Val Phe Leu Ser Pro Leu Pro
                 20                  25                  30

Thr Phe Tyr Arg Val Tyr Arg Lys Lys Ser Thr Glu Gly Phe Gln Ser
                 35                  40                  45

Thr Pro Tyr Leu Val Thr Leu Phe Ser Cys Leu Leu Trp Met Tyr Tyr
 50                  55                  60

Ala Phe Leu Lys Ser Gly Ser Glu Leu Leu Thr Ile Asn Ala Val
 65                  70                  75                  80

Gly Cys Val Ile Glu Ser Leu Tyr Ile Ala Met Tyr Leu Val Tyr Ala
                 85                  90                  95

Pro Lys Ser Ala Arg Leu Leu Thr Ala Lys Leu Phe Ile Gly Leu Asp
                100                 105                 110

Val Gly Leu Phe Gly Leu Ile Ala Leu Val Thr Met Leu Ala Ser His
                115                 120                 125
```

Gly Pro Leu Arg Val Gln Val Val Gly Trp Ile Cys Val Ala Val Ala
            130                 135                 140

Leu Gly Val Phe Ala Ala Pro Leu Ser Ile Ile Arg Leu Val Ile Arg
145                 150                 155                 160

Thr Lys Ser Val Glu Phe Met Pro Phe Ser Leu Ser Phe Phe Leu Val
                165                 170                 175

Leu Ser Ala Val Ile Trp Phe Ala Tyr Gly Ala Leu Lys Lys Asp Ile
                180                 185                 190

Phe Val Ala Met Pro Asn Val Leu Gly Phe Leu Phe Gly Val Ala Gln
                195                 200                 205

Met Ala Leu Tyr Met Ala Tyr Arg Asn Lys Lys Pro Ala Thr Val Ala
210                 215                 220

Val Ile Asp Thr Thr Pro Arg Gln Arg Gln Arg Cys Thr Met Pro Val
225                 230                 235                 240

Gly Arg Gln Thr Arg Arg His Lys Pro Phe Ala Thr Glu Lys Asn Arg
                245                 250                 255

Gly Ser Thr Asn Asp Ala Leu Lys Arg Gly Met Thr Pro Ser Ala Thr
                260                 265                 270

Asp Val Lys Ser Lys Arg Trp Thr Arg Ile Phe Thr Pro Asp Pro Trp
                275                 280                 285

His Leu Glu Gly Thr Leu Asn Asn Ala Pro Lys Arg Glu Ala Thr Leu
                290                 295                 300

Val Gly Ala Gly Val Thr Gly Ala Gly Ala Gln Ser Phe Arg Ser Asp
305                 310                 315                 320

Pro His Lys Cys His Gln Arg Thr His Gly Cys Gln Pro Thr Pro Arg
                325                 330                 335

Arg Glu Val Ile Val Gly Asn Met Pro
                340                 345

<210> SEQ ID NO 53
<211> LENGTH: 290
<212> TYPE: PRT
<213> ORGANISM: Triticum urartu

<400> SEQUENCE: 53

Met Gly Gly Leu Ser Met Glu His Pro Trp Ala Phe Ala Phe Gly Leu
1               5                   10                  15

Leu Gly Asn Val Ile Ser Phe Ser Ser Leu Leu Ala Pro Ile Pro Thr
                20                  25                  30

Phe Tyr Arg Ile Phe Lys Ser Lys Ser Thr Glu Gly Phe Gln Ser Val
                35                  40                  45

Pro Tyr Val Val Ala Leu Phe Ser Ala Met Leu Trp Ile Phe Tyr Ala
50                  55                  60

Leu Val Lys Thr Gly Glu Gly Leu Leu Ile Ser Ile Asn Ala Ala Gly
65                  70                  75                  80

Cys Val Ile Glu Thr Val Tyr Ile Val Met Tyr Leu Val Tyr Ala Pro
                85                  90                  95

Arg Lys Ala Lys Ile Phe Thr Ala Lys Ile Val Leu Leu Asn Ile
                100                 105                 110

Thr Gly Phe Gly Leu Ile Phe Leu Leu Thr Leu Phe Ala Phe His Gly
                115                 120                 125

Glu Thr Arg Val Val Ser Leu Gly Trp Ile Cys Val Gly Phe Ser Val
                130                 135                 140

Cys Val Phe Val Ala Pro Leu Ser Ile Ile Gly Arg Val Ile Lys Thr
145                 150                 155                 160

```
Lys Ser Val Glu Tyr Met Pro Phe Thr Leu Ser Leu Thr Leu
            165                 170                 175

Ser Ala Ile Val Trp Phe Leu Tyr Gly Leu Leu Ile Lys Asp Lys Tyr
            180                 185                 190

Val Ala Leu Pro Asn Ile Leu Gly Phe Thr Phe Gly Val Ile Gln Met
            195                 200                 205

Val Leu Tyr Val Phe Tyr Met Asn Lys Thr Pro Val Ala Ser Glu Val
    210                 215                 220

Lys Glu Gly Lys Glu Ala Trp Lys Ala Pro Ala Glu Asp His Val Val
225                 230                 235                 240

Val Ile Asn Val Gly Lys Thr Asp Lys Gly Ser Cys Ala Glu Val Arg
                245                 250                 255

Pro Val Thr Glu Met Ala Ser Ala Val Asp Val Pro Arg Arg Cys Ala
            260                 265                 270

Ala Glu Ala Ala Ala Pro Gly Val Asp Phe Ala Arg Ser Val Asp
            275                 280                 285

Val Val
    290

<210> SEQ ID NO 54
<211> LENGTH: 310
<212> TYPE: PRT
<213> ORGANISM: Aegilops tauschii

<400> SEQUENCE: 54

Met Ala Phe Leu Asn Met Glu Gln His Thr Trp Ala Phe Thr Phe Gly
1               5                   10                  15

Ile Leu Gly Asn Ile Ile Ser Leu Met Val Phe Leu Ser Pro Leu Pro
            20                  25                  30

Thr Phe Tyr Arg Val Tyr Arg Lys Ser Thr Glu Gly Val Gln Pro
            35                  40                  45

Thr Pro Tyr Leu Val Thr Leu Phe Ser Cys Leu Leu Trp Met Tyr Tyr
    50                  55                  60

Ala Phe Leu Lys Ser Gly Ser Glu Leu Leu Leu Thr Ile Asn Ala Val
65                  70                  75                  80

Gly Cys Val Ile Glu Ser Leu Tyr Ile Ala Met Tyr Leu Val Tyr Ala
                85                  90                  95

Pro Lys Ser Ala Arg Leu Leu Thr Ala Lys Leu Phe Ile Gly Leu Asp
            100                 105                 110

Val Gly Leu Phe Gly Leu Ile Ala Leu Val Thr Met Leu Ala Ser Tyr
            115                 120                 125

Gly Pro Leu Arg Val Gln Val Val Gly Trp Ile Cys Val Ala Val Ala
    130                 135                 140

Leu Gly Val Phe Ala Ala Pro Leu Ser Ile Ile Arg Leu Val Ile Arg
145                 150                 155                 160

Thr Lys Ser Val Glu Phe Met Pro Phe Ser Leu Ser Phe Phe Leu Val
                165                 170                 175

Leu Ser Ala Val Ile Trp Phe Ala Tyr Gly Ala Leu Lys Lys Asp Ile
            180                 185                 190

Phe Val Ala Met Pro Asn Val Leu Gly Leu Phe Gly Val Ala Gln
            195                 200                 205

Met Ala Leu Tyr Met Ala Tyr Arg Asn Lys Lys Pro Ala Thr Val Val
    210                 215                 220

Leu Val His Glu Glu Met Lys Leu Pro Glu His Val Lys Glu Val Ala
```

```
                225                 230                 235                 240

Gly Gly Ala Lys Pro Gln Gly Gly Ala Pro Thr Glu Gly Arg Ile Ser
                245                 250                 255

Cys Gly Ala Glu Val His Pro Ile Asp Val Leu Pro Ala Val Ala Val
                260                 265                 270

Asp Glu Gln Ala Ala Gly Ala Ala Asp Glu Asp Val Ile Arg Asp Asp
                275                 280                 285

Gln Asn Met Leu Arg Pro Glu Gln Pro Val Val Ile Lys Pro Asp Val
                290                 295                 300

Ala Ile Val Val Gln Ala
305                 310

<210> SEQ ID NO 55
<211> LENGTH: 285
<212> TYPE: PRT
<213> ORGANISM: Aegilops tauschii

<400> SEQUENCE: 55

Met Ala Gly Leu Ser Leu Glu His Pro Trp Ala Phe Ala Phe Gly Leu
1               5                   10                  15

Leu Gly Asn Ile Ile Ser Phe Thr Ser Leu Leu Ala Pro Ile Pro Thr
                20                  25                  30

Phe Tyr Arg Ile Phe Lys Ser Lys Ser Thr Glu Gly Phe Gln Ser Val
            35                  40                  45

Pro Tyr Val Val Ala Leu Phe Ser Ala Met Leu Trp Ile Phe Tyr Ala
        50                  55                  60

Leu Val Lys Thr Gly Glu Gly Leu Leu Ile Ser Ile Asn Ala Ala Gly
65                  70                  75                  80

Cys Val Ile Glu Thr Val Tyr Ile Val Met Tyr Leu Val Tyr Ala Pro
                85                  90                  95

Arg Lys Ala Lys Ile Phe Thr Ala Lys Ile Val Leu Leu Asn Val
            100                 105                 110

Ala Gly Phe Gly Leu Ile Leu Leu Thr Leu Phe Ala Phe His Gly
        115                 120                 125

Glu Thr Arg Val Ile Ser Leu Gly Trp Ile Cys Val Gly Phe Ser Val
130                 135                 140

Cys Val Phe Val Ala Pro Leu Ser Ile Ile Gly Arg Val Ile Lys Thr
145                 150                 155                 160

Lys Ser Val Glu Tyr Met Pro Phe Ser Leu Ser Leu Thr Leu Thr Leu
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Thr Phe Gly Met Ile Gln Met
        195                 200                 205

Val Leu Tyr Met Phe Tyr Met Asn Ala Thr Pro Val Val Ser Asp Leu
210                 215                 220

Lys Glu Gly Lys Glu Gly Leu Lys Met Ser Ala Glu His Val Val
225                 230                 235                 240

Val Ile Asn Val Gly Lys Ser Glu Lys Ser Ser Gly Ala Val Val Arg
                245                 250                 255

Pro Val Thr Glu Met Val Lys Ala Val Pro Ala Ala Pro Gly Gln Gln
            260                 265                 270

Val Met Ala Leu Asp Ser Ala Arg Ser Val Asp Val Val
        275                 280                 285
```

<210> SEQ ID NO 56
<211> LENGTH: 287
<212> TYPE: PRT
<213> ORGANISM: Aegilops tauschii

<400> SEQUENCE: 56

Met Gly Gly Leu Ser Leu Gln His Pro Trp Ala Phe Ala Phe Gly Leu
1               5                   10                  15

Leu Gly Asn Val Ile Ser Phe Met Thr Tyr Leu Ala Pro Leu Pro Thr
            20                  25                  30

Phe Tyr Arg Ile Tyr Arg Ser Lys Ser Thr Gln Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asp Glu Leu Leu Ile Thr Ile Asn Ser Ala Gly
65                  70                  75                  80

Cys Ile Ile Glu Thr Ile Tyr Ile Val Met Tyr Leu Ala Tyr Ala Pro
                85                  90                  95

Lys Gln Ala Lys Ile Phe Thr Ala Lys Ile Leu Leu Leu Asn Val
            100                 105                 110

Gly Val Phe Gly Leu Ile Leu Leu Thr Leu Leu Ala Gly Gly
        115                 120                 125

Glu Lys Arg Val Val Met Leu Gly Trp Val Cys Val Gly Phe Ser Val
130                 135                 140

Ser Val Phe Val Ala Pro Leu Ser Ile Ile Arg Leu Val Val Arg Thr
145                 150                 155                 160

Arg Ser Val Glu Phe Met Pro Phe Ser Leu Ser Leu Ser Leu Thr Val
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Ala Phe Gly Val Ile Gln Met
        195                 200                 205

Gly Leu Tyr Ala Ile Tyr Cys Asn Ala Thr Pro Thr Leu Ala Pro Lys
    210                 215                 220

Glu Val Asp Arg Pro Leu Pro Glu His Val Ile Asn Val Ala Lys Leu
225                 230                 235                 240

Gly Pro Thr Ala Thr Ile Glu Leu Asn Met Pro Ala Ala Val Gln Pro
                245                 250                 255

Pro Thr Lys Glu Asn Ile Val Ala Cys Ala Ser Gly Glu Thr Lys Glu
            260                 265                 270

Ile Ser Val Glu Lys Val Asp Met Ala Thr Asn Val Glu His Val
        275                 280                 285

<210> SEQ ID NO 57
<211> LENGTH: 293
<212> TYPE: PRT
<213> ORGANISM: Aegilops tauschii

<400> SEQUENCE: 57

Met Gly Gly Leu Ser Leu Glu His Pro Trp Ala Phe Ala Phe Gly Leu
1               5                   10                  15

Leu Gly Asn Ile Ile Ser Phe Met Thr Tyr Leu Ala Pro Leu Pro Thr
            20                  25                  30

Phe Tyr Arg Ile Tyr Arg Ser Lys Ser Thr Gln Gly Phe Gln Ser Val
        35                  40                  45

```
Pro Tyr Val Val Ala Leu Phe Ser Ala Met Leu Trp Ile Tyr Tyr Ala
    50                  55                  60

Leu Leu Lys Ser Asp Glu Leu Leu Ile Thr Ile Asn Ser Ala Gly
 65              70                  75                  80

Cys Val Ile Glu Thr Ile Tyr Ile Ile Met Tyr Leu Thr Tyr Ala Pro
                85                  90                  95

Lys Gln Ala Lys Leu Phe Thr Ala Lys Ile Leu Leu Leu Leu Asn Val
            100                 105                 110

Gly Val Phe Gly Leu Ile Leu Leu Thr Leu Leu Leu Ala Gly Gly
            115                 120                 125

Glu Lys Arg Val Met Leu Gly Trp Val Cys Val Gly Phe Ser Val
    130                 135                 140

Ser Val Phe Val Ala Pro Leu Ser Val Ile Arg Leu Val Arg Thr
145                 150                 155                 160

Arg Ser Val Glu Phe Met Pro Phe Ser Leu Ser Leu Ser Leu Thr Val
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Ala Phe Gly Val Ile Gln Met
    195                 200                 205

Gly Leu Tyr Ala Leu Tyr Cys Asn Ala Met Pro Arg Gln Ala Pro Lys
    210                 215                 220

Glu Val Asp Asp Pro Met Ser Asp His Gly Ala Val Lys Ala Pro
225                 230                 235                 240

Glu His Val Val Asn Ile Ser Lys Leu Ser Pro Ala Ala Gly Ile Glu
                245                 250                 255

Leu Asn Thr Thr Val Asn Ala Glu Pro Pro Leu Lys Ser Leu Gly Val
                260                 265                 270

Ala Cys Ala Asn Glu Glu Thr Ile Gly Val Ser Val Asp Lys Ala Thr
            275                 280                 285

His Ile Glu Gln Val
            290

<210> SEQ ID NO 58
<211> LENGTH: 290
<212> TYPE: PRT
<213> ORGANISM: Aegilops tauschii

<400> SEQUENCE: 58

Met Gly Gly Leu Ser Met Glu His Pro Trp Ala Phe Ala Phe Gly Leu
 1               5                  10                  15

Leu Gly Asn Val Ile Ser Phe Ser Ser Leu Leu Ala Pro Ile Pro Thr
                20                  25                  30

Phe Tyr Arg Ile Phe Lys Ser Lys Ser Thr Glu Gly Phe Gln Ser Val
            35                  40                  45

Pro Tyr Val Val Ala Leu Phe Ser Ala Met Leu Trp Ile Phe Tyr Ala
    50                  55                  60

Leu Val Lys Thr Gly Glu Gly Leu Leu Ile Ser Ile Asn Ala Ala Gly
 65              70                  75                  80

Cys Val Ile Glu Thr Val Tyr Ile Val Met Tyr Leu Val Tyr Ala Asp
                85                  90                  95

Arg Lys Ala Lys Ile Phe Thr Ala Lys Ile Val Leu Leu Asn Ile
            100                 105                 110

Ala Gly Phe Gly Leu Ile Phe Leu Leu Thr Leu Phe Ala Phe His Gly
            115                 120                 125
```

```
Glu Thr Arg Val Val Thr Leu Gly Trp Ile Cys Val Gly Phe Ser Val
            130                 135                 140

Cys Val Phe Val Ala Pro Leu Ser Ile Ile Gly Arg Val Ile Lys Thr
145                 150                 155                 160

Lys Ser Val Glu Tyr Met Pro Phe Thr Leu Ser Leu Thr Leu Thr Leu
                165                 170                 175

Ser Ala Ile Val Trp Phe Leu Tyr Gly Leu Leu Ile Lys Asp Lys Tyr
            180                 185                 190

Val Ala Leu Pro Asn Ile Leu Gly Phe Thr Phe Gly Val Ile Gln Met
            195                 200                 205

Val Leu Tyr Val Phe Tyr Met Asn Lys Thr Pro Val Ala Ser Gln Val
            210                 215                 220

Lys Glu Gly Lys Glu Ala Trp Lys Ala Pro Ala Glu Asp His Val Val
225                 230                 235                 240

Val Ile Asn Val Gly Lys Ala Asp Lys Ser Ser Cys Ala Glu Val Arg
                245                 250                 255

Pro Val Thr Glu Met Ala Gly Ala Val Asp Val Pro Arg Arg Cys Ala
                260                 265                 270

Ala Glu Ala Ala Ala Pro Gly Val Asp Phe Ala Arg Ser Val Asn
            275                 280                 285

Val Val
    290

<210> SEQ ID NO 59
<211> LENGTH: 237
<212> TYPE: PRT
<213> ORGANISM: Aegilops tauschii

<400> SEQUENCE: 59

Met Gly Ala Val Gly Ser Pro Leu Val Phe Ala Val Gly Ile Leu Gly
1               5                   10                  15

Asn Ile Leu Ser Phe Leu Val Ile Leu Ala Pro Val Pro Thr Phe Tyr
                20                  25                  30

Arg Val Tyr Lys Arg Lys Ser Thr Glu Ser Phe Gln Ser Val Pro Tyr
            35                  40                  45

Ala Met Ala Leu Leu Ser Ala Met Leu Trp Leu Tyr Tyr Ala Leu Leu
50                  55                  60

Thr Lys Asp Leu Leu Leu Leu Thr Ile Asn Thr Val Gly Cys Val Val
65              70                  75                  80

Glu Ser Ala Tyr Leu Ala Ile Tyr Leu Ala Tyr Ala Pro Lys Gln Ala
                85                  90                  95

Arg Thr Phe Thr Ala Lys Leu Val Cys Ile Met Asn Val Ala Leu Tyr
            100                 105                 110

Gly Ala Met Val Cys Val Leu Gln Leu Leu Val Lys Asp Gly Glu Ser
            115                 120                 125

Arg Val Thr Ile Ala Gly Gly Ile Gly Ser Ala Phe Ala Leu Ala Val
            130                 135                 140

Phe Val Ala Pro Leu Ala Ile Ile Arg Gln Val Ile Arg Thr Lys Ser
145                 150                 155                 160

Val Glu Phe Leu Pro Phe Trp Leu Ser Phe Phe Leu Thr Ile Ser Ala
                165                 170                 175

Val Val Trp Phe Phe Tyr Gly Leu Leu Met Lys Asp Phe Phe Val Ala
            180                 185                 190

Thr Pro Asn Val Leu Gly Leu Leu Phe Gly Leu Ala Gln Met Ser Leu
```

```
                    195                 200                 205
His Leu Val Tyr Lys Asn Pro Lys Lys Gly Ala Val Ser Glu Val
    210                 215                 220

Gln Tyr Ser Ile Gly Leu Leu Val Trp Ala Arg Leu Ile
225                 230                 235

<210> SEQ ID NO 60
<211> LENGTH: 275
<212> TYPE: PRT
<213> ORGANISM: Aegilops tauschii

<400> SEQUENCE: 60

Met Ala Gly Gly Leu Phe Asp Met Ser His Pro Ala Ser Ala Leu Ala
1               5                   10                  15

Gly Ile Ala Gly Asn Ile Val Ser Phe Phe Val Phe Leu Ala Pro Met
                20                  25                  30

Ala Thr Phe Leu Gln Ile Tyr Arg Lys Lys Thr Thr Gly Gly Phe Ser
            35                  40                  45

Ser Val Pro Tyr Val Val Ala Leu Phe Ser Cys Ser Leu Leu Ile Phe
        50                  55                  60

Tyr Ala Leu Leu Lys Thr Asp Ser Pro Leu Leu Leu Thr Ile Asn Ser
65                  70                  75                  80

Phe Gly Cys Cys Ile Glu Thr Val Tyr Ile Val Ala Tyr Leu Val Tyr
                85                  90                  95

Ala Pro Pro Arg Ala Arg Leu Arg Thr Leu Ala Tyr Phe Phe Val Leu
            100                 105                 110

Asp Val Ala Ala Phe Gly Leu Val Leu Val Val Thr Met Tyr Ala Phe
        115                 120                 125

Ala Pro Ala His Arg Val Lys Phe Leu Gly Ser Val Cys Leu Ala Phe
    130                 135                 140

Ser Met Ala Val Phe Val Ala Pro Leu Ser Ile Ile Val Lys Val Ile
145                 150                 155                 160

Lys Thr Lys Ser Val Glu Phe Leu Pro Val Gly Leu Ser Phe Cys Leu
                165                 170                 175

Val Leu Ser Ala Val Ala Trp Phe Cys Tyr Gly Leu Phe Thr Lys Asp
            180                 185                 190

Pro Phe Val Met Tyr Pro Asn Val Gly Gly Phe Phe Phe Ser Cys Val
        195                 200                 205

Gln Ile Gly Leu Tyr Cys Trp Tyr Arg Lys Pro Ser Asn Ala Val Leu
    210                 215                 220

Pro Thr Thr Thr Ala Asp Ala Gly Asn Gly Asn Gly Pro Thr Pro
225                 230                 235                 240

Ala Ala Gly Ala Glu Gln Gln Thr Val Ile Asp Val Lys Asp Ala Ala
                245                 250                 255

Arg Ala Ala Glu Val Asp Gln Pro Glu Val Ile Glu Ile Val Pro Ala
            260                 265                 270

Pro Ala Val
        275

<210> SEQ ID NO 61
<211> LENGTH: 290
<212> TYPE: PRT
<213> ORGANISM: Capsella rubella

<400> SEQUENCE: 61

Met Ala Ile Ser Gln Ala Val Leu Ala Thr Val Phe Gly Ile Leu Gly
```

```
            1               5                  10                 15
Asn Val Ile Ser Phe Val Cys Leu Ala Pro Ile Pro Thr Phe Ile
            20                 25                 30
Arg Ile Tyr Lys Arg Lys Ser Ser Glu Gly Tyr Gln Ser Val Pro Tyr
            35                 40                 45
Val Ile Ser Leu Phe Ser Ala Met Leu Trp Leu Tyr Ala Met Ile
            50                 55                 60
Lys Lys Asp Ala Val Met Leu Ile Thr Ile Asn Ser Phe Ala Phe Val
65                 70                 75                 80
Ile Gln Ile Val Tyr Ile Ser Leu Phe Phe Tyr Ala Pro Lys Lys
                    85                 90                 95
Asp Lys Ile Leu Thr Val Lys Phe Val Leu Phe Val Asp Val Phe Ala
                    100                105                110
Phe Gly Leu Ile Phe Phe Ser Thr Tyr Phe Pro Ile His Gly Asn Lys
                    115                120                125
Arg Val Gln Val Leu Gly Tyr Ile Cys Met Val Phe Ala Leu Ser Val
            130                135                140
Phe Val Ala Pro Leu Gly Ile Ile Arg Lys Val Ile Lys Thr Lys Ser
145                150                155                160
Ala Glu Phe Met Pro Phe Gly Leu Ser Phe Phe Leu Thr Leu Ser Ala
                    165                170                175
Val Met Trp Phe Phe Tyr Gly Leu Leu Leu Lys Asp Lys Asn Ile Ala
                    180                185                190
Leu Pro Asn Val Leu Gly Phe Ile Phe Gly Val Leu Gln Met Val Leu
            195                200                205
Phe Val Ile Tyr Lys Lys Pro Gly Thr Lys Val Leu Glu Pro Ser Val
210                215                220
Ile Lys Leu Gln Asp Ile Ser Glu His Val Val Asp Val Val Arg Leu
225                230                235                240
Ser Ser Met Val Cys Asn Ser Gln Met Arg Thr Leu Val Pro Gln Asp
                    245                250                255
Ser Ala Asp Met Glu Asp Thr Ile Asp Ile Glu Glu Lys Met Lys Gly
                    260                265                270
Asp Ile Glu Lys Asn Lys Asp Asn Asn Lys Glu Ala Phe Leu Ile Ser
                    275                280                285
Lys Asn
        290

<210> SEQ ID NO 62
<211> LENGTH: 292
<212> TYPE: PRT
<213> ORGANISM: Capsella rubella

<400> SEQUENCE: 62

Met Ala Leu Thr His Asn Val Trp Ala Phe Val Phe Gly Ile Met Gly
1               5                  10                 15
Asn Ile Ile Ser Phe Val Val Phe Leu Ala Pro Val Pro Thr Phe Ile
                    20                 25                 30
Arg Ile Cys Lys Lys Lys Ser Thr Glu Gly Phe Gln Ser Leu Pro Tyr
                    35                 40                 45
Leu Ser Ala Ile Phe Ser Ala Met Leu Trp Ile Tyr Tyr Ala Met Gln
                    50                 55                 60
Lys Asp Gly Ser Gly Phe Leu Leu Ile Thr Ile Asn Ala Val Gly Cys
65                 70                 75                 80
```

Val Ile Glu Thr Ile Tyr Ile Val Leu Phe Val Thr Tyr Ala Asn Lys
            85                  90                  95

Lys Thr Arg Ile Ser Thr Leu Lys Val Leu Gly Leu Leu Asn Phe Leu
        100                 105                 110

Gly Phe Ala Ala Ile Val Leu Val Cys Glu Leu Leu Thr Lys Gly Ser
        115                 120                 125

Thr Arg Ala Lys Val Leu Gly Gly Ile Cys Val Gly Phe Ser Val Ser
130                 135                 140

Val Phe Ala Ala Pro Leu Ser Ile Met Arg Leu Val Val Arg Thr Arg
145                 150                 155                 160

Ser Val Glu Phe Met Pro Phe Ser Leu Ser Leu Phe Leu Thr Leu Ser
                165                 170                 175

Ala Val Thr Trp Leu Phe Tyr Gly Leu Ala Ile Lys Asp Phe Tyr Val
                180                 185                 190

Ala Leu Pro Asn Val Leu Gly Ala Phe Leu Gly Ala Val Gln Met Ile
            195                 200                 205

Leu Tyr Ile Val Phe Lys Tyr Tyr Met Thr Pro Val Ala Glu Lys Thr
    210                 215                 220

Asp Lys Ser Lys Ala Val Ser Ser Asp His Ser Ile Asp Ile Ala Lys
225                 230                 235                 240

Leu Thr Thr Val Ile Pro Gly Ser Thr Val His Glu Pro Pro Ala Val
                245                 250                 255

His Asn Val Pro Glu Thr Gln Ile Gln Val Thr Glu Val Lys Ser Gln
                260                 265                 270

Asn Met Thr Glu Pro Asn Asp Gln Thr Thr Ser Lys Asp Val Gln Asn
            275                 280                 285

Gln Asn Gln Val
    290

<210> SEQ ID NO 63
<211> LENGTH: 278
<212> TYPE: PRT
<213> ORGANISM: Capsella rubella

<400> SEQUENCE: 63

Met Val Leu Ala His Asn Val Leu Ala Val Thr Phe Gly Val Met Gly
1               5                   10                  15

Asn Ile Ile Ser Phe Ile Val Phe Leu Ala Pro Val Pro Thr Phe Val
                20                  25                  30

Arg Ile Cys Lys Lys Lys Ser Thr Glu Gly Phe Glu Ser Leu Pro Tyr
            35                  40                  45

Val Ser Ala Leu Phe Ser Ala Met Leu Trp Ile Tyr Tyr Ala Met Gln
50                  55                  60

Lys Asp Gly Ala Gly Phe Leu Leu Ile Thr Ile Asn Ala Val Gly Cys
65                  70                  75                  80

Phe Ile Glu Thr Ile Tyr Ile Ile Leu Phe Leu Thr Tyr Ala Asn Lys
            85                  90                  95

Lys Ala Arg Ile Ser Thr Leu Lys Val Leu Gly Leu Leu Asn Phe Leu
        100                 105                 110

Gly Phe Ala Ala Ile Ile Leu Val Cys Glu Leu Leu Thr Lys Gly Ser
        115                 120                 125

Asn Arg Glu Lys Val Leu Gly Gly Ile Cys Val Gly Phe Ser Val Cys
130                 135                 140

Val Phe Ala Ala Pro Leu Ser Ile Met Arg Val Val Ile Arg Thr Lys
145                 150                 155                 160

Ser Val Glu Phe Met Pro Phe Ser Leu Ser Phe Leu Thr Leu Ser
            165                 170                 175

Ala Ile Thr Trp Leu Phe Tyr Gly Leu Ala Ile Lys Asp Phe Tyr Val
            180                 185                 190

Ala Leu Pro Asn Ile Met Gly Ala Phe Leu Gly Ala Val Gln Met Ile
            195                 200                 205

Leu Tyr Val Ile Phe Lys Tyr Tyr Lys Ser Pro Val Val Asp Glu
            210                 215                 220

Thr Glu Lys Pro Lys Thr Val Ser Ala Asp His Ser Ile Asn Met Ala
225                 230                 235                 240

Lys Leu Ser Ser Thr Pro Ala Ser Gly Glu Leu Thr Val His Ser Ser
            245                 250                 255

Gln Thr Asn Pro Val Gln Thr Gly Ala Gly Asp Leu Glu Asp Gln Met
            260                 265                 270

Asp Lys Lys Ile Ser Asn
            275

<210> SEQ ID NO 64
<211> LENGTH: 287
<212> TYPE: PRT
<213> ORGANISM: Capsella rubella

<400> SEQUENCE: 64

Met Ala Leu Phe Asp Thr His Asn Thr Trp Ala Phe Val Phe Gly Leu
1               5                   10                  15

Leu Gly Asn Leu Ile Ser Phe Ala Val Phe Leu Ser Pro Val Pro Thr
            20                  25                  30

Phe Tyr Arg Ile Cys Lys Lys Thr Thr Glu Gly Phe Gln Ser Ile
            35                  40                  45

Pro Tyr Val Val Ala Leu Phe Ser Ala Met Leu Trp Leu Tyr Tyr Ala
50                  55                  60

Thr Gln Lys Lys Asp Val Phe Leu Leu Val Thr Ile Asn Ser Phe Gly
65                  70                  75                  80

Cys Phe Ile Glu Thr Ile Tyr Ile Ser Ile Phe Leu Ala Phe Ala Thr
            85                  90                  95

Lys Asn Ala Arg Met Leu Thr Val Lys Leu Leu Leu Met Asn Val
            100                 105                 110

Gly Gly Phe Cys Ala Ile Leu Leu Leu Cys Gln Phe Leu Ala Lys Gly
            115                 120                 125

Ala Thr Arg Ala Lys Ile Ile Gly Gly Ile Cys Val Gly Phe Ser Val
            130                 135                 140

Cys Val Phe Ala Ala Pro Leu Ser Ile Ile Arg Thr Val Ile Lys Thr
145                 150                 155                 160

Lys Ser Val Glu Tyr Met Pro Phe Ser Leu Ser Leu Thr Leu Thr Ile
            165                 170                 175

Ser Ala Val Ile Trp Leu Leu Tyr Gly Leu Ala Leu Lys Asp Ile Tyr
            180                 185                 190

Val Ala Phe Pro Asn Val Ile Gly Phe Ala Leu Gly Ala Leu Gln Met
            195                 200                 205

Ile Leu Tyr Val Val Tyr Lys Tyr Cys Lys Thr Ser Ser Asp Leu Val
            210                 215                 220

Glu Lys Glu Leu Glu Asn Ala Lys Leu Pro Glu Val Ser Ile Asp Met
225                 230                 235                 240

Leu Lys Leu Gly Gly Ala Ala Glu Pro Ala Cys Gly Ile Thr Val Val 245                 250                 255
Arg Ser Val Asn Met Cys Asn Cys Asn Asp Arg Arg Val Glu Ile Glu
            260                 265                 270
Asn Gly His Gly Leu Val Arg Asn Ser Ala Thr Ala Ala Ala Thr
        275                 280                 285

<210> SEQ ID NO 65
<211> LENGTH: 286
<212> TYPE: PRT
<213> ORGANISM: Capsella rubella

<400> SEQUENCE: 65

Met Gly Val Val Met Asn His His Leu Leu Thr Ile Ile Phe Gly Ile
1               5                   10                  15
Leu Gly Asn Ala Val Ser Phe Leu Val Leu Val Ala Pro Leu Pro Thr
            20                  25                  30
Phe Tyr Arg Ile Tyr Lys Lys Lys Ser Thr Glu Ser Phe Gln Ser Leu
        35                  40                  45
Pro Tyr Gln Val Ser Leu Phe Ser Cys Met Leu Trp Leu Tyr Tyr Ala
    50                  55                  60
Leu Ile Lys Lys Asn Ala Phe Leu Leu Ile Thr Ile Asn Ser Phe Gly
65                  70                  75                  80
Cys Val Val Gln Thr Ile Tyr Ile Ala Met Phe Leu Ala Tyr Ala Thr
                85                  90                  95
Arg Asp Lys Arg Ile Ser Ala Met Lys Leu Phe Ile Ala Ile Asn Val
            100                 105                 110
Val Phe Phe Ser Leu Ile Leu Leu Val Thr His Phe Val Val Lys Thr
        115                 120                 125
Pro Thr Leu Gln Val Ser Val Leu Gly Trp Ile Cys Val Ala Ile Ser
    130                 135                 140
Val Ala Val Phe Ala Ala Pro Leu Met Ile Val Ala Arg Val Val Lys
145                 150                 155                 160
Thr Lys Ser Val Glu Tyr Met Pro Phe Thr Leu Ser Phe Phe Leu Thr
                165                 170                 175
Ile Ser Ala Val Met Trp Phe Gly Tyr Gly Leu Phe Leu Asn Asp Ile
            180                 185                 190
Cys Ile Ala Ile Pro Asn Val Val Gly Phe Val Leu Gly Met Leu Gln
        195                 200                 205
Met Val Leu Tyr Cys Val Tyr Arg Asn Ala Ser Glu Lys Pro Glu Ile
    210                 215                 220
Glu Lys Lys Ile Asn Leu Ser Glu Gln Gln Leu Lys Ser Ile Val Val
225                 230                 235                 240
Met Ser Pro Leu Gly Val Ser Glu Val His Pro Val Val Thr Ala Ser
                245                 250                 255
Val Gly Pro Pro Ser Asp Ala Val His His Glu Glu Pro Ser Asn Gly
            260                 265                 270
Asn Arg Lys Cys His Val Glu Thr Ser Arg Pro Glu Asn Val
        275                 280                 285

<210> SEQ ID NO 66
<211> LENGTH: 291
<212> TYPE: PRT
<213> ORGANISM: Capsella rubella

<400> SEQUENCE: 66

Met Thr Leu Phe Asn Thr Glu Asn Thr Trp Ala Phe Val Phe Gly Leu

```
            1               5                  10                 15
          Leu Gly Asn Val Ile Ser Phe Ala Val Phe Leu Ser Pro Val Pro Thr
                          20                  25                 30

Phe Tyr Arg Ile Trp Lys Lys Thr Thr Glu Gly Phe Gln Ser Ile
                          35                  40              45

Pro Tyr Val Val Ala Leu Phe Ser Ala Thr Leu Trp Leu Tyr Tyr Ala
                          50                  55                 60

Thr Gln Lys Lys Asp Val Phe Leu Leu Val Thr Ile Asn Ala Phe Gly
          65                  70                  75                 80

Cys Phe Ile Glu Thr Ile Tyr Ile Ser Met Phe Leu Ala Tyr Ala Pro
                          85                  90                 95

Lys Pro Ala Arg Met Leu Thr Val Lys Ile Leu Leu Met Asn Phe
                          100                 105             110

Gly Gly Phe Cys Leu Ile Leu Leu Cys Gln Leu Leu Leu Lys Gly
                          115                 120             125

Ala Thr Arg Ala Lys Ile Ile Gly Gly Ile Cys Val Gly Phe Ser Val
                          130                 135                140

Cys Val Phe Ala Ala Pro Leu Ser Ile Ile Arg Thr Val Ile Lys Thr
          145                 150                 155                160

Arg Ser Val Glu Tyr Met Pro Phe Ser Leu Ser Leu Thr Leu Thr Ile
                          165                 170             175

Ser Ala Ile Ile Trp Phe Leu Tyr Gly Leu Ala Leu Lys Asp Ile Tyr
                          180                 185             190

Val Ala Phe Pro Asn Val Leu Gly Phe Ala Leu Gly Ala Leu Gln Met
                          195                 200             205

Ile Leu Tyr Val Val Tyr Lys Tyr Cys Lys Thr Ser Pro His Pro His
                          210                 215             220

Leu Gly Glu Lys Glu Val Glu Ala Ala Lys Leu Pro Glu Val Val Thr
          225                 230                 235                240

Leu Asp Met Leu Lys Leu Gly Ala Val Ala Ser Pro Asp Pro Gly His
                          245                 250             255

Val Val Arg Gln Cys Asn Lys Cys Thr Cys Gly Asn Asp Arg Arg Val
                          260                 265             270

Ala Glu Ile Glu Asp Gly Arg Gln Thr Pro Arg Asn Ser Ser Ala
                          275                 280             285

Ala Ala Thr
              290

<210> SEQ ID NO 67
<211> LENGTH: 260
<212> TYPE: PRT
<213> ORGANISM: Capsella rubella

<400> SEQUENCE: 67

Met Val Phe Ile Lys Val His Gln Leu Ala Phe Phe Gly Leu Met
          1               5                   10                 15

Gly Asn Ile Val Ser Phe Gly Val Phe Leu Ser Pro Val Pro Thr Phe
                          20                  25                 30

Tyr Gly Ile Tyr Lys Lys Lys Ser Ser Lys Gly Phe Gln Ser Ile Pro
                          35                  40              45

Tyr Ile Cys Ala Leu Ala Ser Ala Thr Leu Leu Tyr Tyr Gly Ile
                          50                  55              60

Met Lys Thr His Ala Tyr Leu Ile Ile Ser Ile Asn Thr Phe Gly Cys
          65                  70                  75                 80
```

-continued

```
Phe Ile Glu Ile Thr Tyr Leu Phe Leu Tyr Ile Phe Tyr Ala Pro Arg
                85                  90                  95

Glu Ala Arg Ile Phe Thr Leu Lys Leu Ile Val Ile Cys Asn Ile Gly
            100                 105                 110

Gly Leu Gly Leu Leu Ile Leu Leu Val Asn Leu Leu Val Pro Lys Pro
        115                 120                 125

His Arg Val Ser Thr Val Gly Trp Val Cys Ala Ala Tyr Ser Leu Ala
    130                 135                 140

Val Phe Ala Ser Pro Leu Ser Val Met Arg Lys Val Ile Lys Thr Lys
145                 150                 155                 160

Ser Val Glu Tyr Met Pro Phe Leu Leu Ser Leu Ser Leu Thr Leu Asn
                165                 170                 175

Ala Val Met Trp Phe Phe Tyr Gly Leu Leu Ile Lys Asp Lys Phe Ile
            180                 185                 190

Ala Met Pro Asn Ile Leu Gly Phe Leu Phe Gly Val Ala Gln Met Ile
        195                 200                 205

Leu Tyr Met Met Tyr Gln Gly Ser Thr Lys Thr Asp Leu Pro Thr Glu
    210                 215                 220

His Gln Leu Gly Asn Lys Thr Asp Val Asn Glu Ile Ala Val Val Ala
225                 230                 235                 240

Val Glu Leu Pro Asp Ala Arg Leu Asp Asn Val Glu Gly Ser Ala Arg
                245                 250                 255

Pro Ala Met Lys
            260

<210> SEQ ID NO 68
<211> LENGTH: 344
<212> TYPE: PRT
<213> ORGANISM: Zea mays

<400> SEQUENCE: 68

Met Ala Gly Leu Ser Leu Gln His Pro Met Ala Phe Ala Phe Gly Leu
1               5                   10                  15

Leu Gly Asn Ile Ile Ser Phe Met Thr Tyr Leu Ala Pro Leu Pro Thr
            20                  25                  30

Phe Cys Arg Ile Tyr Arg Asn Lys Ser Thr Glu Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asn Glu Phe Leu Leu Ile Thr Ile Asn Ser Ala Gly
65              70                  75                  80

Cys Val Ile Glu Thr Leu Tyr Ile Ala Thr Tyr Leu Leu Tyr Ala Pro
                85                  90                  95

Asn Lys Ala Lys Leu Phe Thr Ala Lys Ile Leu Leu Leu Leu Asn Val
            100                 105                 110

Gly Val Phe Gly Leu Ile Leu Leu Thr Leu Leu Ser Ala Gly
        115                 120                 125

Pro His Arg Val Val Leu Gly Trp Val Cys Val Ala Phe Ser Val
    130                 135                 140

Ser Val Phe Val Ala Pro Leu Ser Ile Ile Arg Gln Val Arg Thr
145                 150                 155                 160

Arg Ser Val Glu Phe Met Pro Phe Ser Leu Ser Phe Ser Leu Thr Ala
                165                 170                 175

Ser Ala Val Val Trp Phe Leu Tyr Gly Leu Leu Ile Lys Asp Lys Tyr
            180                 185                 190
```

```
Val Ala Leu Pro Asn Val Leu Gly Phe Thr Phe Gly Val Val Gln Met
            195                 200                 205

Gly Met Tyr Ala Leu Tyr Arg Asn Ala Thr Pro Arg Val Pro Ala Ala
        210                 215                 220

Lys Glu Ala Ala Ala Ala Asp Asp Gly Asn Thr Phe Asn Phe Lys
225                 230                 235                 240

Ala Pro Gly Glu His Val Val Thr Ile Ala Lys Leu Thr Ala Ala
            245                 250                 255

Pro Ala Thr Ala Ala Glu Leu Ile Ile Lys Ala Arg Asp Asp Ala Gln
        260                 265                 270

His Pro Pro Glu Glu Ala Ala Ala Lys Ala Pro Ala Lys
            275                 280                 285

Ser Lys Leu Leu Ile Pro Leu Pro Glu His Ala Tyr Ala Cys Met Cys
        290                 295                 300

Ile Ile Arg Ser Gly Ser His His Lys Leu Gly Arg Ala Cys Leu Leu
305                 310                 315                 320

Gly Thr Ser Thr Arg Pro Pro Ala Cys Leu Pro Ala Arg Met Ile Gln
                325                 330                 335

Ser Ser Cys Tyr Ile Arg Lys Gly
            340

<210> SEQ ID NO 69
<211> LENGTH: 295
<212> TYPE: PRT
<213> ORGANISM: Zea mays

<400> SEQUENCE: 69

Met Ala Gly Leu Ser Leu Gln His Pro Trp Ala Phe Thr Phe Gly Leu
1               5                   10                  15

Leu Gly Asn Val Ile Ser Phe Met Thr Phe Leu Ala Pro Ile Pro Thr
            20                  25                  30

Phe Tyr Arg Ile Tyr Lys Ser Lys Ser Thr Glu Gly Phe Gln Ser Val
        35                  40                  45

Pro Tyr Val Val Ala Leu Phe Ser Ala Met Leu Trp Ile Phe Tyr Ala
    50                  55                  60

Leu Ile Lys Ser Asn Glu Thr Phe Leu Ile Thr Ile Asn Ala Ala Gly
65                  70                  75                  80

Cys Val Ile Glu Thr Val Tyr Val Val Met Tyr Phe Val Tyr Ala Thr
                85                  90                  95

Lys Lys Gly Arg Met Phe Thr Ala Lys Ile Met Leu Leu Leu Asn Val
            100                 105                 110

Gly Ala Phe Gly Ala Ile Leu Leu Leu Thr Leu Leu Leu Phe Lys Gly
        115                 120                 125

Asp Lys Arg Val Val Met Leu Gly Trp Ile Cys Val Gly Phe Ser Val
    130                 135                 140

Ser Val Phe Val Ala Pro Leu Ser Ile Met Arg Arg Val Ile Gln Thr
145                 150                 155                 160

Lys Ser Val Glu Tyr Met Pro Phe Ser Leu Ser Leu Ser Leu Thr Leu
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Thr Phe Gly Val Val Gln Met
        195                 200                 205

Val Leu Tyr Val Val Tyr Met Asn Lys Thr Pro Leu Pro Val Ala Asp
```

```
                210                 215                 220
Gly Lys Ala Ala Gly Lys Leu Pro Ser Ala Ala Asp Glu His Val Val
225                 230                 235                 240

Val Asn Val Thr Lys Leu Ser Pro Gly Arg Leu Pro Pro Val Thr Gln
                245                 250                 255

Met Ala Ala Val Pro Thr Lys Ser Cys Ala Thr Glu Ala Ala Ala Pro
                260                 265                 270

Ala Thr Leu Pro Ser Arg Asp Val Val Asp Val Leu Val Asn Arg His
                275                 280                 285

Ser Pro Ala Val His Val Thr
                290                 295

<210> SEQ ID NO 70
<211> LENGTH: 301
<212> TYPE: PRT
<213> ORGANISM: Zea mays

<400> SEQUENCE: 70

Met Ala Gly Leu Ser Leu Glu His Pro Trp Ala Phe Ala Phe Gly Leu
1               5                   10                  15

Leu Gly Asn Val Ile Ser Phe Met Thr Phe Leu Ala Pro Ile Pro Thr
                20                  25                  30

Phe Tyr Arg Ile Tyr Lys Ser Lys Ser Thr Glu Gly Phe Gln Ser Val
            35                  40                  45

Pro Tyr Val Val Ala Leu Phe Ser Ala Met Leu Trp Ile Phe Tyr Ala
50                  55                  60

Leu Ile Lys Ser Asn Glu Thr Phe Leu Ile Thr Ile Asn Ala Ala Gly
65                  70                  75                  80

Cys Val Ile Glu Thr Ile Tyr Ile Val Met Tyr Phe Val Tyr Ala Pro
                85                  90                  95

Lys Lys Ala Lys Leu Phe Thr Ala Lys Ile Met Ala Leu Leu Asn Gly
            100                 105                 110

Gly Val Phe Gly Val Ile Leu Leu Thr Leu Leu Leu Phe Lys Gly
            115                 120                 125

Ser Lys Arg Val Val Leu Leu Gly Trp Ile Cys Val Gly Phe Ser Val
130                 135                 140

Ser Val Phe Val Ala Pro Leu Ser Ile Met Arg Arg Val Ile Gln Thr
145                 150                 155                 160

Lys Ser Val Glu Tyr Met Pro Phe Ser Leu Ser Leu Ser Leu Thr Leu
                165                 170                 175

Ser Ala Val Val Trp Phe Leu Tyr Gly Leu Leu Ile Lys Asp Lys Tyr
                180                 185                 190

Val Ala Leu Pro Asn Val Leu Gly Phe Ile Phe Gly Val Val Gln Met
            195                 200                 205

Val Leu Tyr Val Phe Tyr Met Asn Lys Thr Pro Val Ala Ala Ala Val
210                 215                 220

Gly Lys Asp Ala Gly Lys Leu Pro Ser Ala Ala Asp Glu His Val Leu
225                 230                 235                 240

Val Asn Ile Ala Lys Leu Asn Pro Ala Leu Pro Glu Arg Thr Ser Gly
                245                 250                 255

Met His Pro Val Thr Gln Met Ala Ala Val Pro Ala Arg Ser Cys Ala
                260                 265                 270

Ala Glu Ala Ile Ala Pro Ala Met Leu Pro Asn Arg Asp Val Val Asp
            275                 280                 285
```

-continued

```
Val Phe Val Ser Arg His Ser Pro Ala Val His Val Val
    290                 295                 300

<210> SEQ ID NO 71
<211> LENGTH: 310
<212> TYPE: PRT
<213> ORGANISM: Zea mays

<400> SEQUENCE: 71

Met Ala Gly Gly Leu Phe Ser Met Ala His Pro Ala Val Thr Leu Ser
1               5                   10                  15

Gly Ile Ala Gly Asn Ile Ile Ser Phe Leu Val Phe Leu Ala Pro Val
            20                  25                  30

Ala Thr Phe Leu Gln Val Tyr Arg Lys Lys Ser Thr Gly Gly Phe Ser
        35                  40                  45

Ser Val Pro Tyr Val Val Ala Leu Phe Ser Ser Val Leu Trp Ile Phe
    50                  55                  60

Tyr Ala Leu Val Lys Thr Asn Ser Arg Pro Leu Leu Thr Ile Asn Ala
65                  70                  75                  80

Phe Gly Cys Gly Val Glu Ala Ala Tyr Ile Val Leu Tyr Leu Ala Tyr
                85                  90                  95

Ala Pro Arg Arg Ala Arg Leu Arg Thr Leu Ala Tyr Phe Phe Leu Leu
            100                 105                 110

Asp Val Ala Ala Phe Ala Leu Val Val Ala Val Thr Leu Phe Ala Val
        115                 120                 125

Arg Glu Pro His Arg Val Lys Phe Leu Gly Ser Val Cys Leu Ala Phe
    130                 135                 140

Ser Met Ala Val Phe Val Ala Pro Leu Ser Ile Ile Val Lys Val Val
145                 150                 155                 160

Lys Thr Lys Ser Val Glu Phe Leu Pro Ile Ser Leu Ser Phe Cys Leu
                165                 170                 175

Thr Leu Ser Ala Val Ala Trp Phe Cys Tyr Gly Leu Phe Thr Lys Asp
            180                 185                 190

Pro Phe Val Met Tyr Pro Asn Val Gly Gly Phe Phe Phe Ser Cys Val
        195                 200                 205

Gln Met Gly Leu Tyr Phe Trp Tyr Arg Lys Pro Arg Pro Ala Ala Lys
    210                 215                 220

Asn Asn Ala Val Leu Pro Thr Thr Thr Asp Gly Gly Asn Ala Val Gln
225                 230                 235                 240

Val Gln Gly Gln Val Ile Glu Leu Ala Pro Asn Thr Val Ala Ile Leu
                245                 250                 255

Ser Val Ser Pro Ile Pro Ile Val Gly Val His Lys Ile Glu Val Val
            260                 265                 270

Glu Gln Gln His Lys Glu Ala Ala Val Ala Ala Glu Thr Arg Arg Met
        275                 280                 285

Ala Ala Ala Asn Pro Asp Gly Ala Met Pro Glu Val Ile Glu Ile Val
    290                 295                 300

Pro Ala Ala Ala Ala Val
305                 310

<210> SEQ ID NO 72
<211> LENGTH: 307
<212> TYPE: PRT
<213> ORGANISM: Zea mays

<400> SEQUENCE: 72
```

Met Ala Phe Leu Asn Met Glu Gln Gln Thr Trp Ala Phe Thr Phe Gly
1               5                   10                  15

Ile Leu Gly Asn Ile Val Ser Leu Met Val Phe Leu Ser Pro Leu Pro
            20                  25                  30

Thr Phe Tyr Arg Val Tyr Arg Asn Lys Ser Thr Glu Gly Phe Gln Ser
        35                  40                  45

Thr Pro Tyr Val Val Thr Leu Phe Ser Cys Met Leu Trp Ile Leu Tyr
    50                  55                  60

Ala Leu Leu Lys Pro Gly Ala Glu Leu Leu Val Thr Ile Asn Gly Val
65                  70                  75                  80

Gly Cys Val Val Glu Thr Val Tyr Leu Ala Met Tyr Leu Val Tyr Ala
                85                  90                  95

Pro Lys Ala Ala Arg Val Leu Ala Ala Lys Met Leu Leu Gly Leu Asn
            100                 105                 110

Val Ala Val Phe Gly Leu Val Ala Leu Val Thr Met Leu Leu Ser Asp
            115                 120                 125

Ala Gly Leu Arg Val His Val Leu Gly Trp Ile Cys Val Ser Val Ser
            130                 135                 140

Leu Ser Val Phe Ala Ala Pro Leu Ser Ile Met Arg Gln Val Ile Arg
145                 150                 155                 160

Thr Lys Ser Val Glu Phe Met Pro Ile Ser Leu Ser Phe Phe Leu Val
                165                 170                 175

Leu Ser Ala Val Val Trp Phe Ala Tyr Gly Ala Leu Lys Lys Asp Val
            180                 185                 190

Phe Val Ala Phe Pro Asn Val Leu Gly Phe Val Phe Gly Leu Ala Gln
            195                 200                 205

Met Ala Leu Tyr Met Ala Tyr Ser Arg Asn Arg Lys Pro Ala Ala Ala
            210                 215                 220

Leu Val Ile Leu Pro Glu Gln Ser Lys Glu Glu Ala Ala Glu Gly Lys
225                 230                 235                 240

Ala Ser Cys Gly Gly Ala Glu Val His Pro Ile Asp Ile Ala Glu Val
                245                 250                 255

His Asp Leu Gln Ala Val Val Val Asp Val Asp Val Glu Pro Val Thr
            260                 265                 270

Tyr Ala Ala Ala Ser Gly Met Val Asp Gly Ser Val Gly Arg Pro Arg
            275                 280                 285

Ala Pro Glu Gln Leu Val Ile Lys Pro Asp Met Val Thr Val Ile Ala
            290                 295                 300

Ala Glu Ala
305

<210> SEQ ID NO 73
<211> LENGTH: 260
<212> TYPE: PRT
<213> ORGANISM: Glycine max

<400> SEQUENCE: 73

Met Ala Ile Asn His Glu Thr Trp Ala Phe Val Phe Gly Leu Leu Gly
1               5                   10                  15

Asn Val Ile Ser Phe Met Val Phe Leu Ala Pro Leu Pro Thr Phe Tyr
            20                  25                  30

Gln Ile Tyr Lys Lys Lys Ser Thr Glu Glu Phe Gln Ser Leu Pro Tyr
        35                  40                  45

Val Val Ala Leu Phe Ser Ser Met Leu Trp Ile Tyr Tyr Ala Leu Val
    50                  55                  60

```
Lys Lys Asp Ala Ser Leu Leu Ile Thr Ile Asn Ser Phe Gly Cys
 65                  70                  75                  80

Val Ile Glu Thr Ile Tyr Leu Ala Ile Phe Leu Ile Tyr Ala Pro Ser
                 85                  90                  95

Lys Thr Arg Leu Trp Thr Ile Lys Leu Leu Met Leu Asn Val Phe
            100                 105                 110

Gly Phe Gly Ala Met Leu Leu Ser Thr Leu Tyr Leu Thr Thr Gly Ser
            115                 120                 125

Lys Arg Leu Thr Val Ile Gly Trp Ile Cys Leu Val Phe Asn Ile Ser
        130                 135                 140

Val Phe Ala Ala Pro Leu Cys Ile Ile Lys Arg Val Ile Lys Thr Lys
145                 150                 155                 160

Ser Val Glu Phe Met Pro Phe Ser Leu Ser Phe Leu Thr Ile Asn
                    165                 170                 175

Ala Val Met Trp Phe Phe Tyr Gly Leu Leu Leu Lys Asp Tyr Tyr Val
                180                 185                 190

Ala Leu Pro Asn Thr Leu Gly Phe Leu Phe Ser Ile Ile Gln Met Val
            195                 200                 205

Leu Tyr Leu Ile Tyr Arg Asn Ala Lys Thr Pro Asp Leu Pro Met Lys
        210                 215                 220

Leu Gln Glu Leu Asn Ser His Thr Ile Asp Val Gly Lys Leu Ser Arg
225                 230                 235                 240

Met Glu Pro Ser Glu Pro Asn His Val Thr Lys Asn Gly Thr Leu Thr
                    245                 250                 255

Glu Arg Glu Ile
            260

<210> SEQ ID NO 74
<211> LENGTH: 268
<212> TYPE: PRT
<213> ORGANISM: Glycine max

<400> SEQUENCE: 74

Met Ala Ile Ser His Ser Thr Leu Ala Phe Ala Phe Gly Met Leu Gly
1               5                  10                  15

Asn Val Ile Ser Phe Leu Val Phe Leu Ala Pro Ile Thr Thr Phe Tyr
                20                  25                  30

Arg Ile Phe Lys Lys Ser Thr Glu Gly Phe Gln Ser Leu Pro Tyr
            35                  40                  45

Leu Val Ala Leu Phe Ser Ser Met Leu Trp Leu Tyr Tyr Ala Leu Leu
        50                  55                  60

Lys Lys Asp Ala Met Leu Leu Leu Thr Ile Asn Ser Phe Gly Cys Val
 65                  70                  75                  80

Ile Glu Val Ile Tyr Ile Ile Leu Tyr Ile Thr Tyr Ala Thr Arg Asp
                 85                  90                  95

Ala Arg Asn Leu Thr Leu Lys Leu Phe Ala Met Asn Val Gly Ala
            100                 105                 110

Phe Ala Leu Ile Leu Leu Val Thr His Phe Ala Val His Gly Ser Leu
        115                 120                 125

Arg Val Gln Val Leu Gly Trp Ile Cys Val Ser Leu Ser Ile Ser Val
        130                 135                 140

Phe Ala Ala Pro Leu Ser Ile Val Ala Gln Val Val Arg Thr Lys Ser
145                 150                 155                 160

Val Glu Phe Met Pro Phe Asn Leu Ser Phe Thr Leu Thr Leu Ser Ala
```

```
            165                 170                 175
Ile Met Trp Phe Gly Tyr Gly Leu Phe Leu Lys Asp Ile Cys Ile Ala
            180                 185                 190

Leu Pro Asn Val Leu Gly Phe Ala Leu Gly Leu Leu Gln Met Leu Leu
            195                 200                 205

Tyr Ala Ile Tyr Arg Asn Gly Asn Lys Lys Val Asp Lys Ile Met Glu
            210                 215                 220

Lys Lys Ala Pro Leu Glu Pro Leu Lys Thr Val Val Ile Glu Thr Gly
225                 230                 235                 240

Leu Glu Glu Lys Gln Gln Gly Lys Lys Ser Lys Glu Asn Ser Glu Glu
                245                 250                 255

Lys Glu Lys Ser Asp Glu Pro Asn Asp Cys Ala Val
                260                 265
```

<210> SEQ ID NO 75
<211> LENGTH: 257
<212> TYPE: PRT
<213> ORGANISM: Glycine max

<400> SEQUENCE: 75

```
Met Thr Met His Arg Glu Ser Trp Ala Phe Val Phe Gly Val Met Gly
1               5                   10                  15

Asn Ile Ile Ser Phe Gly Val Phe Leu Ala Pro Leu Pro Thr Phe Tyr
                20                  25                  30

Gln Ile Tyr Lys Lys Ser Thr Glu Gly Phe Gln Ser Leu Pro Tyr
                35                  40                  45

Val Val Ala Leu Phe Ser Ala Met Leu Trp Ile Tyr Tyr Ala Phe Val
    50                  55                  60

Lys Arg Glu Ala Ala Leu Leu Leu Ile Thr Ile Asn Thr Phe Gly Ile
65                  70                  75                  80

Val Val Glu Ser Ile Tyr Leu Ala Ile Phe Leu Leu Tyr Ala Pro Arg
                85                  90                  95

Lys Pro Arg Leu Thr Thr Ile Lys Leu Leu Leu Leu Asn Val Phe
                100                 105                 110

Gly Phe Gly Ala Met Leu Leu Ser Thr Leu Tyr Leu Ser Lys Gly Ala
            115                 120                 125

Lys Arg Leu Ala Ile Ile Gly Trp Ile Cys Leu Val Phe Asn Ile Ser
130                 135                 140

Val Phe Ala Ala Pro Leu Phe Ile Ile Arg Arg Val Ile Lys Thr Arg
145                 150                 155                 160

Ser Val Glu Tyr Met Pro Phe Thr Leu Ser Met Phe Leu Thr Ile Asn
                165                 170                 175

Ala Val Met Trp Phe Phe Tyr Gly Leu Leu Leu Arg Asp Tyr Tyr Val
                180                 185                 190

Ala Leu Pro Asn Thr Leu Gly Phe Val Phe Gly Ile Ile Gln Met Gly
                195                 200                 205

Met Tyr Leu Met Tyr Arg Asn Ala Thr Pro Val Ala Leu Glu Glu Pro
            210                 215                 220

Val Lys Ala Gln Glu Leu Asn Gly His Ile Ile Asp Val Gly Lys Met
225                 230                 235                 240

Gly Thr Met Glu Pro Asn His Ala Ala Thr Ala Gly Ala Val Gly Lys
                245                 250                 255

Val
```

<210> SEQ ID NO 76
<211> LENGTH: 258
<212> TYPE: PRT
<213> ORGANISM: Glycine max

<400> SEQUENCE: 76

Met Ala Ile Asn His Glu Thr Trp Ala Phe Ile Phe Gly Leu Leu Gly
1               5                   10                  15

Asn Val Ile Ser Phe Met Val Phe Leu Ala Ser Leu Pro Thr Leu Tyr
            20                  25                  30

Gln Ile Tyr Lys Lys Ser Thr Asp Gly Phe Gln Ser Leu Pro Tyr
        35                  40                  45

Ile Val Ala Leu Phe Ser Ser Met Leu Trp Ile Tyr Tyr Ala Leu Val
    50                  55                  60

Lys Lys Asp Ala Ser Leu Leu Ile Thr Ile Asn Ser Phe Gly Cys
65                  70                  75                  80

Val Ile Glu Thr Ile Tyr Leu Ala Ile Phe Leu Ile Tyr Ala Pro Ser
                85                  90                  95

Lys Thr Arg Leu Trp Thr Ile Lys Leu Leu Leu Met Leu Asn Val Phe
            100                 105                 110

Gly Phe Gly Ala Met Leu Leu Ser Thr Leu Tyr Leu Thr Thr Gly Ser
            115                 120                 125

Lys Arg Leu Ser Val Ile Gly Trp Ile Cys Leu Val Leu Asn Ile Ser
130                 135                 140

Val Phe Ala Ala Pro Leu Cys Ile Met Lys Arg Val Ile Lys Thr Lys
145                 150                 155                 160

Ser Val Glu Phe Met Pro Phe Ser Leu Ser Phe Phe Leu Thr Ile Asn
                165                 170                 175

Ala Val Met Trp Phe Phe Tyr Gly Leu Leu Lys Asp Tyr Tyr Ile
            180                 185                 190

Ala Leu Pro Asn Thr Leu Gly Phe Leu Phe Gly Ile Ile Gln Met Val
        195                 200                 205

Leu Tyr Leu Ile Tyr Arg Asn Ala Lys Pro Gln Gly Leu Glu Glu Pro
210                 215                 220

Thr Lys Val Gln Glu Leu Asn Gly His Ile Ile Asp Val Val Lys Pro
225                 230                 235                 240

Asn His Val Thr Lys Asn Gly Pro Val Pro Val Ile Glu Thr Ala Ser
                245                 250                 255

Asn Val

<210> SEQ ID NO 77
<211> LENGTH: 289
<212> TYPE: PRT
<213> ORGANISM: Vitis vinifera

<400> SEQUENCE: 77

Met Ala Met Ala Met Ala Asn His His Thr Leu Gly Leu Ile Phe Gly
1               5                   10                  15

Ile Leu Gly Asn Ile Ile Ser Phe Leu Val Tyr Phe Ala Pro Ala Pro
            20                  25                  30

Thr Phe Tyr Arg Ile Tyr Lys Arg Lys Ser Ala Glu Gly Phe His Ser
        35                  40                  45

Leu Pro Tyr Ile Val Ala Leu Phe Ser Ala Met Leu Trp Leu Tyr Tyr
    50                  55                  60

Ala Leu Leu Lys Lys Asp Ala Phe Leu Leu Ile Thr Ile Asn Ser Phe
65                  70                  75                  80

```
Gly Cys Ala Ile Glu Ser Phe Tyr Ile Leu Leu Tyr Phe Phe Tyr Ala
                85                  90                  95
Pro Met Gln Ala Lys Lys Gln Thr Leu Lys Val Val Ile Ser Leu Asn
            100                 105                 110
Val Gly Val Phe Ser Ile Leu Val Val Leu Ile Gln Phe Leu Leu Lys
        115                 120                 125
Gly Ser Asn Arg Ile Asn Val Phe Gly Trp Ile Cys Ala Ser Phe Ser
130                 135                 140
Val Ala Val Phe Ala Ala Pro Leu Ser Ile Val Ala Lys Val Ile Arg
145                 150                 155                 160
Thr Lys Ser Val Glu Phe Met Pro Phe Ser Leu Ser Phe Phe Leu Thr
                165                 170                 175
Leu Ser Ala Ile Met Trp Phe Ala Tyr Gly Leu Leu Lys Asn Asp Pro
            180                 185                 190
Cys Val Ala Ile Pro Asn Ile Leu Gly Val Ile Leu Gly Leu Val Gln
        195                 200                 205
Met Val Leu Tyr Gly Phe Tyr Arg Asn Ala Gly Lys Glu Lys Met Glu
210                 215                 220
Lys Lys Leu Pro Glu His Ile Ile Asp Met Val Met Leu Ser Thr Leu
225                 230                 235                 240
Gly Thr Ser Asp Ile His Pro Ile Gly Ala Gln Gln Asn Gly Ile Lys
                245                 250                 255
Lys Ser Gly Ser Glu Asp Val Lys Asp Asp Glu Glu Thr Gly Asn Arg
            260                 265                 270
Glu Lys Ser Thr Glu Asn Ser Gly Glu Leu Gln Pro Asn Gly Ser Thr
        275                 280                 285
Val

<210> SEQ ID NO 78
<211> LENGTH: 278
<212> TYPE: PRT
<213> ORGANISM: Vitis vinifera

<400> SEQUENCE: 78

Met Ala Val Val Thr Val Lys Gln Leu Ala Phe Ile Phe Gly Leu Leu
1               5                   10                  15
Gly Asn Leu Val Ser Phe Met Val Tyr Leu Ser Pro Val Pro Thr Phe
            20                  25                  30
Phe Lys Ile Tyr Lys Arg Lys Thr Ser Glu Gly Tyr Gln Ala Leu Pro
        35                  40                  45
Tyr Ser Val Gly Leu Leu Cys Ala Ser Leu Phe Leu Tyr Tyr Ala Leu
50                  55                  60
Leu Gln Ser Gly Lys Phe Leu Ile Leu Ser Ile Asn Thr Ile Gly Ser
65                  70                  75                  80
Thr Ile Gln Ala Thr Tyr Leu Val Leu Phe Ile Ile Tyr Ser Pro Arg
                85                  90                  95
Ala Gly Lys Val Ala Thr Leu Lys Met Ile Leu Ile Leu Asn Val Ala
            100                 105                 110
Ser Leu Gly Leu Val Leu Leu Leu Thr Thr Leu Phe Ser Lys Gly Lys
        115                 120                 125
Thr Arg Ile Gln Val Val Gly Trp Ile Ser Ala Gly Val Asn Ile Gly
130                 135                 140
Thr Phe Val Ala Pro Leu Ser Ile Ile Lys Arg Val Ile Glu Thr Arg
145                 150                 155                 160
```

```
Ser Val Glu Tyr Met Pro Phe Asn Leu Ser Phe Phe Leu Thr Ile Cys
                165                 170                 175

Ala Thr Met Trp Phe Phe Tyr Gly Ile Phe Val Arg Asp Phe Phe Ile
            180                 185                 190

Ala Ile Pro Asn Val Val Gly Phe Val Phe Gly Ile Ala Gln Met Phe
        195                 200                 205

Leu Tyr Ile Ile Tyr Lys Tyr Met Met Lys Ser Asp Glu Thr Thr Leu
    210                 215                 220

Glu Gln Leu Glu Glu Thr Thr Glu Arg Pro Leu Tyr Val Pro Thr Ala
225                 230                 235                 240

Asn His Glu Pro Ser Gly Gln Glu Leu Lys Ala Val Thr Ile Thr Ser
                245                 250                 255

Pro Arg Gln Val Asp Tyr Phe Thr Glu His His Pro Met Phe Met Glu
            260                 265                 270

Arg Asp Glu Tyr Leu Ser
            275

<210> SEQ ID NO 79
<211> LENGTH: 270
<212> TYPE: PRT
<213> ORGANISM: Vitis vinifera

<400> SEQUENCE: 79

Met Ala Leu Phe Pro Ile His His Pro Leu Val Phe Ile Phe Gly Ile
1               5                   10                  15

Leu Gly Asn Leu Ile Ser Phe Met Val Tyr Leu Ala Pro Leu Pro Thr
            20                  25                  30

Phe Tyr Gln Ile Tyr Lys Arg Lys Ser Thr Glu Gly Phe Gln Ser Val
        35                  40                  45

Pro Tyr Val Val Ala Leu Phe Ser Ala Met Leu Trp Ile Tyr Tyr Ala
    50                  55                  60

Phe Leu Asn Thr Asp Ala Ser Leu Leu Ile Thr Ile Asn Ser Val Gly
65                  70                  75                  80

Cys Val Ile Glu Thr Ser Tyr Ile Val Met Phe Leu Val Tyr Ala Pro
                85                  90                  95

Lys Lys Ala Arg Ile Thr Thr Val Lys Leu Val Phe Leu Met Asn Ile
            100                 105                 110

Cys Gly Phe Gly Ser Ile Leu Leu Leu Thr Leu Leu Leu Ala Glu Gly
        115                 120                 125

Ala Asn Arg Val Arg Ile Leu Gly Trp Val Cys Leu Val Phe Ser Leu
    130                 135                 140

Ser Val Phe Leu Ala Pro Leu Cys Ile Met Arg Gln Val Ile Arg Thr
145                 150                 155                 160

Lys Ser Val Glu Tyr Met Pro Phe Leu Leu Ser Phe Phe Leu Thr Leu
                165                 170                 175

Ser Ala Val Met Trp Phe Phe Tyr Gly Leu Met Leu Lys Asp Phe Tyr
            180                 185                 190

Ile Ala Gly Pro Asn Ile Leu Gly Phe Val Phe Gly Ile Val Gln Met
        195                 200                 205

Val Leu Tyr Leu Ile Tyr Arg Asn Arg Lys Val Leu Glu Asn Glu
    210                 215                 220

Lys Leu Pro Glu Leu Ser Glu Gln Ile Ile Asp Val Val Lys Leu Ser
225                 230                 235                 240

Thr Met Val Cys Ser Glu Val Asn Leu Thr Asn Gln Gln His Ser Asn
```

```
                      245                 250                 255
Glu Gly His Gly Thr Thr Gly Leu Glu Val Ile Val Ala Leu
            260                 265                 270

<210> SEQ ID NO 80
<211> LENGTH: 217
<212> TYPE: PRT
<213> ORGANISM: Populus trichocarpa

<400> SEQUENCE: 80

Met Thr Gly Asn Ile Ile Ser Phe Met Val Tyr Leu Ala Pro Val Pro
1               5                   10                  15

Thr Phe Ile Arg Ile Leu Arg Lys Lys Ser Thr Glu Asp Phe Gln Ser
            20                  25                  30

Leu Pro Tyr Leu Val Ala Leu Phe Ser Ser Met Leu Trp Leu Tyr Tyr
        35                  40                  45

Ala Met Leu Lys Asn Asp Glu Ile Leu Leu Val Thr Ile Asn Ser Phe
    50                  55                  60

Gly Cys Val Ile Glu Thr Ile Tyr Ile Ala Ile Tyr Ile Ala Tyr Ala
65                  70                  75                  80

Thr Arg Glu Ser Lys Val Ser Thr Ile Lys Leu Leu Ser Met Asn
                85                  90                  95

Met Gly Leu Phe Ser Leu Ile Ile Leu Leu Thr His Phe Leu Ala Ser
            100                 105                 110

Gly Ser Thr Arg Val Lys Ala Leu Gly Trp Leu Cys Val Ala Phe Ser
        115                 120                 125

Val Cys Val Phe Ala Ala Pro Leu Asn Ile Val Lys Gln Ile Ile Arg
    130                 135                 140

Thr Lys Ser Val Glu Phe Met Pro Phe Thr Leu Ser Phe Phe Leu Thr
145                 150                 155                 160

Leu Ser Ala Val Ile Trp Phe Ala Tyr Gly Leu Phe Ile Lys Asp Met
                165                 170                 175

Cys Val Ala Leu Pro Asn Ile Leu Gly Phe Val Leu Gly Leu Leu Gln
            180                 185                 190

Met Leu Leu Tyr Gly Ile Tyr Arg Asn Ala Glu Lys Lys Lys Ile Pro
        195                 200                 205

Ala Glu Asn Leu Lys Ser Ile Val Ile
    210                 215

<210> SEQ ID NO 81
<211> LENGTH: 269
<212> TYPE: PRT
<213> ORGANISM: Populus trichocarpa

<400> SEQUENCE: 81

Met Ala Leu His Phe Thr Trp Val Phe Gly Phe Gly Leu Leu Gly Asn
1               5                   10                  15

Ile Ile Ser Cys Leu Val Cys Leu Ala Pro Leu Pro Thr Phe Tyr Gln
            20                  25                  30

Ile Cys Lys Lys Lys Thr Ser Gln Gly Phe Gln Ser Ile Pro Tyr Val
        35                  40                  45

Ile Ala Leu Phe Ser Ala Met Leu Trp Leu Phe Tyr Ala Ser Phe Ser
    50                  55                  60

Glu Asn Ala Met Leu Leu Ile Thr Ile Asn Ser Phe Ala Phe Phe Met
65                  70                  75                  80

Glu Ile Gly Tyr Ile Ala Val Tyr Leu Phe Tyr Ala Thr Lys Lys Asp
```

```
                85                  90                  95
Lys Ile Leu Thr Phe Lys Leu Leu Leu Phe Asn Ile Phe Gly Phe
            100                 105                 110

Gly Leu Ile Cys Ala Leu Ser Leu Leu Thr Glu Gly Thr Lys Arg
            115                 120                 125

Val His Val Leu Gly Trp Ile Cys Met Val Phe Ala Leu Cys Val Phe
130                 135                 140

Val Ala Pro Leu Gly Val Val Arg Lys Val Ile Arg Thr Lys Ser Val
145                 150                 155                 160

Glu Phe Met Pro Phe Ser Leu Ser Phe Phe Leu Thr Leu Ser Ala Val
                165                 170                 175

Met Trp Phe Phe Tyr Gly Tyr Leu Lys Lys Asp Lys Phe Val Ala Ile
                180                 185                 190

Pro Asn Ile Leu Gly Phe Ile Phe Gly Ile Leu Gln Met Val Leu Tyr
            195                 200                 205

Leu Ile Tyr Arg Asn Pro Lys Lys Asn Glu Val Ala Glu Pro Arg Thr
210                 215                 220

Gln Glu Leu Ser Glu Gln Tyr Cys Ser Asp Ile Asn Ile Ala Met Pro
225                 230                 235                 240

Lys Leu Asn Glu Gly Gly Asn Glu Val Phe Glu Ala His Ser Ala Lys
                245                 250                 255

Asp Gln Thr Lys Glu Ala Met Asp Val Thr Asn Lys Val
                260                 265

<210> SEQ ID NO 82
<211> LENGTH: 283
<212> TYPE: PRT
<213> ORGANISM: Populus trichocarpa

<400> SEQUENCE: 82

Met Ala Leu His Leu Thr Trp Met Leu Ala Phe Gly Leu Leu Gly Asn
1               5                   10                  15

Leu Ile Ser Cys Leu Val Cys Leu Ala Pro Leu Pro Thr Phe Tyr Gln
            20                  25                  30

Ile Tyr Lys Lys Lys Thr Ser Glu Gly Phe Gln Ser Ile Pro Tyr Val
        35                  40                  45

Ile Ala Leu Phe Ser Ala Met Leu Trp Leu Phe Tyr Ala Ile Phe Ser
50                  55                  60

Glu Asp Ala Ile Leu Leu Ile Thr Ile Asn Thr Phe Ala Phe Phe Met
65                  70                  75                  80

Glu Phe Gly Tyr Ile Thr Val Tyr Leu Leu Tyr Ala Thr Lys Lys Asp
                85                  90                  95

Lys Ile Leu Thr Phe Lys Leu Leu Leu Phe Asn Ser Phe Gly Phe
            100                 105                 110

Gly Leu Ile Cys Val Leu Thr Leu Phe Leu Thr Gln Gly Gln Lys Arg
            115                 120                 125

Val Gln Val Leu Gly Trp Ile Cys Met Ile Phe Ser Leu Cys Val Phe
145                 135                 140

Val Ala Pro Leu Phe Ile Val Arg Glu Val Ile Lys Thr Lys Ser Val
145                 150                 155                 160

Glu Phe Met Pro Phe Ser Leu Ser Phe Phe Leu Thr Leu Ser Ala Val
                165                 170                 175

Met Trp Phe Phe Tyr Gly Tyr Leu Lys Lys Asp Gln Phe Val Ala Val
                180                 185                 190
```

```
Pro Asn Ile Leu Gly Phe Leu Phe Gly Ile Ile Gln Met Val Leu Tyr
            195                 200                 205

Val Ile Tyr Arg Asn Pro Met Lys Ile Leu Val Val Glu Pro Lys Leu
    210                 215                 220

Gln Glu Leu Ser His Glu His Ile Val Asp Ile Arg Lys Leu Gly Thr
225                 230                 235                 240

Ala Ile Cys Ser Glu Ile Asn Ile Val Ile Pro Gln Leu Asn Asp Ser
                245                 250                 255

Gly Lys Val Val Phe Glu Asp Gln Ile Ala Lys Glu Leu Thr Lys Gln
                260                 265                 270

Thr Gln Glu Ile Thr Asn Ala Thr Asn Lys Ile
            275                 280
```

<210> SEQ ID NO 83
<211> LENGTH: 283
<212> TYPE: PRT
<213> ORGANISM: Populus trichocarpa

<400> SEQUENCE: 83

```
Met Ala Leu His Leu Thr Trp Val Phe Gly Phe Gly Leu Leu Gly Asn
1               5                   10                  15

Phe Ile Ser Cys Leu Val Cys Leu Ala Pro Leu Pro Thr Phe Tyr Arg
                20                  25                  30

Ile Cys Lys Lys Thr Ser Gln Gly Phe His Ser Ile Pro Tyr Val
            35                  40                  45

Ile Ala Leu Phe Ser Ala Met Leu Trp Leu Tyr Ala Leu Phe Lys
        50                  55                  60

Glu Asp Ala Leu Leu Ile Thr Ile Asn Ser Phe Thr Phe Phe Met
65                  70                  75                  80

Glu Ile Gly Tyr Ile Phe Met Tyr Leu Leu Tyr Ala Thr Lys Lys Asp
                85                  90                  95

Lys Ile Leu Thr Phe Lys Leu Leu Leu Phe Phe Asn Val Phe Gly Phe
            100                 105                 110

Gly Leu Ile Cys Val Leu Thr Arg Phe Leu Thr Gln Arg Gln Lys Arg
        115                 120                 125

Val Gln Val Leu Gly Trp Ile Cys Met Thr Phe Ser Leu Cys Val Phe
130                 135                 140

Val Ala Pro Leu Phe Ile Val Arg Lys Val Ile Arg Thr Lys Ser Val
145                 150                 155                 160

Glu Phe Met Pro Phe Ser Leu Ser Phe Phe Leu Thr Leu Ser Ala Val
                165                 170                 175

Met Trp Phe Phe Tyr Gly Phe Leu Lys Lys Asp Gln Phe Val Ala Val
            180                 185                 190

Pro Asn Ile Leu Gly Leu Leu Phe Gly Ile Leu Gln Met Val Leu Tyr
            195                 200                 205

Met Ile Tyr Gly Asn Ser Lys Lys Val Val Leu Glu Pro Lys Leu
    210                 215                 220

Lys Leu Asp Ile Ser Glu His Val Val Asp Leu Glu Lys Leu Gly Ala
225                 230                 235                 240

Ala Ile Cys Ser Glu Ile Ala Ile Gly Ile Pro Lys Leu Asn Asp Gly
                245                 250                 255

Gly Asp Gly Ile Ile Glu Asp Gln Asn Ala Lys Glu Gln Thr Lys Lys
                260                 265                 270

Ile Met Lys Ala Met Asp Val Thr Asn Lys Leu
            275                 280
```

```
<210> SEQ ID NO 84
<211> LENGTH: 259
<212> TYPE: PRT
<213> ORGANISM: Populus trichocarpa

<400> SEQUENCE: 84

Met Gly Phe Leu Ser Asn Asp Gln Leu Thr Phe Leu Phe Gly Leu Leu
1               5                   10                  15

Gly Asn Ile Val Ala Ala Gly Met Phe Leu Ala Pro Val Pro Thr Phe
                20                  25                  30

Tyr Thr Ile Phe Lys Arg Lys Ser Ser Glu Gly Phe Gln Ser Ile Pro
            35                  40                  45

Tyr Ser Val Ala Leu Met Ser Ala Ser Leu Leu Leu Tyr Tyr Gly Leu
        50                  55                  60

Leu Lys Thr Asn Ala Tyr Leu Leu Ile Ser Ile Asn Ser Ile Gly Cys
65                  70                  75                  80

Ala Phe Glu Val Thr Tyr Leu Ile Ile Tyr Leu Ile Tyr Ala Pro Lys
                85                  90                  95

Gln Glu Lys Met His Thr Met Lys Leu Leu Leu Ile Phe Asn Met Gly
            100                 105                 110

Ser Phe Gly Val Val Leu Leu Leu Thr Met Leu Leu Met Lys Gly Lys
        115                 120                 125

Pro Arg Leu Ser Val Val Gly Trp Ile Cys Ala Val Phe Ser Val Ala
130                 135                 140

Val Cys Ala Ala Pro Leu Ser Ile Met Arg Arg Val Val Arg Thr Lys
145                 150                 155                 160

Ser Val Glu Tyr Leu Pro Phe Thr Leu Ser Ala Ser Ile Thr Leu Asn
                165                 170                 175

Ala Val Met Trp Phe Phe Tyr Gly Leu Leu Gln His Asp Tyr Tyr Ile
            180                 185                 190

Ala Leu Pro Asn Val Leu Gly Phe Leu Phe Gly Ile Ala Gln Met Ile
        195                 200                 205

Leu Tyr Met Val Tyr Lys Asn Leu Lys Lys Asn Val Glu Glu Lys Ser
    210                 215                 220

Glu Gln Leu Ala Gly Asn Met Glu Val Val Gln Met Thr Lys Glu Thr
225                 230                 235                 240

Glu Ser Cys Thr Val Asp Asp Pro His Met Glu Thr Lys Ile Cys Ile
                245                 250                 255

Cys Asp Leu

<210> SEQ ID NO 85
<211> LENGTH: 302
<212> TYPE: PRT
<213> ORGANISM: Sorghum bicolor

<400> SEQUENCE: 85

Met Ala Gly Leu Ser Leu Gln His Pro Trp Ala Phe Ala Phe Gly Leu
1               5                   10                  15

Leu Gly Asn Val Ile Ser Phe Leu Thr Phe Leu Ala Pro Ile Pro Thr
                20                  25                  30

Phe Tyr Arg Ile Tyr Lys Ser Lys Ser Thr Glu Gly Phe Gln Ser Val
            35                  40                  45

Pro Tyr Val Val Ala Leu Phe Ser Ala Met Leu Trp Ile Phe Tyr Ala
        50                  55                  60
```

Leu Ile Lys Ser Asn Glu Thr Phe Leu Ile Thr Ile Asn Ala Ala Gly
65                  70                  75                  80

Cys Val Ile Glu Thr Ile Tyr Ile Val Met Tyr Phe Val Tyr Ala Pro
                85                  90                  95

Lys Lys Ala Lys Leu Phe Thr Ala Lys Ile Met Leu Leu Leu Asn Val
                100                 105                 110

Gly Val Phe Gly Val Ile Leu Leu Val Thr Leu Leu Leu Phe Lys Gly
                115                 120                 125

Asp Lys Arg Val Val Met Leu Gly Trp Ile Cys Val Gly Phe Ser Val
            130                 135                 140

Ser Val Phe Val Ala Pro Leu Ser Ile Met Arg Arg Val Ile Gln Thr
145                 150                 155                 160

Lys Ser Val Glu Tyr Met Pro Phe Ser Leu Ser Leu Ser Leu Thr Leu
                165                 170                 175

Ser Ala Val Val Trp Phe Leu Tyr Gly Leu Leu Ile Lys Asp Lys Tyr
                180                 185                 190

Val Ala Leu Pro Asn Ile Leu Gly Phe Thr Phe Gly Val Val Gln Met
                195                 200                 205

Val Leu Tyr Val Leu Tyr Met Asn Lys Thr Pro Val Ala Val Ala Glu
210                 215                 220

Gly Lys Asp Ala Gly Val Lys Leu Pro Ser Ala Ala Asp Glu His Val
225                 230                 235                 240

Leu Val Asn Ile Thr Lys Leu Ser Pro Ala Leu Pro Asp Arg Ser Ser
                245                 250                 255

Gly Val His Arg Ala Thr Gln Met Ala Ala Val Pro Ala Ser Ser Cys
                260                 265                 270

Ala Ala Glu Ala Ala Ala Pro Ala Met Leu Pro Asn Arg Asp Val Val
                275                 280                 285

Asp Val Phe Val Ser Arg Gln Ser Pro Ala Val His Val Val
                290                 295                 300

<210> SEQ ID NO 86
<211> LENGTH: 302
<212> TYPE: PRT
<213> ORGANISM: Sorghum bicolor

<400> SEQUENCE: 86

Met Ala Gly Leu Ser Leu Gln His Pro Trp Ala Phe Ala Phe Gly Leu
1               5                   10                  15

Leu Gly Asn Leu Ile Ser Phe Leu Thr Phe Leu Ala Pro Ile Pro Thr
                20                  25                  30

Phe Tyr Arg Ile Tyr Lys Thr Lys Ser Thr Glu Gly Phe Gln Ser Val
                35                  40                  45

Pro Tyr Val Val Ala Leu Phe Ser Ala Met Leu Trp Ile Phe Tyr Ala
                50                  55                  60

Leu Ile Lys Ser Asn Glu Thr Phe Leu Ile Thr Ile Asn Ala Ala Gly
65                  70                  75                  80

Cys Val Ile Glu Thr Ile Tyr Ile Val Met Tyr Phe Val Tyr Ala Pro
                85                  90                  95

Lys Lys Ala Lys Leu Phe Thr Ala Lys Ile Met Leu Leu Leu Asn Val
                100                 105                 110

Gly Val Phe Gly Val Ile Leu Leu Val Thr Leu Leu Leu Phe Lys Gly
                115                 120                 125

Asp Lys Arg Val Val Met Leu Gly Trp Ile Cys Val Gly Phe Ser Val
            130                 135                 140

```
Ser Val Phe Val Ala Pro Leu Ser Ile Met Arg Arg Val Ile Gln Thr
145                 150                 155                 160

Lys Ser Met Glu Tyr Met Pro Phe Ser Leu Ser Leu Ser Leu Thr Leu
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Thr Phe Gly Met Val Gln Met
        195                 200                 205

Val Leu Tyr Val Leu Tyr Met Asn Lys Thr Pro Val Ala Val Ala Glu
    210                 215                 220

Gly Lys Asp Ala Gly Lys Leu Pro Ser Ala Gly Asp Lys His Val
225                 230                 235                 240

Leu Val Asn Ile Ala Lys Leu Ser Pro Ala Leu Pro Glu Arg Ser Ser
                245                 250                 255

Gly Val His Arg Ala Thr Gln Met Ser Ala Val Pro Ala Lys Ser Cys
            260                 265                 270

Ala Ala Glu Ala Thr Ala Pro Lys Val Met Leu Pro Asn Arg Asp Val
        275                 280                 285

Val Asp Val Phe Leu Ser Gln Ala Leu His Arg Lys Gln Ala
    290                 295                 300
```

<210> SEQ ID NO 87
<211> LENGTH: 309
<212> TYPE: PRT
<213> ORGANISM: Sorghum bicolor

<400> SEQUENCE: 87

```
Met Ala Gly Gly Leu Phe Ser Met Ala His Pro Ala Ile Thr Leu Ser
1               5                   10                  15

Gly Ile Ala Gly Asn Ile Ile Ser Phe Leu Val Phe Leu Ala Pro Val
                20                  25                  30

Ala Thr Phe Leu Gln Val Tyr Arg Lys Lys Ser Thr Gly Gly Phe Ser
            35                  40                  45

Ser Val Pro Tyr Val Val Ala Leu Phe Ser Ser Val Leu Trp Ile Phe
50                  55                  60

Tyr Ala Leu Val Lys Thr Asn Ser Arg Pro Leu Leu Thr Ile Asn Ala
65                  70                  75                  80

Phe Gly Cys Gly Val Glu Ala Ala Tyr Ile Val Phe Tyr Leu Ala Tyr
                85                  90                  95

Ala Pro Arg Lys Ala Arg Leu Arg Thr Leu Ala Tyr Phe Phe Leu Leu
            100                 105                 110

Asp Val Ala Ala Phe Ala Leu Val Val Val Thr Leu Phe Val Val
        115                 120                 125

Arg Glu Pro His Arg Val Lys Phe Leu Gly Ser Val Cys Leu Ala Phe
    130                 135                 140

Ser Met Ala Val Phe Val Ala Pro Leu Ser Ile Ile Val Lys Val Val
145                 150                 155                 160

Lys Thr Lys Ser Val Glu Phe Leu Pro Ile Ser Leu Ser Phe Cys Leu
                165                 170                 175

Thr Leu Ser Ala Val Ala Trp Phe Cys Tyr Gly Leu Phe Thr Lys Asp
            180                 185                 190

Pro Phe Val Met Tyr Pro Asn Val Gly Gly Phe Phe Phe Ser Cys Val
        195                 200                 205

Gln Met Gly Leu Tyr Phe Trp Tyr Arg Lys Pro Arg Pro Ala Lys Asn
```

```
                210                 215                 220
Asn Ala Val Leu Pro Thr Thr Thr Asp Gly Ala Ser Ala Val Gln Met
225                 230                 235                 240

Gln Gly Gln Val Ile Glu Leu Ala Pro Asn Thr Val Ala Ile Leu Ser
                245                 250                 255

Val Ser Pro Ile Pro Ile Val Gly Val His Lys Ile Glu Val Val Glu
                260                 265                 270

Gln Gln His Lys Glu Ala Ala Val Ala Ala Glu Thr Arg Arg Met Ala
                275                 280                 285

Ala Ala Asn Pro Asp Gly Ala Met Pro Glu Val Ile Glu Ile Val Pro
                290                 295                 300

Ala Val Ala Thr Val
305

<210> SEQ ID NO 88
<211> LENGTH: 291
<212> TYPE: PRT
<213> ORGANISM: Sorghum bicolor

<400> SEQUENCE: 88

Met Ala Gly Leu Ser Leu Gln His Pro Met Ala Phe Ala Phe Gly Leu
1               5                   10                  15

Leu Gly Asn Ile Ile Ser Phe Met Thr Tyr Leu Ala Pro Leu Tyr Arg
                20                  25                  30

Pro Thr Phe Tyr Arg Ile Tyr Lys Ser Lys Ser Thr Gln Gly Phe Gln
                35                  40                  45

Ser Val Pro Tyr Val Val Ala Leu Phe Ser Ala Met Leu Trp Ile Tyr
50                  55                  60

Tyr Ala Leu Leu Lys Ser Asn Glu Phe Leu Leu Ile Thr Ile Asn Ser
65                  70                  75                  80

Ala Gly Cys Val Ile Glu Thr Leu Tyr Ile Val Met Tyr Leu Leu Tyr
                85                  90                  95

Ala Pro Lys Lys Ala Lys Leu Phe Thr Ala Lys Ile Leu Leu Leu Leu
                100                 105                 110

Asn Val Gly Val Phe Gly Leu Ile Leu Leu Leu Thr Leu Leu Leu Ser
                115                 120                 125

Ala Gly Gln His Arg Val Val Val Leu Gly Trp Val Cys Val Ala Phe
                130                 135                 140

Ser Val Ser Val Phe Val Ala Pro Leu Ser Ile Ile Arg Gln Val Val
145                 150                 155                 160

Arg Thr Arg Ser Val Glu Phe Met Pro Phe Ser Leu Ser Leu Ser Leu
                165                 170                 175

Thr Val Ser Ala Val Val Trp Phe Leu Tyr Gly Leu Leu Ile Lys Asp
                180                 185                 190

Lys Tyr Val Ala Leu Pro Asn Val Leu Gly Phe Ser Phe Gly Val Val
                195                 200                 205

Gln Met Gly Leu Tyr Ala Leu Tyr Arg Asn Ala Thr Pro Arg Val Pro
                210                 215                 220

Pro Ala Lys Glu Val Thr Asp Asp Ala Ala Ala Asp Gly Thr Phe
225                 230                 235                 240

Lys Leu Pro Gly Glu His Val Val Thr Ile Ala Lys Leu Thr Ala Val
                245                 250                 255

Pro Ala Val Ser Pro Gln Leu Gln Glu Glu Ala Lys Pro Ala Asp Asn
                260                 265                 270
```

Gly Thr Thr Pro Ala Pro Ala Pro Ala Asn Asp Val Gln Leu Asn Ala
            275                 280                 285

Glu Gln Val
    290

<210> SEQ ID NO 89
<211> LENGTH: 336
<212> TYPE: PRT
<213> ORGANISM: Sorghum bicolor

<400> SEQUENCE: 89

Met Ala Phe Leu Asn Met Glu Gln Gln Thr Trp Ala Phe Thr Phe Gly
1               5                   10                  15

Ile Leu Gly Asn Ile Ile Ser Leu Met Val Phe Leu Ser Pro Leu Pro
            20                  25                  30

Thr Phe Tyr Arg Val Tyr Arg Lys Lys Ser Thr Glu Gly Phe Gln Ser
        35                  40                  45

Thr Pro Tyr Val Val Thr Leu Phe Ser Cys Met Leu Trp Ile Phe Tyr
    50                  55                  60

Ala Leu Leu Lys Ser Gly Ala Glu Leu Leu Val Thr Ile Asn Gly Val
65                  70                  75                  80

Gly Cys Val Ile Glu Thr Val Tyr Leu Gly Met Tyr Leu Leu Tyr Ala
                85                  90                  95

Pro Lys Ala Ala Arg Val Leu Thr Ala Lys Met Leu Leu Gly Leu Asn
            100                 105                 110

Val Gly Val Phe Gly Leu Val Ala Leu Val Thr Met Val Leu Ser Asn
        115                 120                 125

Gly Gly Leu Arg Val Lys Val Leu Gly Trp Ile Cys Val Ser Val Ala
    130                 135                 140

Leu Ser Val Phe Ala Ala Pro Leu Ser Ile Met Arg Gln Val Ile Arg
145                 150                 155                 160

Thr Lys Ser Val Glu Phe Met Pro Ile Ser Leu Ser Phe Phe Leu Val
                165                 170                 175

Leu Ser Ala Val Ile Trp Phe Ala Tyr Gly Ala Leu Lys Lys Asp Val
            180                 185                 190

Phe Val Ala Ala Pro Asn Val Leu Gly Phe Val Phe Gly Leu Ala Gln
        195                 200                 205

Met Ala Leu Tyr Met Ala Tyr Arg Asn Lys Lys Pro Ala Ala Ala Ala
    210                 215                 220

Val Ile Met Val Glu Glu Val Lys Leu Pro Ala Glu Gln Tyr Ala Ser
225                 230                 235                 240

Lys Glu Val Ala Pro Pro Ala Ala Ala His Glu Gly Ser Arg Ala Ser
                245                 250                 255

Cys Gly Ala Glu Val His Pro Ile Asp Ile Asp Thr Leu Pro Val Ala
            260                 265                 270

Asp Val Gly Arg His His Asp Ser Gln Ala Val Val Ile Asp Val
        275                 280                 285

Asp Val Glu Pro Ala Ala Thr Cys Ala Ala Ala Ala Ala Ala Gly
    290                 295                 300

Gly Val Arg Gly Asp Gly Ala Ala Gly Val Val Thr Ala Gly Pro Glu
305                 310                 315                 320

Gln Pro Ala Ala Met Lys Pro Val Asp Met Ala Ile Ala Val Glu Ala
                325                 330                 335

<210> SEQ ID NO 90

<211> LENGTH: 273
<212> TYPE: PRT
<213> ORGANISM: Sorghum bicolor

<400> SEQUENCE: 90

Met Ala Gly Gly Leu Phe Ser Met Glu His Pro Trp Val Ser Ala Phe
1               5                   10                  15

Gly Ile Leu Gly Asn Ile Ile Ser Phe Leu Val Phe Leu Ala Pro Val
            20                  25                  30

Pro Thr Phe Leu Arg Val Tyr Arg Lys Lys Ser Thr Glu Gly Phe Ser
        35                  40                  45

Ser Val Pro Tyr Val Val Ala Leu Phe Ser Cys Thr Leu Trp Ile Leu
50                  55                  60

Tyr Ala Val Val Lys Thr Asn Ser Ser Pro Leu Leu Thr Ile Asn Ala
65                  70                  75                  80

Phe Gly Cys Val Val Glu Ala Thr Tyr Ile Leu Leu Tyr Leu Ile Tyr
                85                  90                  95

Ala Pro Arg Ala Ala Arg Leu Arg Ala Leu Ala Phe Phe Phe Leu Leu
            100                 105                 110

Asp Val Ala Ala Leu Ala Leu Ile Val Val Val Val Val Val Leu Val
        115                 120                 125

Ala Glu Pro His Arg Val Lys Val Leu Gly Ser Ile Cys Leu Ala Phe
130                 135                 140

Ser Met Ala Val Phe Val Ala Pro Leu Ser Val Ile Phe Val Val Ile
145                 150                 155                 160

Arg Thr Lys Ser Ala Glu Phe Met Pro Phe Thr Leu Ser Phe Phe Leu
                165                 170                 175

Thr Leu Ser Ala Val Ala Trp Phe Leu Tyr Gly Ile Phe Thr Lys Asp
            180                 185                 190

Pro Tyr Val Thr Leu Pro Asn Val Gly Gly Phe Phe Gly Cys Ile
        195                 200                 205

Gln Met Val Leu Tyr Cys Cys Tyr Arg Lys Pro Ser Ala Ser Val Val
210                 215                 220

Leu Pro Thr Thr Thr Asp Ala Ala Ala Thr Glu Met Glu Leu Pro Leu
225                 230                 235                 240

Ala Ala His Gln Ala Val Ala Pro Val Leu Ala Glu Leu Gln Lys Leu
                245                 250                 255

Glu Glu Ala Met Gly Ser Pro Arg Lys His Gly Gly Val Val Lys Val
            260                 265                 270

Val

<210> SEQ ID NO 91
<211> LENGTH: 313
<212> TYPE: PRT
<213> ORGANISM: Sorghum bicolor

<400> SEQUENCE: 91

Met Ile Thr Val Gly His Pro Val Phe Ala Val Gly Ile Leu Gly
1               5                   10                  15

Asn Ile Leu Ser Phe Leu Val Thr Leu Ala Pro Val Pro Thr Phe Tyr
            20                  25                  30

Arg Val Tyr Lys Lys Lys Ser Thr Glu Ser Phe Gln Ser Val Pro Tyr
        35                  40                  45

Val Val Ala Leu Leu Ser Ala Met Leu Trp Leu Tyr Tyr Ala Leu Leu
50                  55                  60

-continued

Ser Ile Asp Val Leu Leu Leu Ser Ile Asn Thr Ile Ala Cys Val Val
65                  70                  75                  80

Glu Ser Val Tyr Leu Ala Ile Tyr Leu Thr Tyr Ala Pro Lys Pro Ala
                85                  90                  95

Met Ala Phe Thr Leu Lys Leu Leu Phe Thr Met Asn Met Gly Leu Phe
            100                 105                 110

Gly Ala Met Val Ala Phe Leu Gln Phe Tyr Val Asp Gly Gln Arg Arg
        115                 120                 125

Val Ser Ile Ala Gly Gly Val Gly Ala Ala Phe Ala Leu Ala Val Phe
    130                 135                 140

Val Ala Pro Leu Thr Ile Ile Arg Gln Val Ile Arg Thr Lys Ser Val
145                 150                 155                 160

Glu Tyr Met Pro Phe Trp Leu Ser Phe Leu Thr Ile Ser Ala Val
                165                 170                 175

Val Trp Phe Phe Tyr Gly Leu Leu Met Lys Asp Phe Phe Val Ala Met
                180                 185                 190

Pro Asn Val Leu Gly Leu Leu Phe Gly Leu Ala Gln Met Ala Leu Tyr
            195                 200                 205

Phe Val Tyr Arg Asn Arg Asn Pro Lys Gln Asn Gly Ala Val Ser Glu
        210                 215                 220

Met Gln Gln Gln Ala Ala Val Gln Ala Asp Ala Asp Ala Lys Lys
225                 230                 235                 240

Glu Gln Gln Leu Arg Gln Ala His Ala Asp Ala Gly Ala Asp Gly Glu
                245                 250                 255

Ala Val Ala Val Arg Ile Asp Asp Glu Glu Pro Lys Asn Val Val
                260                 265                 270

Val Asp Ile Met Pro Pro Pro Pro Leu Leu Pro Ala Glu Arg Ala
            275                 280                 285

Ser Pro Pro Leu Pro Leu Pro Pro Pro Ala Met Val Met Met Thr
    290                 295                 300

Ala His Gln Thr Ala Val Glu Val Val
305                 310

<210> SEQ ID NO 92
<211> LENGTH: 297
<212> TYPE: PRT
<213> ORGANISM: Ricinus communis

<400> SEQUENCE: 92

Met Ala Ile Phe Asn Thr His Asn Pro Ser Val Phe Val Phe Gly Leu
1               5                   10                  15

Leu Gly Asn Ile Val Ser Phe Val Phe Leu Ala Pro Val Pro Thr
            20                  25                  30

Phe Leu Arg Val Cys Lys Lys Ser Thr Glu Gly Phe Gln Ser Phe
        35                  40                  45

Pro Tyr Val Val Ser Leu Phe Ser Ala Met Leu Trp Leu Tyr Tyr Ala
    50                  55                  60

Ser Leu Lys Ser Asp Ala Phe Leu Leu Ile Thr Ile Asn Ser Val Gly
65                  70                  75                  80

Cys Leu Ile Glu Thr Ile Tyr Ile Thr Leu Phe Ile Tyr Ala Pro
                85                  90                  95

Lys Gln Ala Arg Ile Thr Thr Leu Lys Ile Leu Leu Leu Asn Phe
        100                 105                 110

Gly Gly Phe Cys Leu Ile Leu Leu Leu Ser His Phe Leu Ala Lys Gly
            115                 120                 125

```
Ser Glu Arg Ala Thr Ile Leu Gly Trp Val Cys Val Ile Phe Ser Val
            130                 135                 140
Ser Val Phe Ala Ala Pro Leu Ser Val Met Arg Ile Val Ile Arg Thr
145                 150                 155                 160
Lys Ser Val Glu Phe Met Pro Phe Tyr Leu Ser Phe Leu Thr Leu
                165                 170                 175
Ser Ala Ile Met Trp Leu Phe Tyr Gly Leu Leu Lys Asp Leu Tyr
            180                 185                 190
Ile Ala Val Pro Asn Ile Leu Gly Leu Val Phe Gly Val Leu Gln Met
            195                 200                 205
Ile Leu Tyr Val Ile Tyr Lys Asn Val Lys Thr Val Val Glu Glu Pro
            210                 215                 220
Lys Leu Pro Glu His Asn Val Asp Asn Val Lys Leu Ser Ala Val Ile
225                 230                 235                 240
Thr Cys Glu Val Gln Gln Glu Val Cys Ser Gln Ser Gln Pro Asn Gly
                245                 250                 255
Asp Asp Gly Ala His Asn Lys Glu Gln Lys Met His Asp Asn Pro Ala
            260                 265                 270
Asn Ala Val Thr Glu Tyr Gln Arg His Ser Gly Met Asp Ala Ser Ile
            275                 280                 285
Ala Asp Gln Ser Ile Ala Cys Arg Val
            290                 295

<210> SEQ ID NO 93
<211> LENGTH: 277
<212> TYPE: PRT
<213> ORGANISM: Ricinus communis

<400> SEQUENCE: 93

Met Ala Tyr His Leu Ser Leu Glu Phe Leu Phe Gly Val Leu Ala Asn
1               5                   10                  15
Ile Ile Ser Ser Met Val Cys Leu Ala Pro Leu Pro Thr Phe Tyr Gln
                20                  25                  30
Ile Cys Lys Lys Lys Thr Ser Glu Gly Phe Gln Ser Val Pro Tyr Val
            35                  40                  45
Ile Ala Leu Phe Ser Ala Met Leu Trp Leu Phe Tyr Ala Thr Phe Asp
        50                  55                  60
Asp Asn Ala Thr Leu Leu Ile Thr Ile Asn Ser Phe Thr Phe Phe Met
65                  70                  75                  80
Glu Val Gly Tyr Leu Ser Val Tyr Leu Phe Tyr Gly Thr Arg Lys Asp
                85                  90                  95
Arg Met Leu Thr Thr Lys Leu Val Leu Phe Asn Val Phe Gly Phe
            100                 105                 110
Gly Met Ile Ala Ile Leu Thr Leu Phe Leu Thr His Gly Arg Lys Arg
            115                 120                 125
Val Asp Val Leu Gly Trp Ile Cys Met Ile Phe Ala Leu Cys Val Phe
            130                 135                 140
Val Ala Pro Leu Gly Ile Met Arg Lys Val Ile Lys Thr Lys Ser Val
145                 150                 155                 160
Glu Phe Met Pro Phe Ser Leu Ser Phe Leu Thr Leu Ser Ala Val
                165                 170                 175
Met Trp Phe Phe Tyr Gly Phe Leu Lys Lys Asp Ile Tyr Val Tyr Ile
            180                 185                 190
Pro Asn Val Leu Gly Phe Phe Phe Gly Ile Val Gln Met Ile Leu Tyr
```

```
                195                 200                 205
Leu Ile Tyr Arg Asn Ser Lys Lys Pro Val Glu Glu Pro Lys Ser Gln
    210                 215                 220

Glu Phe Ser Glu His Ile Val Asp Val Ala Lys Leu Ser Ala Val Ile
225                 230                 235                 240

Cys Ser Glu Leu Lys Thr Met Val Val Ala Lys Leu Asn Asp Asn Gly
                245                 250                 255

Asn Glu Val Val Lys Glu Thr Lys Asn Thr Lys Gln Glu Met Glu
            260                 265                 270

Ala Ser Asn Lys Val
        275

<210> SEQ ID NO 94
<211> LENGTH: 279
<212> TYPE: PRT
<213> ORGANISM: Ricinus communis

<400> SEQUENCE: 94

Met Ala Phe His Leu Thr Leu Ala Phe Ala Phe Gly Leu Leu Gly Asn
1               5                   10                  15

Ile Ile Ser Phe Leu Val Cys Leu Ala Pro Met Pro Thr Phe Tyr Gln
            20                  25                  30

Ile Cys Lys Lys Lys Thr Ser Glu Gly Phe Gln Ser Ile Pro Tyr Val
        35                  40                  45

Ile Ala Leu Phe Ser Ala Thr Leu Trp Leu Phe Tyr Ala Ile Phe Ala
    50                  55                  60

Asn Asp Ala Thr Leu Leu Ile Thr Ile Asn Ser Phe Ala Phe Phe Met
65                  70                  75                  80

Glu Thr Ala Tyr Ile Ala Ile Tyr Leu Phe Tyr Ala Val Lys Lys Asp
                85                  90                  95

Arg Leu Phe Thr Thr Lys Leu Val Leu Ser Leu Asn Ile Phe Ala Phe
            100                 105                 110

Gly Ser Ile Cys Val Ile Ala Met Phe Leu Thr His Gly Gln Lys Arg
        115                 120                 125

Val Gln Leu Leu Gly Trp Ile Cys Met Val Phe Ala Leu Cys Val Phe
    130                 135                 140

Val Ala Pro Leu Ala Ile Val Arg Lys Val Ile Lys Thr Lys Ser Val
145                 150                 155                 160

Glu Phe Met Pro Phe Ser Leu Ser Phe Phe Leu Thr Leu Ser Ala Val
                165                 170                 175

Met Trp Phe Phe Tyr Gly Phe Leu Lys Lys Asp Leu Tyr Val Ala Val
            180                 185                 190

Pro Asn Ile Leu Gly Phe Met Phe Gly Val Leu Gln Met Ile Leu Tyr
        195                 200                 205

Leu Ile Tyr Arg Asn Pro Lys Lys Thr Gly Asp Asp Gln Lys Ala
    210                 215                 220

Asn Glu Leu Pro Asn Gln His Ser Ile Ile Asp Val Ala Lys Leu Asn
225                 230                 235                 240

Thr Arg Val Ser Cys Cys Glu Pro Asn Ala Thr Thr Val Ala His Ser
                245                 250                 255

Arg Asn Asp Arg Glu Glu Gln Thr Met Gln Ile Asn Arg Glu Asp
            260                 265                 270

Lys Asp Ala Thr Asn Thr Val
        275
```

<210> SEQ ID NO 95
<211> LENGTH: 272
<212> TYPE: PRT
<213> ORGANISM: Ricinus communis

<400> SEQUENCE: 95

Met Ala Ile Ile Ser Thr His Pro Pro Leu Ala Phe Ala Phe Gly Ile
1               5                   10                  15

Leu Gly Asn Ile Ile Ser Ile Leu Val Tyr Leu Ala Pro Val Pro Thr
            20                  25                  30

Phe Tyr Arg Ile Tyr Arg Lys Lys Ser Thr Glu Gly Phe Gln Ser Leu
        35                  40                  45

Pro Tyr Leu Val Ala Leu Phe Ser Ser Met Leu Trp Leu Tyr Tyr Ala
    50                  55                  60

Met Leu Lys Lys Asp Val Phe Leu Leu Val Thr Ile Asn Ala Phe Gly
65                  70                  75                  80

Cys Val Ile Glu Thr Ile Tyr Ile Ile Met Tyr Ile Ile Tyr Ala Thr
                85                  90                  95

Lys Lys Asn Arg Val Ser Thr Phe Lys Val Leu Thr Ser Met Asn Leu
            100                 105                 110

Gly Leu Phe Ala Phe Ile Ile Leu Phe Ser His Phe Leu Val Lys Ser
        115                 120                 125

Ser Val Arg Ala Gln Val Leu Gly Trp Ile Cys Val Ala Val Ser Val
    130                 135                 140

Cys Val Phe Ala Ala Pro Leu Ser Ile Val Ala Gln Val Ile Lys Thr
145                 150                 155                 160

Arg Ser Val Glu Phe Met Pro Phe Asn Leu Ser Phe Leu Thr Leu
                165                 170                 175

Ser Ala Ile Met Trp Phe Ala Tyr Gly Leu Ser Thr Lys Asp Thr Cys
            180                 185                 190

Val Ala Leu Pro Asn Val Leu Gly Phe Ile Leu Gly Leu Leu Gln Met
        195                 200                 205

Val Leu Tyr Val Ile Tyr Arg Lys Ala Lys Lys Val Ile Leu Glu Glu
    210                 215                 220

Lys Leu Pro Glu His Leu Lys Thr Ile Val Val Leu Ser Thr Leu Gly
225                 230                 235                 240

Asn Ser Glu Gln Gln Leu Val Thr Pro Val Gly Ser Leu Leu Ile Phe
                245                 250                 255

Gly Gln Phe Arg Asp Val Ala Thr Cys Arg Arg Phe Gln Ile Leu Leu
            260                 265                 270

<210> SEQ ID NO 96
<211> LENGTH: 286
<212> TYPE: PRT
<213> ORGANISM: Ricinus communis

<400> SEQUENCE: 96

Met Ala Leu Asn Asp Pro Arg Phe Ile Leu Ala Phe Gly Ile Leu Gly
1               5                   10                  15

Asn Ile Val Ser Phe Leu Val Tyr Leu Ala Pro Leu Pro Thr Phe Trp
            20                  25                  30

Arg Ile Val Lys Lys Lys Ser Thr Glu Gly Phe Gln Ser Ile Pro Tyr
        35                  40                  45

Ser Val Ala Leu Phe Ser Ala Met Leu Thr Leu Tyr Tyr Ala Thr Leu
    50                  55                  60

Lys Glu Asn Ala Ile Leu Leu Ile Thr Ile Asn Ser Ile Gly Cys Leu
65                  70                  75                  80

Ile Glu Gly Ile Tyr Leu Thr Ile Tyr Met Ile Tyr Ala Thr Gln Thr
                85                  90                  95

Ser Arg Val Gln Ile His Phe Lys Leu Leu Ile Leu Phe Asn Leu Gly
            100                 105                 110

Thr Tyr Leu Leu Ile Val Met Leu Ala Ser Glu Leu Thr His Gly Thr
        115                 120                 125

Leu Arg Val Gln Val Val Gly Trp Ile Cys Ala Val Phe Ser Val Cys
    130                 135                 140

Val Phe Ala Ala Pro Leu Ser Ile Met Arg Leu Val Ile Lys Thr Lys
145                 150                 155                 160

Ser Val Glu Tyr Met Pro Phe Ser Leu Ser Phe Phe Leu Thr Leu Cys
                165                 170                 175

Ala Ile Ser Trp Leu Gly Tyr Gly Leu Ala Val Asn Asp Tyr Phe Ile
            180                 185                 190

Ala Ser Pro Asn Ile Leu Gly Phe Leu Phe Gly Ile Val Gln Met Val
        195                 200                 205

Leu Tyr Met Ile Tyr Lys Asn Lys Asn Glu Ile Leu Pro Thr Ser
    210                 215                 220

Thr Ser Gln Glu Leu Ala Val Ser Lys Pro Glu Thr Ser Gln Asp Arg
225                 230                 235                 240

Glu Asn Ser Asn Ser Ser Leu Asn Gln Gln Asp Leu Glu Ala Ala
                245                 250                 255

Lys Asp Asp Arg Arg Glu Asn Lys Ala Val Pro Glu Glu Ala Ser
        260                 265                 270

Glu Arg Asn Gly Tyr Arg Ala Thr Cys Phe Gly Ile Ser Phe
    275                 280                 285

<210> SEQ ID NO 97
<211> LENGTH: 294
<212> TYPE: PRT
<213> ORGANISM: Arabiopsis lyrata

<400> SEQUENCE: 97

Met Ala Leu Thr His Asn Val Trp Ala Phe Val Phe Gly Met Leu Gly
1               5                   10                  15

Asn Ile Ile Ser Phe Val Val Phe Leu Ala Pro Val Pro Thr Phe Val
                20                  25                  30

Arg Ile Cys Lys Lys Lys Ser Thr Glu Gly Phe Gln Ser Leu Pro Tyr
            35                  40                  45

Val Ser Ala Leu Phe Ser Ala Met Leu Trp Ile Tyr Tyr Ala Met Gln
50                  55                  60

Lys Asp Gly Ser Gly Phe Leu Leu Ile Thr Ile Asn Ala Val Gly Cys
65                  70                  75                  80

Val Ile Glu Thr Ile Tyr Ile Val Leu Phe Val Thr Tyr Ala Asn Lys
                85                  90                  95

Lys Thr Arg Ile Ser Thr Leu Lys Val Leu Gly Leu Leu Asn Phe Leu
            100                 105                 110

Gly Phe Ala Ala Ile Val Leu Val Cys Glu Leu Leu Thr Glu Gly Ser
        115                 120                 125

Thr Arg Glu Lys Val Leu Gly Gly Ile Cys Val Gly Phe Ser Val Ser
    130                 135                 140

Val Phe Ala Ala Pro Leu Ser Ile Met Arg Val Val Arg Thr Arg
145                 150                 155                 160

```
Ser Val Glu Phe Met Pro Phe Ser Leu Ser Leu Phe Leu Thr Ile Ser
                165                 170                 175

Ala Val Thr Trp Leu Phe Tyr Gly Leu Ala Ile Lys Asp Phe Tyr Val
            180                 185                 190

Ala Leu Pro Asn Val Leu Gly Ala Phe Leu Gly Ala Val Gln Met Ile
        195                 200                 205

Leu Tyr Ile Ile Phe Lys Tyr Tyr Lys Ile Pro Met Ala Gln Lys Thr
    210                 215                 220

Asp Lys Ser Lys Ala Val Ser Asp His Ser Ile Asp Ile Ala Lys Leu
225                 230                 235                 240

Thr Thr Val Thr Pro Gly Pro Ile Ser Asp Ser Ala Val His Gln Pro
                245                 250                 255

Pro Leu Ile His Asn Val Pro Glu Thr Gln Ile Gln Val Thr Glu Val
            260                 265                 270

Lys Ser Gln Asn Ile Thr Asp Pro Lys Asp Gln Ile Asn Lys Asp Val
        275                 280                 285

Glu Asn Gln Ser Gln Val
    290

<210> SEQ ID NO 98
<211> LENGTH: 262
<212> TYPE: PRT
<213> ORGANISM: Glycine max

<400> SEQUENCE: 98

Met Val Ser Ile Ser Asp His Glu Leu Val Leu Ile Phe Gly Leu Leu
1               5                   10                  15

Gly Asn Ile Val Ser Phe Met Val Phe Leu Ala Pro Leu Pro Thr Phe
            20                  25                  30

Tyr Thr Ile Tyr Lys Lys Lys Ser Ser Glu Gly Phe Gln Ser Ile Pro
        35                  40                  45

Tyr Ala Val Ala Leu Leu Ser Ala Leu Leu Leu Tyr Tyr Gly Phe
    50                  55                  60

Ile Lys Thr Asn Ala Thr Leu Ile Ile Thr Ile Asn Cys Ile Gly Cys
65                  70                  75                  80

Val Ile Glu Val Ser Tyr Leu Thr Met Tyr Ile Ile Tyr Ala Pro Arg
                85                  90                  95

Lys Gln Lys Ile Ser Thr Leu Val Met Ile Leu Ile Ala Asp Ile Gly
            100                 105                 110

Gly Phe Gly Leu Thr Met Leu Ile Thr Thr Phe Ala Val Lys Gly Ile
        115                 120                 125

Asn Arg Val His Ala Val Gly Trp Ile Cys Ala Ile Phe Asn Ile Ala
    130                 135                 140

Val Phe Ala Ala Pro Leu Ser Ile Met Arg Arg Val Ile Lys Thr Lys
145                 150                 155                 160

Ser Val Glu Phe Met Pro Phe Ser Leu Ser Leu Phe Leu Thr Leu Cys
                165                 170                 175

Ala Thr Met Trp Phe Phe Tyr Gly Phe Phe Asp Lys Asp Asp Phe Ile
            180                 185                 190

Met Phe Pro Asn Val Leu Gly Phe Ile Phe Gly Ile Ser Gln Met Ile
        195                 200                 205

Leu Tyr Met Ile Tyr Lys Asn Ser Lys Lys Asn Gly Glu Thr Asn Cys
    210                 215                 220

Thr Glu Gln Gln Glu Ser Glu Gly Thr Val Asn Ser Lys Gln His Ser
```

```
                225                 230                 235                 240
Cys Asp Gly Asn Lys Leu Asp Phe Pro Ser Leu Val Glu Met Lys Glu
                    245                 250                 255

Asn Gln Leu Asn Gln Val
            260

<210> SEQ ID NO 99
<211> LENGTH: 258
<212> TYPE: PRT
<213> ORGANISM: Glycine max

<400> SEQUENCE: 99

Met Ala Ile Ser His Glu Thr Trp Ala Phe Ile Phe Gly Leu Leu Gly
1               5                   10                  15

Asn Val Ile Ser Phe Met Val Phe Leu Ala Pro Leu Pro Thr Phe Tyr
            20                  25                  30

Gln Ile Tyr Lys Lys Lys Ser Ser Glu Gly Phe Gln Ser Leu Pro Tyr
        35                  40                  45

Val Val Ala Leu Phe Ser Ser Met Leu Trp Ile Tyr Tyr Ala Leu Val
    50                  55                  60

Lys Lys Asp Ala Ser Leu Leu Ile Thr Ile Asn Ser Phe Gly Cys
65                  70                  75                  80

Val Ile Glu Thr Ile Tyr Leu Ala Ile Phe Leu Val Tyr Ala Pro Ser
                85                  90                  95

Lys Thr Arg Leu Trp Thr Ile Lys Leu Leu Leu Met Leu Asn Val Phe
            100                 105                 110

Gly Phe Gly Gly Met Leu Leu Ser Thr Leu Tyr Leu Thr Thr Gly Ser
        115                 120                 125

Lys Arg Leu Ser Val Ile Gly Trp Ile Cys Leu Val Phe Asn Ile Ser
    130                 135                 140

Val Phe Ala Ala Pro Leu Cys Ile Met Lys Arg Val Ile Lys Thr Arg
145                 150                 155                 160

Ser Val Glu Phe Met Pro Phe Ser Leu Ser Leu Ser Leu Thr Ile Asn
                165                 170                 175

Ala Val Met Trp Phe Phe Tyr Gly Leu Leu Leu Lys Asp Tyr Tyr Ile
            180                 185                 190

Ala Leu Pro Asn Thr Leu Gly Phe Leu Phe Gly Ile Ile Gln Met Val
        195                 200                 205

Leu Tyr Leu Val Tyr Arg Asn Ala Lys Pro Gln Thr Leu Glu Glu Pro
    210                 215                 220

Thr Lys Val Gln Glu Leu Asn Gly His Ile Ile Asp Val Val Lys Pro
225                 230                 235                 240

Asn His Ala Thr Lys Asn Gly His Val Pro Val Ile Glu Ile Ala Ser
                245                 250                 255

Ser Val

<210> SEQ ID NO 100
<211> LENGTH: 283
<212> TYPE: PRT
<213> ORGANISM: Glycine max

<400> SEQUENCE: 100

Met Ala Ile Phe Asn Gly His Asn His Leu Ala Leu Gly Phe Gly Met
1               5                   10                  15

Leu Gly Asn Val Ile Ser Phe Met Val Tyr Leu Ala Pro Leu Pro Thr
            20                  25                  30
```

Phe Tyr Arg Ile Tyr Lys Lys Ser Thr Glu Gly Phe Gln Ser Leu
            35                  40                  45

Pro Tyr Leu Val Ala Leu Phe Ser Ser Met Leu Trp Leu Tyr Tyr Ala
        50                  55                  60

Ser Leu Lys Pro Ala Asp Ala Thr Leu Leu Ile Thr Ile Asn Ser Leu
65                  70                  75                  80

Gly Cys Val Ile Glu Ile Val Tyr Ile Ile Met Phe Thr Ile Tyr Ala
                    85                  90                  95

Thr Lys Asp Ala Arg Asn Leu Thr Val Lys Leu Phe Met Val Met Asn
                100                 105                 110

Val Gly Ser Phe Ala Leu Ile Phe Leu Val Thr Tyr Phe Ala Met His
            115                 120                 125

Gly Ser Leu Arg Val Gln Val Gly Trp Val Cys Val Ser Ile Ala
        130                 135                 140

Val Gly Val Phe Ala Ala Pro Leu Ser Ile Val Ala Gln Val Ile Arg
145                 150                 155                 160

Thr Lys Asn Val Glu Phe Met Pro Phe Asn Leu Ser Leu Phe Leu Thr
                165                 170                 175

Ile Ser Ala Val Met Trp Phe Tyr Gly Leu Leu Leu Lys Asp Ile
            180                 185                 190

Cys Ile Ala Ile Pro Asn Ile Leu Gly Phe Thr Leu Gly Leu Leu Gln
        195                 200                 205

Met Leu Leu Tyr Ala Ile Tyr Arg Asn Gly Lys Thr Asn Asn Lys Glu
    210                 215                 220

Val Val Thr Lys Glu Glu His Ala Leu Glu Ala Met Lys Asn Val Val
225                 230                 235                 240

Val Val Asn Pro Leu Gly Thr Cys Glu Val Tyr Pro Val Ile Gly Lys
                245                 250                 255

Glu Ile Asn Asn Asn Gly Gln Gly Ile Glu Gly Ala Glu Glu Lys Glu
                260                 265                 270

Lys Gly Val Glu Leu Gly Lys Glu Cys Pro Val
            275                 280

<210> SEQ ID NO 101
<211> LENGTH: 272
<212> TYPE: PRT
<213> ORGANISM: Glycine max

<400> SEQUENCE: 101

Met Val Ile Thr His His Thr Leu Ala Phe Thr Phe Gly Met Leu Gly
1               5                   10                  15

Asn Val Ile Ser Phe Leu Val Phe Leu Ala Pro Val Pro Thr Phe Tyr
            20                  25                  30

Arg Ile Tyr Lys Lys Lys Ser Thr Glu Ser Phe Gln Ser Leu Pro Tyr
        35                  40                  45

Leu Val Ala Leu Phe Ser Ser Met Leu Trp Leu Tyr Tyr Ala Leu Leu
    50                  55                  60

Lys Arg Asp Ala Val Leu Leu Ile Thr Ile Asn Ser Phe Gly Cys Val
65                  70                  75                  80

Ile Glu Ile Ile Tyr Ile Val Leu Tyr Ile Thr Tyr Ala Thr Arg Asp
                85                  90                  95

Ala Arg Asn Leu Thr Ile Lys Leu Phe Ser Ala Met Asn Met Thr Ser
                100                 105                 110

Phe Ala Val Ile Leu Leu Val Thr His Phe Gly Val His Gly Pro Leu

```
            115                 120                 125
Arg Val Gln Val Leu Gly Trp Ile Cys Val Ser Ile Ser Val
    130                 135                 140

Phe Ala Ala Pro Leu Ser Ile Val Ala Gln Val Val Arg Thr Lys Ser
145                 150                 155                 160

Val Glu Phe Met Pro Phe Asn Leu Ser Phe Thr Leu Thr Leu Ser Ala
                    165                 170                 175

Ile Met Trp Phe Gly Tyr Gly Leu Phe Leu Lys Asp Ile Cys Ile Ala
                180                 185                 190

Leu Pro Asn Val Leu Gly Phe Val Leu Gly Leu Leu Gln Met Leu Leu
                195                 200                 205

Tyr Thr Ile Tyr Arg Lys Gly Asn Lys Lys Thr Asn Thr Asn Glu Lys
    210                 215                 220

Ser Leu Ser Val Lys Pro Leu Lys Asn Ile Ala Val Val Asn Pro Leu
225                 230                 235                 240

Gly Thr Gly Glu Val Phe Pro Val Glu Glu Asp Glu Gln Ala Ala Lys
                    245                 250                 255

Lys Ser Gln Gly Asp Gly Glu Asp Lys Lys Ala Glu Asp Cys Leu Val
                260                 265                 270

<210> SEQ ID NO 102
<211> LENGTH: 268
<212> TYPE: PRT
<213> ORGANISM: Glycine max
<220> FEATURE:
<221> NAME/KEY: misc_feature
<222> LOCATION: (244)..(244)
<223> OTHER INFORMATION: Xaa can be any naturally occurring amino acid

<400> SEQUENCE: 102

Met Pro Thr His His Ala Ser Ala Ala Ile Phe Gly Ile Ile Gly Asn
1               5                   10                  15

Met Ile Ser Val Met Val Tyr Leu Ala Pro Val Pro Thr Phe Tyr Gln
                20                  25                  30

Ile Tyr Lys Lys Lys Cys Thr Asp Gly Phe His Ser Leu Pro Tyr Leu
            35                  40                  45

Leu Ser Leu Met Ser Ser Met Leu Trp Leu Tyr Tyr Ala Phe Leu Lys
    50                  55                  60

Ile His Asp Gly Val Val Pro Leu Ile Thr Ile Asn Ser Ile Gly Cys
65                  70                  75                  80

Val Ile Glu Leu Ile Tyr Ile Leu Thr Tyr Ile Lys Tyr Ala His Lys
                85                  90                  95

Asp Ala Arg Asn Leu Thr Tyr Thr Leu Phe Ala Ala Met Asn Ile Ala
            100                 105                 110

Phe Leu Thr Leu Val Leu Ser Ser His Phe Ala Leu His Gly Ser His
        115                 120                 125

Arg Val Lys Val Ile Gly Trp Ile Cys Asp Ala Val Ser Leu Ser Val
    130                 135                 140

Phe Ala Ser Pro Leu Ser Ile Met Ala Lys Val Ile Arg Thr Lys Ser
145                 150                 155                 160

Val Gln Phe Met Pro Phe Tyr Leu Ser Phe Leu Thr Leu Asn Ala
                    165                 170                 175

Ile Thr Trp Phe Val Tyr Gly Leu Ser Ile Gln Asp Lys Cys Ile Tyr
                180                 185                 190

Val Pro Asn Val Gly Gly Phe Gly Leu Gly Leu Val Gln Met Val Leu
                195                 200                 205
```

```
Tyr Gly Ile Tyr Arg Asn Gly Gly Glu Ser Glu Lys Glu Gln Ala Leu
        210                 215                 220

Ala Glu Gly Ala Ile Asn Ile Val Val Val Asn Pro Leu Gly Pro Ala
225                 230                 235                 240

Glu Val Phe Xaa Ile Ala Glu Gly Val Asp Asp Lys Val Lys Glu
            245                 250                 255

Gly Leu Val Val Asp Gln Glu Lys Asp Ala Lys Asp
        260                 265

<210> SEQ ID NO 103
<211> LENGTH: 298
<212> TYPE: PRT
<213> ORGANISM: Brachypodium distachyon

<400> SEQUENCE: 103

Met Ala Ala Ile Gly Asn Pro Trp Val Phe Ala Val Gly Ile Leu Gly
1                   5                   10                  15

Asn Ile Leu Ser Phe Leu Val Ile Leu Ala Pro Val Pro Thr Phe His
                20                  25                  30

Arg Val Tyr Lys Arg Lys Ser Thr Glu Ser Phe Gln Ser Ala Pro Tyr
            35                  40                  45

Ala Met Ala Leu Leu Ser Ala Met Leu Trp Leu Tyr Tyr Ala Leu Leu
        50                  55                  60

Thr Ala Asp Leu Leu Leu Leu Ser Ile Asn Ala Val Gly Cys Val Val
65                  70                  75                  80

Glu Thr Ala Tyr Leu Ala Val Tyr Leu Ala Tyr Ala Pro Lys Gln Ala
                85                  90                  95

Arg Ala Phe Thr Val Lys Leu Val Phe Val Met Asn Val Ala Leu Tyr
            100                 105                 110

Gly Ala Met Val Ala Phe Leu Gln Leu Tyr Val Arg Asp Gly Asp Arg
        115                 120                 125

Arg Val Ala Ile Ala Gly Gly Val Gly Ala Ala Phe Ala Phe Ala Val
    130                 135                 140

Phe Val Ala Pro Leu Ala Ile Ile Arg Gln Val Ile Arg Thr Lys Ser
145                 150                 155                 160

Val Glu Phe Leu Pro Phe Trp Leu Ser Phe Phe Leu Thr Ile Ser Ala
                165                 170                 175

Val Val Trp Phe Phe Tyr Gly Leu Leu Met Lys Asp Phe Phe Val Ala
            180                 185                 190

Met Pro Asn Val Leu Gly Leu Leu Phe Gly Leu Ala Gln Met Ala Leu
        195                 200                 205

His Leu Val Tyr Lys Asn Pro Lys Lys Lys Gly Ala Val Ser Glu
        210                 215                 220

Ala Gly Gln Ala Ala Val Ala Ala Asp Gly Glu Lys Gln Asn Gln Leu
225                 230                 235                 240

Glu Leu Gln Gln Gln His Gln Gln Ala Ala Ala Thr Ile Asn Ala
                245                 250                 255

Asp Asp Ala Glu Asp Ala Ser Lys Val Gln Gln Ser Val Thr Val Val
            260                 265                 270

Val Asp Ile Pro Leu Pro Pro Glu Glu His Pro Ala Pro Met Pro
        275                 280                 285

Pro Pro Ile Arg Thr Ala Val Glu Val Val
        290                 295
```

<210> SEQ ID NO 104
<211> LENGTH: 299
<212> TYPE: PRT
<213> ORGANISM: Brachypodium distachyon

<400> SEQUENCE: 104

Met Ala Ala Gly Phe Leu Ser Met Ala His Pro Ala Ile Thr Leu Ser
1               5                   10                  15

Gly Ile Ala Gly Asn Val Ile Ser Phe Leu Val Phe Leu Ala Pro Val
            20                  25                  30

Thr Thr Phe Val Gln Val Val Arg Lys Lys Thr Thr Gly Gly Phe Ser
        35                  40                  45

Ala Val Pro Tyr Val Val Ala Leu Phe Ser Ser Thr Leu Trp Ile Leu
    50                  55                  60

Tyr Ala Leu Leu Lys Gly Asn Ser Arg Pro Leu Leu Thr Ile Asn Gly
65                  70                  75                  80

Phe Gly Cys Gly Val Glu Leu Ala Tyr Val Ala Tyr Leu Leu Tyr
                85                  90                  95

Ala Pro Arg Lys Ala Arg Leu Arg Ala Leu Ala Tyr Phe Leu Ala Leu
            100                 105                 110

Asp Val Ala Ala Phe Ala Ile Val Ala Ala Val Ala Leu Leu Gly Val
        115                 120                 125

Ala Pro Glu His Arg Val Lys Phe Leu Gly Ser Val Cys Leu Ala Phe
    130                 135                 140

Ser Met Ala Val Phe Val Ala Pro Leu Ser Ile Ile Phe Lys Val Ile
145                 150                 155                 160

Lys Thr Lys Ser Val Glu Phe Met Pro Ile Ser Leu Ser Phe Cys Leu
                165                 170                 175

Val Leu Ser Ala Val Ala Trp Phe Cys Tyr Gly Tyr Phe Thr Lys Asp
            180                 185                 190

Pro Tyr Val Met Tyr Pro Asn Val Gly Gly Phe Phe Phe Ser Cys Val
        195                 200                 205

Gln Met Gly Leu Tyr Phe Tyr Tyr Arg Arg Pro Ser Asn Ala Ala Val
    210                 215                 220

Leu Pro Thr Thr Ala Asp Gly Ala Thr Gly Gly Ala Val Gln Ala
225                 230                 235                 240

Gln Val Ile Glu Leu Pro Pro His Ala Val Ala Ile Leu Ser Val Ser
                245                 250                 255

Asn Ile Pro Ile Leu Gly Met His Lys Ile Glu Val Met Ala Ala Pro
            260                 265                 270

Glu Gln Gln Asp Ala Lys Ala Ala Asp Ile Val Asp Lys Ala Ala Pro
        275                 280                 285

Ala Pro Glu Ala Val Glu Ile Ala Gly Thr Val
    290                 295

<210> SEQ ID NO 105
<211> LENGTH: 309
<212> TYPE: PRT
<213> ORGANISM: Brachypodium distachyon

<400> SEQUENCE: 105

Met Ala Phe Leu Asn Met Glu Gln His Thr Trp Ala Phe Thr Phe Gly
1               5                   10                  15

Ile Leu Gly Asn Ile Ile Ser Leu Met Val Phe Leu Ser Pro Leu Pro
            20                  25                  30

Thr Phe Tyr Arg Val Tyr Arg Lys Lys Ser Thr Glu Gly Phe Gln Ser

```
            35                  40                  45
Thr Pro Tyr Val Val Thr Leu Phe Ser Cys Leu Leu Trp Met Tyr Tyr
    50                  55                  60

Ala Phe Leu Lys Ser Gly Ala Glu Leu Leu Thr Ile Asn Gly Val
65                  70                  75                  80

Gly Cys Gly Ile Glu Thr Leu Tyr Ile Ala Met Tyr Leu Ile Tyr Ala
                85                  90                  95

Pro Lys Ser Ala Arg Leu Leu Thr Ala Lys Leu Phe Leu Gly Leu Asp
            100                 105                 110

Val Gly Leu Phe Gly Leu Ile Ala Leu Val Thr Met Leu Val Ser Ala
        115                 120                 125

Gly Thr Leu Arg Val Gln Ile Val Gly Trp Ile Cys Val Ala Val Ala
    130                 135                 140

Leu Gly Val Phe Ala Ala Pro Leu Ser Ile Ile Arg Leu Val Ile Arg
145                 150                 155                 160

Thr Lys Ser Val Glu Phe Met Pro Ile Ser Leu Ser Phe Phe Leu Val
                165                 170                 175

Leu Ser Ala Val Ile Trp Phe Ala Tyr Gly Leu Leu Lys Lys Asp Val
            180                 185                 190

Phe Val Ala Val Pro Asn Val Leu Gly Phe Val Phe Gly Val Ala Gln
        195                 200                 205

Met Ala Leu Tyr Met Ala Tyr Arg Asn Lys Ser Pro Ala Ile Thr Val
    210                 215                 220

Val His Gln Glu Met Lys Leu Pro Glu His Val Lys Glu Val Thr Thr
225                 230                 235                 240

Asn Thr Lys Leu Gly Gly Ala Pro Thr Glu Gly Arg Ile Ser Cys Gly
                245                 250                 255

Ala Glu Val His Pro Ile Asp Val Met Pro Thr Ser Ala Ala Ala Gly
            260                 265                 270

Ala Asp Glu Gln Ala Ile Asn Val Glu Glu Ala Ala Ala Gly Arg Asp
        275                 280                 285

Asp His Asn Met Leu Arg Pro Glu Gln Val Ile Lys Pro Asp Met Ala
    290                 295                 300

Ile Val Val Glu Val
305

<210> SEQ ID NO 106
<211> LENGTH: 300
<212> TYPE: PRT
<213> ORGANISM: Brachypodium distachyon

<400> SEQUENCE: 106

Met Ala Gly Leu Ser Leu Gln His Pro Trp Ala Phe Ala Phe Gly Leu
1               5                   10                  15

Leu Gly Asn Val Ile Ser Phe Met Thr Tyr Leu Ala Pro Leu Ser Thr
            20                  25                  30

Phe Tyr Arg Ile Tyr Lys Asn Lys Ser Thr Gln Gly Phe Gln Ser Val
        35                  40                  45

Pro Tyr Val Val Ala Leu Phe Ser Ala Met Leu Trp Ile Tyr Tyr Ala
    50                  55                  60

Leu Leu Lys Ser Asp Gly Cys Leu Leu Ile Thr Ile Asn Thr Ala Gly
65                  70                  75                  80

Cys Val Ile Glu Thr Ile Tyr Ile Val Val Tyr Leu Ala Tyr Ala Pro
                85                  90                  95
```

```
Lys Gln Ala Lys Leu Phe Thr Ala Lys Ile Leu Leu Leu Asn Val
            100                 105                 110

Gly Val Phe Gly Met Ile Leu Leu Thr Leu Leu Leu Ser Glu Gly
            115                 120                 125

Glu Lys Arg Val Val Met Leu Gly Trp Val Cys Val Gly Phe Ser Val
            130                 135                 140

Ser Val Phe Val Ala Pro Leu Ser Val Ile Arg Leu Val Val Arg Thr
145                 150                 155                 160

Arg Ser Val Glu Phe Met Pro Phe Asn Leu Ser Leu Ser Leu Thr Leu
                165                 170                 175

Ser Ala Val Val Trp Phe Leu Tyr Gly Leu Leu Ile Lys Asp Lys Tyr
            180                 185                 190

Val Ala Leu Pro Asn Ile Leu Gly Phe Ala Phe Gly Val Ile Gln Met
            195                 200                 205

Gly Leu Tyr Ala Leu Tyr Arg Asn Ser Thr Pro Arg Pro Val Thr Lys
            210                 215                 220

Glu Val Asp Ala Glu Ser His Asp Gly Ala Ala Pro Lys Val Pro Glu
225                 230                 235                 240

His Val Val Asn Ile Gly Lys Leu Gly Ala Val Glu Leu Lys Thr Thr
                245                 250                 255

Glu Val Phe Ile His Pro Ala Ile Glu Ser Pro Pro Thr Lys Glu Asn
                260                 265                 270

Gly Val Ala His Gly Ala Glu Gln Ser Arg Glu Gly Val Val Val
            275                 280                 285

Glu Lys Val Asp Glu Ala Ser Gln Val Glu Gln Val
290                 295                 300

<210> SEQ ID NO 107
<211> LENGTH: 292
<212> TYPE: PRT
<213> ORGANISM: Brachypodium distachyon

<400> SEQUENCE: 107

Met Ala Gly Leu Ser Leu Glu His Pro Trp Ala Phe Ala Phe Gly Leu
1               5                   10                  15

Leu Gly Asn Val Ile Ser Phe Met Ser Tyr Leu Ala Pro Ile Pro Thr
            20                  25                  30

Phe Ile Arg Ile Tyr Lys Ser Lys Ser Thr Glu Gly Phe Gln Ser Val
            35                  40                  45

Pro Tyr Val Val Ala Leu Phe Ser Ala Met Leu Trp Ile Tyr Tyr Ala
50                  55                  60

Leu Val Lys Ser Asn Glu Ser Leu Leu Ile Thr Ile Asn Ala Ala Gly
65                  70                  75                  80

Cys Val Ile Glu Thr Ile Tyr Val Val Met Tyr Phe Val Tyr Ala Pro
                85                  90                  95

Arg Lys Ala Lys Leu Phe Thr Ala Lys Ile Met Leu Leu Leu Asn Gly
            100                 105                 110

Gly Val Phe Gly Val Ile Leu Phe Cys Thr Leu Phe Leu Ala His Gly
            115                 120                 125

Glu Lys Arg Val Val Ser Leu Gly Trp Ile Cys Val Ala Phe Ser Val
            130                 135                 140

Ser Val Phe Val Ala Pro Leu Ser Ile Ile Gly Arg Val Ile Lys Thr
145                 150                 155                 160

Arg Ser Val Glu Tyr Met Pro Phe Ser Leu Ser Leu Ser Leu Thr Leu
                165                 170                 175
```

```
Ser Ala Val Val Trp Phe Leu Tyr Gly Leu Leu Ile Lys Asp Lys Tyr
            180                 185                 190

Val Ala Leu Pro Asn Ile Leu Gly Phe Ser Phe Gly Val Val Gln Met
            195                 200                 205

Ala Leu Tyr Met Phe Tyr Met Asn Lys Thr Pro Ile Val Arg Gly Asp
210                 215                 220

Gly Lys Glu Gly Lys Leu Pro Ala Ala Glu His Val Val Asn
225                 230                 235                 240

Met Ala Lys Leu Gly Gly Ala Thr Pro Asp Asn Lys Asn Cys Gly
                245                 250                 255

Ser Glu Val Tyr Pro Val Glu Val Lys Ala Leu Pro Lys Ser Cys Ala
            260                 265                 270

Ala Gly Val Asp Arg Pro Leu Val Asp Pro Thr Ala Arg Pro Ala Thr
            275                 280                 285

Val Glu Val Val
    290

<210> SEQ ID NO 108
<211> LENGTH: 291
<212> TYPE: PRT
<213> ORGANISM: Brachypodium distachyon

<400> SEQUENCE: 108

Met Ala Gly Ala Leu Phe Ser Met Ala His Pro Trp Ala Ser Ala Phe
1               5                   10                  15

Gly Ile Leu Gly Asn Ile Ile Ser Phe Leu Val Phe Leu Ala Pro Thr
            20                  25                  30

Pro Thr Phe Leu Arg Val Tyr Arg Lys Lys Ser Thr Glu Gly Phe Ser
            35                  40                  45

Ser Val Pro Tyr Val Val Ala Leu Phe Ser Cys Thr Leu Trp Ile Leu
        50                  55                  60

Tyr Ala Leu Val Lys Thr Asn Ser Ser Pro Leu Leu Thr Ile Asn Ala
65                  70                  75                  80

Phe Gly Cys Val Val Glu Ala Ala Tyr Ile Val Leu Tyr Leu Val Tyr
                85                  90                  95

Ala Pro Arg Pro Ala Arg Leu Arg Thr Leu Ala Ser Phe Leu Leu Leu
            100                 105                 110

Asn Val Ala Ala Phe Ser Leu Ile Val Ala Val Thr Val Phe Leu Val
            115                 120                 125

Ala Pro Met His Arg Val Lys Val Leu Gly Ser Ile Cys Leu Ala Phe
        130                 135                 140

Ser Met Ala Val Phe Val Ala Pro Leu Ser Val Ile Phe Val Val Ile
145                 150                 155                 160

Lys Thr Lys Ser Ala Glu Tyr Met Pro Phe Ser Leu Ser Phe Phe Leu
                165                 170                 175

Thr Leu Ser Ala Val Ala Trp Phe Phe Tyr Gly Leu Thr Lys Asp
            180                 185                 190

Ile Tyr Val Thr Leu Pro Asn Val Gly Gly Phe Phe Gly Ile Ala
            195                 200                 205

Gln Met Thr Leu Tyr Phe Cys Tyr Arg Lys Pro Gly Thr Ser Ala Leu
        210                 215                 220

Val Leu Pro Thr Ser Ile Asp Asp Val Ser Thr Glu Pro Ala Ala Ser
225                 230                 235                 240

Ala Ala Ala Asp Gln Glu Val Glu Leu Pro Ala Gly Thr His Pro Ala
```

```
                    245                 250                 255
Val Ala Met Leu Thr Val Ser Thr Leu Pro Val Leu Ala Glu Leu Gln
            260                 265                 270

Lys Met Gln Glu Ile Gly Thr Pro Thr Arg Lys Gly Tyr Ile
        275                 280                 285

Lys Ala Phe
        290

<210> SEQ ID NO 109
<211> LENGTH: 292
<212> TYPE: PRT
<213> ORGANISM: Cucumis sativus

<400> SEQUENCE: 109

Met Ala Ile Ser Pro Gln Thr Leu Ala Phe Val Phe Gly Leu Leu Gly
1               5                   10                  15

Asn Ile Ile Ser Phe Met Val Phe Leu Ala Pro Leu Pro Thr Phe Tyr
            20                  25                  30

Lys Ile Tyr Lys Lys Lys Ser Ala Glu Gly Tyr Gln Ser Val Pro Tyr
        35                  40                  45

Val Val Ala Leu Phe Ser Ala Met Leu Trp Ile Tyr Tyr Ala Leu Leu
    50                  55                  60

Lys Thr Asn Ala Thr Phe Leu Ile Thr Ile Asn Ser Phe Gly Cys Val
65                  70                  75                  80

Ile Glu Ser Leu Tyr Ile Leu Leu Phe Ile Ile Tyr Ala Pro Thr Lys
                85                  90                  95

Leu Arg Phe Gln Thr Ala Lys Val Ile Phe Leu Leu Asn Val Leu Gly
            100                 105                 110

Phe Gly Leu Met Leu Ala Leu Thr Leu Val Leu Ala Lys Gly Glu Lys
        115                 120                 125

Arg Leu Lys Val Leu Gly Trp Ile Cys Leu Val Phe Asn Leu Ser Val
    130                 135                 140

Phe Ala Ala Pro Leu Phe Ile Met Gly Lys Val Ile Lys Thr Lys Ser
145                 150                 155                 160

Val Glu Tyr Met Pro Phe Ala Leu Ser Phe Phe Leu Thr Leu Asn Ala
                165                 170                 175

Val Met Trp Phe Phe Tyr Gly Leu Leu Leu Lys Asp Tyr Tyr Ile Ala
            180                 185                 190

Leu Pro Asn Val Val Gly Phe Val Phe Gly Ile Ile Gln Met Ile Leu
        195                 200                 205

Tyr Val Ile Val Lys His Ile Gly Asn Lys Ser Arg Ile Pro Val Lys
    210                 215                 220

Asp Glu Lys Ala Ala Pro Pro Gln Leu His Glu Leu Ser Glu Gln
225                 230                 235                 240

Ile Ile Asp Ala Val Lys Leu Gly Thr Met Val Cys Thr Glu Leu Asn
                245                 250                 255

Pro Val Pro Val Thr Val Leu Gln Pro Asn Met Asp Val Val Asp Ala
            260                 265                 270

Val Val Glu Ala Val Ile Asp Asn Ile Gln Lys Lys Lys Asp Gln Asp
        275                 280                 285

Ile Ile Thr Asn
        290

<210> SEQ ID NO 110
<211> LENGTH: 302
```

<212> TYPE: PRT
<213> ORGANISM: Cucumis sativus

<400> SEQUENCE: 110

Met Ala Leu Ser Phe Met Asn His Asn Pro Trp Ile Phe Ala Phe Gly
1               5                   10                  15

Leu Leu Gly Asn Ile Phe Ser Phe Ile Val Phe Leu Ala Pro Val Pro
                20                  25                  30

Thr Phe Ile Arg Val Cys Arg Lys Lys Ser Thr Glu Gly Phe Gln Ser
            35                  40                  45

Ile Pro Tyr Val Val Ala Leu Phe Ser Ala Leu Leu Ile Tyr Tyr
        50                  55                  60

Ser Thr Leu Asn Ala Asp Glu Phe Phe Leu Met Thr Ile Asn Ser Val
65                  70                  75                  80

Gly Cys Phe Ile Glu Thr Ile Tyr Ile Ala Leu Tyr Ile Ala Tyr Ala
                85                  90                  95

Pro Lys Lys Ala Arg Ile Phe Thr Val Arg Phe Val Leu Leu Leu Asp
            100                 105                 110

Val Val Gly Phe Cys Ser Ile Leu Val Val Thr Gln Phe Leu Val Lys
        115                 120                 125

Arg Ala Tyr Arg Ala Arg Val Ile Gly Phe Ile Cys Gly Gly Leu Ser
130                 135                 140

Val Ser Val Phe Ala Ala Pro Leu Ser Ile Met Lys Arg Val Ile Arg
145                 150                 155                 160

Thr Arg Ser Val Glu Tyr Met Pro Phe Ser Leu Ser Phe Phe Leu Thr
                165                 170                 175

Leu Ser Ala Val Met Trp Leu Cys Tyr Gly Leu Phe Leu Lys Asp Leu
            180                 185                 190

Tyr Val Ala Leu Pro Asn Thr Leu Gly Phe Thr Phe Gly Met Ala Gln
        195                 200                 205

Met Ile Leu Tyr Ala Ile Tyr Arg Asn Ala Lys Pro Leu Pro Ser Glu
210                 215                 220

Glu Lys Leu Pro Gln His Lys Ala Asp Ile Glu Thr Gln Ile Val Ile
225                 230                 235                 240

Thr Ala Thr Pro Thr Asn Pro Asp Asp His Gln Gly Asp Glu His Gln
                245                 250                 255

Asn Gln Asp Gln Val Ile Asn Val Pro Pro Pro Pro Gln Ser Asn
            260                 265                 270

Thr Asn His Ala Pro Ser Val Cys Asn Asn Asp Lys Tyr Cys Met
        275                 280                 285

Asp Asn Asn Met Ala Pro Pro Met Val Lys Cys Glu Ala
290                 295                 300

<210> SEQ ID NO 111
<211> LENGTH: 236
<212> TYPE: PRT
<213> ORGANISM: Cucumis sativus

<400> SEQUENCE: 111

Met Asn Gly Leu Ser Val His Gln Leu Gln Phe Ile Phe Gly Leu Leu
1               5                   10                  15

Gly Asn Ile Ile Ser Phe Leu Val Phe Leu Ala Pro Met Pro Thr Phe
                20                  25                  30

Trp Thr Ile Tyr Lys Lys Lys Thr Ser Glu Gly Phe Gln Ser Ile Pro
            35                  40                  45

```
Tyr Val Val Ala Leu Met Ser Ala Met Leu Leu Tyr Tyr Ala Ala
    50              55                  60

Leu Lys Thr Asn Ala Tyr Leu Leu Val Ser Ile Asn Ser Phe Gly Cys
65              70                  75                  80

Val Ile Glu Val Ile Tyr Ile Ala Leu Tyr Leu Phe Tyr Ala Pro Lys
            85                  90                  95

Lys Gln Lys Ile Phe Thr Leu Lys Leu Phe Ile Ile Phe Asn Leu Gly
                100                 105                 110

Phe Ser Gly Val Met Val Gly Gly Thr Met Phe Phe Leu His Gly Met
            115                 120                 125

Lys Arg Thr Asn Ala Val Gly Trp Ile Cys Ala Ala Phe Asn Leu Ser
130                 135                 140

Val Phe Ala Ser Pro Leu Ser Ile Met Lys Arg Val Ile Thr Thr Lys
145                 150                 155                 160

Ser Val Glu Tyr Met Pro Phe Ser Leu Ser Phe Phe Leu Thr Leu Ser
                165                 170                 175

Ala Thr Met Trp Phe Phe Tyr Gly Phe Phe Ile Lys Asp Leu Phe Ile
            180                 185                 190

Ala Leu Pro Asn Val Val Gly Phe Leu Leu Gly Met Val Gln Met Ile
            195                 200                 205

Met Tyr Ile Tyr Ile Leu Leu Leu Leu Leu His Tyr Thr Thr Pro
210                 215                 220

His Ala Asp Val Leu Gln Ile Phe Ser Leu Leu Ile
225                 230                 235

<210> SEQ ID NO 112
<211> LENGTH: 274
<212> TYPE: PRT
<213> ORGANISM: Cucumis sativus

<400> SEQUENCE: 112

Met Lys Gly Leu Ser Val His Gln Leu Gln Phe Ile Phe Gly Leu Leu
1               5                   10                  15

Gly Asn Ile Ile Ser Phe Met Val Phe Leu Ala Pro Val Pro Thr Phe
            20                  25                  30

Trp Thr Val Tyr Lys Lys Thr Ser Glu Gly Phe Gln Cys Ile Pro
        35                  40                  45

Tyr Val Val Ala Leu Met Ser Ala Met Leu Leu Leu Tyr Tyr Ala Val
    50                  55                  60

Leu Lys Thr Asn Ala Tyr Leu Leu Ile Ser Ile Asn Ser Phe Gly Cys
65              70                  75                  80

Val Ile Glu Leu Ile Tyr Ile Ala Leu Tyr Phe Tyr Ala Pro Lys
            85                  90                  95

Lys Leu Lys Ile Phe Thr Leu Lys Leu Leu Met Ile Leu Asn Leu Gly
                100                 105                 110

Ser Tyr Gly Val Met Val Gly Gly Thr Met Leu Ile Leu His Gly Asn
            115                 120                 125

Lys Arg Thr His Ala Val Gly Trp Ile Cys Ala Ala Phe Asn Leu Ala
130                 135                 140

Val Phe Ala Ser Pro Leu Ala Ile Met Lys Arg Val Ile Thr Thr Lys
145                 150                 155                 160

Ser Val Glu Tyr Met Pro Phe Ser Leu Ser Phe Phe Leu Thr Leu Ser
                165                 170                 175

Ala Thr Met Trp Phe Phe Tyr Gly Phe Phe Ile Lys Asp Leu Phe Ile
            180                 185                 190
```

```
Ala Leu Pro Asn Ile Val Gly Phe Leu Leu Gly Met Val Gln Met Ile
            195                 200                 205

Met Tyr Met Ile Tyr Lys Asp Arg Lys Gly Asn Ser Leu Glu Glu Lys
            210                 215                 220

Leu Glu Glu Gly Gly Lys Lys Tyr Val Asp Asp Gln Ser Leu Ser
225                 230                 235                 240

Lys Tyr Lys Gly Gln Ile Arg Arg Ile Leu Asp Leu Val Leu Glu Glu
            245                 250                 255

Tyr Arg Phe Ser Arg Glu Asn Tyr Asn Ala Leu Asp Val Val Glu Pro
            260                 265                 270

Thr Thr

<210> SEQ ID NO 113
<211> LENGTH: 277
<212> TYPE: PRT
<213> ORGANISM: Cucumis sativus

<400> SEQUENCE: 113

Met Thr Ile Phe His Ser Pro His Leu Leu Val Phe Thr Phe Gly Leu
1               5                   10                  15

Leu Gly Asn Ile Ile Ser Phe Phe Val Tyr Leu Ala Pro Leu Pro Thr
            20                  25                  30

Phe Tyr Arg Ile Trp Gln Lys Lys Ser Thr Glu Gly Phe His Ala Leu
            35                  40                  45

Pro Tyr Leu Val Ala Leu Phe Ser Ser Ala Leu Trp Leu Cys Tyr Ala
        50                  55                  60

Phe Leu Lys Thr Asn Thr Phe Leu Leu Ile Thr Ile Asn Ser Phe Gly
65                  70                  75                  80

Cys Val Ile Glu Phe Leu Tyr Phe Ile Val Phe Ile Val Phe Ala Ala
                85                  90                  95

Asn Ser Val Arg Met Leu Thr Ile Arg Ile Phe Ala Met Met Asn Met
            100                 105                 110

Gly Leu Phe Gly Leu Ile Leu Val Ala Ile His Phe Ile Pro Asn Pro
        115                 120                 125

Ser Asn Arg Thr Asp Val Met Gly Trp Ile Cys Val Ala Val Ser Val
    130                 135                 140

Ser Val Phe Ala Ala Pro Leu Ser Ile Leu Arg Gln Val Met Thr Thr
145                 150                 155                 160

Lys Ser Val Glu Phe Met Pro Phe Thr Leu Ser Phe Phe Leu Thr Leu
                165                 170                 175

Ser Ala Ile Met Trp Phe Ala Tyr Gly Leu Leu Leu Asn Asp Ile Cys
            180                 185                 190

Ile Ala Ile Pro Asn Val Val Gly Phe Ile Leu Gly Leu Leu Gln Met
        195                 200                 205

Val Val Tyr Ala Ile Tyr Arg Lys Arg Lys Ile Val Ile Met Glu Glu
    210                 215                 220

Lys Lys Gln Pro Glu Gln Val Val Leu Lys Ser Ile Ala Val Ser Glu
225                 230                 235                 240

Val Phe Ala Met Lys Lys Pro Asn Gly Asn Asp Ala Gln Leu Lys Glu
                245                 250                 255

Val Ile Ile Ile Lys Gln Glu Ala Gln Glu Asp Asp Lys Leu Ser Cys
            260                 265                 270

Asp Lys Ile Asn Thr
            275
```

<210> SEQ ID NO 114
<211> LENGTH: 291
<212> TYPE: PRT
<213> ORGANISM: Cucumis sativus

<400> SEQUENCE: 114

Met Ala Leu Phe Asp Thr His His Pro Gly Val Phe Ala Phe Gly Leu
1               5                   10                  15

Leu Gly Asn Ile Ile Ser Phe Ile Val Phe Leu Ala Pro Val Pro Thr
            20                  25                  30

Phe Met Arg Ile Tyr Lys Lys Ser Thr Glu Gly Phe Gln Ser Val
        35                  40                  45

Pro Tyr Val Val Ala Leu Phe Ser Ala Met Leu Trp Leu Tyr Tyr Ala
    50                  55                  60

Ser Phe Asn Ser Asn Glu Thr Leu Leu Ile Thr Ile Asn Ser Val Gly
65                  70                  75                  80

Cys Leu Ile Glu Thr Leu Tyr Ile Ala Ile Phe Ile Val Phe Ala Pro
                85                  90                  95

Lys Gln Ile Arg Val Ser Thr Leu Arg Phe Val Leu Leu Asn Phe
            100                 105                 110

Gly Gly Phe Cys Ile Ile Leu Leu Val Thr His Phe Leu Val His Gly
        115                 120                 125

Ser Asn Gln Val Lys Val Val Gly Trp Ile Cys Val Ala Phe Ser Val
    130                 135                 140

Ser Val Phe Ala Ala Pro Leu Thr Ile Met Arg Leu Val Ile Arg Thr
145                 150                 155                 160

Lys Ser Val Glu Phe Met Pro Phe Ser Leu Ser Phe Phe Leu Thr Leu
                165                 170                 175

Ser Ala Ile Thr Trp Leu Leu Tyr Gly Val Phe Leu Lys Asp Ile Tyr
            180                 185                 190

Val Ala Leu Pro Asn Val Leu Gly Phe Ile Phe Gly Val Ala Gln Met
        195                 200                 205

Ile Leu Tyr Leu Ile Tyr Arg Lys Tyr Glu Ile Ala Ile Ala Lys Glu
    210                 215                 220

Met Lys Leu Pro Glu Gln Thr Thr Val Asp Ile Val Met Lys Gln Lys
225                 230                 235                 240

Gln Asp Ser Ser Val Glu Ala Ile Glu Val Ile Lys Thr Asn Ile
                245                 250                 255

Glu Glu Ile Glu Leu Ser Asn Gly Asn Asn Asn Asp Asn Asp Lys
            260                 265                 270

His Asn His Lys Thr Leu Glu Val Ser His Gln Ile Thr Asp His Leu
        275                 280                 285

Asn His Val
    290

<210> SEQ ID NO 115
<211> LENGTH: 295
<212> TYPE: PRT
<213> ORGANISM: Cucumis sativus

<400> SEQUENCE: 115

Met Ala Leu Ser Phe Asn Thr His Asn Pro Ala Ala Phe Thr Phe Gly
1               5                   10                  15

Leu Leu Gly Asn Ile Ile Ser Phe Ile Val Phe Leu Ala Pro Val Pro
            20                  25                  30

```
Thr Phe Met Arg Ile Tyr Lys Lys Ser Thr Glu Gly Phe Gln Ser
            35                  40                  45

Ile Pro Tyr Val Val Ala Leu Phe Ser Ala Met Leu Trp Leu Tyr Tyr
 50                  55                  60

Ala Ser Phe Asn Pro Asn Glu Thr Leu Leu Ile Thr Ile Asn Ser Val
 65                  70                  75                  80

Gly Cys Leu Ile Glu Thr Ile Tyr Leu Ala Ile Phe Ile Val Phe Ala
                85                  90                  95

Pro Lys Gln Ile Arg Val Ser Thr Leu Arg Phe Val Leu Leu Leu Asn
                100                 105                 110

Phe Gly Gly Phe Cys Ile Ile Leu Leu Val Thr His Phe Leu Val His
                115                 120                 125

Gly Ser Asn Arg Val Lys Val Val Gly Trp Ile Cys Val Ala Phe Ser
130                 135                 140

Ile Ser Val Phe Ala Ala Pro Leu Thr Ile Ile Arg Leu Val Ile Arg
145                 150                 155                 160

Thr Lys Ser Val Glu Phe Met Pro Phe Tyr Leu Ser Phe Phe Leu Thr
                165                 170                 175

Leu Ser Ala Thr Ser Trp Leu Leu Tyr Gly Val Phe Leu Lys Asp Ile
                180                 185                 190

Tyr Ile Ala Val Pro Asn Ile Pro Gly Phe Met Phe Gly Ile Ala Gln
                195                 200                 205

Met Ile Leu Tyr Leu Ile Tyr Lys Lys Arg Glu Thr Ala Met Glu Met
                210                 215                 220

Gln Leu Pro Gln His Ser Thr Asp Asn Ile Val Ile Val Ser Ala Ala
225                 230                 235                 240

Thr Asn Ser Asp Lys Gln Lys Gln His Ser Ser Leu Pro Ser Asn
                245                 250                 255

Asn Leu Val Gly Ala Ala Val Asp Asp Asp Val Thr Thr Thr Thr
                260                 265                 270

Lys Asn Gly Ile Asp Pro Ile Asn Asn Leu Glu Gln Asn His Gln Val
                275                 280                 285

Lys Asp Gln Leu Asn His Val
                290                 295

<210> SEQ ID NO 116
<211> LENGTH: 294
<212> TYPE: PRT
<213> ORGANISM: Cucumis sativus

<400> SEQUENCE: 116

Met Ala Leu Ser Phe Asn Thr His Asn Pro Ala Ala Phe Thr Phe Gly
 1               5                  10                  15

Leu Leu Gly Asn Ile Ile Ser Phe Ile Val Phe Leu Ala Pro Val Pro
                20                  25                  30

Thr Phe Met Arg Ile Tyr Lys Lys Ser Thr Glu Gly Phe Gln Ser
            35                  40                  45

Ile Pro Tyr Val Val Ala Leu Phe Ser Ala Met Leu Trp Leu Tyr Tyr
 50                  55                  60

Ala Ser Phe Asn Pro Asn Glu Thr Leu Leu Ile Thr Ile Asn Ser Val
 65                  70                  75                  80

Gly Cys Leu Ile Glu Thr Ile Tyr Leu Ala Ile Phe Ile Val Phe Ala
                85                  90                  95

Pro Lys Gln Ile Arg Val Ser Thr Leu Arg Phe Val Leu Leu Leu Asn
```

```
            100                 105                 110
Phe Gly Gly Phe Cys Ile Ile Leu Leu Val Thr His Phe Leu Val His
        115                 120                 125

Gly Ser Asn Arg Val Lys Val Gly Trp Ile Cys Val Ala Phe Ser
130                 135                 140

Ile Ser Val Phe Ala Ala Pro Leu Thr Ile Ile Arg Leu Val Ile Arg
145                 150                 155                 160

Thr Lys Ser Val Glu Phe Met Pro Phe Tyr Leu Ser Phe Phe Leu Thr
                165                 170                 175

Leu Ser Ala Thr Ser Trp Leu Leu Tyr Gly Val Phe Leu Lys Asp Ile
                180                 185                 190

Tyr Ile Ala Val Pro Asn Ile Pro Gly Phe Met Phe Gly Ile Ala Gln
            195                 200                 205

Met Ile Leu Tyr Leu Ile Tyr Lys Lys Arg Glu Thr Ala Met Glu Met
210                 215                 220

Gln Leu Pro Gln His Ser Thr Asp Asn Thr Val Ile Val Ser Ala Ala
225                 230                 235                 240

Thr Asn Ser Asp Lys Gln Lys Gln His Ser Ser Leu Pro Ser Asn
                245                 250                 255

Asn Leu Val Gly Ala Ala Val Asp Asp Val Thr Thr Thr Lys
            260                 265                 270

Asn Gly Ile Asp Pro Ile Asn Asn Leu Glu Glu Asn His Gln Val Lys
            275                 280                 285

Asp Gln Leu Asn His Val
        290

<210> SEQ ID NO 117
<211> LENGTH: 300
<212> TYPE: PRT
<213> ORGANISM: Solanum lycopersicum

<400> SEQUENCE: 117

Met Ala Val Asp Phe Gly His Tyr Ala Phe Ala Phe Gly Val Leu Gly
1               5                   10                  15

Asn Ile Ile Ser Phe Ile Val Phe Leu Ser Pro Ile Pro Thr Phe Tyr
                20                  25                  30

Ser Ile Tyr Lys Lys Lys Ser Thr Glu Gly Tyr Gln Ser Ile Pro Tyr
            35                  40                  45

Val Val Ala Leu Phe Ser Ser Met Leu Trp Ile Tyr Tyr Ala Leu Leu
        50                  55                  60

Lys Ser Asn Met Pro Leu Leu Ile Thr Ile Asn Ser Phe Gly Met Phe
65                  70                  75                  80

Ile Glu Thr Ile Tyr Val Gly Phe Tyr Leu Phe Tyr Ala Pro Lys Lys
                85                  90                  95

Ala Arg Val His Thr Ile Lys Met Leu Met Leu Ser Val Val Gly Gly
            100                 105                 110

Phe Gly Ala Ile Val Leu Val Thr Glu Phe Leu Phe Lys Gly Val Val
        115                 120                 125

Arg Gly Gln Ile Val Gly Trp Ile Cys Leu Ile Phe Ser Leu Cys Val
130                 135                 140

Phe Val Ala Pro Leu Gly Ile Val Arg Gln Val Ile Lys Thr Lys Ser
145                 150                 155                 160

Val Glu Tyr Met Pro Leu Leu Leu Ser Val Phe Leu Thr Leu Ser Ala
                165                 170                 175
```

Val Met Trp Phe Phe Tyr Gly Leu Leu Leu Lys Asp Ile Asn Ile Ala
            180                 185                 190

Ala Pro Asn Val Leu Gly Phe Ile Phe Gly Ile Leu Gln Ile Ile Leu
            195                 200                 205

Tyr Ala Ile Tyr Ser Lys Lys Glu Lys Ser Ile Lys Glu Gln Lys
            210                 215                 220

Leu Pro Glu Ile Gln Lys Thr Glu Val Ile Val Lys Asp Glu Asn Met
225                 230                 235                 240

Asn Ala Asn Lys Lys Leu Pro Glu Leu Thr Gln Glu Gln Ile Ile Asp
                245                 250                 255

Ile Val Lys Leu Ala Gly Leu Leu Val Val Thr Asp Lys Thr Asn Val
            260                 265                 270

Ala Thr Cys Pro Asn Asp Thr Asn Cys Gly Val Lys Ala Val Asn Lys
            275                 280                 285

Ile Glu Asn Met Pro Lys Leu Gln Thr Val Ala Thr
            290                 295                 300

<210> SEQ ID NO 118
<211> LENGTH: 296
<212> TYPE: PRT
<213> ORGANISM: Solanum lycopersicum

<400> SEQUENCE: 118

Met Ala Phe Ser Ala Asp His Trp Ala Phe Val Phe Gly Val Leu Gly
1               5                   10                  15

Asn Ile Val Ser Phe Ile Val Phe Leu Ser Pro Leu Pro Thr Phe Tyr
            20                  25                  30

Thr Ile Tyr Lys Lys Lys Thr Ala Glu Gly Tyr Gln Ser Ile Pro Tyr
            35                  40                  45

Val Val Ala Leu Phe Ser Ser Met Leu Trp Ile Tyr Tyr Ala Phe Leu
        50                  55                  60

Lys Thr Asn Thr Thr Leu Leu Ile Thr Ile Asn Thr Phe Gly Val Phe
65              70                  75                  80

Val Glu Thr Ile Tyr Val Val Phe Tyr Leu Ile Tyr Ala Pro Lys Lys
            85                  90                  95

Ser Arg Val Gln Thr Ile Lys Met Leu Ser Leu Phe Val Val Gly Gly
            100                 105                 110

Phe Gly Ala Ile Ile Leu Val Thr Gln Phe Leu Phe Lys Gly Val Ile
            115                 120                 125

Arg Gly Gln Val Val Gly Trp Ile Cys Leu Ile Phe Ser Leu Cys Val
            130                 135                 140

Phe Val Ala Pro Leu Gly Ile Val Arg Lys Val Ile Lys Thr Lys Ser
145                 150                 155                 160

Val Glu Tyr Met Pro Leu Leu Leu Ser Val Phe Leu Thr Leu Ser Ala
            165                 170                 175

Val Met Trp Phe Phe Tyr Gly Leu Leu Leu Lys Asp Ile Asn Ile Ala
            180                 185                 190

Ala Pro Asn Ile Leu Gly Phe Ile Phe Gly Val Leu Gln Met Ile Leu
            195                 200                 205

Tyr Val Ile Tyr Ser Lys Lys Glu Lys Ala Ile Leu Lys Glu Gln Lys
            210                 215                 220

Leu Pro Glu Ile Gln Lys Gly Glu Val Ile Val Lys Asp Glu Asn Met
225                 230                 235                 240

Asn Ala Asp Lys Lys Phe Pro Glu Leu Thr Gln Glu Gln Ile Ile Asp
                245                 250                 255

```
Ile Val Arg Leu Gly Leu Met Val Cys Lys Gly Lys Val His Val Ala
            260                 265                 270

Thr Cys Pro His Gly Thr Thr Cys Glu Pro Lys Val Asp Glu Asn Glu
            275                 280                 285

Pro Lys Leu Gln Thr Val Glu Val
            290                 295

<210> SEQ ID NO 119
<211> LENGTH: 298
<212> TYPE: PRT
<213> ORGANISM: Solanum lycopersicum

<400> SEQUENCE: 119

Met Val Phe Asn His Trp Ala Phe Ala Phe Gly Val Leu Gly Asn Ile
1               5                   10                  15

Val Ser Phe Ile Val Phe Leu Ser Pro Ile Pro Thr Phe Tyr Asn Ile
            20                  25                  30

Tyr Lys Lys Lys Ser Thr Glu Gly Tyr Gln Ser Ile Pro Tyr Val Val
            35                  40                  45

Ala Leu Phe Ser Ser Met Leu Trp Ile Tyr Tyr Ala Leu Leu Lys Ser
50                  55                  60

Asn Met Pro Leu Leu Ile Thr Ile Asn Ser Phe Gly Met Phe Ile Glu
65                  70                  75                  80

Thr Ile Tyr Val Gly Leu Tyr Leu Leu Tyr Ala Pro Asn Lys Ala Arg
            85                  90                  95

Val His Thr Ile Lys Met Leu Met Leu Ser Val Val Gly Gly Phe Gly
            100                 105                 110

Ala Ile Val Leu Ile Thr Glu Phe Leu Phe Lys Gly Val Val Arg Gly
            115                 120                 125

Gln Ile Val Gly Trp Ile Cys Leu Ile Phe Ser Leu Cys Val Phe Val
130                 135                 140

Ala Pro Leu Gly Ile Val Arg Lys Val Ile Lys Thr Lys Ser Val Glu
145                 150                 155                 160

Tyr Met Pro Leu Leu Leu Ser Val Phe Leu Thr Leu Ser Ala Val Met
            165                 170                 175

Trp Phe Phe Tyr Gly Leu Leu Leu Lys Asp Ile Asn Ile Ala Ala Pro
            180                 185                 190

Asn Val Leu Gly Phe Ile Phe Gly Ile Leu Gln Ile Val Leu Tyr Ala
            195                 200                 205

Ile Tyr Ser Lys Lys Glu Lys Val Ile Leu Lys Glu Gln Lys Leu Pro
210                 215                 220

Glu Ile Gln Thr Pro Ala Val Ile Val Lys Asn Glu Asn Met Met Asn
225                 230                 235                 240

Thr Thr Lys Lys Leu Pro Glu Leu Thr Gln Glu Ile Ile Asp Ile
            245                 250                 255

Val Lys Leu Gly Leu Leu Val Cys Ser Asp Lys Thr Gln Val Ala Thr
            260                 265                 270

Cys Pro Asn Asp Thr Asn Cys Gly Val Lys Asp Thr Asn Asn Asn Val
            275                 280                 285

Val Asn Met Pro Lys Leu Gln Thr Val Ala
            290                 295

<210> SEQ ID NO 120
<211> LENGTH: 282
<212> TYPE: PRT
```

<213> ORGANISM: Solanum lycopersicum

<400> SEQUENCE: 120

Met Ala Ile Ala Gly His Trp Ala Phe Val Phe Gly Val Leu Gly Asn
1               5                   10                  15

Ile Ile Ser Phe Ile Val Phe Leu Ser Pro Ile Pro Thr Phe Asn Lys
            20                  25                  30

Ile Tyr Lys Lys Lys Ser Thr Glu Gly Tyr Gln Ser Ile Pro Tyr Val
        35                  40                  45

Ile Ala Leu Phe Ser Cys Met Leu Trp Ile Tyr Tyr Ala Phe Leu Lys
    50                  55                  60

Thr Asn Thr Thr Leu Leu Ile Thr Ile Asn Ser Phe Gly Met Leu Ile
65                  70                  75                  80

Glu Thr Ile Tyr Val Ser Leu Phe Leu Tyr Tyr Ala Pro Lys Lys Ala
                85                  90                  95

Arg Val Asn Thr Val Lys Met Leu Leu Leu Thr Val Val Gly Gly Phe
            100                 105                 110

Gly Ala Ile Ile Leu Val Thr Gln Phe Leu Phe Lys Gly Val Val Arg
        115                 120                 125

Gly Gln Ile Val Gly Trp Ile Cys Leu Ile Phe Ser Leu Cys Val Phe
    130                 135                 140

Val Ala Pro Leu Gly Ile Val Arg Gln Val Ile Lys Thr Lys Ser Val
145                 150                 155                 160

Glu Tyr Met Pro Ile Leu Leu Ser Val Phe Leu Thr Ile Ser Ala Val
                165                 170                 175

Met Trp Phe Phe Tyr Gly Leu Leu Leu Lys Asp Val Asn Ile Ala Ala
            180                 185                 190

Pro Asn Ile Leu Gly Phe Ile Phe Gly Ile Leu Gln Met Ile Leu Tyr
        195                 200                 205

Ala Met Tyr Arg Lys Lys His Lys Pro Ile Val Asn Val Asn Val Glu
    210                 215                 220

Val Gln Asn Pro Val Ile Ile Leu Asp Asp Asn Lys Lys Ile Pro Glu
225                 230                 235                 240

Leu Thr Glu Glu Gln Ile Ile Asp Ile Val Lys Leu Gly Lys Leu Val
                245                 250                 255

Cys Ser Gly Lys Ile Gln Met Ala Ser Thr Leu Asn Gly Asn Ala Ser
            260                 265                 270

Lys Glu Val Lys Gln Gln Thr Glu Glu Ala
        275                 280

<210> SEQ ID NO 121
<211> LENGTH: 295
<212> TYPE: PRT
<213> ORGANISM: Solanum lycopersicum

<400> SEQUENCE: 121

Met Thr Thr His Leu Ala Phe Val Phe Gly Leu Leu Gly Asn Ile Val
1               5                   10                  15

Ser Phe Met Val Tyr Leu Ala Pro Val Pro Thr Phe Tyr Lys Ile Tyr
            20                  25                  30

Lys Lys Lys Ser Thr Glu Gly Phe Gln Ser Val Pro Tyr Val Val Gly
        35                  40                  45

Leu Phe Ser Ala Met Leu Trp Ile Tyr Tyr Ala Phe Leu Lys Pro Asp
    50                  55                  60

Thr Thr Leu Leu Ile Thr Ile Asn Ser Val Gly Cys Phe Ile Gln Thr

```
                65                  70                  75                  80
        Phe Tyr Ile Cys Phe Phe Leu Phe Tyr Ala Thr Lys Ala Lys Met
                        85                  90                  95

Asp Thr Met Lys Leu Leu Leu Ser Met Asn Val Val Gly Leu Gly Leu
                       100                 105                 110

Ile Ile Phe Leu Thr Gln Phe Phe Ala Lys Gly Ser Asn Arg Ala Gln
                       115                 120                 125

Ile Val Gly Trp Ile Cys Leu Ile Phe Ser Phe Cys Val Phe Val Ala
                       130                 135                 140

Pro Leu Gly Val Leu Arg Gln Val Ile Arg Thr Lys Ser Val Glu Tyr
        145                 150                 155                 160

Met Pro Phe Gln Leu Ser Phe Phe Leu Thr Leu Ser Ala Val Met Trp
                       165                 170                 175

Phe Leu Tyr Gly Leu Leu Arg Lys Asp Tyr Asn Ile Ala Ile Pro Asn
                       180                 185                 190

Val Leu Gly Phe Ser Leu Gly Val Ile Gln Met Thr Leu Tyr Leu Ile
                       195                 200                 205

Tyr Lys Asn Ala Lys Lys Val Thr Lys Glu Val Lys Leu Glu Val Thr
                       210                 215                 220

Glu Ile Val Ala Asp Asp Lys Glu Leu Lys Leu Ser Glu Glu Ile Leu
        225                 230                 235                 240

Lys Asp Gln Ile Ile Asp Val Val Lys Leu Ser Ala Ile Val Cys Ser
                       245                 250                 255

Glu Ile Ile Pro Met Val Thr Gly Asn Glu Leu Lys Asn Glu Ile Asn
                       260                 265                 270

Leu Pro Gln Leu Asn Val Ile Ile Asn Glu Asp Met Met Ile Lys Pro
                       275                 280                 285

Lys Ala Ile Ile Glu Ala Ser
                       290                 295

<210> SEQ ID NO 122
<211> LENGTH: 297
<212> TYPE: PRT
<213> ORGANISM: Solanum lycopersicum

<400> SEQUENCE: 122

Met Ala Gly Ile Ser Gly His Trp Ala Phe Ala Phe Gly Val Leu Gly
        1               5                   10                  15

Asn Ile Val Ser Phe Ile Val Phe Leu Ser Pro Leu Pro Thr Phe Tyr
                        20                  25                  30

Lys Ile Tyr Lys Lys Ser Thr Asp Gly Tyr Gln Ser Ile Pro Tyr
                        35                  40                  45

Val Val Ala Leu Phe Ser Ser Met Leu Trp Ile Tyr Tyr Ala Phe Leu
                        50                  55                  60

Lys Thr Asn Thr Thr Leu Leu Ile Thr Ile Asn Ser Phe Gly Val Phe
        65                  70                  75                  80

Ile Glu Thr Ile Tyr Val Gly Phe Tyr Leu Phe Tyr Ala Pro Lys Lys
                        85                  90                  95

Asp Arg Val Gln Thr Ile Lys Met Leu Met Leu Ser Val Gly Gly
                       100                 105                 110

Phe Gly Ala Ile Val Leu Ile Thr Glu Phe Leu Phe Lys Gly Val Val
                       115                 120                 125

Arg Gly Gln Ile Val Gly Trp Ile Cys Leu Ile Phe Ser Leu Cys Val
                       130                 135                 140
```

```
Phe Val Ala Pro Leu Gly Ile Val Lys Gln Val Ile Lys Thr Lys Ser
145                 150                 155                 160

Val Glu Tyr Met Pro Leu Leu Leu Ser Ile Phe Leu Thr Leu Ser Ala
                165                 170                 175

Val Val Trp Phe Phe Tyr Gly Leu Leu Leu Lys Asp Ile Asn Ile Ala
            180                 185                 190

Ile Pro Asn Val Leu Gly Phe Ile Leu Gly Ile Leu Gln Met Val Leu
        195                 200                 205

Tyr Val Ile Tyr Asn Lys Lys Glu Lys Ala Ile Leu Lys Glu Gln Lys
    210                 215                 220

Leu Pro Glu Lys Leu Gln Asn His Met Ile Ile Ser Met Asp Glu Lys
225                 230                 235                 240

Asn Lys Asn Ser Pro Gly Leu Thr Glu Glu Gln Ile Ile Asp Ile Val
                245                 250                 255

Lys Leu Gly Ser Leu Ile Ser Ser Gly Lys Ile His Ile Ala Ser Cys
            260                 265                 270

Leu His Asp Ala Met Cys Ala Ser Ala Lys Ile Glu Asn Thr Pro Asn
        275                 280                 285

Asn Leu Glu Thr Val Glu Ala Ile Asn
    290                 295

<210> SEQ ID NO 123
<211> LENGTH: 276
<212> TYPE: PRT
<213> ORGANISM: Solanum lycopersicum

<400> SEQUENCE: 123

Met Thr Ser Val Ser His Thr His Pro Leu Val Tyr Thr Phe Gly Ile
1               5                   10                  15

Leu Gly Asn Leu Val Ser Phe Met Val Phe Ile Ala Pro Val Pro Thr
                20                  25                  30

Phe Tyr Arg Ile Val Lys Lys Lys Ser Ser Glu Gly Phe His Ser Leu
            35                  40                  45

Pro Tyr Val Val Gly Leu Phe Ser Ala Met Leu Trp Ile Tyr Tyr Ala
        50                  55                  60

Met Val Lys Thr Asn Val Thr Leu Leu Ile Thr Ile Asn Ser Phe Gly
65                  70                  75                  80

Cys Ile Ala Glu Thr Ile Tyr Val Ala Ile Tyr Phe Thr Tyr Ala Thr
                85                  90                  95

Lys Lys Ala Arg Met Lys Thr Leu Gly Leu Val Leu Leu Leu Asn Phe
            100                 105                 110

Gly Val Phe Gly Leu Ile Leu Phe Leu Thr Gln Ile Leu Cys Gln Gly
        115                 120                 125

Thr Lys Arg Ala Glu Val Ile Gly Trp Ile Cys Met Ala Phe Ser Ile
    130                 135                 140

Ser Val Phe Val Ala Pro Leu Ser Ile Met Gly Arg Val Ile Arg Thr
145                 150                 155                 160

Lys Ser Val Glu Phe Met Pro Phe Asn Leu Ser Leu Ala Leu Thr Val
                165                 170                 175

Ser Ala Val Met Trp Phe Leu Tyr Gly Leu Leu Leu Lys Asp Val Tyr
            180                 185                 190

Val Ala Val Pro Asn Ile Pro Gly Met Ile Leu Gly Val Leu Gln Met
        195                 200                 205

Ile Leu Tyr Gly Ile Tyr Arg Asn Ser Lys Ser Asn Asn Val Ala Thr
    210                 215                 220
```

```
Glu Lys Glu Leu Pro Ile Val Val Lys Val Asp Gln Glu Gln Pro Thr
225                 230                 235                 240

Lys Val Asn Ser Glu Val Tyr Pro Val Asn Ile Ser Ser Leu Asp Ser
            245                 250                 255

Glu Asn Gly Glu Ala Lys Asp Gly Lys Asn Leu Gln Asp Pro Gln Met
        260                 265                 270

Asn Ser Gln Val
        275

<210> SEQ ID NO 124
<211> LENGTH: 287
<212> TYPE: PRT
<213> ORGANISM: Solanum lycopersicum

<400> SEQUENCE: 124

Met Ala Gly Phe Ser Asp His Trp Thr Phe Ala Phe Gly Val Leu Gly
1               5                   10                  15

Asn Ile Ile Ser Phe Val Phe Leu Ser Pro Leu Pro Thr Phe Tyr
                20                  25                  30

Asn Ile Tyr Lys Lys Lys Ser Thr Glu Gly Tyr Gln Ser Ile Pro Tyr
            35                  40                  45

Val Val Ala Leu Phe Ser Ala Met Leu Trp Ile Tyr Tyr Ala Phe Leu
50                  55                  60

Lys Thr Asn Thr Thr Leu Leu Val Thr Ile Asn Thr Phe Gly Cys Phe
65                  70                  75                  80

Ile Glu Thr Leu Tyr Val Gly Phe Tyr Leu Phe Tyr Ala Pro Lys Lys
                85                  90                  95

Ala Arg Val Gln Thr Ile Lys Leu Leu Leu Leu Val Val Gly Gly
            100                 105                 110

Phe Gly Ala Ile Ile Leu Ile Thr Gln Phe Leu Phe Lys Gly Ala Ile
        115                 120                 125

Arg Ala Gln Ile Val Gly Trp Ile Cys Leu Val Phe Ser Leu Cys Val
130                 135                 140

Phe Val Ala Pro Leu Cys Ile Val Arg Gln Val Ile Lys Thr Lys Ser
145                 150                 155                 160

Val Glu Tyr Met Pro Phe Leu Leu Ser Val Phe Leu Thr Leu Ser Ala
                165                 170                 175

Val Met Trp Phe Phe Tyr Gly Leu Leu Leu Lys Asp Phe Asn Ile Ala
            180                 185                 190

Ile Pro Asn Val Leu Gly Phe Ile Phe Gly Ile Leu Gln Met Ile Leu
        195                 200                 205

Tyr Val Met Tyr Asn Lys Lys Glu Lys Val Val Ile Lys Glu Gln Asn
210                 215                 220

Leu Pro Glu Leu Lys Asp His Val Ile Ile Glu Asp Asp Lys Lys
225                 230                 235                 240

Lys Leu Pro Glu Leu Ser Glu Glu Gln Ile Ile Asn Ile Ile Lys Leu
                245                 250                 255

Gly Ser Leu Val Tyr Ser Asp Lys Asn Tyr Gly Asn Leu Thr Glu Val
            260                 265                 270

Ala Lys Asn Asp Lys Ala Ile Ser Lys Leu Gln Thr Leu Glu Ala
        275                 280                 285

<210> SEQ ID NO 125
<211> LENGTH: 286
<212> TYPE: PRT
```

<213> ORGANISM: Solanum lycopersicum

<400> SEQUENCE: 125

```
Met Pro Leu Phe Thr Thr Leu Gln Leu Ala Phe Ala Phe Gly Ile Leu
1               5                   10                  15

Gly Asn Gly Val Ser Phe Leu Val Tyr Leu Ser Pro Leu Pro Thr Phe
            20                  25                  30

Tyr Arg Ile Phe Lys Arg Lys Ser Thr Glu Gly Phe Gln Ser Ile Pro
        35                  40                  45

Tyr Ser Val Ser Leu Phe Ser Ala Met Leu Tyr Leu Tyr Tyr Ala Tyr
    50                  55                  60

Leu Lys Lys Asn Glu Ile Leu Leu Ile Thr Ile Asn Ser Phe Gly Thr
65                  70                  75                  80

Gly Ile Gln Leu Ile Tyr Leu Thr Ile Phe Met Ile Tyr Ala Thr Lys
                85                  90                  95

Ser Ala Lys Ile Phe Ala Thr Lys Leu Leu Ile Gly Phe Asn Leu Val
            100                 105                 110

Ala Phe Gly Ala Ile Val Gly Leu Thr Tyr Val Phe Ala Asn Glu Asn
        115                 120                 125

Asp Leu Arg Ile Ser Ile Val Gly Trp Ile Cys Ala Val Phe Ser Val
    130                 135                 140

Ser Val Phe Ala Ala Pro Leu Ser Ile Met Arg Arg Val Ile Gln Thr
145                 150                 155                 160

Lys Ser Val Glu Phe Met Pro Phe Pro Leu Ser Phe Leu Thr Ile
                165                 170                 175

Cys Ala Val Met Trp Phe Phe Tyr Gly Leu Leu Lys Lys Asp Met Tyr
            180                 185                 190

Ile Ala Met Pro Asn Ile Leu Gly Phe Ser Phe Gly Ile Ala Gln Met
        195                 200                 205

Ile Leu Tyr Ala Ile Tyr Arg Asn Arg Lys Gln Gln Val Leu Pro Asp
    210                 215                 220

Leu Ser Leu Met Asp Leu Lys Glu Ile Ala Ile Asp Met Lys Ala Val
225                 230                 235                 240

Val Val Glu Ile Ile Gln Glu Asn Val Asp Asp Glu Asn Lys Asn Lys
                245                 250                 255

Ile Asn Lys Gln Glu Glu Val Val Ser Val Asp Glu Lys Lys Asp Val
            260                 265                 270

Glu Tyr Asp Lys Gln Asp Val Ala Leu Thr Thr Ser Asn Val
        275                 280                 285
```

<210> SEQ ID NO 126
<211> LENGTH: 310
<212> TYPE: PRT
<213> ORGANISM: Fragaria vesca

<400> SEQUENCE: 126

```
Met Thr Ser Ser His Ser Pro Leu Ala Phe Ala Phe Gly Ile Leu Gly
1               5                   10                  15

Asn Ile Val Ser Phe Ile Val Phe Leu Ala Pro Val Pro Thr Phe Tyr
            20                  25                  30

Arg Val Tyr Lys Lys Lys Ser Thr Glu Gly Phe Gln Ser Ile Pro Tyr
        35                  40                  45

Ile Phe Ala Leu Phe Ser Ala Thr Ile Trp Ile Tyr Tyr Ala Ser Leu
    50                  55                  60

Lys Ser Asp Glu Met Leu Leu Ile Thr Ile Asn Gly Phe Gly Cys Val
```

```
                        65                  70                  75                  80
Ile Glu Thr Ile Tyr Ile Ala Met Tyr Ile Thr Tyr Ala Pro Lys Lys
                        85                  90                  95

Ala Arg Val Asn Thr Leu Arg Leu Leu Leu Val Asn Phe Gly Gly
                100                 105                 110

Phe Cys Leu Ile Leu Phe Leu Ser His Phe Leu Thr Gln Gly Pro Thr
            115                 120                 125

Arg Val Lys Val Leu Gly Trp Val Cys Val Ala Phe Ser Val Ser Val
    130                 135                 140

Phe Ala Ala Pro Leu Ser Ile Met Arg Leu Val Ile Arg Thr Lys Ser
145                 150                 155                 160

Val Glu Phe Met Pro Phe Ser Leu Ser Phe Phe Leu Thr Leu Ser Ala
                165                 170                 175

Ile Met Trp Leu Phe Tyr Gly Leu Leu Leu Lys Asp Leu Tyr Val Ala
                180                 185                 190

Ala Pro Asn Ile Leu Gly Phe Ser Phe Gly Val Val Gln Met Ile Leu
            195                 200                 205

Tyr Ala Ala Tyr Arg Asn Lys Lys Thr Val Leu Val Asp Glu Glu Lys
    210                 215                 220

Val Pro Glu His Lys Thr Ala Asp Asp Phe Val Lys Gln Ile Asn Ile
225                 230                 235                 240

Thr Val Leu Pro Ser Pro Lys Ala Gln Val Gln Val Lys Glu Glu Ala
                245                 250                 255

Val Ser Pro Ala Arg Ala Asp Ser Ser Asp Glu Ser Ser Asp Asp His
                260                 265                 270

Glu Gln Asn Val His Asp Gln Gln Arg Glu His Val Pro Gln Pro Cys
            275                 280                 285

His Val Asp Ala Gln Gly Ala Asp Leu Ile Ser Lys Gln Val Pro Ala
    290                 295                 300

Leu Val Gln Cys Glu Val
305                 310

<210> SEQ ID NO 127
<211> LENGTH: 292
<212> TYPE: PRT
<213> ORGANISM: Fragaria vesca

<400> SEQUENCE: 127

Met Ala Ile His His Pro Leu Thr Leu Ala Phe Gly Leu Leu Gly Asn
1               5                   10                  15

Ile Ile Ser Phe Met Val Phe Leu Ala Pro Met Pro Thr Phe Tyr Lys
                20                  25                  30

Ile Tyr Lys Lys Lys Thr Thr Glu Gly Phe Gln Ala Leu Pro Tyr Ala
            35                  40                  45

Val Ala Leu Phe Ser Cys Met Leu Trp Ile Tyr Tyr Ala Leu Leu Lys
    50                  55                  60

Gln Asp Ala Thr Phe Leu Ile Thr Ile Asn Ser Val Gly Cys Val Ile
65                  70                  75                  80

Glu Thr Val Tyr Leu Ala Ile Phe Leu Phe Tyr Ser Pro Lys Lys Ala
                85                  90                  95

Arg Ile Ser Thr Val Lys Phe Leu Leu Leu Asn Val Leu Gly Tyr
            100                 105                 110

Gly Leu Met Leu Val Leu Thr Leu Phe Leu Ala Lys Gly Glu Ile Arg
    115                 120                 125
```

-continued

```
Leu Lys Val Val Gly Trp Ile Cys Leu Val Phe Asn Leu Thr Val Phe
    130                 135                 140
Ala Ala Pro Leu Cys Ile Leu Lys Lys Val Ile Arg Thr Lys Ser Val
145                 150                 155                 160
Glu Phe Met Pro Phe Pro Leu Ser Phe Phe Leu Thr Leu Gly Ala Val
                165                 170                 175
Met Trp Phe Phe Tyr Gly Phe Leu Leu Lys Asp Tyr Asn Ile Ala Phe
            180                 185                 190
Pro Asn Ile Leu Gly Phe Met Phe Gly Ile Ala Gln Met Val Leu Tyr
        195                 200                 205
Ile Val Tyr Lys Asn Ala Lys Lys Val Val Leu Glu Glu Pro Ser
    210                 215                 220
Lys Val Gln Glu Leu Ser Asp His Ile Ile Glu Val Met Lys Ile Ser
225                 230                 235                 240
Thr Met Val Cys Pro Asp Leu Thr Pro Val Val Leu Gln Pro Asn Asp
                245                 250                 255
Ile Asn Ile Asp Leu Ile Glu Val Ile Pro Leu Asp Pro Asn Asn Val
            260                 265                 270
Val Lys Gly Ile Asn Ala Glu Glu Ser Lys Glu Asp Met Asp Asp Ala
        275                 280                 285
Ser Thr Lys Val
    290

<210> SEQ ID NO 128
<211> LENGTH: 291
<212> TYPE: PRT
<213> ORGANISM: Fragaria vesca
<220> FEATURE:
<221> NAME/KEY: misc_feature
<222> LOCATION: (137)..(137)
<223> OTHER INFORMATION: Xaa can be any naturally occurring amino acid

<400> SEQUENCE: 128

Met Ser Met Tyr Asn Ser Gln His His Leu Ala Phe Ile Phe Val Val
1               5                   10                  15
Ile Gly Asp Val Ile Ser Phe Met Val Tyr Leu Ala Pro Val Pro Thr
            20                  25                  30
Phe Tyr Arg Ile Tyr Lys Lys Thr Thr Glu Gly Phe Gln Ser Leu
        35                  40                  45
Pro Tyr Leu Val Ala Leu Phe Gly Ser Thr Leu Trp Leu Tyr Tyr Gly
    50                  55                  60
Ile Val Lys Gln Asn Met Val Leu Leu Ile Thr Ile Asn Thr Phe Gly
65                  70                  75                  80
Ser Val Met Glu Thr Leu Tyr Ile Ala Met Tyr Ile Val Tyr Ala Thr
                85                  90                  95
Asn Ala Ser Arg Lys Leu Thr Ile Lys Leu Phe Gly Phe Met Asn Leu
            100                 105                 110
Gly Leu Phe Ser Leu Ile Val Val Cys Ile Ser Tyr Ala Val His Ser
        115                 120                 125
Glu Tyr Arg Ala Leu Val Leu Gly Xaa Ile Asn Val Ala Val Thr Ile
    130                 135                 140
Cys Ala Ser Ala Ala Pro Leu Ser Ile Val Ala Gln Val Ile Arg Thr
145                 150                 155                 160
Gly Ser Val Glu Phe Met Pro Phe Thr Leu Ser Phe Phe Leu Thr Leu
                165                 170                 175
Ser Gly Val Leu Trp Phe Ser Tyr Gly Met Leu Leu Lys Asp Ile Phe
```

```
                180             185             190
Ile Ala Leu Pro Asn Gly Leu Gly Phe Val Leu Gly Leu Leu Gln Met
        195                 200                 205

Leu Phe Tyr Ala Ile Tyr Arg Asn Arg Lys Gln Val Thr Val Asp Gln
        210                 215                 220

Arg Asn Lys Leu Pro Ala Pro Glu His Val Thr Asp Thr Val Ile Leu
225                 230                 235                 240

Ser Ile Ala Thr Ser Glu Val Gln Ser Val Asp Ala Lys Gln Cys Tyr
                245                 250                 255

Asp Tyr Asp Gly Lys Asp Gly Ser Lys Glu Ser Asp Gly Asp Glu His
                260                 265                 270

Glu Lys Cys Val Val Glu Met Val Asp Val Asp Ala Ser Gly Asp Leu
        275                 280                 285

Ala Ser Leu
        290

<210> SEQ ID NO 129
<211> LENGTH: 257
<212> TYPE: PRT
<213> ORGANISM: Fragaria vesca

<400> SEQUENCE: 129

Met Ala Tyr Ser Thr Thr Glu Gln Leu Ala Phe Ser Phe Gly Leu Leu
1               5                   10                  15

Gly Asn Ile Val Ser Phe Met Val Phe Leu Ala Pro Met Pro Thr Phe
                20                  25                  30

Tyr Arg Ile Tyr Lys Lys Lys Ser Glu Gly Phe Gln Ser Ile Pro
        35                  40                  45

Tyr Val Val Ala Leu Leu Ser Ala Met Leu Leu Tyr Tyr Gly Val
    50                  55                  60

Ile Lys Thr Asn Ala Ile Leu Ile Ser Ile Asn Ala Phe Gly Ile
65                  70                  75                  80

Val Ile Glu Val Ala Tyr Leu Ile Phe Tyr Leu Thr Tyr Ala Pro Lys
                85                  90                  95

Lys Gln Arg Ile Phe Thr Leu Asn Leu Ile Leu Leu Val Asn Val Ala
                100                 105                 110

Phe Gly Leu Thr Leu Ala Ala Thr Ile Phe Leu Leu Ser Gly Thr Lys
            115                 120                 125

Arg Val Ala Ala Val Gly Trp Ile Cys Ala Val Phe Asn Ile Ala Val
130                 135                 140

Phe Ala Ala Pro Leu Ser Ile Met Arg Glu Val Ile Arg Thr Lys Ser
145                 150                 155                 160

Val Glu Phe Met Pro Phe Gly Leu Ser Leu Phe Leu Thr Leu Cys Ala
                165                 170                 175

Thr Thr Trp Phe Phe Tyr Gly Leu Phe Thr Lys Asp Tyr Tyr Ile Ala
            180                 185                 190

Leu Pro Asn Val Leu Gly Phe Leu Gly Ile Ala Gln Met Ile Leu
        195                 200                 205

Tyr Met Val Tyr Arg Asn Ser Gly Lys Asp His Asp Glu Val Glu Ala
        210                 215                 220

Lys Thr Arg Thr Asn Gly Asp Asp Leu Glu Met Arg Tyr Lys Val Ile
225                 230                 235                 240

Ser Lys Ser Lys Thr Thr Asn His Asn Lys Leu Tyr Arg Ser Val Ser
                245                 250                 255
```

Thr

```
<210> SEQ ID NO 130
<211> LENGTH: 254
<212> TYPE: PRT
<213> ORGANISM: Cicer arietinum

<400> SEQUENCE: 130
```

Met Ser Lys Met Phe Thr Phe Ser Asp His Glu Met Val Leu Ile Phe
1               5                   10                  15

Gly Leu Leu Gly Asn Ile Val Ser Phe Leu Val Phe Leu Ala Pro Leu
            20                  25                  30

Pro Thr Phe Tyr Ser Ile Cys Lys Lys Thr Ser Glu Gly Phe Gln
        35                  40                  45

Ser Ile Pro Tyr Val Val Ala Leu Leu Ser Ala Met Leu Leu Leu Tyr
50                  55                  60

Tyr Gly Leu Leu Lys Thr Asn Ala Ile Leu Ile Thr Ile Asn Cys
65                  70                  75                  80

Ile Gly Cys Val Ile Glu Val Leu Tyr Leu Ile Ile Tyr Ile Tyr
                85                  90                  95

Ala Pro Arg Lys Leu Lys Ile Ser Thr Leu Ala Leu Ile Leu Val Ala
            100                 105                 110

Asp Leu Gly Gly Leu Gly Leu Thr Leu Ile Ile Thr Asn Phe Ile Val
            115                 120                 125

Lys Ser Tyr Tyr Arg Val His Ala Val Gly Leu Ile Cys Ala Ile Phe
130                 135                 140

Asn Ile Ala Val Phe Ala Ala Pro Leu Ser Ile Met Arg Lys Val Ile
145                 150                 155                 160

Lys Thr Arg Ser Val Glu Tyr Met Pro Phe Phe Leu Ser Leu Phe Leu
                165                 170                 175

Thr Leu Cys Ala Thr Met Trp Phe Phe Tyr Gly Leu Phe Asp Lys Asp
            180                 185                 190

Asn Tyr Ile Met Leu Pro Asn Val Leu Gly Phe Leu Phe Gly Ile Ser
            195                 200                 205

Gln Met Ile Leu Tyr Leu Ile Tyr Lys Asn Ala Lys Asn Lys Val Glu
210                 215                 220

Ala Asn Ser Asn Glu Gln Gln Glu Tyr Gly Asp Asp Asp Gly Asn Lys
225                 230                 235                 240

Glu Asp Phe Pro Ser Ile Val Glu Met Lys Glu Asn Ile Val
                245                 250

```
<210> SEQ ID NO 131
<211> LENGTH: 255
<212> TYPE: PRT
<213> ORGANISM: Cicer arietinum

<400> SEQUENCE: 131
```

Met Ala Met Thr Arg Glu Ser Trp Ala Phe Val Phe Gly Leu Leu Gly
1               5                   10                  15

Asn Ile Ile Ser Phe Ala Val Phe Leu Ser Pro Leu Pro Thr Phe Tyr
            20                  25                  30

Leu Ile Phe Lys Lys Lys Ser Thr Glu Gly Phe Gln Ser Leu Pro Tyr
        35                  40                  45

Val Val Ala Leu Phe Ser Ala Met Leu Trp Ile Tyr Tyr Ala Phe Val
50                  55                  60

Lys Arg Glu Ala Ala Leu Leu Leu Ile Thr Ile Asn Thr Phe Gly Ile

```
                65                  70                  75                  80
Val Val Glu Ser Cys Tyr Leu Ile Val Phe Leu Ile Tyr Ala Thr Lys
                    85                  90                  95

Lys Ser Arg Leu Ser Thr Ile Lys Leu Leu Leu Leu Asn Val Phe
            100                 105                 110

Gly Phe Gly Ala Met Leu Leu Ser Thr Leu Tyr Leu Ala Lys Gly Ala
        115                 120                 125

Lys Arg Leu Ala Ile Ile Gly Trp Ile Cys Leu Val Phe Asn Ile Thr
130                 135                 140

Val Phe Ala Ala Pro Leu Phe Ile Ile Ser Arg Val Ile Arg Thr Arg
145                 150                 155                 160

Ser Val Glu Tyr Met Pro Phe Phe Leu Ser Phe Leu Thr Ile Asn
                165                 170                 175

Ala Val Met Trp Phe Phe Tyr Gly Leu Leu Lys Asp Tyr Tyr Val
            180                 185                 190

Ala Leu Pro Asn Thr Leu Gly Phe Val Phe Gly Ile Ile Gln Met Val
        195                 200                 205

Met Tyr Leu Ile Tyr Arg Asn Ala Thr Pro Val Pro Leu Asp Gly Pro
    210                 215                 220

Val Lys Gly Gln Glu Leu Ser Gly Gly His Ile Val Asp Val Val Lys
225                 230                 235                 240

Ile Gly Ser Asp Pro Asn Arg Gly Gly Ala Val Ser Lys Val
                245                 250                 255

<210> SEQ ID NO 132
<211> LENGTH: 302
<212> TYPE: PRT
<213> ORGANISM: Artificial Sequence
<220> FEATURE:
<223> OTHER INFORMATION: Synthetic amino acid sequence

<400> SEQUENCE: 132

Met Gly Ala Val Gly Ser Pro Trp Ala Phe Phe Gly Val Leu Gly
1               5                   10                  15

Asn Val Val Ser Phe Leu Val Tyr Leu Ser Pro Val Pro Thr Phe Tyr
                20                  25                  30

Gln Val Phe Lys Lys Lys Ser Thr Gly Gly Phe Ser Ser Ile Pro Tyr
            35                  40                  45

Leu Val Ala Leu Leu Ser Ala Met Leu Trp Leu Tyr Tyr Ala Met Leu
50                  55                  60

Thr Thr Gly Ser Phe Leu Leu Ile Ser Ile Asn Gly Ala Gly Cys Val
65                  70                  75                  80

Ile Glu Ser Val Tyr Val Val Tyr Val Ala Tyr Ala Pro Arg Lys
                85                  90                  95

Ala Lys Leu Arg Thr Ala Lys Leu Ile Gly Leu Met Asp Val Gly Gly
            100                 105                 110

Phe Gly Ile Val Leu Leu Val Thr His Val Leu Val His Gly Ser Lys
        115                 120                 125

Arg Val Gln Ile Val Gly Trp Val Cys Leu Ala Phe Ser Met Cys Val
130                 135                 140

Phe Val Ala Pro Leu Ser Val Ile Arg Arg Val Ile Gln Ser Lys Ser
145                 150                 155                 160

Val Glu Tyr Met Pro Phe Thr Leu Ser Leu Phe Leu Thr Val Cys Ala
                165                 170                 175

Thr Met Trp Leu Ala Tyr Gly Leu Leu Lys Lys Asp Tyr Cys Ile Ala
```

```
                180                 185                 190
Leu Pro Asn Val Leu Gly Phe Val Phe Gly Ile Ala Gln Met Gly Leu
            195                 200                 205

Tyr Val Phe Tyr Arg Asn Arg Lys Pro Val Ile Phe Asp Pro Glu Asp
        210                 215                 220

Lys Leu Arg Ala Pro Glu Gln Met Lys Ser Ile Val Ile Leu Ser Thr
225                 230                 235                 240

Ile Pro Thr Ser Glu Val His Pro Val Asp Ala Lys His Cys Asp Gly
                245                 250                 255

Asn Asp Gly Glu Asp Val Asp Gly Lys Asp Gly Asn Lys Glu Gly Asp
            260                 265                 270

Gly Asp Glu His Glu Lys Cys Val Val Leu Val Asp Met Asp Ala
        275                 280                 285

Ser Gly Glu Leu Gln Leu Lys Ser Asp Glu Pro Cys Val Glu
        290                 295                 300

<210> SEQ ID NO 133
<211> LENGTH: 288
<212> TYPE: PRT
<213> ORGANISM: Artificial Sequence
<220> FEATURE:
<223> OTHER INFORMATION: Synthetic amino acid sequence

<400> SEQUENCE: 133

Met Ala Met Asn His Ser Thr Leu Ala Phe Val Gly Leu Ile Gly
1               5                   10                  15

Asn Ile Val Ser Phe Leu Val Phe Leu Ser Pro Val Pro Thr Phe Tyr
            20                  25                  30

Arg Val Cys Lys Ser Lys Ser Ala Glu Gly Tyr His Ser Ile Pro Tyr
        35                  40                  45

Val Met Ala Leu Phe Ser Cys Met Leu Trp Ile Phe Tyr Gly Phe Val
    50                  55                  60

Thr Ser Gly Asp Phe Leu Leu Ile Thr Ile Asn Ser Val Gly Cys Leu
65                  70                  75                  80

Ile Glu Ser Val Tyr Val Ile Val Phe Met Ile Tyr Ala Pro Arg Lys
                85                  90                  95

Ala Arg Ile Arg Thr Ala Arg Leu Leu Leu Leu Leu Asp Ile Gly Leu
            100                 105                 110

Phe Gly Ile Ile Leu Leu Leu Thr Leu Val Leu Thr His Gly Asp Lys
        115                 120                 125

Arg Val Val Ile Ile Gly Trp Ile Cys Leu Gly Phe Asn Val Ala Val
    130                 135                 140

Phe Ala Ala Pro Leu Ser Val Val Ala Lys Val Val Lys Ser Arg Ser
145                 150                 155                 160

Val Glu Phe Met Pro Phe Ser Leu Ser Leu Phe Leu Thr Val Cys Ala
                165                 170                 175

Val Ala Trp Phe Phe Tyr Gly Phe Leu Leu Lys Asp Tyr Asn Val Ala
            180                 185                 190

Leu Pro Asn Ile Ile Gly Leu Val Leu Gly Ile Leu Gln Met Ile Leu
        195                 200                 205

Tyr Phe Met Tyr Met Asn Lys Thr Pro Val Ala Ser Gln Val Lys Glu
    210                 215                 220

Gly Lys Glu Ala Trp Lys Ala Pro Ala Glu Asp His Val Val Val Ile
225                 230                 235                 240

Asn Val Gly Lys Ala Asp Lys Ser Ser Cys Ala Glu Val Arg Pro Val
```

```
                    245                 250                 255
Thr Glu Met Ala Gly Ala Val Asp Val Pro Arg Arg Cys Ala Ala Glu
            260                 265                 270
Ala Ala Ala Ala Pro Gly Val Asp Phe Ala Arg Ser Val Asn Val Val
            275                 280                 285

<210> SEQ ID NO 134
<211> LENGTH: 333
<212> TYPE: PRT
<213> ORGANISM: Artificial Sequence
<220> FEATURE:
<223> OTHER INFORMATION: Synthetic amino acid sequence

<400> SEQUENCE: 134

Met Ala Met Asn His Ser Thr Leu Ala Phe Val Phe Gly Met Ile Gly
1               5                   10                  15

Asn Ile Ile Ser Phe Ile Val Phe Leu Ser Pro Leu Pro Thr Phe Tyr
            20                  25                  30

Gln Val Phe Lys Lys Thr Ser Glu Gly Tyr His Ser Val Pro Tyr
        35                  40                  45

Val Val Ala Leu Phe Ser Ser Met Leu Trp Leu Tyr Tyr Ala Leu Val
    50                  55                  60

Lys Ser Gly Ser Phe Leu Leu Ile Thr Ile Asn Ser Phe Gly Cys Val
65                  70                  75                  80

Val Glu Ser Val Tyr Val Val Met Phe Val Leu Tyr Ala Pro Arg Lys
                85                  90                  95

Ala Arg Val Ser Thr Leu Arg Met Ile Leu Leu Leu Val Ile Gly Gly
            100                 105                 110

Phe Gly Leu Ile Leu Leu Leu Thr His Leu Leu Ser His Gly Pro Leu
        115                 120                 125

Arg Val Gln Val Ile Gly Trp Val Cys Leu Gly Phe Asn Ile Ser Val
    130                 135                 140

Phe Val Ala Pro Leu Ser Ile Met Ala Lys Val Ile Gln Thr Lys Ser
145                 150                 155                 160

Val Glu Phe Met Pro Leu Ser Leu Ser Leu Phe Leu Thr Val Cys Ala
                165                 170                 175

Ile Ala Trp Phe Ala Tyr Gly Phe Phe Leu Lys Asp Tyr Asn Ile Ala
            180                 185                 190

Leu Pro Asn Val Ile Gly Leu Val Gly Ile Val Gln Met Leu Leu
        195                 200                 205

Tyr Met Ile Tyr Arg Asn Lys Lys Pro Ala Ala Ala Val Ile Met
    210                 215                 220

Val Glu Glu Val Lys Leu Pro Ala Glu Gln Tyr Ala Ser Lys Glu Val
225                 230                 235                 240

Ala Pro Pro Ala Ala Ala His Glu Gly Ser Arg Ala Ser Cys Gly Ala
                245                 250                 255

Glu Val His Pro Ile Asp Ile Asp Thr Leu Pro Val Ala Asp Val Gly
            260                 265                 270

Arg His His Asp Ser Gln Ala Val Val Ile Asp Val Asp Val Glu
        275                 280                 285

Pro Ala Thr Cys Ala Ala Ala Ala Ala Gly Gly Val Arg
    290                 295                 300

Gly Asp Gly Ala Ala Gly Val Val Thr Ala Gly Pro Glu Gln Pro Ala
305                 310                 315                 320

Ala Met Lys Pro Val Asp Met Ala Ile Ala Val Glu Ala
```

325                330

<210> SEQ ID NO 135
<211> LENGTH: 296
<212> TYPE: PRT
<213> ORGANISM: Artificial Sequence
<220> FEATURE:
<223> OTHER INFORMATION: Synthetic amino acid sequence

<400> SEQUENCE: 135

Met Gly Ala Val Gly Ser Pro Trp Ala Phe Leu Phe Gly Val Ile Gly
1               5                   10                  15

Asn Val Val Ser Phe Leu Val Tyr Leu Ala Pro Val Pro Thr Phe Tyr
            20                  25                  30

Arg Val Cys Lys Lys Lys Thr Thr Gln Gly Phe His Ser Leu Pro Tyr
        35                  40                  45

Ile Met Ala Leu Leu Ser Ala Met Leu Trp Leu Phe Tyr Gly Phe Val
    50                  55                  60

Lys Thr Gly Glu Leu Leu Leu Ile Ser Ile Asn Gly Phe Gly Cys Phe
65                  70                  75                  80

Ile Glu Thr Val Tyr Leu Val Leu Phe Met Ile Tyr Ala Pro Lys Lys
                85                  90                  95

Ala Lys Val Ser Thr Leu Arg Ile Ile Gly Leu Leu Asn Phe Gly Val
            100                 105                 110

Phe Gly Ile Ile Leu Leu Val Thr His Phe Leu Thr Lys Ala Glu Lys
        115                 120                 125

Arg Val Val Ile Leu Gly Trp Val Cys Val Ala Phe Ser Ile Cys Val
    130                 135                 140

Phe Ala Ala Pro Leu Ser Val Met Arg Val Val Val Lys Ser Arg Ser
145                 150                 155                 160

Val Glu Tyr Met Pro Phe Thr Leu Ser Phe Phe Leu Thr Leu Cys Ala
                165                 170                 175

Thr Met Trp Phe Phe Tyr Gly Leu Phe Leu Lys Asp Tyr Cys Ile Ala
            180                 185                 190

Leu Pro Asn Thr Val Gly Leu Thr Phe Gly Val Ile Gln Met Val Leu
        195                 200                 205

Tyr Val Phe Tyr Ser Lys Lys Glu Lys Ala Ile Leu Lys Glu Gln Lys
    210                 215                 220

Leu Pro Glu Ile Gln Lys Gly Glu Val Ile Val Lys Asp Glu Asn Met
225                 230                 235                 240

Asn Ala Asp Lys Lys Phe Pro Glu Leu Thr Gln Glu Gln Ile Ile Asp
                245                 250                 255

Ile Val Arg Leu Gly Leu Met Val Cys Lys Gly Lys Val His Val Ala
            260                 265                 270

Thr Cys Pro His Gly Thr Thr Cys Glu Pro Lys Val Asp Glu Asn Glu
        275                 280                 285

Pro Lys Leu Gln Thr Val Glu Val
    290                 295

<210> SEQ ID NO 136
<211> LENGTH: 292
<212> TYPE: PRT
<213> ORGANISM: Artificial Sequence
<220> FEATURE:
<223> OTHER INFORMATION: Synthetic amino acid sequence

<400> SEQUENCE: 136

Met Gly Ala Val Gly Ser Pro Trp Ala Phe Ile Phe Gly Val Leu Gly
1               5                   10                  15

Asn Val Ile Ser Phe Leu Val Phe Leu Ala Pro Leu Pro Thr Phe Tyr
            20                  25                  30

Gln Val Tyr Lys Lys Lys Ser Thr Glu Gly Phe Ser Ser Val Pro Tyr
        35                  40                  45

Ile Met Ala Leu Leu Ser Cys Met Leu Trp Leu Phe Tyr Ala Leu Leu
50                  55                  60

Thr Thr Asn Ser Leu Leu Leu Ile Thr Ile Asn Ser Ala Gly Cys Leu
65                  70                  75                  80

Ile Glu Thr Ile Tyr Val Ile Leu Tyr Phe Ile Tyr Ala Pro Lys Lys
                85                  90                  95

Ala Lys Ile Phe Thr Ala Lys Met Val Leu Leu Asn Ile Gly Gly
                100                 105                 110

Phe Gly Val Val Leu Leu Thr Val Phe Leu Thr Lys Ala Glu Lys
            115                 120                 125

Arg Val Gln Ile Ile Gly Trp Ile Cys Val Gly Phe Ala Ile Ala Val
    130                 135                 140

Phe Val Ala Pro Leu Ser Val Ile Ala Lys Val Ile Gln Thr Lys Ser
145                 150                 155                 160

Val Glu Phe Met Pro Leu Thr Leu Ser Phe Phe Leu Thr Val Ser Ala
                165                 170                 175

Val Val Trp Phe Leu Tyr Gly Ile Leu Thr Lys Asp Lys Tyr Ile Ala
            180                 185                 190

Leu Pro Asn Thr Leu Gly Phe Leu Leu Gly Leu Ala Gln Met Gly Leu
            195                 200                 205

Tyr Ala Phe Tyr Lys Lys Arg Glu Thr Ala Met Glu Met Gln Leu Pro
    210                 215                 220

Gln His Ser Thr Asp Asn Ile Val Ile Val Ser Ala Ala Thr Asn Ser
225                 230                 235                 240

Asp Lys Gln Lys Gln His Ser Ser Ser Leu Pro Ser Asn Asn Leu Val
                245                 250                 255

Gly Ala Ala Val Asp Asp Asp Val Thr Thr Thr Thr Lys Asn Gly
            260                 265                 270

Ile Asp Pro Ile Asn Asn Leu Glu Gln Asn His Gln Val Lys Asp Gln
        275                 280                 285

Leu Asn His Val
    290

<210> SEQ ID NO 137
<211> LENGTH: 287
<212> TYPE: PRT
<213> ORGANISM: Artificial Sequence
<220> FEATURE:
<223> OTHER INFORMATION: Synthetic amino acid sequence

<400> SEQUENCE: 137

Met Gly Ala Val Gly Ser Pro Trp Ala Phe Leu Phe Gly Val Leu Gly
1               5                   10                  15

Asn Val Val Ser Phe Leu Val Tyr Leu Ser Pro Val Pro Thr Phe Tyr
            20                  25                  30

Gln Val Phe Lys Lys Lys Ser Thr Gly Gly Phe Ser Ser Ile Pro Tyr
        35                  40                  45

Leu Val Ala Leu Leu Ser Ala Met Leu Trp Leu Tyr Tyr Ala Met Leu
50                  55                  60

```
Thr Thr Gly Ser Phe Leu Leu Ile Ser Ile Asn Gly Ala Gly Cys Val
 65                  70                  75                  80

Ile Glu Ser Val Tyr Val Val Tyr Val Ala Tyr Ala Pro Arg Lys
                 85                  90                  95

Ala Lys Leu Arg Thr Ala Lys Leu Ile Gly Leu Met Asp Val Gly Gly
            100                 105                 110

Phe Gly Ile Val Leu Leu Val Thr His Val Leu Val His Gly Ser Lys
        115                 120                 125

Arg Val Gln Ile Val Gly Trp Val Cys Leu Ala Phe Ser Met Cys Val
    130                 135                 140

Phe Val Ala Pro Leu Ser Val Ile Arg Arg Val Ile Gln Ser Lys Ser
145                 150                 155                 160

Val Glu Tyr Met Pro Phe Thr Leu Ser Leu Phe Leu Thr Val Cys Ala
                165                 170                 175

Thr Met Trp Leu Ala Tyr Gly Leu Leu Lys Lys Asp Tyr Cys Ile Ala
            180                 185                 190

Leu Pro Asn Val Leu Gly Phe Val Phe Gly Ile Ala Gln Met Gly Leu
        195                 200                 205

Tyr Val Phe Tyr Lys Tyr Cys Lys Thr Ser Pro His Leu Gly Glu Lys
    210                 215                 220

Glu Val Glu Ala Ala Lys Leu Pro Glu Val Ser Leu Asp Met Leu Lys
225                 230                 235                 240

Leu Gly Thr Val Ser Ser Pro Glu Pro Ile Ser Val Val Arg Gln Ala
                245                 250                 255

Asn Lys Cys Thr Cys Gly Asn Asp Arg Arg Ala Glu Ile Glu Asp Gly
            260                 265                 270

Gln Thr Pro Lys His Gly Lys Gln Ser Ser Ser Ala Ala Ala Thr
        275                 280                 285

<210> SEQ ID NO 138
<211> LENGTH: 36
<212> TYPE: DNA
<213> ORGANISM: Artificial Sequence
<220> FEATURE:
<223> OTHER INFORMATION: Synthetic DNA

<400> SEQUENCE: 138
taatgtcgac atgaacatcg ctcacactat cttcgg                         36

<210> SEQ ID NO 139
<211> LENGTH: 39
<212> TYPE: DNA
<213> ORGANISM: Artificial Sequence
<220> FEATURE:
<223> OTHER INFORMATION: Synthetic DNA

<400> SEQUENCE: 139
tatgagctct taaacttgaa ggtcttgctt tccattaac                      39

<210> SEQ ID NO 140
<211> LENGTH: 36
<212> TYPE: DNA
<213> ORGANISM: Artificial Sequence
<220> FEATURE:
<223> OTHER INFORMATION: Synthetic DNA

<400> SEQUENCE: 140
taatgtcgac atggatgttt ttgctttcaa tgcttc                         36
```

```
<210> SEQ ID NO 141
<211> LENGTH: 36
<212> TYPE: DNA
<213> ORGANISM: Artificial Sequence
<220> FEATURE:
<223> OTHER INFORMATION: Synthetic DNA

<400> SEQUENCE: 141
tatgagctct cacacgtaag aaacaatcaa aggctc                                36

<210> SEQ ID NO 142
<211> LENGTH: 37
<212> TYPE: DNA
<213> ORGANISM: Artificial Sequence
<220> FEATURE:
<223> OTHER INFORMATION: Synthetic DNA

<400> SEQUENCE: 142
taatgtcgac atgggtgata aacttcgatt atccatc                               37

<210> SEQ ID NO 143
<211> LENGTH: 37
<212> TYPE: DNA
<213> ORGANISM: Artificial Sequence
<220> FEATURE:
<223> OTHER INFORMATION: Synthetic DNA

<400> SEQUENCE: 143
tatgagctct tagatcgatg aggcattgtt agaattc                               37

<210> SEQ ID NO 144
<211> LENGTH: 41
<212> TYPE: DNA
<213> ORGANISM: Artificial Sequence
<220> FEATURE:
<223> OTHER INFORMATION: Synthetic DNA

<400> SEQUENCE: 144
taatgtcgac atggttaacg ctacagttgc gagaaacatt g                          41

<210> SEQ ID NO 145
<211> LENGTH: 38
<212> TYPE: DNA
<213> ORGANISM: Artificial Sequence
<220> FEATURE:
<223> OTHER INFORMATION: Synthetic DNA

<400> SEQUENCE: 145
tatgagctct caagctgaaa ctcgtttagc ttgtccac                              38

<210> SEQ ID NO 146
<211> LENGTH: 40
<212> TYPE: DNA
<213> ORGANISM: Artificial Sequence
<220> FEATURE:
<223> OTHER INFORMATION: Synthetic DNA

<400> SEQUENCE: 146
taatgtcgac atgacggacc cccacaccgc ccggacgatc                            40

<210> SEQ ID NO 147
<211> LENGTH: 40
<212> TYPE: DNA
<213> ORGANISM: Artificial Sequence
<220> FEATURE:
<223> OTHER INFORMATION: Synthetic DNA
```

<400> SEQUENCE: 147
tatgagctct caagcctggc caagttcgat tccagcattc                            40

<210> SEQ ID NO 148
<211> LENGTH: 43
<212> TYPE: DNA
<213> ORGANISM: Artificial Sequence
<220> FEATURE:
<223> OTHER INFORMATION: Synthetic DNA

<400> SEQUENCE: 148
taatgtcgac atggtgcatg aacagttgaa tcttattcgg aag                       43

<210> SEQ ID NO 149
<211> LENGTH: 41
<212> TYPE: DNA
<213> ORGANISM: Artificial Sequence
<220> FEATURE:
<223> OTHER INFORMATION: Synthetic DNA

<400> SEQUENCE: 149
tatgagctct caaacgccgc taactctttt gtttaaatat g                         41

<210> SEQ ID NO 150
<211> LENGTH: 38
<212> TYPE: DNA
<213> ORGANISM: Artificial Sequence
<220> FEATURE:
<223> OTHER INFORMATION: Synthetic DNA

<400> SEQUENCE: 150
taatgtcgac atggtgtttg cacatttgaa ccttcttc                             38

<210> SEQ ID NO 151
<211> LENGTH: 40
<212> TYPE: DNA
<213> ORGANISM: Artificial Sequence
<220> FEATURE:
<223> OTHER INFORMATION: Synthetic DNA

<400> SEQUENCE: 151
tatgagctct taaacattgt taggttcttg gttggtattc                           40

<210> SEQ ID NO 152
<211> LENGTH: 41
<212> TYPE: DNA
<213> ORGANISM: Artificial Sequence
<220> FEATURE:
<223> OTHER INFORMATION: Synthetic DNA

<400> SEQUENCE: 152
taatgtcgac atgttcctca aggttcatga aattgctttt c                         41

<210> SEQ ID NO 153
<211> LENGTH: 36
<212> TYPE: DNA
<213> ORGANISM: Artificial Sequence
<220> FEATURE:
<223> OTHER INFORMATION: Synthetic DNA

<400> SEQUENCE: 153
tatgagctct cacttcattg gcctcaccga tccttc                               36

<210> SEQ ID NO 154
<211> LENGTH: 39

```
<212> TYPE: DNA
<213> ORGANISM: Artificial Sequence
<220> FEATURE:
<223> OTHER INFORMATION: Synthetic DNA

<400> SEQUENCE: 154
taatgtcgac atgagtctct tcaacactga aaacacatg                              39

<210> SEQ ID NO 155
<211> LENGTH: 36
<212> TYPE: DNA
<213> ORGANISM: Artificial Sequence
<220> FEATURE:
<223> OTHER INFORMATION: Synthetic DNA

<400> SEQUENCE: 155
tatgagctct catgtagctg ctgcggaaga ggactg                                 36

<210> SEQ ID NO 156
<211> LENGTH: 39
<212> TYPE: DNA
<213> ORGANISM: Artificial Sequence
<220> FEATURE:
<223> OTHER INFORMATION: Synthetic DNA

<400> SEQUENCE: 156
taatgtcgac atggctctct tcgacactca taacacatg                              39

<210> SEQ ID NO 157
<211> LENGTH: 38
<212> TYPE: DNA
<213> ORGANISM: Artificial Sequence
<220> FEATURE:
<223> OTHER INFORMATION: Synthetic DNA

<400> SEQUENCE: 157
tatgagctct caagtagttg cagcactgtt tctaactc                               38

<210> SEQ ID NO 158
<211> LENGTH: 41
<212> TYPE: DNA
<213> ORGANISM: Artificial Sequence
<220> FEATURE:
<223> OTHER INFORMATION: Synthetic DNA

<400> SEQUENCE: 158
ggaattccat atggctctaa ctaacaattt atgggcattt g                           41

<210> SEQ ID NO 159
<211> LENGTH: 41
<212> TYPE: DNA
<213> ORGANISM: Artificial Sequence
<220> FEATURE:
<223> OTHER INFORMATION: Synthetic DNA

<400> SEQUENCE: 159
taatgtcgac ttaaacttga ctttgtttct ggacatcctt g                           41

<210> SEQ ID NO 160
<211> LENGTH: 40
<212> TYPE: DNA
<213> ORGANISM: Artificial Sequence
<220> FEATURE:
<223> OTHER INFORMATION: Synthetic DNA

<400> SEQUENCE: 160
```

```
taatgtcgac atgggagtca tgatcaatca ccatttcctc                    40
```

<210> SEQ ID NO 161
<211> LENGTH: 36
<212> TYPE: DNA
<213> ORGANISM: Artificial Sequence
<220> FEATURE:
<223> OTHER INFORMATION: Synthetic DNA

<400> SEQUENCE: 161

```
tatgagctct caaacggttt caggacgagt agcctc                        36
```

<210> SEQ ID NO 162
<211> LENGTH: 39
<212> TYPE: DNA
<213> ORGANISM: Artificial Sequence
<220> FEATURE:
<223> OTHER INFORMATION: Synthetic DNA

<400> SEQUENCE: 162

```
taatgtcgac atggcagagg caagtttcta tatcggagt                     39
```

<210> SEQ ID NO 163
<211> LENGTH: 38
<212> TYPE: DNA
<213> ORGANISM: Artificial Sequence
<220> FEATURE:
<223> OTHER INFORMATION: Synthetic DNA

<400> SEQUENCE: 163

```
tatgagctct taagagagga gaggttcaac acgtgatg                      38
```

<210> SEQ ID NO 164
<211> LENGTH: 20
<212> TYPE: DNA
<213> ORGANISM: Artificial Sequence
<220> FEATURE:
<223> OTHER INFORMATION: Synthetic DNA

<400> SEQUENCE: 164

```
gtaaaacgac cagtcttaag                                          20
```

<210> SEQ ID NO 165
<211> LENGTH: 17
<212> TYPE: DNA
<213> ORGANISM: Artificial Sequence
<220> FEATURE:
<223> OTHER INFORMATION: Synthetic DNA

<400> SEQUENCE: 165

```
caggaaacag ctatgac                                             17
```

<210> SEQ ID NO 166
<211> LENGTH: 21
<212> TYPE: DNA
<213> ORGANISM: Artificial Sequence
<220> FEATURE:
<223> OTHER INFORMATION: Synthetic DNA

<400> SEQUENCE: 166

```
tgctgtactt gcttggtatt g                                        21
```

<210> SEQ ID NO 167
<211> LENGTH: 18
<212> TYPE: DNA
<213> ORGANISM: Artificial Sequence

```
<220> FEATURE:
<223> OTHER INFORMATION: Synthetic DNA

<400> SEQUENCE: 167
ggaccagacc agacaacc                                                    18

<210> SEQ ID NO 168
<211> LENGTH: 909
<212> TYPE: DNA
<213> ORGANISM: Artificial Sequence
<220> FEATURE:
<223> OTHER INFORMATION: Synthetic DNA

<400> SEQUENCE: 168
atgggtgctg ttggttctcc ttgggctttc cttttggtg tgttgggtaa tgttgtttct        60
ttcttggttt atttgtctcc tgttcctact ttctaccaag ttttcaagaa aaagagtaca      120
ggaggttttt cttcaattcc ttacttggtt gctctttgt ctgcaatgct ttggttgtat       180
tacgctatgc ttactacagg atcattcctc ctcatatcta ttaacggagc aggttgtgtg      240
atcgaatcag tttatgttgt ggtttatgtt gcttacgcac caagaaaggc taagttgagg      300
accgcaaaat tgattggact catggatgtt ggaggttttg gtatcgttct tttggtgaca      360
catgttcttg tgcacggatc aaagagagtt caaattgtgg gttgggtttg tttggctttt      420
tctatgtgcg ttttcgtggc acctctctca gtgatcagaa gggttataca gagtaaatct      480
gtggagtaca tgccttttac tctctctta ttccttacag tttgtgctac catgtggttg       540
gcttatggac tcttaaaaaa ggattactgc atagctttac ctaatgtgct tggatttgtt     600
ttcggtattg cacaaatggg tctttatgtg ttttacagaa acaggaagcc tgttatcttc     660
gatccagaag ataaattaag agcacctgag cagatgaagt ctatagttat tctctcaacc    720
atacctacta gtgaagtgca tccagttgat gctaaacact gtgatggaaa tgatggtgaa    780
gatgttgatg aaaagatgg taacaaggag ggagatggag atgaacatga gaagtgcgtg     840
gttgtgctcg tggatatgga tgctagtgga gagttacagt tgaagtctga tgaaccttgt    900
gtggaatga                                                             909

<210> SEQ ID NO 169
<211> LENGTH: 867
<212> TYPE: DNA
<213> ORGANISM: Artificial Sequence
<220> FEATURE:
<223> OTHER INFORMATION: Synthetic DNA

<400> SEQUENCE: 169
atggctatga accactctac tctcgctttt gttttcggat tgatcggtaa tatcgtttct       60
ttcttagttt tcctcagtcc tgtgcctact ttctacagag tttgtaagag taaatctgct      120
gaaggttatc attcaatacc ttacgttatg gctctttta gttgcatgtt gtggatcttt       180
tacggattcg ttacctctgg agattttctt ttgataacta tcaatagtgt gggatgtttg      240
attgagtctg tgtatgttat tgtgtttatg atctatgctc caagaaaggc aagaattagg      300
acagctaggc tcttacttt gctcgatatc ggacttttcg gtattatcct ccttttgact      360 cttgtttga cacacggaga taaagagtt gtgataattg gatggatctg tctcggtttt       420
aacgttgctg tgttcgctgc acctctttct gttgtggcaa aggttgtgaa atcaaggagt     480
gttgaattca tgccattctc tctctcatta tttcttaccg tttgcgctgt ggcatggttt     540
ttctatggat tcctcttaaa ggattacaat gttgctttgc ctaacatcat aggattggtg     600
```

| | |
|---|---|
| ctcggtatcc tccaaatgat actctacttc atgtacatga ataagacacc tgttgcttca | 660 |
| caggtgaagg aaggaaaaga ggcatggaaa gctccagcag aggatcatgt tgtggttatt | 720 |
| aacgttggaa aggctgataa atcttcatgc gcagaagtta gacctgtgac cgagatggct | 780 |
| ggagcagttg atgtgccaag aaggtgtgca gcagaagcag cagcagcacc tggagtggat | 840 |
| ttcgcaagga gtgtgaatgt tgtttga | 867 |

<210> SEQ ID NO 170
<211> LENGTH: 1002
<212> TYPE: DNA
<213> ORGANISM: Artificial Sequence
<220> FEATURE:
<223> OTHER INFORMATION: Synthetic DNA

<400> SEQUENCE: 170

| | |
|---|---|
| atggctatga accactctac tctcgctttt gtgtttggta tgatcggaaa tattatctct | 60 |
| tttatcgtgt ttttgtctcc actccctact ttctaccaag tgttcaagaa aaagacaagt | 120 |
| gaaggatatc attctgttcc ttacgttgtg gctcttttct cttcaatgct ttggttgtat | 180 |
| tacgctttgg ttaaaagtgg atcttttctt ttgattacca tcaattcatt cggttgtgtt | 240 |
| gtggagagtg tgtatgttgt gatgtttgtt ctctacgctc ctagaaaggc aagggtgagt | 300 |
| acattgagaa tgatcctctt acttgttata ggaggtttcg gacttatctt gctcttaacc | 360 |
| catcttttgt cacacggtcc actcagggtg caagttatag gatgggtttg tttaggtttt | 420 |
| aacatttctg tgttcgttgc tcctttgtca attatggcaa aagtgatcca gaccaagtct | 480 |
| gttgaattca tgccactctc attaagtctt ttcttgactg tttgcgctat tgcatggttc | 540 |
| gcttatggat ttttccttaa ggattacaac atagctttgc ctaacgttat tggactcgtg | 600 |
| ttaggtatcg ttcaaatgct cctctacatg atctacagaa ataagaagcc tgctgcagct | 660 |
| gcagtgataa tggttgaaga ggtgaaactt ccagctgaac agtacgcatc taaggaggtt | 720 |
| gctcctccag ctgcagctca tgaaggatct agagcttcat gtggtgcaga ggttcaccct | 780 |
| atagatattg atacattgcc agttgctgat gtgggaaggc atcacgattc acaggctgtt | 840 |
| gtggttatcg atgtggatgt tgagccagca gctacttgcg ctgcagcagc tgcagctgca | 900 |
| ggaggtgtta gaggagatgg tgctgctggt gtggttacag ctggtcctga caacctgct | 960 |
| gctatgaaac ctgtggatat ggctattgct gtggaggcat ga | 1002 |

<210> SEQ ID NO 171
<211> LENGTH: 891
<212> TYPE: DNA
<213> ORGANISM: Artificial Sequence
<220> FEATURE:
<223> OTHER INFORMATION: Synthetic DNA

<400> SEQUENCE: 171

| | |
|---|---|
| atgggtgctg tgggtagtcc ttgggctttt ctcttcggtg ttattggtaa tgttgtgtct | 60 |
| ttcctcgtgt atctcgctcc tgttccaact ttctacagag tttgtaagaa aaagactaca | 120 |
| caaggattcc atagtttgcc ttatattatg gctctttttgt ctgcaatgtt gtggctcttt | 180 |
| tacggattcg ttaagaccgg tgaacttctc cttatatcta ttaacggatt tggttgcttc | 240 |
| atcgaaactg tgtatcttgt tctttttatg atatacgctc caaaaaaggc aaaagtttca | 300 |
| actcttagaa ttatcggatt gctcaacttt ggagtgttcg gtataattct ccttgttacc | 360 |
| cacttcttaa ctaaagctga aagagggtt tgattcttg gtgggtgtg tgttgcattt | 420 |
| tcaatctgcg tgttcgctgc accttttgagt gttatgagag ttgtggttaa atctagatca | 480 |

```
gttgaataca tgccttttac tctctctttc tttcttacac tctgtgctac catgtggttt    540
ttctatggat tattccttaa ggattactgc atagcattgc ctaatactgt gggactcaca    600
tttggtgtta tccagatggt gttgtatgtt ttctactcaa aaaggagaa ggctattctc    660 aaggaacaaa agcttcctga gatacagaaa ggtgaagtga ttgttaagga tgaaaacatg    720
aacgctgata agaagttccc agaacttaca caagagcaga tcatagatat cgtgaggttg    780
ggactcatgg tttgtaaagg aaaggtgcat gttgctacct gcccacacgg aaccacctgt    840
gaacctaaag ttgatgagaa cgaaccaaag ttgcagactg ttgaagtgtg a            891
```

<210> SEQ ID NO 172
<211> LENGTH: 879
<212> TYPE: DNA
<213> ORGANISM: Artificial Sequence
<220> FEATURE:
<223> OTHER INFORMATION: Synthetic DNA

<400> SEQUENCE: 172

```
atgggtgctg ttggtagtcc ttgggctttt atctttggtg tgttgggtaa tgtgatttct     60
ttcttggtgt tccttgctcc tcttcctaca ttctaccaag tttacaagaa aaagtcaacc    120
gaaggattct cttcagtgcc ttatatcatg gctctttga gttgtatgtt atggcttttc    180
tatgcactcc tcactacaaa ctctcttttg ctcataacta ttaactcagc tggttgcctt    240
attgagacaa tctatgttat tttgtacttc atctacgctc aaaaaaggc aaagattttc    300 actgctaaga tggttctcct tttgaacatt ggaggtttcg gagttgtgct cttacttact    360
gttttcttga caaaagctga aaagagagtt caaattatcg gatggatatg tgtgggtttt    420
gctattgcag ttttcgtggc tcctctcagt gttattgcaa agtgatcca gacaaagtct    480 gttgagttta tgccattgac cctctcattt ttccttactg tgagtgctgt tgtgtggttc    540
ttatatggaa tccttaccaa ggataagtac atagcattgc ctaatacact cggattttg    600 ctcggtttag ctcagatggg tctttatgca ttctacaaaa agagggaaac tgctatggag    660
atgcaacttc ctcagcattc aactgataat atcgttatag tgagtgctgc aacaaactct    720
gataaacaaa agcagcacag ttcttcattg ccatctaata acctcgttgg agctgcagtg    780
gatgatgatg atgttaccac tacaaccaaa aacggtatag atccaatcaa caacctcgaa    840
cagaatcatc aagtgaaaga tcagttaaac cacgtttga                           879
```

<210> SEQ ID NO 173
<211> LENGTH: 864
<212> TYPE: DNA
<213> ORGANISM: Artificial Sequence
<220> FEATURE:
<223> OTHER INFORMATION: Synthetic DNA

<400> SEQUENCE: 173

```
atgggtgctg tgggttctcc ttgggctttt ctctttggtg ttctcggtaa tgtggtttct     60
tttcttgtgt atttgagtcc tgttccaaca ttctaccaag ttttcaagaa aaagtcaacc    120
ggaggttttt cttcaatacc ttacttggtt gctcttttga gtgcaatgct ttggttgtat    180
tacgctatgc tcactacagg atctttcctc ctcatatcta ttaacggagc tggttgtgtt    240
atcgagtctg tgtatgttgt ggtttatgtt gcttacgcac caagaaaggc taagttgagg    300
accgcaaaat taatcggact tatggatgtt ggaggttttg gtatagtgct tttggttaca    360
catgtgcttg ttcacggtag taagagagtg caaattgttg gttgggtgtg tttggctttt    420
```

| | |
|---|---|
| agtatgtgcg tgttcgttgc acctctctct gttataagaa gagttattca gtcaaaaagt | 480 |
| gttgaataca tgcctttac tctctcatta ttccttaccg tgtgtgctac tatgtggttg | 540 |
| gcttatggac tcttaaaaaa ggattactgc attgctttgc ctaacgttct cggatttgtg | 600 |
| ttcggtatcg ctcaaatggg actttatgtt ttctataagt actgcaagac atctcctcat | 660 |
| cttggtgaaa aagaggttga agctgcaaag ttaccagagg tgtctcttga tatgttgaaa | 720 |
| ctcggaactg ttagttctcc tgaaccaatc tcagtggtta dacaggctaa taagtgtaca | 780 |
| tgcggtaacg atagaagggc agagatagaa gatggtcaaa cacctaagca cggaaagcag | 840 |
| tcaagttcag cagcagcaac atga | 864 |

<210> SEQ ID NO 174
<211> LENGTH: 909
<212> TYPE: DNA
<213> ORGANISM: Artificial Sequence
<220> FEATURE:
<223> OTHER INFORMATION: Synthetic DNA

<400> SEQUENCE: 174

| | |
|---|---|
| atgggagcag tcggttcgcc gtgggccttt tgttcggag ttcttggtaa tgtggtctcg | 60 |
| tttctcgtgt atctctcacc cgttcctacg ttctaccagg tgttcaagaa gaagtccact | 120 |
| ggcgggttct ccagcatccc gtatctggtg gctctcctgt ctgcaatgct ctggctgtac | 180 |
| tatgccatgc ttaccacagg atcgttcctt ttgatcagta ttaacggcgc ggggtgcgtt | 240 |
| attgagtcag tctacgtggt cgtttacgtc gcctatgcac caagaaaggc aaagctcagg | 300 |
| accgcaaagc tgatcggact tatggacgtg ggaggtttcg gtattgtcct cctggttaca | 360 |
| cacgtgctcg tccatggcag caagcgggtg cagatcgtcg ggtgggtttg cctggccttc | 420 |
| tcaatgtgtg tttttgtggc gccgctttcg gtcatccgca gggttattca atctaagtca | 480 |
| gtcgaataca tgccattcac cctttccttg tttctcaccg tttgcgctac aatgtggctg | 540 |
| gcatacggcc ttttgaagaa ggattattgt atcgctttgc ctaacgtgct cggcttcgtc | 600 |
| tttgggattg cacagatggg cctctacgtt ttctatcgga atagaaagcc ggtcatcttt | 660 |
| gacccagagg ataagttgag ggctcccgaa cagatgaagt ccatcgtcat tctcagcacg | 720 |
| attcctactt ctgaggtgca ccccgtcgac gcgaagcatt gcgacggcaa cgatggggag | 780 |
| gacgtggatg gaaaggatgg taataaggaa ggagacggcg acgagcacga aaagtgtgtg | 840 |
| gtcgttttgg tggatatgga tgccagcggg gaattgcagt tgaagagtga tgaaccctgt | 900 |
| gtggagtga | 909 |

<210> SEQ ID NO 175
<211> LENGTH: 879
<212> TYPE: DNA
<213> ORGANISM: Artificial Sequence
<220> FEATURE:
<223> OTHER INFORMATION: Synthetic DNA

<400> SEQUENCE: 175

| | |
|---|---|
| atgggggcag tgggttcgcc ttgggccttt atttttgggg tcctcggcaa tgtgatttcc | 60 |
| tttctggttt tcctggctcc tcttcctacg ttctaccagg tttacaagaa gaagtccact | 120 |
| gagggctttt ccagcgtgcc gtacattatg gccctcctgt cctgcatgtt gtggctcttc | 180 |
| tatgcgcttt tgaccacaaa ctcactcctg cttatcacca ttaattcggc cggatgtctc | 240 |
| atcgaaacaa tctacgtgat cctgtacttc atctacgctc caagaaaggc aaagatcttt | 300 |
| acggcgaaga tggtgttgct cctgaacatc ggcgggttcg gcgtggtcct tttgctcacg | 360 |

```
gtctttctga ctaaggctga gaagcgcgtg cagatcattg gctggatttg cgtcgggttc      420
gccatcgcgg tctttgttgc cccgctcagt gttattgcga aggtcatcca aacaaagtct      480
gtcgaattca tgccactgac ccttagcttc tttctcacag tttctgctgt tgtgtggttc      540
ttgtacggca ttctcacgaa ggacaagtat atcgcactgc cgaacactct tggattcctg      600
cttggtttgg ctcaaatggg gctctacgca ttttataaga agagggagac cgcgatggaa      660
atgcagctcc ctcaacactc aaccgacaac atcgtgattg tcagtgccgc gacaaattcc      720
gataagcaga agcaacattc ttcatcgctg cccagcaaca atcttgtcgg agctgcagtt      780
gacgatgacg atgtcacgac taccacaaag aatggtatcg acccaatcaa taacctggag      840
caaaaccatc aagtgaagga ccaactgaat catgtgtga                             879
```

TRANSFORMED PLANT AND METHOD FOR PRODUCING EXUDATE CONTAINING SUGAR USING TRANSFORMED PLANT

CROSS REFERENCE TO RELATED APPLICATIONS

This application is a National Stage of International Application No. PCT/JP2014/084316 filed Dec. 25, 2014, claiming priority based on Japanese Patent Application No. 2013-273128 filed Dec. 27, 2013, the contents of all of which are incorporated herein by reference in their entirety.

TECHNICAL FIELD

The present invention relates to a transformed plant that has gained an excellent trait by introduction of a given gene and a method for producing an exudate containing sugar using the transformed plant.

BACKGROUND ART

For stable production of biofuel or bioplastics, low cost and stable supply of their raw material sugar is desired. The representative example of the raw material sugar is sugar accumulated in sugarcane. Extraction of sugar from sugarcane generally requires processes such as cutting down of sugarcane at a predetermined harvest time, crushing, pressing, concentration, and purification. Moreover, after harvest, the farmland requires management work such as maintenance of farm for new cultivation, planting, and spraying herbicides and insecticides. The production of the raw material sugar with plants such as sugarcane has been conventionally a process requiring a great deal of cost such as that for the production process and the cultivation, as described above.

Patent Literature 1 discloses a method for recovering a heterologous protein encoded by a heterologous gene from a plant transformed to express the heterologous gene. The method disclosed in Patent Literature 1 comprises collecting an exudate from a plant transformed to express a heterologous gene and recovering the heterologous protein from the collected exudate. Examples of the exudate in Patent Literature 1 include exudate from the rhizome and the guttation exuded from a plant as an exudate through the hydathode of the leaf.

Patent Literature 2 and Non Patent Literature 1 disclose transporter proteins involved in sugar transport in plant in *Arabidopsis thaliana* and rice (*Oryza sativa*). The transporter proteins disclosed in Patent Literature 2 and Non Patent Literature 1 are known as GLUE proteins or SWEET proteins. Introduction of a nucleic acid encoding a transporter protein disclosed in Patent Literature 2 and Non Patent Literature 1 into a plant may improve the amount of sugar transport to root.

Non Patent Literature 2 describes the confirmation of function of a cell membrane small molecule transporter by artificially localizing the cell membrane transporter on the endoplasmic reticulum (ER) and measuring the small molecule transporter activity of the ER. In particular, the glucose transporters GLUTs and SGLTs were localized on the ER and their original functions were speculated using FRET (Forster resonance energy transfer or fluorescence resonance energy transfer).

CITATION LIST

Patent Literature

Patent Literature 1
JP Patent Publication (Kohyou) No. 2002-501755 A
Patent Literature 2
JP Patent Publication (Kohyou) No. 2012-525845 A Non Patent Literature Non Patent Literature 1
Nature (2010) 468, 527-534
Non Patent Literature 2
FASEB J. (2010) 24, 2849-2858

SUMMARY OF INVENTION

Technical Problem

As described in the foregoing, large cost of producing sugar using plants has been a big problem. The aforementioned problem may be however solved by including sugar at a high concentration in the exudate derived from a plant and collecting the exudate. Patent Literature 1 discloses the collection of a heterologous protein from exudate, but no technique to collect sugar from the exudate. Patent Literature 2 and Non Patent Literature 1 disclose the transporter proteins, designated as SWEETs, involved in sugar transportation and nucleic acids encoding them, but no relation between these transporter proteins or nucleic acids encoding them and the sugar content in the exudate.

Accordingly, in view of the circumstances described above, an object of the present invention is to provide a transformed plant that produces an exudate containing sugar at a high concentration and a method for producing sugar using the transformed plant.

Solution to Problem

As a result of diligent studies to achieve the purpose described above, the present inventors have found that high sugar contents in exudate are achieved in the transformed plant in which a nucleic acid encoding a SWEET protein in a certain group (clade) is introduced and expression of the protein is enhanced, thereby completing the present invention.

The present invention encompasses the following:
(1) A transformed plant or a transformed plant cell in which a nucleic acid encoding a transporter protein having a consensus sequence comprising the following amino acid sequence: (L/I/V/M/F)x(G/A)xx(I/L/V/M/F)xxxx(L/I/V/F)(A/S)(P/S) [SEQ ID NO: 1] (1-3aa)(P/S/T/A)T(F/L)xx(I/V)xxxKxxxxxxxxPYxxx(L/I)xxxx(L/I)x(I/L/M/V/F)xY(A/S/G) [SEQ ID NO: 2] (7-13aa)(I/L/V/M)(1-2aa)(I/V)Nxxxxxx(E/Q)xxYxxx(Y/F)xx(Y/F)(A/G/S) [SEQ ID No: 3] (35-36aa)(R/Q/H)xxxxGx(V/I/L)xxxxx(V/M/L/I/F)xxxx(A/S/T)P(L/M)x(I/V)(I/M/V/L) [SEQ ID NO: 4] (2-7aa)(V/I)(V/I/M)x(T/S)x(S/N)xx(F/Y)(M/L)(P/S)(F/I/V/L)xLSxx(L/I)(T/V)xx(A/G)xxW(F/L)x YGxxxxDxx(V/I)xxPNxxGxx(F/L)(G/S)xxCXM/I)x(L/M/I/V/F)(Y/H/F) [SEQ ID NO: 5] and being involved in sugar transportation is introduced and/or expression of the protein is enhanced.
(2) The transformed plant or transformed plant cell according to (1), wherein the transporter protein is a protein in the clade III among the clades I to V of taxonomic groups based on the amino acid sequences of the SWEET proteins.

(3) The transformed plant or transformed plant cell according to (1), wherein the transporter protein is a protein of any of the following (a) and (b):
(a) a protein comprising an amino acid sequence set forth in any of SEQ ID NOs: 15 to 137;
(b) a protein having an amino acid sequence having an identity of 90% or more to an amino acid sequence set forth in any of SEQ ID NOs: 15 to 137 and having transporter activity involved in sugar transportation.
(4) The transformed plant or transformed plant cell according to (1), wherein the consensus sequence comprises the following amino acid sequence: G(L/I/V/F/M)xGx(I/V/L)(I/V/L)(S/T)xxxxL(A/S)P(L/V/I/M)(P/S/T/A)TFxx(I/V)x(K/R)xK(S/T) xxx(F/Y)x(S/A)xPYxx(A/S/T)LxSxxLx(L/I/M/V)(Y/F)Y(A/G) [SEQ ID NO: 6] (7-9aa)(L/I)(I/V/L)(T/S)INxx(G/A)xx(I/V/M)(E/Q)xxYxxx(F/Y)(L/I/V/F)x(Y/F)Ax(K/R/N)xxxxx(T/A) [SEQ ID NO: 7] (7-8aa)(V/F/L/I/M)(18-19aa)(R/Q/H)xxxxGx(I/V)xxxxx(V/I/L/M)x(V/M)F(A/V)(A/S/T)PLx(I/V)(I/M/V/L)xxV(I/V)(K/R/Q)(T/S)(K/R)S(V/A)x(F/Y)MP(F/I/L)xLS(L/F/V)xL(T/V)(L/I)xAxxW(F/L)xYG(L/F)xxxDx x(V/I)xxPNxxGxx(L/F)(G/S)xxQMx(L/V/I)(Y/F)xx(Y/F) [SEQ ID NO: 8.]
(5) The transformed plant or transformed plant cell according to (4), wherein the transporter protein is a protein of any of the following (a) and (b):
(a) a protein comprising an amino acid sequence set forth in any of SEQ ID NOs: 15 to 35;
(b) a protein having an amino acid sequence having an identity of 90% or more to an amino acid sequence set forth in any of SEQ ID NOs: 15 to 35 and having transporter activity involved in sugar transportation.
(6) The transformed plant or transformed plant cell according to (1), wherein the consensus sequence comprises the following amino acid sequence: (A/V)xxxG(I/L/V)xGN(I/L/V)(I/L/V)S(F/L)x(V/T)xL(A/S)P(V/L/I)(P/A)TFxx(I/V)x(K/R)xK(S/T)xx(G/S)(F/Y)(Q/S/E)SxPYxx(A/S/T)LxS(A/C/S)xLx(L/I/M)(Y/F)Y(A/G)xx(K/T) [SEQ ID NO: 9] (3-5aa)(L/M/P)(L/I)(I/L/V)(T/S)INxx(G/A)xx(I/V)(E/Q) xxY(I/L)x(L/M/V/I)(F/Y)(L/I/V/F)x(Y/F) Ax(K/R)xxxxx(T/A)xx(L/M/F/V/I)(L/F/V/I)xxx(N/D)(F/V/I/L)xx(F/L)xx(I/L/V)xxxxxxx(L/I/V) [SEQ ID NO: 10] (5-6aa)(R/Q)xxxxGx(I/V)xxxx(S/A)(V/L/M)(C/S/A)VF(A/V)(A/S)PLx(I/V)(I/M/V)xxV(I/V)(K/R/Q)(T/S)(K/R)S(V/A)E(F/Y)MP(F/I)xLS(L/F/V)xL(T/V)(L/I)(S/N)A(V/I)xW(F/L)xYGLxx(K/N)Dxx(V/I)xxPN(V/I)xGxx(F/L)(G/S)xxQMxL(Y/F)xx(Y/F) [SEQ ID NO: 11].
(7) The transformed plant or transformed plant cell according to (6), wherein the transporter protein is a protein of any of the following (a) and (b):
(a) a protein comprising an amino acid sequence set forth in any of SEQ ID NOs: 15 to 26;
(b) a protein having an amino acid sequence having an identity of 90% or more to an amino acid sequence set forth in any of SEQ ID NOs: 15 to 26 and having transporter activity involved in sugar transportation.
(8) The transformed plant or transformed plant cell according to (1), wherein the consensus sequence comprises the following amino acid sequence: (M/L/V)xx(T/K/N/S)xxxx-AxxFG(L/I/V)LGN(I/L/V)(I/V)SFxVxL(S/A)P(V/I)PT-FxxIxK(K/R)K (S/T)x(E/K)(G/S)(F/Y)(Q/E)S(I/L)PYxx(A/S)LxS(A/C)xLx(L/I/M)YY(A/G)xxK [SEQ ID NO: 12] (4-5aa)(L/M)(L/I)(I/V)(T/S)IN(A/S/T)(F/V)(G/A)x(F/V)(I/V)(E/Q)xxY(I/L)x(L/M/I)(F/Y)(F/V/I/L )x(Y/F)Ax(K/R)xx(R/K)xx(T/A)(L/V/M)K(V/L/M/F)(L/I/V/F)xxx(N/D)(F/V/I)xx(F/L)xx(I/L)(L/I/V/F)(L/M/V)(L/V)xx(F/L)(L/I/V) [SEQ ID NO: 13] (5-6aa)(R/Q)x(K/S/Q)x(L/I/V)Gx(I/V)Cxxx(S/A)(V/L)(S/C/A)VF(A/V)(A/S)PLx(I/V)(M/I/V) xxV(I/V)(K/R)T(K/R)S(V/A)E(Y/F)MPFxLS(L/F)xLT(I/L)(S/N)A(V/I)xW(L/F)xYGLx(L/I)(K/N)D xx(V/I)A(L/F/I/M)PN(V/I)(L/I/V)Gxx(L/F)GxxQM(I/V)L(Y/F)(V/L/I/M)(V/L/I/M)(Y/F)(K/R/Q [SEQ ID NO: 14].
(9) The transformed plant or transformed plant cell according to (8), wherein the transporter protein is a protein of any of the following (a) and (b):
(a) a protein comprising an amino acid sequence set forth in any of SEQ ID NOs: 15 to 21;
(b) a protein having an amino acid sequence having an identity of 90% or more to an amino acid sequence set forth in any of SEQ ID NOs: 15 to 21 and having transporter activity involved in sugar transportation.
(10) The transformed plant or transformed plant cell according to (1), wherein the transformed plant is a phanerogam.
(11) The transformed plant or transformed plant cell according to (10), wherein the phanerogam is an angiosperm.
(12) The transformed plant or transformed plant cell according to (11), wherein the angiosperm is a monocot.
(13) The transformed plant or transformed plant cell according to (12), wherein the monocot is a plant of the family Poaceae.
(14) The transformed plant or transformed plant cell according to (13), wherein the plant of the family Poaceae is a plant of the genus *Oryza*.
(15) The transformed plant or transformed plant cell according to (11), wherein the angiosperm is a dicot.
(16) The transformed plant or transformed plant cell according to (15), wherein the dicot is a plant of the family Brassicaceae.
(17) The transformed plant or transformed plant cell according to (16), wherein the plant of the family Brassicaceae is a plant of the genus *Arabidopsis*.
(18) A method for producing an exudate, comprising the steps of cultivating a transformed plant according to any of the above (1) to (17); and collecting an exudate from the transformed plant.
(19) A method for producing an exudate according to (18), wherein the transformed plant is cultivated under conditions at a relative humidity of 80% RH or more.
(20) The method for producing an exudate according to (18), wherein the exudate is guttation.

The description of the present application encompasses the contents described in the description and/or the drawings of JP patent application No. 2013-273128, which is the basics of the priority of the present application.

Advantageous Effects of Invention

According to the present invention, the sugar content in the exudate derived from plants can be greatly increased. Accordingly, transformed plants according to the present invention can produce exudate having a property such as high sugar content by introducing a nucleic acid encoding a particular transporter protein involved in sugar transportation and/or enhancing expression of the protein. Also, the method for producing an exudate according to the present invention can produce an exudate with a high sugar content by using a transformed plant in which a nucleic acid encoding a particular transporter protein involved in sugar transportation is introduced and/or expression of the protein is enhanced. Furthermore, the exudate collected from the transformed plant can be used as a raw material for producing alcohol, organic acid, alkane, and terpenoids because of its high sugar content.

BRIEF DESCRIPTION OF DRAWINGS

FIG. 1-2 is an extended view of a part of the phylogenetic tree shown in FIG. 1-1.

FIG. 1-3 is an extended view of a part of the phylogenetic tree shown in FIG. 1-1.

FIG. 2-1 illustrates a result of multiple alignment analysis of the proteins contained in the phylogenetic tree illustrated in FIG. 1-1 [XP 004235326 *Solanum* (SEQ ID NO: 1171, XP 004235334 *Solanum* (SEQ ID NO: 119), ACV71016 *Capsicum* (SEQ ID NO: 361, XP 004235333 *Solanum* (SEQ ID NO: 118), XP 004235342 *Solanum* (SEQ ID NO: 122), XP 004235339 *Solanum* (SEQ ID NO: 120), XP 004241452 *Solanum* (SEQ ID NO: 1241, XP 004235340 *Solanum* (SEQ ID NO: 121), AFK35161 *Medicago* (SEQ ID NO: 29), CAC44123 *Medicago* (SEQ ID NO: 30), XP 004503778 *Cicer* (SEQ ID NO: 131), AFK48645 *Lotus* (SEQ ID NO: 38), NP 001241307 *Glycine* (SEQ ID NO: 75), NP 001242732 *Glycine* (SEQ ID NO: 76), XP 003523161 *Glycine* (SEQ ID NO: 99), NP 001237418 *Glycine* (SEQ ID NO: 73), XP 003602780 *Medicago* (SEQ ID NO: 28), XP 004138032 *Cucumis* (SEQ ID NO: 109). EMJ10621 *Prunus* (SEQ ID NO: 49), XP 004297512 *Fragaria* (SEQ ID NO: 127), XP 002284244 *Vitis* (SEQ ID NO: 79), EOA14646 *Capsella* (SEQ ID NO: 60. NP 199892 AtSW10 (SEQ ID NO: 16), XP 002321731 *Populus* (SEQ ID NO: 82), XP 002322281 *Populus* (SEQ ID NO: 83), XP 002321730 *Populus* (SEQ ID NO: 81), XP 002511127 *Ricinus* (SEQ ID NO: 93). XP 002511128 *Ricinus* (SEQ ID NO: 94), CBI32263 *Vitis* (SEQ ID NO: 46), EMJ01437 *Prunus* (SEQ ID NO: 48), XP 002520679 *Ricinus* (SEQ ID NO: 961, XP 004247459 *Solanum* (SEQ ID NO: 125), EOA28959 *Capsella* (SEQ ID NO: 67), NP 181439 AtSW09 (SEQ ID NO: 15), XP 002333315 *Populus* (SEQ ID NO: 84), NEC1 PETHY *Petunia* (SEQ ID NO: 35), XP 002267792 *Vitis* (SEQ ID NO: 78), XP 004138978 *Cucumis* (SEQ ID NO: 111), XP 004138979 *Cucumis* (SEQ ID NO: 112), XP 003518628 *Glycine* (SEQ ID NO: 98), XP 004489106 *Cicer* (SEQ ID NO: 130), XP 003617528 *Medicago* (SEQ ID NO: 27), XP 004302124 *Fragaria* (SEQ ID NO: 129), NOD3 MEDTR *Medicago* (SEQ ID NO: 31), NP 001239695 *Glycine* (SEQ ID NO: 74), AFK39311 *Lotus* (SEQ ID NO: 37), XP 003620983 *Medicago* (SEQ ID NO: 32), XP 003530901 *Glycine* (SEQ ID NO: 101), XP 003524088 *Glycine* (SEQ ID NO: 1001, XP 003615405 Medicare (SEQ ID NO: 33), XP 003547573 *Glycine* (SEQ ID NO: 102)].

FIG. 2-2 is a diagram illustrating a result of multiple alignment analysis of the protein contained in the phylogenetic tree illustrated in FIG. 1-1, and following below FIG. 2-1 [XP 003593107 Medicare (SEQ ID NO: 34), EOA22072 *Capsella* (SEQ ID NO: 65), NP 196821 AtSW15 (SEQ ID NO: 21), EMJ23678 *Prunus* (SEQ ID NO: 501, XP 004301046 *Fragaria* (SEQ ID NO: 128), XP 002299333 *Populus* (SEQ ID NO: 801, XP 002514863 *Ricinus* (SEQ ID NO: 951, XP 004140547 *Cucumis* (SEC) ID NO: 113), XP 002264875 *Vitis* (SEQ ID NO: 77), NP 199893 AtSW13 (SEQ ID NO: 19), XP 002862913 *Arabiopsis* (SEQ ID NO: 97), EOA14916 *Capsella* (SEQ ID NO: 62k EOA17919 *Capsella* (SEQ ID NO: 63), NP 194231 AtSW14 (SEQ ID NO: 201. EOA21276 *Capsella* (SEQ ID NO: 64), NP 197755 AtSW12 (SEQ ID NO: 18), EOA24501 *Capsella* (SEQ ID NO: 66), NP 190443 AtSW11 (SEQ ID NO: 171, XP 002511126 *Ricinus* (SEQ ID NO: 92), XP 004297511 *Fragaria* (SEQ ID NO: 126), XP 004153501 *Cucumis* (SEQ ID NO: 1151, XP 004161952 *Cucumis* (SEQ ID NO: 116), XP 004145146 *Cucumis* (SEQ ID NO: 114), XP 004138250 *Cucumis* (SEQ ID NO: 110), XP 004235470 *Solanum* (SEQ ID NO: 123), CBI15715 *Vitis* (SEQ ID NO: 451. AFW71563 *Zea* (SEQ ID NO: 39), NP 001149028 *Zea* (SEQ ID NO: 721, XP 002453892 *Sorghum* (SEQ ID NO: 89), EMT09236 *Aegilops* (SEQ ID NO: 54), XP 003575028 *Brachypodium* (SEQ ID NO: 105), NP 001046944 OsSW15 (SEQ ID NO: 26), EMS46194 *Triticum* (SEQ ID NO: 52), AFW88409 *Zea* (SEQ ID NO: 40), XP 002465280 *Sorghum* (SEQ ID NO: 91), BAJ99068 *Hordeum* (SEQ ID NO: 43), EMT31030 *Aegilops* (SEQ ID NO: 59), XP 003561640 *Brachypodium* (SEQ ID NO: 103), NP 001050099 OsSW12 (SEQ ID NO: 23), BAK07340 *Hordeum* (SEQ ID NO: 44), EMS45810 *Triticum* (SEQ ID NO: 51), XP 003578398 *Brachypodium* (SEQ ID NO: 1081, XP 002462642 *Sorghum* (SEQ ID NO: 90), EAZ09693 *Oryza* (SEQ ID NO: 47), NP 001148964 *Zea* (SEQ ID NO: 71), XP 002444688 *Sorghum* (SEQ ID NO: 87), XP 003572455 *Brachypodium* (SEQ ID NO: 104), NP 001062354 OsSW11 (SEQ ID NO: 22), EMT31640 *Aegilops* (SEQ ID NP: 60), EMS51422 *Triticum* (SEQ ID NO: 53), EMT20808 *Aegilops* (SEQ ID NO: 58)].

FIG. 2-3 is a diagram illustrating a result of multiple alignment analysis of the protein contained in the phylogenetic tree illustrated in FIG. 1-1, and following below FIG. 2-2 [BAJ85621 *Hordeum* (SEQ ID NO: 41), EMT11081 *Aegilops* (SEQ ID NO: 55), XP 002442119 *Sorghum* (SEQ ID NO: 85), XP 002443167 *Sorghum* (SEQ ID NO: 86), NP 001141654 *Zea* (SEQ ID NO: 70), NP 001141106 *Zea* (SEQ ID NO: 69), SWT13 ORYSJ OsSW13 *Oryza* (SEQ ID NO: 24), XP 003576225 *Brachypodium* (SEQ ID NO: 107), BAJ94651 *Hordeum* (SEQ ID NO: 421, XP 003576036 *Brachypodium* (SEQ ID NO: 106), EMT20480 *Aegilops* (SEQ ID NO: 56), EMT20481 *Aegilops* (SEQ ID NO: 57), NP 001132836 *Zea* (SEQ ID NO: 68), XP 002450786 *Sorghum* (SEQ ID NO: 88), NP 001067955 OsSW14 (SEQ ID NO: 25)].

FIG. 2-4 is a diagram illustrating a result of multiple alignment analysis of the protein contained in the phylogenetic tree illustrated in FIG. 1-1, and following the right of FIG. 2-1 [XP 004235326 *Solanum* (SEQ ID NO: 117), XP 004235334 *Solanum* (SEQ ID NO: 119), ACV71016 *Capsicum* (SEQ ID NO: 36), XP 004235333 *Solanum* (SEQ ID NO: 118), XP 004235342 *Solanum* (SEQ ID NO: 122), XP 004235339 *Solanum* (SEQ ID NO: 120), XP 004241452 *Solanum* (SEQ ID NO: 124), XP 004235340 *Solanum* (SEQ ID NO: 121), AFK35161 *Medicago* (SEQ ID NO: 29), CAC44123 *Medicago* (SEQ ID NO: 30), XP 004503778 *Cicer* (SEQ ID NO: 131), AFK48645 *Lotus* (SEQ ID NO: 38), NP 001241307 *Glycine* (SEQ ID NO: 75), NP 001242732 *Glycine* (SEQ ID NO: 76), XP 003523161 *Glycine* (SEQ ID NO: 99), NP 001237418 *Glycine* (SEQ ID NO: 73), XP 003602780 *Medicago* (SEQ ID NO: 28), XP 004138032 *Cucumis* (SEQ ID NO: 109), EMJ10621 *Prunus* (SEQ ID NO: 49), XP 004297512 *Fragaria* (SEQ ID NO: 127), XP 002284244 *Vitis* (SEQ ID NO: 79), EOA14646 *Capsella* (SEQ ID NO: 61), NP 199892 AtSW10 (SEQ ID NO: 161, XP 002321731 *Populus* (SEQ ID NO: 82), XP 002322281 *Populus* (SEQ ID NO: 83), XP 002321730 *Populus* (SEQ ID NO: 81), XP 002511127 *Ricinus* (SEQ ID NO: 93), XP 002511128 *Ricinus* (SEQ ID NO: 94), CBI32263 *Vitis* (SEQ ID NO: 46), EMJ01437 *Prunus* (SEQ ID NO: 48), XP 002520679 *Ricinus* (SEQ ID NO: 961, XP 004247459 *Solanum* (SEQ ID NO: 125), EOA28959 *Capsella* (SEQ ID NO: 67), NP 181439 AtSW09 (SEQ ID NO: 15), XP 002333315 *Populus* (SEQ ID NO: 84), NEC1 PETHY *Petunia* (SEQ ID NO: 35), XP 002267792 *Vitis* (SEQ ID NO: 78), XP 004138978 *Cucumis* (SEQ ID NO:

111), XP 004138979 *Cucumis* (SEQ ID NO: 112), XP 003518628 *Glycine* (SEQ ID NO: 98), XP 004489106 *Cicer* (SEQ ID NO: 130), XP 003617528 *Medicago* (SEQ ID NO: 27), XP 004302124 *Fragaria* (SEQ ID NO: 129), NOD3 MEDTR *Medicago* (SEQ ID NO: 31), NP 001239695 *Glycine* (SEQ ID NO: 74), AFK39311 *Lotus* (SEQ ID NO: 37), XP 003620983 *Medicago* (SEQ ID NO: 321, XP 003530901 *Glycine* (SEQ ID NO: 101), XP 003524088 *Glycine* (SEQ ID NO: 1001, XP 003615405 *Medicago* (SEQ ID NO: 33), XP 003547573 *Glycine* (SEQ ID NO: 102)].

Figure 1:
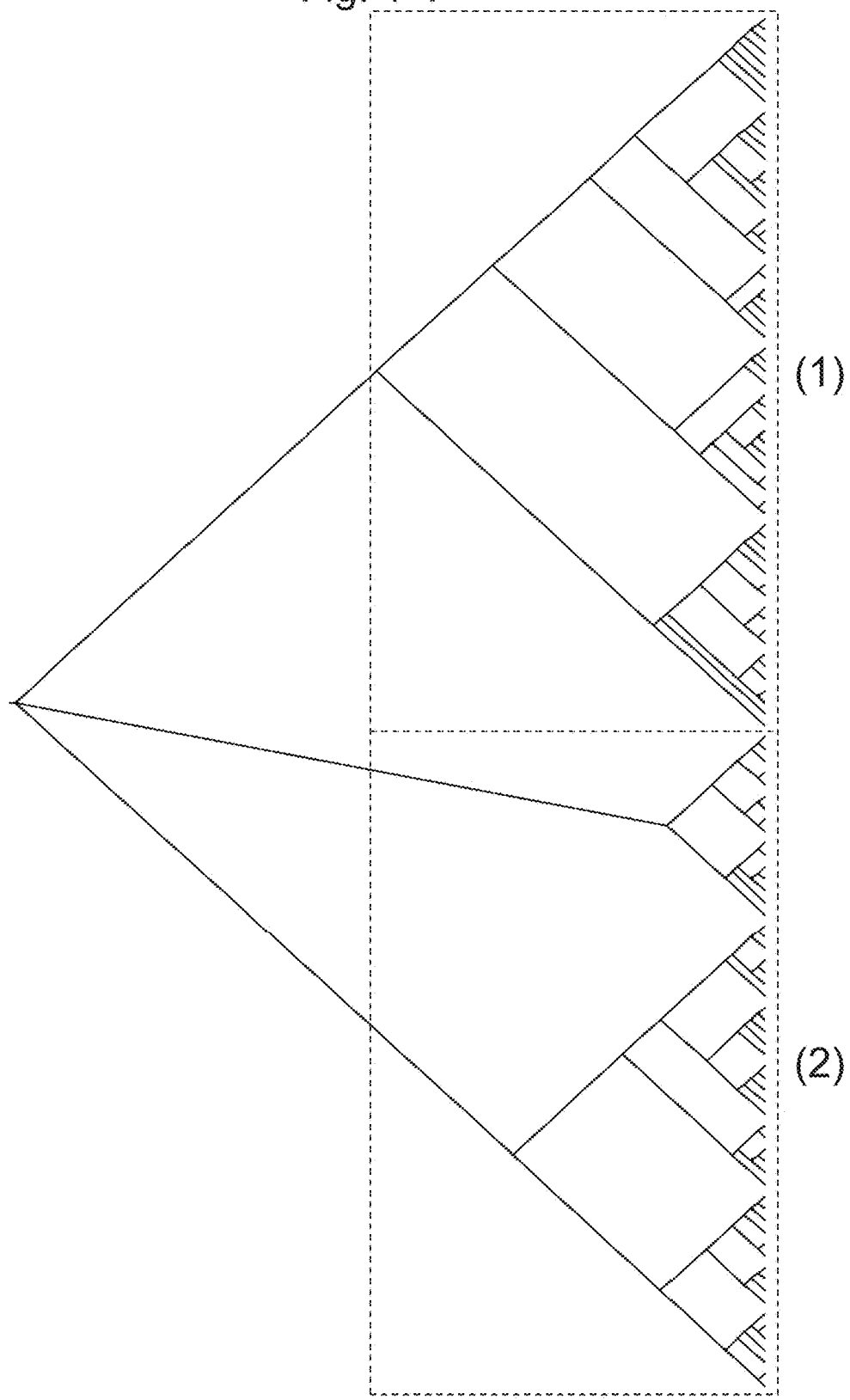
FIG. 1-1 is a schematic view of a phylogenetic tree made based on the information of amino acid sequences of SWEET proteins in the clade III defined in Non-Patent Literature 1 (Nature (2010) 468, 527-532) collected from the GenBank database provided at National Center for Biotechnology Information (NCBI).
Figures 1, 2:

FIG. 2-5 is a diagram illustrating a result of multiple alignment analysis of the protein contained in the phylogenetic tree illustrated in FIG. 1-1, and following the right of FIG. 2-2 [XP 003593107 *Medicago* (SEQ ID NO: 34), EOA22072 *Capsella* (SEQ ID NO: 65), NP 196821 AtSW15 (SEQ ID NO: 21), EMJ23678 *Prunus* (SEQ ID NO: 50), XP 004301046 *Fragaria* (SEQ ID NO: 128), XP 002299333 *Populus* (SEQ ID NO: 80), XP 002514863 *Ricinus* (SEQ ID NO: 951, XP 004140547 *Cucumis* (SEQ ID NO: 113), XP 002264875 *Vitis* (SEQ ID NO: 77), NP 199893 AtSW13 (SEQ ID NO: 19), XP 002862913 *Arabiopsis* (SEQ ID NO: 97), EOA14916 *Capsella* (SEQ ID NO: 62), EOA17919 *Capsella* (SEQ ID NO: 63), NP 194231 AtSW14 (SEQ ID NO: 20), EOA21276 *Capsella* (SEQ ID NO: 64), NP 197755 AtSW12 (SEQ ID NO: 18), EOA24501 *Capsella* (SEQ ID NO: 66), NP 190443 AtSW11 (SEQ ID NO: 171, XP 002511126 *Ricinus* (SEQ ID NO: 92), XP 004297511 *Fragaria* (SEQ ID NO: 126), XP 004153501 *Cucumis* (SEQ ID NO: 1151, XP 004161952 *Cucumis* (SEQ ID NO: 116), XP 004145146 *Cucumis* (SEQ ID NO: 114), XP 004138250 *Cucumis* (SEQ ID NO: 110), XP 004235470 *Solanum* (SEQ ID NO: 123), CBI15715 *Vitis* (SEC) ID NO: 451. AFW71563 *Zea* (SEQ ID NO: 39), NP 001149028 *Zea* (SEQ ID NO: 721, XP 002453892 *Sorghum* (SEQ ID NO: 89), EMT09236 *Aegilops* (SEQ ID NO: 54), XP 003575028 *Brachypodium* (SEQ ID NO: 105), NP 001046944 OsSW15 (SEQ ID NO: 26), EMS46194 *Triticum* (SEQ ID NO: 52), AFW88409 *Zea* (SEQ ID NO: 401, XP 002465280 *Sorghum* (SEQ ID NO: 91), BAJ99068 *Hordeum* (SEQ ID NO: 43), EMT31030 *Aegilops* (SEQ ID NO: 59), XP 003561640 *Brachypodium* (SEQ ID NO: 103), NP 001050099 OsSW12 (SEQ ID NO: 23). BAK07340 *Hordeum* (SEQ ID NO: 44), EMS45810 *Triticum* (SEQ ID NO: 51), XP 003578398 *Brachypodium* (SEQ ID NO: 1081, XP 002462642 *Sorghum* (SEQ ID NO: 90), EAZ09693 *Oryza* (SEQ ID NO: 47), NP 001148964 *Zea* (SEQ ID NO: 71), XP 002444688 *Sorghum* (SEQ ID NO: 87), XP 003572455 *Brachypodium* (SEQ ID NO: 104), NP 001062354 OsSW11 (SEQ ID NO: 22), EMT31640 *Aegilops* (SEQ ID NP: 60), EMS51422 *Triticum* (SEQ ID NO: 531. EMT20808 *Aegilops* (SEQ ID NO: 58)].

Figures 1, 2, 3:

FIG. 2-6 is a diagram illustrating a result of multiple alignment analysis of the protein contained in the phylogenetic tree illustrated in FIG. 1-1, and following the right of FIG. 2-3 [BAJ85621 *Hordeum* (SEQ ID NO: 41), EMT11081 *Aegilops* (SEQ ID NO: 55), XP 002442119 *Sorghum* (SEQ ID NO: 85), XP 002443167 *Sorghum* (SEQ ID NO: 86), NP 001141654 *Zea* (SEQ ID NO: 70), NP 001141106 *Zea* (SEQ ID NO: 69), SWT13 ORYSJ OsSW13 *Oryza* (SEQ ID NO: 24), XP 003576225 *Brachypodium* (SEQ ID NO: 107), BAJ94651 *Hordeum* (SEQ ID NO: 421, XP 003576036 *Brachypodium* (SEQ ID NO: 106), EMT20480 *Aegilops* (SEQ ID NO: 56), EMT20481 *Aegilops* (SEQ ID NO: 57), NP 001132836 *Zea* (SEQ ID NO: 68), XP 002450786 *Sorghum* (SEQ ID NO: 88k NP 001067955 OsSW14 (SEQ ID NO: 25)].

FIG. 2-7 is a diagram illustrating a result of multiple alignment analysis of the protein contained in the phylogenetic tree illustrated in FIG. 1-1, and following the right of FIG. 2-4 [XP 004235326 *Solanum* (SEQ ID NO: 117), XP 004235334 *Solanum* (SEQ ID NO: 119), ACV71016 *Capsicum* (SEQ ID NO: 36), XP 004235333 *Solanum* (SEQ ID NO: 118), XP 004235342 *Solanum* (SEQ ID NO: 122), XP 004235339 *Solanum* (SEQ ID NO: 120), XP 004241452 *Solanum* (SEQ ID NO: 124), XP 004235340 *Solanum* (SEQ ID NO: 121), AFK35161 *Medicago* (SEQ ID NO: 29), CAC44123 *Medicago* (SEQ ID NO: 30), XP 004503778 *Cicer* (SEQ ID NO: 131), AFK48645 *Lotus* (SEQ ID NO: 38), NP 001241307 *Glycine* (SEQ ID NO: 75), NP 001242732 *Glycine* (SEQ ID NO: 76), XP 003523161 *Glycine* (SEQ ID NO: 991. NP 001237418 *Glycine* (SEQ ID NO: 731, XP 003602780 *Medicago* (SEQ ID NP: 28), XP 004138032 *Cucumis* (SEQ ID NO: 109), EMJ10621 *Prunus* (SEQ ID NO: 49k XP 004297512 *Fragaria* (SEQ ID NO: 1271, XP 002284244 *Vitis* (SEQ ID NO: 79), EOA14646 *Capsella* (SEQ ID NO: 61), NP 199892 AtSW10 (SEQ ID NO: 16), XP 002321731 *Populus* (SEQ ID NO: 82), XP 002322281 *Populus* (SEQ ID NO: 83), XP 002321730 *Populus* (SEQ ID NP: 81), XP 002511127 *Ricinus* (SEQ ID NO: 93), XP 002511128 *Ricinus* (SEQ ID NO: 94), CBI32263 *Vitis* (SEQ ID NO: 46), EMJ01437 *Prunus* (SEQ ID NO: 481, XP 002520679 *Ricinus* (SEQ ID NO: 96), XP 004247459 *Solanum* (SEQ ID NO: 125), EOA28959 *Capsella* (SEQ ID NO: 67), NP 181439 AtSW09 (SEQ ID NO: 15), XP 002333315 *Populus* (SEQ ID NO: 84), NEC1 PETHY *Petunia* (SEQ ID NO: 35), XP 002267792 *Vitis* (SEQ ID NO: 78), XP 004138978 *Cucumis* (SEQ ID NO: 111), XP 004138979 *Cucumis* (SEQ ID NO: 112), XP 003518628 *Glycine* (SEQ ID NO: 98), XP 004489106 *Cicer* (SEQ ID NO: 130), XP 003617528 *Medicago* (SEQ ID NO: 27), XP 004302124 *Fragaria* (SEQ ID NO: 129), NOD3 MEDTR *Medicago* (SEQ ID NO: 311. NP 001239695 *Glycine* (SEQ ID NO: 74), AFK39311 *Lotus* (SEQ ID NO: 37), XP 003620983 *Medicago* (SEQ ID NO: 321, XP 003530901 *Glycine* (SEQ ID NO: 101), XP 003524088 *Glycine* (SEQ ID NO: 100), XP 003615405 *Medicago* (SEQ ID NO: 33), XP 003547573 *Glycine* (SEQ ID NO: 102)].

FIG. 2-8 is a diagram illustrating a result of multiple alignment analysis of the protein contained in the phylogenetic tree illustrated in FIG. 1-1, and following the right of FIG. 2-5 [XP 003593107 *Medicago* (SEQ ID NO: 34), EOA22072 *Capsella* (SEQ ID NO: 65), NP 196821 AtSW15 (SEQ ID NO: 21), EMJ23678 *Prunus* (SEQ ID NO: 50), XP 004301046 *Fragaria* (SEQ ID NO: 128), XP 002299333 *Populus* (SEQ ID NO: 80), XP 002514863 *Ricinus* (SEQ ID NO: 95), XP 004140547 *Cucumis* (SEQ ID NO: 113), XP 002264875 *Vitis* (SEQ ID NO: 77), NP 199893 AtSW13 (SEQ ID NO: 19), XP 002862913 *Arabiopsis* (SEC) ID NO: 97), EOA14916 *Capsella* (SEQ ID NO: 62), EOA17919 *Capsella* (SEQ ID NO: 63), NP 194231 AtSW14 (SEQ ID NO: 20), EOA21276 *Capsella* (SEQ ID NO: 64), NP 197755 AtSW12 (SEQ ID NO: 18), EOA24501 *Capsella* (SEQ ID NO: 66), NP 190443 AtSW11 (SEQ ID NO: 17), XP 002511126 *Ricinus* (SEQ ID NO: 92), XP 004297511 *Fragaria* (SEQ ID NO: 1261, XP 004153501 *Cucumis* (SEQ ID NO: 115), XP 004161952 *Cucumis* (SEQ ID NO: 1161, XP 004145146 *Cucumis* (SEQ ID NO: 114), XP 004138250 *Cucumis* (SEQ ID NO: 110), XP 004235470 *Solanum* (SEQ ID NO: 123), CB115715 *Vitis* (SEQ ID NO: 45). AFW71563 *Zea* (SEQ ID NO: 39), NP 001149028 *Zea* (SEQ ID NO: 72), XP 002453892 *Sorghum* (SEQ ID NO: 89), EMT09236 *Aegilops* (SEQ ID NO: 54), XP 003575028 *Brachypodium* (SEQ ID NO: 105), NP 001046944 OsSW15 (SEQ ID NO: 26), EMS46194 *Triticum* (SEQ ID NO: 52), AFW88409 *Zea* (SEQ ID NO: 40), XP 002465280 *Sorghum* (SEQ ID NO:

91), BAJ99068 *Hordeum* (SEQ ID NO: 43), EMT31030 *Aegilops* (SEQ ID NO: 59), XP 003561640 *Brachypodium* (SEQ ID NO: 103), NP 001050099 OsSW12 (SEQ ID NO: 23), BAK07340 *Hordeum* (SEQ ID NO: 44), EMS45810 *Triticum* (SEQ ID NO: 51), XP 003578398 *Brachypodium* (SEQ ID NO: 108), XP 002462642 *Sorghum* (SEQ ID NO: 90), EAZ09693 *Oryza* (SEQ ID NO: 47), NP 001148964 *Zea* (SEQ ID NO: 71), XP 002444688 *Sorghum* (SEQ ID NO: 87), XP 003572455 *Brachypodium* (SEQ ID NO: 104), NP 001062354 OsSW11 (SEQ ID NO: 22), EMT31640 *Aegilops* (SEQ ID NP: 60), EMS51422 *Triticum* (SEQ ID NO: 53), EMT20808 *Aegilops* (SEQ ID NO: 58)].

FIG. 2-9 is a diagram illustrating a result of multiple alignment analysis of the protein contained in the phylogenetic tree illustrated in FIG. 1-1, and following the right of FIG. 2-6 [BAJ85621 *Hordeum* (SEQ ID NO: 41), EMT11081 *Aegilops* (SEQ ID NO: 55), XP 002442119 *Sorghum* (SEQ ID NO: 85), XP 002443167 *Sorghum* (SEQ ID NO: 86), NP 001141654 *Zea* (SEQ ID NO: 70), NP 001141106 *Zea* (SEQ ID NO: 69), SWT13 ORYSJ OsSW13 *Oryza* (SEQ ID NO: 24), XP 003576225 *Brachypodium* (SEQ ID NO: 107), BAJ94651 *Hordeum* (SEQ ID NO: 42), XP 003576036 *Brachypodium* (SEQ ID NO: 106), EMT20480 *Aegilops* (SEQ ID NO: 56), EMT20481 *Aegilops* (SEQ ID NO: 57), NP 001132836 *Zea* (SEQ ID NO: 68), XP 002450786 *Sorghum* (SEQ ID NO: 88), NP 001067955 OsSW14 (SEQ ID NO: 25)].

FIG. 2-10 is a diagram illustrating a result of multiple alignment analysis of the protein contained in the phylogenetic tree illustrated in FIG. 1-1, and following the right of FIG. 2-7 [XP 004235326 *Solanum* (SEQ ID NO: 117), XP 004235334 *Solanum* (SEQ ID NO: 119), ACV71016 *Capsicum* (SEQ ID NO: 36), XP 004235333 *Solanum* (SEQ ID NO: 118), XP 004235342 *Solanum* (SEQ ID NO: 122), XP 004235339 *Solanum* (SEQ ID NO: 120), XP 004241452 *Solanum* (SEQ ID NO: 124), XP 004235340 *Solanum* (SEQ ID NO: 121), AFK35161 *Medicago* (SEQ ID NO: 29), CAC44123 *Medicago* (SEQ ID NO: 30), XP 004503778 *Cicer* (SEQ ID NO: 131), AFK48645 *Lotus* (SEQ ID NO: 38), NP 001241307 *Glycine* (SEQ ID NO: 75), NP 001242732 *Glycine* (SEQ ID NO: 76), XP 003523161 *Glycine* (SEQ ID NO: 99), NP 001237418 *Glycine* (SEQ ID NO: 73), XP 003602780 *Medicago* (SEQ ID NO: 28), XP 004138032 *Cucumis* (SEQ ID NO: 109), EMJ10621 *Prunus* (SEQ ID NO: 49), XP 004297512 *Fragaria* (SEQ ID NO: 1271, XP 002284244 *Vitis* (SEQ ID NO: 79), EOA14646 *Capsella* (SEQ ID NO: 61), NP 199892 AtSW10 (SEQ ID NO: 16), XP 002321731 *Populus* (SEQ ID NO: 82), XP 002322281 *Populus* (SEQ ID NO: 831, XP 002321730 *Populus* (SEQ ID NO: 81), XP 002511127 *Ricinus* (SEQ ID NO: 93), XP 002511128 *Ricinus* (SEQ ID NO: 94), CBI32263 *Vitis* (SEQ ID NO: 46), EMJ01437 *Prunus* (SEQ ID NO: 481, XP 002520679 *Ricinus* (SEQ ID NO: 961, XP 004247459 *Solanum* (SEQ ID NO: 125), EOA28959 *Capsella* (SEQ ID NO: 67), NP 181439 AtSW09 (SEQ ID NO: 15), XP 002333315 *Populus* (SEQ ID NO: 84), NEC1 PETHY *Petunia* (SEQ ID NO: 35), XP 002267792 *Vitis* (SEQ ID NO: 781, XP 004138978 *Cucumis* (SEQ ID NO: 111), XP 004138979 *Cucumis* (SEQ ID NO: 1121, XP 003518628 *Glycine* (SEQ ID NO: 98), XP 004489106 *Cicer* (SEQ ID NO: 130), XP 003617528 *Medicago* (SEQ ID NO: 27), XP 004302124 *Fragaria* (SEQ ID NO: 129), NOD3 MEDTR *Medicago* (SEQ ID NO: 31), NP 001239695 *Glycine* (SEQ ID NO: 74), AFK39311 *Lotus* (SEQ ID NO: 37), XP 003620983 *Medicago* (SEQ ID NO: 32), XP 003530901 *Glycine* (SEQ ID NO: 101), XP 003524088 *Glycine* (SEQ ID NO: 100), XP 003615405 *Medicago* (SEQ ID NO: 33), XP 003547573 *Glycine* (SEQ ID NO: 102)].

FIG. 2-11 is a diagram illustrating a result of multiple alignment analysis of the protein contained in the phylogenetic tree illustrated in FIG. 1-1, and following the right of FIG. 2-8 [XP 003593107 *Medicago* (SEQ ID NO: 34), EOA22072 *Capsella* (SEQ ID NO: 65), NP 196821 AtSW15 (SEQ ID NO: 21), EMJ23678 *Primus* (SEQ ID NO: 50), XP 004301046 *Fragaria* (SEQ ID NO: 128), XP 002299333 *Populus* (SEQ ID NO: 80), XP 002514863 *Ricinus* (SEC) ID NO: 95), XP 004140547 *Cucumis* (SEQ ID NO: 113), XP 002264875 *Vitis* (SEQ ID NO: 77), NP 199893 AtSW13 (SEQ ID NO: 19), XP 002862913 *Arabiopsis* (SEQ ID NO: 97), EOA14916 *Capsella* (SEQ ID NO: 62), EOA17919 *Capsella* (SEQ ID NO: 63), NP 194231 AtSW14 (SEQ ID NO: 20), EOA21276 *Capsella* (SEQ ID NO: 64), NP 197755 AtSW12 (SEQ ID NO: 18), EOA24501 *Capsella* (SEQ ID NO: 66), NP 190443 AtSW11 (SEQ ID NO: 17), XP 002511126 *Ricinus* (SEQ ID NO: 92), XP 004297511 *Fragaria* (SEQ ID NP: 126), XP 004153501 *Cucumis* (SEQ ID NO: 115), XP 004161952 *Cucumis* (SEQ ID NO: 116), XP 004145146 *Cucumis* (SEQ ID NO: 114), XP 004138250 *Cucumis* (SEQ ID NO: 110), XP 004235470 *Solanum* (SEQ ID NO: 123), CB115715 *Vitis* (SEQ ID NO: 45). AFW71563 *Zea* (SEQ ID NO: 39), NP 001149028 *Zea* (SEQ ID NO: 72), XP 002453892 *Sorghum* (SEQ ID NO: 89), EMT09236 *Aegilops* (SEQ ID NO: 54), XP 003575028 *Brachypodium* (SEQ ID NO: 105), NP 001046944 OsSW15 (SEQ ID NO: 26), EMS46194 *Triticum* (SEQ ID NO: 52), AFW88409 *Zea* (SEQ ID NO: 40), XP 002465280 *Sorghum* (SEQ ID NO: 91), BAJ99068 *Hordeum* (SEQ ID NO: 43), EMT31030 *Aegilops* (SEQ ID NO: 59), XP 003561640 *Brachypodium* (SEQ ID NO: 103), NP 001050099 OsSW12 (SEQ ID NO: 23). BAK07340 *Hordeum* (SEQ ID NO: 44), EMS45810 *Triticum* (SEQ ID NO: 51), XP 003578398 *Brachypodium* (SEQ ID NO: 108), XP 002462642 *Sorghum* (SEQ ID NO: 90), EAZ09693 *Oryza* (SEQ ID NO: 47), NP 001148964 *Zea* (SEQ ID NO: 71), XP 002444688 *Sorghum* (SEQ ID NO: 87), XP 003572455 *Brachypodium* (SEQ ID NO: 104), NP 001062354 OsSW11 (SEQ ID NO: 22), EMT31640 *Aegilops* (SEQ ID NP: 60), EMS51422 *Triticum* (SEQ ID NO: 53), EMT20808 *Aegilops* (SEQ ID NO: 58)].

FIG. 2-12 is a diagram illustrating a result of multiple alignment analysis of the protein contained in the phylogenetic tree illustrated in FIG. 1-1, and following the right of FIG. 2-9 [BAJ85621 *Hordeum* (SEQ ID NO: 41), EMT11081 *Aegilops* (SEQ ID NO: 551. XP 002442119 *Sorghum* (SEQ ID NO: 85), XP 002443167 *Sorghum* (SEQ ID NO: 86), NP 001141654 *Zea* (SEQ ID NO: 70), NP 001141106 *Zea* (SEQ ID NO: 69). SWT13 ORYSJ OsSW13 *Oryza* (SEQ ID NO: 24), XP 003576225 *Brachypodium* (SEQ ID NO: 107), BAJ94651 *Hordeum* (SEQ ID NO: 42), XP 003576036 *Brachypodium* (SEQ ID NO: 106), EMT20480 *Aegilops* (SEQ ID NO: 56), EMT20481 *Aegilops* (SEQ ID NO: 57), NP 001132836 *Zea* (SEQ ID NO: 68), XP 002450786 *Sorghum* (SEQ ID NO: 88), NP 001067955 OsSW14 (SEQ ID NO: 25)].

FIG. 2-13 is a diagram illustrating a result of multiple alignment analysis of the protein contained in the phylogenetic tree illustrated in FIG. 1-1, and following the right of FIG. 2-10 [XP 004235326 *Solanum* (SEQ ID NO: 117), XP 004235334 *Solanum* (SEQ ID NO: 119), ACV71016 *Capsicum* (SEQ ID NO: 36), XP 004235333 *Solanum* (SEQ ID NO: 118), XP 004235342 *Solanum* (SEQ ID NO: 122), XP 004235339 *Solanum* (SEQ ID NO: 120), XP 004241452 *Solanum* (SEQ ID NO: 124), XP 004235340 *Solanum* (SEQ ID NO: 121), AFK35161 *Medicago* (SEQ ID NO: 29), CAC44123 *Medicago* (SEQ ID NO: 30), XP 004503778 *Cicer* (SEQ ID NO: 131), AFK48645 *Lotus* (SEQ ID NO: 38), NP 001241307 *Glycine* (SEQ ID NO: 75), NP 001242732 *Glycine* (SEQ ID NO: 76), XP 003523161 *Glycine* (SEQ ID NO: 99), NP 001237418 *Glycine* (SEQ ID NO: 73), XP 003602780 *Medicago* (SEQ ID NO: 28), XP 004138032 *Cucumis* (SEQ ID NO: 109), EMJ10621 *Prunus* (SEQ ID NO: 49), XP 004297512 *Fragaria* (SEQ ID NO: 127), XP 002284244 *Vitis* (SEQ ID NO: 79). EOA14646 *Capsella* (SEQ ID NO: 61), NP 199892 AtSW10 (SEQ ID NO: 161, XP 002321731 *Populus* (SEQ ID NO: 82), XP 002322281 *Populus* (SEQ ID NO: 83), XP 002321730 *Populus* (SEQ ID NO: 81), XP 002511127 *Ricinus* (SEQ ID NO: 93), XP 002511128 *Ricinus* (SEQ ID NO: 94), CBI32263 *Vitis* (SEQ ID NO: 46), EMJ01437 *Prunus* (SEQ ID NO: 48), XP 002520679 *Ricinus* (SEQ ID NO: 96), XP 004247459 *Solanum* (SEQ ID NO: 125), EOA28959 *Capsella* (SEQ ID NO: 67), NP 181439 AtSW09 (SEQ ID NO: 15), XP 002333315 *Populus* (SEQ ID NO: 84), NEC1 PETHY *Petunia* (SEQ ID NO: 35), XP 002267792 *Vitis* (SEQ ID NO: 78), XP 004138978 *Cucumis* (SEQ ID NO: 111), XP 004138979 *Cucumis* (SEQ ID NO: 112), XP 003518628 *Glycine* (SEQ ID NO: 98), XP 004489106 *Cicer* (SEQ ID NO: 130), XP 003617528 *Medicago* (SEQ ID NO: 27), XP 004302124 *Fragaria* (SEQ ID NO: 129), NOD3 MEDTR *Medicago* (SEQ ID NO: 311. NP 001239695 *Glycine* (SEQ ID NO: 74), AFK39311 *Lotus* (SEQ ID NO: 37), XP 003620983 *Medicago* (SEQ ID NO: 321, XP 003530901 *Glycine* (SEQ ID NO: 101), XP 003524088 *Glycine* (SEQ ID NO: 100), XP 003615405 *Medicago* (SEQ ID NO: 33), XP 003547573 *Glycine* (SEQ ID NO: 102)].

FIG. 2-14 is a diagram illustrating a result of multiple alignment analysis of the protein contained in the phylogenetic tree illustrated in FIG. 1-1, and following the right of FIG. 2-11 [XP 003593107 *Medicago* (SEQ ID NO: 34), EOA22072 *Capsella* (SEQ ID NO: 65), NP 196821 AtSW15 (SEQ ID NO: 21), EMJ23678 *Prunus* (SEQ ID NO: 50), XP 004301046 *Fragaria* (SEQ ID NO: 128), XP 002299333 *Populus* (SEQ ID NO: 80), XP 002514863 *Ricinus* (SEQ ID NO: 95), XP 004140547 *Cucumis* (SEQ ID NO: 113), XP 002264875 *Vitis* (SEQ ID NO: 77), NP 199893 AtSW13 (SEQ ID NO: 19), XP 002862913 *Arabiopsis* (SEQ ID NO: 97), EOA14916 *Capsella* (SEQ ID NO: 62), EOA17919 *Capsella* (SEQ ID NO: 63), NP 194231 AtSW14 (SEQ ID NO: 20), EOA21276 *Capsella* (SEQ ID NO: 64), NP 197755 AtSW12 (SEQ ID NO: 18), EOA24501 *Capsella* (SEQ ID NO: 66), NP 190443 AtSW11 (SEQ ID NO: 17), XP 002511126 *Ricinus* (SEQ ID NO: 92), XP 004297511 *Fragaria* (SEQ ID NP: 126), XP 004153501 *Cucumis* (SEQ ID NO: 115), XP 004161952 *Cucumis* (SEQ ID NO: 116), XP 004145146 *Cucumis* (SEQ ID NO: 114), XP 004138250 *Cucumis* (SEQ ID NO: 110), XP 004235470 *Solanum* (SEQ ID NO: 123), CB115715 *Vitis* (SEQ ID NO: 45), AFW71563 *Zea* (SEQ ID NO: 39), NP 001149028 *Zea* (SEQ ID NO: 72), XP 002453892 *Sorghum* (SEQ ID NO: 89), EMT09236 *Aegilops* (SEQ ID NO: 54), XP 003575028 *Brachypodium* (SEQ ID NO: 105), NP 001046944 OsSW15 (SEQ ID NO: 26), EMS46194 *Triticum* (SEQ ID NO: 52), AFW88409 *Zea* (SEQ ID NO: 401, XP 002465280 *Sorghum* (SEQ ID NO: 91), BAJ99068 *Hordeum* (SEQ ID NO: 43), EMT31030 *Aegilops* (SEQ ID NO: 59), XP 003561640 *Brachypodium* (SEQ ID NO: 103), NP 001050099 OsSW12 (SEQ ID NO: 23). BAK07340 *Hordeum* (SEQ ID NO: 44), EMS45810 *Triticum* (SEQ ID NO: 51), XP 003578398 *Brachypodium* (SEQ ID NO: 108), XP 002462642 *Sorghum* (SEQ ID NO: 90), EAZ09693 *Oryza* (SEQ ID NO: 47), NP 001148964 *Zea* (SEQ ID NO: 71), XP 002444688 *Sorghum* (SEQ ID NO: 87), XP 003572455 *Brachypodium* (SEQ ID NO: 104), NP 001062354 OsSW11 (SEQ ID NO: 22), EMT31640 *Aegilops* (SEQ ID NP: 60), EMS51422 *Triticum* (SEQ ID NO: 53), EMT20808 *Aegilops* (SEQ ID NO: 58)].

FIG. 2-15 is a diagram illustrating a result of multiple alignment analysis of the protein contained in the phylogenetic tree illustrated in FIG. 1-1, and following the right of FIG. 2-12 [BAJ85621 *Hordeum* (SEQ ID NO: 41), EMT11081 *Aegilops* (SEQ ID NO: 55), XP 002442119 *Sorghum* (SEQ ID NO: 85), XP 002443167 *Sorghum* (SEQ ID NO: 86), NP 001141654 *Zea* (SEQ ID NO: 70), NP 001141106 *Zea* (SEQ ID NO: 69), SWT13 ORYSJ OsSW13 *Oryza* (SEQ ID NO: 24), XP 003576225 *Brachypodium* (SEQ ID NO: 107), BAJ94651 *Hordeum* (SEQ ID NO: 42), XP 003576036 *Brachypodium* (SEQ ID NO: 106), EMT20480 *Aegilops* (SEQ ID NO: 56), EMT20481 *Aegilops* (SEQ ID NO: 57), NP 001132836 *Zea* (SEQ ID NO: 68), XP 002450786 *Sorghum* (SEQ ID NO: 88), NP 001067955 OsSW14 (SEQ ID NO: 25)].

FIG. 3-1 is a diagram illustrating a result of multiple alignment analysis of the amino acid sequences of the SWEET proteins classified in the clade III in Non-Patent Literature 1 (Nature (2010) 468, 527-532) [AtSW09 (SEQ ID NO: 15). PhNEC1 (SEQ ID NO: 35), XP 003617528 *Medicago* (SEQ ID NO: 27), NOD3 MEDTR *Medicago* (SEQ ID NO: 31), XP 003620983 *Medicago* (SEQ ID NO: 32). AtSW15 (SEQ ID NO: 21), XP 003615405 *Medicago* (SEQ ID NO: 33), XP 003593107 *Medicago* (SEQ ID NO: 34), AtSW11 (SEQ ID NO: 17), AtSW12 (SEQ ID NO: 18), AtSW13 (SEQ ID NO: 19), AtSW14 (SEQ ID NO: 20), OsSW13 (SEQ ID NO: 24), OsSW14 (SEQ ID NO: 25), OsSW15 (SEQ ID NO: 26), AFK35161 *Medicago* (SEQ ID NO: 29), CAC44123 *Medicago* (SEQ ID NO: 30), XP 003602780 *Medicago* (SEQ ID NO: 28), AtSW10 (SEQ ID NO: 16), OsSW12 (SEQ ID NO: 23), OsSW11 (SEQ ID NO: 22)], FIG. 3-2 is a diagram illustrating a result of multiple alignment analysis of the amino acid sequences of the SWEET proteins classified in the clade III in Non-Patent Literature 1 (Nature (2010) 468, 527-532), and following below FIG. 3-1 [AtSW09(SEQ ID NO: 15). PhNEC1 (SEQ ID NO: 35), XP 003617528 *Medicago* (SEQ ID NO: 27), NOD3 MEDTR *Medicago* (SEQ ID NO: 31), XP 003620983 *Medicago* (SEQ ID NO: 32). AtSW15 (SEQ ID NO: 21), XP 003615405 *Medicago* (SEQ ID NO: 33), XP 003593107 *Medicago* (SEQ ID NO: 34), AtSW11 (SEQ ID NO: 17), AtSW12 (SEQ ID NO: 18), AtSW13 (SEQ ID NO: 19), AtSW14 (SEQ ID NO: 20), OsSW13 (SEQ ID NO: 24), OsSW14 (SEQ ID NO: 25), OsSW15 (SEQ ID NO: 26), AFK35161 *Medicago* (SEQ ID NO: 29), CAC44123 *Medicago* (SEQ ID NO: 30), XP 003602780 *Medicago* (SEQ ID NO: 28), AtSW10 (SEQ ID NO: 16), OsSW12 (SEQ ID NO: 23), OsSW11 (SEQ ID NO: 22)].

FIG. 3-3 is a diagram illustrating a result of multiple alignment analysis of the amino acid sequences of the SWEET proteins classified in the clade III in Non-Patent Literature 1 (Nature (2010) 468, 527-532), and following below FIG. 3-2 [AtSW09 (SEQ ID NO: 15), PhNEC1 (SEQ ID NO: 35), XP 003617528 *Medicago* (SEQ ID NO: 27), NOD3 MEDTR *Medicago* (SEQ ID NO: 31), XP 003620983 *Medicago* (SEQ ID NO: 32), AtSW15 (SEQ ID NO: 21), XP 003615405 *Medicago* (SEQ ID NO: 33), XP 003593107 *Medicago* (SEQ ID NO: 34), AtSW11 (SEQ ID NO: 17), AtSW12 (SEQ ID NO: 18), AtSW13 (SEQ ID NO: 19), AtSW14 (SEQ ID NO: 20), OsSW13 (SEQ ID NO: 24), OsSW14 (SEQ ID NO: 25), OsSW15 (SEQ ID NO: 26), AFK35161 *Medicago* (SEQ ID NO: 29), CAC44123 *Med-* icago (SEQ ID NO: 30), XP 003602780 *Medicago* (SEQ ID NO: 28), AtSW10 (SEQ ID NO: 16), OsSW12 (SEQ ID NO: 23), OsSW11 (SEQ ID NO: 22)].

FIG. 4-1 is a diagram illustrating a result of multiple alignment analysis of SWEET proteins derived from *Arabidopsis thaliana* and SWEET proteins derived from *Oryza sativa* in the clade III [At5g50790.1 AtSW10 (SEQ ID NO: 16), At5g13170.1 AtSW15 (SEQ ID NO: 21), At3g48740.1 AtSW11 (SEQ ID NO: 17), At5g23660.1 AtSW12 (SEQ ID NO: 18), At5g50800.1 AtSW13 (SEQ ID NO: 19), At4g25010.1 AtSW14 (SEQ ID NO: 20), Os12g0476200 OsSW13 (SEQ ID NO: 24), Os11g0508600 OsSW14 (SEQ ID NO: 25), Os02g0513100 OsSW15 (SEQ ID NO: 26), At2g39060.1 AtSW09 (SEQ ID NO: 15), Os03g0347500 OsSW12 (SEQ ID NO: 23), Os08g0535200 OsSW11 (SEQ ID NO: 22)].

FIG. 4-2 is a diagram illustrating a result of multiple alignment analysis of SWEET proteins derived from *Arabidopsis thaliana* and SWEET proteins derived from *Oryza sativa* in the clade III, and following below FIG. 4-1 [At5g50790.1 AtSW10 (SEQ ID NO: 161. At5g13170.1 AtSW15 (SEQ ID NO: 21), At3g48740.1 AtSW11 (SEQ ID NO: 17), At5g23660.1 AtSW12 (SEQ ID NO: 18), At5g50800.1 AtSW13 (SEQ ID NO: 19), At4g25010.1 AtSW14 (SEQ ID NO: 20), Os12g0476200 OsSW13 (SEQ ID NO: 24), Os11g0508600 OsSW14 (SEQ ID NO: 25), Os02g0513100 OsSW15 (SEQ ID NO: 26), At2g39060.1 AtSW09 (SEQ ID NO: 15), Os03g0347500 OsSW12 (SEQ ID NO: 23), Os08g0535200 OsSW11 (SEQ ID NO: 22)].

FIG. 5 is a diagram illustrating a result of multiple alignment analysis of SWEET proteins derived from *Arabidopsis thaliana* in the clade III [At5e50790.1 AtSW10 (SEQ ID NO: 16), At5g13170.1 AtSW15 (SEQ ID NO: 21), At3e48740.1 AtSW11 (SEQ ID NO: 17), At5e23660.1 AtSW12 (SEQ ID NO: 18), At5g50800.1 AtSW13 (SEQ ID NO: 19), At4e25010.1 AtSW14 (SEQ ID NO: 20), At2g39060.1 AtSW09 (SEQ ID NO: 15)].

Figure 6:
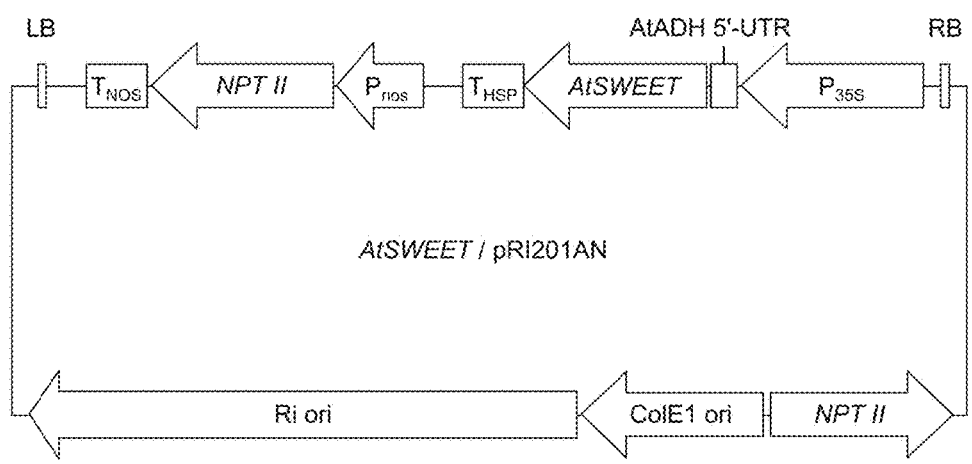

FIG. 6 is a configuration diagram schematically illustrating a physical map of the nucleic acid AtSWEET/pRI201AN prepared in Examples.

FIG. 7 is a photograph of the part producing guttation in *Arabidopsis* under conditions described in Examples.

Figure 8:
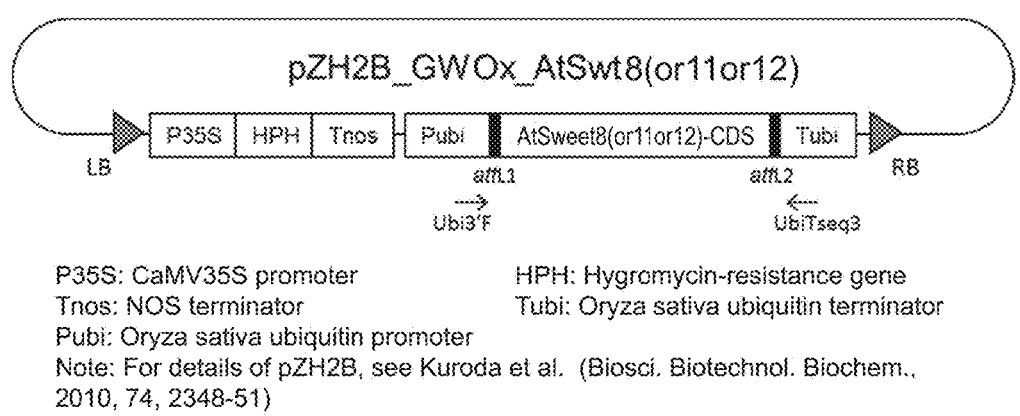

FIG. 8 is a configuration diagram schematically illustrating a physical map of the nucleic acids pZH2B_GWOx_AtSWEET11 and pZH2B_GWOx_AtSWEET12 prepared in Examples.

FIG. 9 FIG. 9 is a photograph of the part producing guttation under conditions described in Examples in rice.

DESCRIPTION OF EMBODIMENTS

The present invention will be described in detail below.

The present invention involves introduction of a nucleic acid encoding a particular transporter protein involved in sugar transportation and/or enhancement of expression of the protein. In this way, exudates with high sugar concentrations can be collected from transformed plants in which the nucleic acid is introduced into cells and/or the expression of the protein is enhanced. As used herein, the exudate refers to a liquid oozed out of tissue in plant, including, for example, root exudate, seed exudate, guttation-liquid oozed out of the hydathode. The phenomenon in which a liquid is oozed out of the hydathode is referred to as guttation. Therefore, guttation-liquid is synonymous with guttation. In particular, the transformed plant in which a nucleic acid encoding a particular transporter protein involved in sugar transportation is introduced into cells and/or the expression of the protein is enhanced can produce guttation with high sugar concentrations.

As used herein, the meaning of nucleic acid includes naturally occurring nucleic acids such as DNA and RNA, artificial nucleic acids such as peptide nucleic acid (PNA) and nucleic acid molecules in which a base, sugar, or phosphodiester moiety is chemically modified. The meaning of the nucleic acid encoding a particular transporter protein involved in sugar transportation includes both of the gene in the genome and the transcription product of the gene.

As used herein, the sugar refers to a substance represented by the chemical formula $C_n(H_2O)_m$, including polysaccharides, oligosaccharides, disaccharides, and monosaccharides, including aldehyde and ketone derivatives of polyol and derivatives and condensation products related thereto. Glucosides in which aglycone such as alcohol, phenol, saponin, or pigment is bound to reduced group of sugar are also included. The monosaccharides may be classified into triose, tetrose, hexose, or pentose based on the number of carbon atoms and they may be classified into aldose, which has an aldehyde group, ketose, which has a ketone group, or the like based on a functional group in the molecule. The sugar may be divided into D-form and L-form according to the conformation at the asymmetric carbon most apart from the aldehyde or ketone group. Specific examples of the monosaccharides include glucose, fructose, galactose, mannose, xylose, xylulose, ribose, erythrose, threose, erythrulose, glyceraldehyde, dihydroxyacetone, etc. and specific examples of the disaccharides include sucrose (saccharose), lactose, maltose, trehalose, cellobiose, etc.

The plants according to the present invention have significantly increased amounts of sugar contained in exudate such as guttation in comparison with the wild type by introducing a nucleic acid encoding a particular transporter protein involved in sugar transportation into cells and/or enhancing expression of the protein. The protein may be expressed at the all cells in the plant tissue or it may be expressed in at least a part of the cells in the plant tissue. As used herein, the meaning of the plant tissue includes the plant organs such as leaf, stem, seed, root, and flower. In the present invention, introducing a nucleic acid means significantly increasing the molecular number per cell of the nucleic acid encoding a transporter protein in comparison with the molecular number in the wild type. In the present invention, enhancing expression of a transporter protein means increasing the expression of its transcription product and/or its translation product by modifying an expression regulatory region of a nucleic acid encoding the transporter protein and/or injecting the nucleic acid itself into a cell.

Transporter Protein Gene Involved in Sugar Transportation

The aforementioned "nucleic acid encoding a particular transporter protein involved in sugar transportation" encodes a transporter protein having a consensus sequence 1 comprising the following amino acid sequence: (L/I/V/M/F)x(G/A)xx(I/L/V/M/F)xxxx(L/I/V/F)(A/S)(P/S) [SEQ ID NO: 1](1-3aa)(P/S/T/A)T(F/L)xx(I/V)xxxKxxxxxxxx-PYxxx(L/I)xxxx(L/I)x(I/L/M/V/F)xY(A/S/G) [SEQ ID NO: 2] (7-13aa)(I/L/V/M)(1-2aa)(I/V)Nxxxxxx(E/Q)xxYxxx(Y/F)xx(Y/F)(A/G/S) [SEQ ID NO: 3] (35-36aa)(R/Q/H)xxxxGx(V/I/L)xxxxx(V/M/L/I/F)xxxx(A/S/T)P(L/M)x(I/V)(I/M/V/L) [SEQ ID NO: 4] (2-7aa)(V/I)(V/I/M)x(T/S)x(S/N)xx(F/Y)(M/L)(P/S)(F/I/V/L)xLSxx(L/I)(T/V)xx(A/G)xxW(F/L)x YGxxxxDxx(V/I)xxPNxxGxx(F/L)(G/S)xxCXM/I)x(L/M/I/V/F)(Y/H/F) [SEQ ID NO: 5] and being involved in sugar transportation.

In the amino acid sequence above, x denotes an arbitrary amino acid residue. In the amino acid sequence, the notations with 2 numbers connected by—and the following "aa" indicate that there is a sequence of arbitrary amino acids at the position and that the sequence consists of a number of amino acid residues, where the number is in the range between the 2 numbers. In the amino acid sequence, the notations with plural amino acids separated by/in a parenthesis indicate that there is one of the plural amino acids at the position. This way of notation is adopted in the description of the amino acid sequences herein.

The amino acid sequence shown above can be in other words an amino acid sequence in which the amino acid sequence set forth in SEQ ID NO: 1, 1 to 3 arbitrary amino acid residues, the amino acid sequence set forth in SEQ ID NO: 2, 7 to 13 arbitrary amino acid residues, the amino acid sequence set forth in SEQ ID NO: 3, any amino acid residue of I/L/V/M, 1 to 2 amino acid residues, the amino acid sequence set forth in SEQ ID NO: 4, 2 to 7 amino acid residues, and the amino acid sequence set forth in SEQ ID NO: 5 are connected in this order from the N-terminus to the C-terminus.

Supplementary FIG. 8 in Nature (2010) 468, 527-534 discloses a phylogenetic tree of SWEETs, transporter proteins involved in sugar transportation, based on the amino acid sequences. The document discloses SWEET proteins from thale cress (*Arabidopsis thaliana*), SWEET proteins from rice (*Oryza sativa*), SWEET proteins from bur clover (*Medicago* truncatula). SWEET proteins from *Chlamydomonas reinhardtii*, SWEET proteins from *Physcomitrella patens*, SWEET proteins from *Petunia hybrida*, SWEET proteins from *Caenorhabditis elegans*, and SWEET proteins from mammals. According to this phylogenetic tree, it is understood that SWEETs, transporter proteins involved in sugar transportation, are classified into five clades of I to V based on the similarity of the amino acid sequence.

TABLE 1

| GenBank (NCBI) ID No. #1 | GenBank (NCBI) ID No. #2 | Index in the Genome | Gene Name | Encoded Protein | Abbreviation of Encoded Protein | SWEET Clade | Organism |
|---|---|---|---|---|---|---|---|
| NP_564140 | SWET1_ARATH | At1g21460 | AtSWEET1 | AtSWEET1 | AtSW01 | I | Arabidopsis thaliana |
| NP_566493 | SWET2_ARATH | At3g14770 | AtSWEET2 | AtSWEET2 | AtSW02 | I | Arabidopsis thaliana |
| NP_200131 | SWET3_ARATH | At5g53190 | AtSWEET3 | AtSWEET3 | AtSW03 | I | Arabidopsis thaliana |
| NP_566829 | SWET4_ARATH | At3g28007 | AtSWEET4 | AtSWEET4 | AtSW04 | II | Arabidopsis thaliana |
| NP_201091 | SWET5_ARATH | At5g62850 | AtSWEET5 | AtSWEET5 | AtSW05 | II | Arabidopsis thaliana |
| NP_176849 | SWET6_ARATH | At1g66770 | AtSWEET6 | AtSWEET6 | AtSW06 | II | Arabidopsis thaliana |
| NP_567366 | SWET7_ARATH | At4g10850 | AtSWEET7 | AtSWEET7 | AtSW07 | II | Arabidopsis thaliana |
| NP_568579 | SWET8_ARATH | At5g40260 | AtSWEET8 | AtSWEET8 | AtSW08 | II | Arabidopsis thaliana |
| NP_181439 | AAM63257 | At2g39060 | AtSWEET9 | AtSWEET9 | AtSW09 | III | Arabidopsis thaliana |
| NP_199892 | AED95992 | At5g50790 | AtSWEET10 | AtSWEET10 | AtSW10 | III | Arabidopsis thaliana |
| NP_190443 | AEE78451 | At3g48740 | AtSWEET11 | AtSWEET11 | AtSW11 | III | Arabidopsis thaliana |
| NP_197755 | AED93195 | At5g23660 | AtSWEET12 | AtSWEET12 | AtSW12 | III | Arabidopsis thaliana |
| NP_199893 | AED95993 | At5g50800 | AtSWEET13 | AtSWEET13 | AtSW13 | III | Arabidopsis thaliana |
| NP_194231 | AEE84991 | At4g25010 | AtSWEET14 | AtSWEET14 | AtSW14 | III | Arabidopsis thaliana |
| NP_196821 | AED91859 | At5g13170 | AtSWEET15 | AtSWEET15 | AtSW15 | III | Arabidopsis thaliana |
| NP_188291 | SWT16_ARATH | At3g16690 | AtSWEET16 | AtSWEET16 | AtSW16 | IV | Arabidopsis thaliana |
| NP_193327 | SWT17_ARATH | At4g15920 | AtSWEET17 | AtSWEET17 | AtSW17 | IV | Arabidopsis thaliana |
| NP_001044998 | SWT1A_ORYSJ | Os01g0881300 | OsSWEET1a | OsSWEET1a | OsSW01a | I | Oryza sativa |
| NP_001055599 | SWT1B_ORYSJ | Os05g0426000 | OsSWEET1b | OsSWEET1b | OsSW01b | I | Oryza sativa |
| NP_001043270 | SWT2A_ORYSJ | Os01g0541800 | OsSWEET2a | OsSWEET2a | OsSW02a | I | Oryza sativa |
| NP_001043983 | SWT2B_ORYSJ | Os01g0700100 | OsSWEET2b | OsSWEET2b | OsSW02b | I | Oryza sativa |
| NP_001054926 | SWT3A_ORYSJ | Os05g0214300 | OsSWEET3a | OsSWEET3a | OsSW03a | I | Oryza sativa |
| NP_001042428 | SWT3B_ORYSJ | Os01g0220700 | OsSWEET3b | OsSWEET3b | OsSW03b | I | Oryza sativa |
| NP_001046621 | SWET4_ORYSJ | Os02g0301100 | OsSWEET4 | OsSWEET4 | OsSW04 | II | Oryza sativa |
| NP_001056475 | SWET5_ORYSJ | Os05g0588500 | OsSWEET5 | OsSWEET5 | OsSW05 | II | Oryza sativa |
| NP_001043523 | SWT6A_ORYSJ | Os01g0606000 | OsSWEET6a | OsSWEET6a | OsSW06a | II | Oryza sativa |
| NP_001043522 | SWT6B_ORYSJ | Os01g0605700 | OsSWEET6b | OsSWEET6b | OsSW06b | II | Oryza sativa |
| NP_001062690 | SWT7A_ORYSJ | Os09g0254600 | OsSWEET7a | OsSWEET7a | OsSW07a | II | Oryza sativa |
| NP_001062702 | SWT7B_ORYSJ | Os09g0258700 | OsSWEET7b | OsSWEET7b | OsSW07b | II | Oryza sativa |
| SWT7C_ORYSJ | — | Os12g0178500 | OsSWEET7c | OsSWEET7c | OsSW07c | II | Oryza sativa |
| NP_001062354 | — | Os08g0535200 | OsSWEET11 | OsSWEET11 | OsSW11 | III | Oryza sativa |
| NP_001050099 | — | Os03g0347500 | OsSWEET12 | OsSWEET12 | OsSW12 | III | Oryza sativa |
| SWT13_ORYSJ | — | Os12g0476200 | OsSWEET13 | OsSWEET13 | OsSW13 | III | Oryza sativa |
| NP_001067955 | — | Os11g0508600 | OsSWEET14 | OsSWEET14 | OsSW14 | III | Oryza sativa |
| NP_001046944 | — | Os02g0513100 | OsSWEET15 | OsSWEET15 | OsSW15 | III | Oryza sativa |
| NP_001050071 | SWT16_ORYSJ | Os03g0341300 | OsSWEET16 | OsSWEET16 | OsSW16 | IV | Oryza sativa |
| XP_003617528 | — | Medtr5g092600 | MtSWEET9 | MtSWEET9 | MtSW09 | III | Medicago truncatula |
| XP_003602780 | — | Medtr3g098930 | MtSWEET10a | MtSWEET10a | MtSW10a | III | Medicago truncatula |
| AFK35161 | — | — | MtSWEET10b | MtSWEET10b | MtSW10b | III | Medicago truncatula |
| CAC44123 | — | — | MtSWEET10c | MtSWEET10c | MtSW10c | III | Medicago truncatula |
| NOD3_MEDTR | — | — | NOD3 | MtSWEET15a | MtSW15a | III | Medicago truncatula |
| XP_003620983 | — | Medtr7g005690 | MtSWEET15b | MtSWEET15b | MtSW15b | III | Medicago truncatula |
| XP_003615405 | — | Medtr5g067530 | MtSWEET15c | MtSWEET15c | MtSW15c | III | Medicago truncatula |
| XP_003593107 | — | Medtr2g007890 | MtSWEET15d | MtSWEET15d | MtSW15d | III | Medicago truncatula |
| NEC1_PETHY | — | — | NEC1 | PhNEC1 | PhNEC1 | III | Petunia hybrida |

As used herein, the word AtSWEET refers to AtSWEET1, AtSWEET2, AtSWEET3, AtSWEET4, AtSWEET5, AtSWEET6, AtSWEET7, AtSWEET8, AtSWEET9, AtSWEET10, AtSWEET11, AtSWEET12, AtSWEET13, AtSWEET14, AtSWEET15, AtSWEET16, and AtSWEETT17 in Table 1 and the word OsSWEET refers to OsSWEET1a, OsSWEET1b, OsSWEET2a, OsSWEET2b, OsSWEET3a, OsSWEET3b, OsSWEET4, OsSWEET5, OsSWEET6a, OsSWEET6b, OsSWEET7a, OsSWEET7b, OsSWEET7c, OsSWEET11, OsSWEET12, OsSWEET13, OsSWEET14, OsSWEET15, and OsSWEET16 in Table 1.

Consensus Sequence 1 described above is an amino acid sequence generated from a phylogenetic tree (FIG. 1-1 to FIG. 1-3) by ClustalW and multiple alignment (FIG. 2-1 to FIG. 2-15) made based on the information on amino acid sequences of SWEET proteins in the clade III defined in the aforementioned document collected from the GenBank database. Accordingly, the aforementioned transporter proteins involved in sugar transportation having Consensus Sequence 1 include the SWEET proteins classified in clade III in the aforementioned document, but no SWEET proteins classified in any of clades I, II, IV, and V in the aforementioned document. In other words, Consensus Sequence 1 described above is a sequence that is characteristic of the SWEET proteins classified in clade III in the aforementioned document and the SWEET proteins collected from the GenBank database and classified in clade III and that is a criterion for the clear distinction from those in clades I, II, IV, and V according to the aforementioned document.

FIG. 1-1 illustrates a whole picture of the phylogenetic tree and FIGS. 1-2 to 1-3 illustrate the enlargement of partial areas of the whole picture shown in FIG. 1-1. The whole picture shown in FIG. 1-1 contains neither GenBank ID nor protein names. The partial areas shown in FIG. 1-2 to 1-3 contain GenBank IDs and protein names.

Specific examples of clade III include SWEET proteins derived from, in addition to besides thale cress (*Arabidopsis thaliana*), rice (*Oryza sativa*), bur clover (*Medicago denticulata*), and petunia (*Petunia hybrida*) listed in Table 1, soybean (*Glycine max*), bird's-foot trefoil (*Lotus japonicus*), tomato (*Solamnum lycopersicum*), red pepper (*Capsicum annuum*), chick-pea (*Cicer arietinum*), cucumber (*Cucumis sativus*), peach (*Prunus persica*), strawberry (*Fragaria vesca*), grape (*Vitisvinifera*), *Capsella rubella*, poplar (*Populus trichocarpa*), castorbean (*Ricinus communis*), corn (*Zea mays*), sorghum (*Sorghum bicolor*), Tausch's goatgrass (*Aegilops tauschii*), purple false brome (*Brachypodium distachyon*), red wild einkorn (*Triticumurartu*), barley (*Hordeum vulgare*), etc., as shown in FIG. 1-1 to 1-3.

Table 2 below shows corresponding GenBank ID numbers, gene names, species of the organisms of origin, and SEQ ID NOs of amino acid sequence of the SWEET proteins derived from *Arabidopsis thaliana, Oryza sativa, Medicago denticulata*, and *Petunia hybrida* listed in Table 1 among these SWEET proteins included in clade III.

Table 1 below shows corresponding GenBank ID numbers, indexes of the protein coding regions calculated from the genome data (Index in the Genome), gene names, protein names, abbreviations of the proteins, SWEET protein clade numbers, and species of the organisms of origin of SWEET proteins from *Arabidopsis thaliana*, SWEET proteins from *Oryza sativa*, and *Medicago* truncatula SWEET proteins and a *Petunia hybrida* SWEET protein among the transporter proteins SWEETs involved in sugar transportation disclosed in the document.

TABLE 2

| GenBank ID | Gene Name | Species of organism of origin | SEQ ID NO of amino acid sequence |
|---|---|---|---|
| NP_181439 | AtSWEET9 | *Arabidopsis thaliana* | SEQ ID NO: 15 |
| NP_199892 | AtSWEET10 | *Arabidopsis thaliana* | SEQ ID NO: 16 |
| NP_190443 | AtSWEET11 | *Arabidopsis thaliana* | SEQ ID NO: 17 |
| NP_197755 | AtSWEET12 | *Arabidopsis thaliana* | SEQ ID NO: 18 |
| NP_199893 | AtSWEET13 | *Arabidopsis thaliana* | SEQ ID NO: 19 |
| NP_194231 | AtSWEET14 | *Arabidopsis thaliana* | SEQ ID NO: 20 |
| NP_196821 | AtSWEET15 | *Arabidopsis thaliana* | SEQ ID NO: 21 |
| NP_001062354 | OsSWEET11 | *Oryza sativa* | SEQ ID NO: 22 |
| NP_00105099 | OsSWEET12 | *Oryza sativa* | SEQ ID NO: 23 |
| SWT13_ORYSJ | OsSWEET13 | *Oryza sativa* | SEQ ID NO: 24 |
| NP_001067955 | OsSWEET14 | *Oryza sativa* | SEQ ID NO: 25 |
| NP_001046944 | OsSWEET15 | *Oryza sativa* | SEQ ID NO: 26 |
| XP_003617528 | MtSWEET9 | *Medicago denticulata* | SEQ ID NO: 27 |
| XP_003602780 | MtSWEET10a | *Medicago denticulata* | SEQ ID NO: 28 |
| AFK35161 | MtSWEET10b | *Medicago denticulata* | SEQ ID NO: 29 |
| CAC44123 | MtSWEET10c | *Medicago denticulata* | SEQ ID NO: 30 |
| NOD3_MEDTR | NOD3 | *Medicago denticulata* | SEQ ID NO: 31 |
| XP_003620983 | MtSWEET15b | *Medicago denticulata* | SEQ ID NO: 32 |
| XP_003615405 | MtSWEET15c | *Medicago denticulata* | SEQ ID NO: 33 |
| XP_003593107 | MtSWEET15d | *Medicago denticulata* | SEQ ID NO: 34 |
| NEC1_PETHY | NEC1 | *Petunia hybrida* | SEQ ID NO: 35 |

Tables 3, 4, and 5 below show corresponding GenBank ID numbers, species of the organisms of origin, and SEQ ID NOs of amino acid sequences of the SWEET proteins shown in FIG. 1-1 to 1-3 derived from organisms of species other than *Arabidopsis thaliana, Oryza saliva, Medicago denticulata*, and *Petunia hybrida*.

TABLE 3

| GenBank ID | Species of organism of origin | SEQ ID NO of amino acid sequence |
|---|---|---|
| ACV71016 | *Capsicum annuum* | SEQ ID NO: 36 |
| AFK39311 | *Lotus japonicus* | SEQ ID NO: 37 |
| AFK48645 | *Lotus japonicus* | SEQ ID NO: 38 |
| AFW71563 | *Zea mays* | SEQ ID NO: 39 |
| AFW88409 | *Zea mays* | SEQ ID NO: 40 |
| BAJ85621 | *Hordeum vulgare* | SEQ ID NO: 41 |
| BAJ94651 | *Hordeum vulgare* | SEQ ID NO: 42 |
| BAJ99068 | *Hordeum vulgare* | SEQ ID NO: 43 |
| BAK07340 | *Hordeum vulgare* | SEQ ID NO: 44 |
| CBI15715 | *Vitis vinifera* | SEQ ID NO: 45 |
| CBI32263 | *Vitis vinifera* | SEQ ID NO: 46 |
| EAZ09693 | *Oryza sativa Indica* | SEQ ID NO: 47 |
| EMJ01437 | *Prunus persica* | SEQ ID NO: 48 |
| EMJ10621 | *Prunus persica* | SEQ ID NO: 49 |
| EMJ23678 | *Prunus persica* | SEQ ID NO: 50 |
| EMS45810 | *Triticum urartu* | SEQ ID NO: 51 |
| EMS46194 | *Triticum urartu* | SEQ ID NO: 52 |
| EMS51422 | *Triticum urartu* | SEQ ID NO: 53 |
| EMT09236 | *Aegilops tauschii* | SEQ ID NO: 54 |
| EMT11081 | *Aegilops tauschii* | SEQ ID NO: 55 |
| EMT20480 | *Aegilops tauschii* | SEQ ID NO: 56 |
| EMT20481 | *Aegilops tauschii* | SEQ ID NO: 57 |

TABLE 3-continued

| GenBank ID | Species of organism of origin | SEQ ID NO of amino acid sequence |
|---|---|---|
| EMT20808 | Aegilops tauschii | SEQ ID NO: 58 |
| EMT31030 | Aegilops tauschii | SEQ ID NO: 59 |
| EMT31640 | Aegilops tauschii | SEQ ID NO: 60 |
| EOA14646 | Capsella rubella | SEQ ID NO: 61 |
| EOA14916 | Capsella rubella | SEQ ID NO: 62 |
| EOA17919 | Capsella rubella | SEQ ID NO: 63 |
| EOA21276 | Capsella rubella | SEQ ID NO: 64 |
| EOA22072 | Capsella rubella | SEQ ID NO: 65 |
| EOA24501 | Capsella rubella | SEQ ID NO: 66 |
| EOA28959 | Capsella rubella | SEQ ID NO: 67 |
| NP_001132836 | Zea mays | SEQ ID NO: 68 |
| NP_001141106 | Zea mays | SEQ ID NO: 69 |
| NP_001141654 | Zea mays | SEQ ID NO: 70 |
| NP_001148964 | Zea mays | SEQ ID NO: 71 |

TABLE 4

| GenBank ID | Species of organism of origin | SEQ ID NO of amino acid sequence |
|---|---|---|
| NP_001149028 | Zea mays | SEQ ID NO: 72 |
| NP_001237418 | Glycine max | SEQ ID NO: 73 |
| NP_001239695 | Glycine max | SEQ ID NO: 74 |
| NP_001241307 | Glycine max | SEQ ID NO: 75 |
| NP_001242732 | Glycine max | SEQ ID NO: 76 |
| XP_002264875 | Vitis vinifera | SEQ ID NO: 77 |
| XP_002267792 | Vitis vinifera | SEQ ID NO: 78 |
| XP_002284244 | Vitis vinifera | SEQ ID NO: 79 |
| XP_002299333 | Populus trichocarpa | SEQ ID NO: 80 |
| XP_002321730 | Populus trichocarpa | SEQ ID NO: 81 |
| XP_002321731 | Populus trichocarpa | SEQ ID NO: 82 |
| XP_002322281 | Populus trichocarpa | SEQ ID NO: 83 |
| XP_002333315 | Populus trichocarpa | SEQ ID NO: 84 |
| XP_002442119 | Sorghum bicolor | SEQ ID NO: 85 |
| XP_002443167 | Sorghum bicolor | SEQ ID NO: 86 |
| XP_002444688 | Sorghum bicolor | SEQ ID NO: 87 |
| XP_002450786 | Sorghum bicolor | SEQ ID NO: 88 |
| XP_002453892 | Sorghum bicolor | SEQ ID NO: 89 |
| XP_002462642 | Sorghum bicolor | SEQ ID NO: 90 |
| XP_002465280 | Sorghum bicolor | SEQ ID NO: 91 |
| XP_002511126 | Ricinus cummunis | SEQ ID NO: 92 |
| XP_002511127 | Ricinus cummunis | SEQ ID NO: 93 |
| XP_002511128 | Ricinus cummunis | SEQ ID NO: 94 |
| XP_002514863 | Ricinus cummunis | SEQ ID NO: 95 |
| XP_002520679 | Ricinus cummunis | SEQ ID NO: 96 |
| XP_002862913 | Arabiopsis lyrata | SEQ ID NO: 97 |
| XP_003518628 | Glycine max | SEQ ID NO: 98 |
| XP_003523161 | Glycine max | SEQ ID NO: 99 |
| XP_003524088 | Glycine max | SEQ ID NO: 100 |
| XP_003530901 | Glycine max | SEQ ID NO: 101 |
| XP_003547573 | Glycine max | SEQ ID NO: 102 |
| XP_003561640 | Brachypodium distachyon | SEQ ID NO: 103 |
| XP_003572455 | Brachypodium distachyon | SEQ ID NO: 104 |
| XP_003575028 | Brachypodium distachyon | SEQ ID NO: 105 |
| XP_003576036 | Brachypodium distachyon | SEQ ID NO: 106 |
| XP_003576225 | Brachypodium distachyon | SEQ ID NO: 107 |

TABLE 5

| GenBank ID | Species of organism of origin | SEQ ID NO of amino acid sequence |
|---|---|---|
| XP_003578398 | Brachypodium distachyon | SEQ ID NO: 108 |
| XP_004138032 | Cucumis sativus | SEQ ID NO: 109 |
| XP_004138250 | Cucumis sativus | SEQ ID NO: 110 |
| XP_004138978 | Cucumis sativus | SEQ ID NO: 111 |
| XP_004138979 | Cucumis sativus | SEQ ID NO: 112 |
| XP_004140547 | Cucumis sativus | SEQ ID NO: 113 |
| XP_004145146 | Cucumis sativus | SEQ ID NO: 114 |
| XP_004153501 | Cucumis sativus | SEQ ID NO: 115 |
| XP_004161952 | Cucumis sativus | SEQ ID NO: 116 |
| XP_004235326 | Solanum lycopersicum | SEQ ID NO: 117 |
| XP_004235333 | Solanum lycopersicum | SEQ ID NO: 118 |
| XP_004235334 | Solanum lycopersicum | SEQ ID NO: 119 |
| XP_004235339 | Solanum lycopersicum | SEQ ID NO: 120 |
| XP_004235340 | Solanum lycopersicum | SEQ ID NO: 121 |
| XP_004235342 | Solanum lycopersicum | SEQ ID NO: 122 |
| XP_004235470 | Solanum lycopersicum | SEQ ID NO: 123 |
| XP_004241452 | Solanum lycopersicum | SEQ ID NO: 124 |
| XP_004247459 | Solanum lycopersicum | SEQ ID NO: 125 |
| XP_004297511 | Fragaria vesca | SEQ ID NO: 126 |
| XP_004297512 | Fragaria vesca | SEQ ID NO: 127 |
| XP_004301046 | Fragaria vesca | SEQ ID NO: 128 |
| XP_004302124 | Fragaria vesca | SEQ ID NO: 129 |
| XP_004489106 | Cicer arietinum | SEQ ID NO: 130 |
| XP_004503778 | Cicer arietinum | SEQ ID NO: 131 |

FIGS. 2-1 to 2-15 illustrate a result of analysis of alignment of the amino acid sequences of the SWEET proteins derived from various organisms listed in Tables 2 to 5 using ClustalW multiple sequence alignment program (available in DDBJ at National Institute of Genetics). The version and various parameters used in the analysis are shown below.

ClustalW Version, 2.1
Pairwise Alignment Parameters
   Alignment Type, Slow
   Slow Pairwise Alignment Options
   Protein Weight Matrix, Gonnet
   Gap Open, 10
   Gap Extension, 0.1
Multiple Sequence Alignment Parameters
   Protein Weight Matrix, Gonnet
   Gap Open, 10
   Gap Extension, 0.20
   Gap Distances, 5
   No End Gaps, no
   Iteration, none
   Numiter, I
   Clustering, NJ
Output Options
   Format, Aln w/numbers
   Order, Aligned The aforementioned SWEET proteins classified in clade III of the SWEET protein are found to have Consensus sequence 1 described above, as shown in FIG. 2-1 to 2-15. The variations of amino acid residues that can occur at the certain positions in Consensus Sequence 1 shown above are based on the following reasons. It is well known that the amino acids are classified according to their side chains of similar properties (chemical properties and the physical size) as described in Reference (1) ("McKee's Biochemistry," 3rd edition, Chapter 5 Amino acid, peptide, protein, 5.1 Amino acid, Japanese Edition supervised by Atsushi Ichikawa, translation supervised by Shinnichi Fukuoka, published by Ryosuke Sone, from Kagaku-Dojin Publishing Company, inc., ISBN4-7598-0944-9). Also, it is well known that substitution process in molecular evolution occurs frequently between amino acid residues classified in a certain group while maintaining the activity of protein. Based on this idea, a score matrix (BLOSUM) for the amino acid residue substitution is proposed in FIG. 2 in References (2): Henikoff S., Henikoff J. G., Amino-acid substitution matrices from protein blocks, Proc. Natl. Acad. Sci. USA, 89, 10915-10919 (1992) and used widely. Reference (2) is based on the findings that the substitution between amino acids having side chains of similar chemical properties has a less impact on the structure and function of the whole protein.

According to References (1) and (2) mentioned above, the groups of side chains of amino acids to be considered in the multiple alignment may be those based on indexes for chemical properties, the physical size, etc. These are shown as the groups of amino acids having scores of 0 or more, or preferably amino acids having 1 or more in the score matrix (BLOSUM) disclosed in References (2). Representative groups include the following 8 groups. Another sub-grouping may be the groups of amino acids having scores of 0 or more, preferably the groups of amino acids having scores of I or more, or more preferably the groups of amino acids having scores of 2 or more.

1) Aliphatic Hydrophobic Amino Acid Group (ILMV Group)

This group is a group of the amino acids having an aliphatic hydrophobic side chain among the neutral non-polar amino acids shown in Reference (1) mentioned above and constituted of valine (V, Val), leucine (L, Leu), isoleucine (I, Ile), and methionine (M, Met). Among the amino acids classified as neutral non-polar amino acids in Reference (1), FGACWP are not included in this "aliphatic hydrophobic amino acid group" for the following reasons. *Glycine* (G, Gly) and alanine (A, Ala) have weak effects of the nonpolar groups because the sizes are not larger than the methyl group. Cysteine (C, Cys) may play an important role in S—S bonding and also have a property of forming hydrogen bonding with the oxygen atom and the nitrogen atom in nature. Phenylalanine (F, Phe) and tryptophan (W, Trp) have a side chain having a high molecular weight and a strong effect of the aromatic group. Proline (P, Pro) has a strong effect of the imino acid group, and fixes the angle of the main chain of polypeptide.

2) Group Having Hydroxy Methylene Group (ST Group)

This group is a group of amino acids having a hydroxy methylene group in the side chain among the neutral polar amino acids, and constituted of serine (S, Ser) and threonine (T, Thr). Because the hydroxyl group in the side chains of S and T is a sugar-binding site, they are often important sites for a particular activity of a certain polypeptide (protein).

3) Acidic Amino Acid (DE Group)

This group is a group of amino acids having an acidic carboxyl group in the side chain, and constituted of aspartic acid (D, Asp) and glutamic acid (E, Glu).

4) Basic Amino Acid (KR Group)

This group is a group of the basic amino acids, and constituted of lysine (K, Lys) and arginine (R, Arg). These K and R are positively charged and display basic characteristics in a wide range of pH. On the other hand, histidine (H, His), which is classified as a basic amino acid, is not classified in this group because it is hardly ionized at pH 7

5) Methylene Group-Polar Group (DHN Group)

In this group, all amino acids characteristically have, as a side chain, a methylene group bound to the α carbon atom and a polar group attached to the methylene group. They are characterized by having a methylene group, which is a nonpolar group, similar in physical size, and the group is constituted of asparagine (N, Asn, the polar group is the amido group), aspartic acid (D, Asp, the polar group is the carboxyl group), and histidine (H, His, the polar group is the imidazole group).

6) Dimethylene Group-Polar Group (EKQR Group)

In this group, all amino acids characteristically have, as a side chain, a linear hydrocarbon equal to or longer than the dimethylene group bound to the α carbon atom and a polar group attached to the hydrocarbon. They are characterized by having a dimethylene group, which is a nonpolar group, similar in physical size. The group is constituted of glutamic acid (E, Glu, the polar group is the carboxyl group), lysine (K, Lys, the polar group is the amino group), glutamine (Q, Gln, the polar group is the amido group), and arginine (R, Arg, the polar groups are the imino group and the amino group).

7) Aromatic (FYW group)

This group is a group of aromatic amino acids, which have a benzene nucleus in the side chain and characterized by chemical properties unique to aromatic groups. The group consists of phenylalanine (F, Phe), tyrosine (Y, Tyr), and tryptophan (W, Trp).

8) Cyclic & Polar (HY Group)

This group is a group of amino acids that has a ring structure and polarity in the side chain, and constituted of histidine (H, His, the ring structure and the polar group are both the imidazole group), tyrosine (Y, Tyr, the ring structure is the benzene nucleus and the polar group is the hydroxyl group).

Based on the aforementioned amino acid groups, substitution of an amino acid residue in the amino acid sequence of a protein having a certain function with an amino acid residue in the same group can be easily expected to result in a novel protein having a similar function. For example, based on the aforementioned "1) Aliphatic hydrophobic amino acid group (ILMV group)," substitution of an isoleucine residue in the amino acid sequence of a protein having a certain function with a leucine residue can be easily expected to result in a novel protein having a similar function. If there are multiple proteins having a certain function, their amino acid sequences may be expressed as a consensus sequence. Also in such a case, substitution of an amino acid residue with an amino acid residue in the same group can be easily expected to result in a novel protein having a similar function. For example, if there are multiple proteins having a certain function and an amino acid residue in the consensus sequence calculated from them is isoleucine or leucine (L/I), based on the aforementioned "1) Aliphatic hydrophobic amino acid group (ILMV group)", substitution of the isoleucine or leucine residue with a methionine or valine residue can be easily expected to result in a novel protein having a similar function.

The aforementioned "particular transporter protein involved in a sugar transportation" can be defined as a protein that has Consensus Sequence 2 consisting of an amino acid sequence in which certain amino acid residues are added at the N-terminal side and the C-terminal side of Consensus Sequence 1 described above and the variation of amino acids that can be present at certain positions are limited. The amino acid sequence of Consensus Sequence 2 is as follows. G(L/I/V/F/M)xGx(I/V/L)(I/V/L)(S/T)xxxxL(A/S)P(L/V/I/M)(P/S/T/A)TFxx(I/V)x(K/R)xK(S/T) xxx(F/Y)x(S/A)xPYxx(A/S/T)LxSxxLx(L/I/M/V)(Y/F)Y(A/G) [SEQ ID NO: 6] (1-9aa)(L/I)(I/V/L)(T/S)INxx(G/A)xx(I/V/M)(E/Q)xxYxxx(F/Y)(L/I/V/F)x(Y/F)Ax(K/R/N)xxxxx(T/A) [SEQ ID NO: 7] (7-8aa)(V/F/L/I/M)(18-19aa)(R/Q/H)xxxxGx(I/V)xxxxx(V/I/L/M)x(V/M)F(A/V)(A/S/T)PLx(I/V)(I/M/V/L)xxV(I/V)(K/R/Q)(T/S)(K/R)S(V/A)x(F/Y)MP(F/I/L)xLS(L/F/V)xL(T/V)(L/I)xAxxW(F/L)xYG(L/F)xxxDx x(V/I)xxPNxxGxx(L/F)(G/S)xxQMx(L/V/I)(Y/F)xx(Y/F) [SEQ ID NO: 8].

The amino acid sequence of Consensus Sequence 2 can be, in other words, an amino acid sequence in which the amino acid sequence set forth in SEQ ID NO: 6, 7 to 9 arbitrary amino acid residues, the amino acid sequence set forth in SEQ ID NO: 7, 7 to 8 arbitrary amino acid residues, any amino acid residue of V/F/L/I/M, 18 to 19 amino acid residues, and the amino acid sequence set forth in SEQ ID NO: 8 are connected in this order from the N-terminus to the C-terminus.

Consensus Sequence 2 is an amino acid sequence that is shared between SWEET proteins classified in clade III in the aforementioned document. More specifically, Consensus Sequence 2 is an amino acid sequence generated from multiple alignment obtained, as described above, by the ClustalW analysis of the transporter proteins involved in sugar transportation derived from *Arabidopsis thaliana*, the transporter proteins involved in sugar transportation derived from *Oryza sativa*, the transporter proteins involved in sugar transportation derived from *Medicago denticulata*, and the transporter proteins involved in sugar transportation derived from *Petunia hybrida* classified in clade III in the aforementioned document. Therefore, Consensus Sequence 2 is a sequence that is characteristic of the SWEET proteins classified in clade III in the aforementioned documents and that is a criterion for the clear distinction from those in clades I, II, IV, and V according to the aforementioned document.

FIGS. 3-1 to 3-3 illustrate a result of analysis of alignment of the amino acid sequences of the SWEET proteins classified in clade III in the aforementioned document using ClustalW multiple sequence alignment program (available in DDBJ at National Institute Genetics; the version and various parameters used in the analysis are as described above). The SWEET protein classified in clade III in the aforementioned document are found to have Consensus Sequence 2 described above, as shown in FIGS. 3-1 to 3-3.

Furthermore, the aforementioned "particular transporter protein involved in a sugar transportation" can be defined as a protein having Consensus Sequence 3 consisting of an amino acid sequence in which certain amino acid residues are added at the N-terminal side of Consensus Sequence 2 described above and the variation of amino acids that can be present at certain positions are limited. The amino acid sequence of Consensus Sequence 3 is as follows. (A/V)xxxG(I/L/V)xGN(I/L/V)(I/L/V)S(F/L)x(V/T)xL(A/S)P(V/L/I)(P/A)TFxx(I/V)x(K/R)xK(S/T)xx(G/S)(F/Y)(Q/S/E)SxPYxx(A/S/T)LxS(A/C/S)xLx(L/I/M)(Y/F)Y(A/G)xx(K/T) [SEQ ID NO: 9](3-5aa)(L/M/P)(L/I)(MW)(T/S)INxx(G/A)xx(I/V)(E/Q)xxY(I/L)x(L/M/V/I)(F/Y)(L/I/V/F)x(Y/F)Ax(K/R)xxxxx(T/A)xx(L/M/F/V/I)(L/F/V/I)xxx(N/D)(F/V/I/L)xx(F/L)xx(I/L/V)xxxxxx(L/I/V) [SEQ ID NO: 10] (5-6aa)(R/Q)xxxxGx(I/V)xxxx(S/A)(V/L/M)(C/S/A)VF(A/V)(A/S)PLx(I/V)(I/M/V)xxV(I/V)(K/R/Q)(T/S)(K/R)S(V/A)E(F/Y)MP(F/I)xLS(L/F/V)xL(T/V)(L/I)(S/N)A(V/I)xW(F/L)xYGLxx(K/N)  DXX(V/I)xxPN(V/I)xGxx(F/L)(G/S)xxQMxL(Y/F)xx(Y/F) [SEQ ID NO: 11].

The amino acid sequence of Consensus Sequence 3 can be, in other words, an amino acid sequence in which the amino acid sequence set forth in SEQ ID NO: 9, 3 to 5 arbitrary amino acid residues, the amino acid sequence set forth in SEQ ID NO: 10, 5 to 6 arbitrary amino acid residues and the amino acid sequence of SEQ ID NO: 11 are connected in this order from the N-terminus to the C-terminus.

Consensus Sequence 3 is an amino acid sequence generated from multiple alignment obtained by ClustalW analysis, as described above, of the amino acid sequence of the transporter proteins involved in sugar transportation derived from *Arabidopsis thaliana* and the transporter proteins involved in sugar transportation from derived *Oryza sativa* among the SWEET proteins classified in clade III in the aforementioned document. Therefore, Consensus Sequence 3 is a sequence that is characteristic of the transporter proteins involved in sugar transportation derived from *Arabidopsis thaliana* and the transporter proteins involved in sugar transportation derived from *Oryza saliva* classified in clade III in the aforementioned document and that is a criterion for the clear distinction from those in clades I, II, IV, and V according to the aforementioned document.

FIGS. 4-1 to 4-2 illustrate a result of analysis of alignment of the amino acid sequence of the transporter proteins involved in sugar transportation derived from *Arabidopsis thaliana* and the transporter proteins involved in sugar transportation derived from *Oryza sativa* classified in clade III in the aforementioned document using ClustalW multiple sequence alignment program (available in DDBJ at National Institute Genetics; the version and various parameters used in the analysis are as described above). The transporter proteins involved in sugar transportation derived from *Arabidopsis thaliana* and the transporter proteins involved in sugar transportation derived from *Oryza sativa* classified in clade III in the aforementioned document are found to have Consensus Sequence 3 described above, as shown in FIGS. 4-1 to 4-2.

Furthermore, the aforementioned "particular transporter protein involved in a sugar transportation" can be defined as a protein having Consensus Sequence 4 consisting of an amino acid sequence in which certain amino acid residues are added at the N-terminal side and the C-terminal side of Consensus Sequence 3 described above and the variation of amino acids that can be present at certain positions are limited. The amino acid sequence of Consensus Sequence 4 is as follows. (M/L/V)xx(T/K/N/S)xxxxAxxFG(L/I/V)LGN (I/L/V)(I/V)SFxVxL(S/A)P(V/I)PTFxxIxK(K/R)K  (S/T)x(E/K)(G/S)(F/Y)(Q/E)S(I/L)PYxx(A/S)LxS(A/C)xLx(L/I/M)YY(A/G)xxK [SEQ ID NO: 12] (4-5aa)(L/M)(L/I)(I/V)(T/S)IN(A/S/T)(F/V)(G/A)x(F/V)(I/V)(E/Q)xxY(I/L)x(L/M/I)(F/Y)(F/V/I/L   )x(Y/F)Ax(K/R)xx(R/K)xx(T/A)(L/V/M)K(V/L/M/F)(L/I/V/F)xxx(N/D)(F/V/I)xx(F/L)xx(I/L)(L/I/V/F)(L/M/V)(L/V)xx(F/L)(L/I/V) [SEQ ID NO: 13] (5-6aa)(R/Q)x(K/S/Q)x(L/I/V)Gx(I/V)Cxxx(S/A)(V/L)(S/C/A)VF(A/V)(A/S)PLx(I/V)(M/I/V)xxV(I/V)(K/R)T(K/R)S(V/A)E(Y/F)MPFxLS(L/F)xLT(I/L)(S/N)A(V/I)xW(L/F)xYGLx(L/I)(K/N)D xx(V/I)A(L/F/I/M)PN(V/I)(L/I/V)Gxx(L/F)GxxQM(I/V)L(Y/F)(V/L/I/M)(V/L/I/M)(Y/F)(K/R/Q) [SEQ ID NO: 14].

The amino acid sequence of Consensus Sequence 4 can be, in other words, an amino acid sequence in which the amino acid sequence of SEQ ID NO: 12, 4 to 5 arbitrary amino acid residues, the amino acid sequence of SEQ ID NO: 13, 5 to 6 arbitrary amino acid residues, and the amino acid sequence of SEQ ID NO: 14 are connected in this order from the N-terminus to the C-terminus.

Consensus sequence 4 is an amino acid sequence generated from multiple alignment obtained by ClustalW analysis, as described above, of the amino acid sequences of the transporter proteins involved in sugar transportation derived from *Arabidopsis thaliana* among the SWEET proteins classified in clade III in the aforementioned document. Therefore, Consensus Sequence 4 is a sequence that is characteristic of the transporter proteins involved in sugar transportation derived from *Arabidopsis thaliana* classified in clade III in the aforementioned document and that is a criterion for the clear distinction from those in clades I, II, IV, and V according to the aforementioned document.

FIG. 5 illustrates a result of analysis of alignment of the amino acid sequence of the transporter proteins involved in sugar transportation derived from *Arabidopsis thaliana* classified in clade III in the aforementioned document using ClustalW multiple sequence alignment program (available in DDBJ at National Institute Genetics; the version and various parameters used in the analysis are as described above). The transporter proteins involved in sugar transportation derived from *Arabidopsis thaliana* classified in clade III in the aforementioned document are found to have Consensus Sequence 4 described above, as shown in FIG. 5.

As described in the foregoing, the "nucleic acids encoding a particular transporter protein involved in sugar transportation" that can be used in the present invention are not particularly limited, as long as they encode a particular transporter protein involved in sugar transportation having Consensus Sequence 1, 2, 3, or 4 described above. In other words, the nucleic acids are not limited to those encoding the specific SWEET proteins listed Tables 2 to 5, but include those encoding SWEET proteins derived from organisms of species other than those listed in Tables 2 to 5. For example, nucleic acids that are derived from organisms whose sequence data is not stored in databases such as GenBank and that encode transporter proteins involved in sugar transportation having Consensus Sequence 1, 2, 3, or 4 can be also used.

Specific examples of the particular transporter protein involved in a sugar transportation can include proteins comprising an amino acid sequence set forth in any of SEQ ID NOs: 15 to 131, as illustrated in Tables 2 to 5. In particular, the particular transporter protein involved in a sugar transportation may be preferably a protein comprising an amino acid sequence set forth in any of SEQ ID NOs: 15 to 35 (Table 2), more preferably a protein comprising an amino acid sequence set forth in any of SEQ ID NOs: 15 to 26 (derived from *Arabidopsis thaliana* or *Oryza sativa*), or further preferably a protein comprising an amino acid sequence set forth in any of SEQ ID NOs: 15 to 21 (derived from *Arabidopsis thaliana*). The most preferred examples of the particular transporter protein involved in a sugar transportation are AtSWEET11 comprising the amino acid sequence set forth in SEQ ID NO: 17, AtSWEET12 comprising the amino acid sequence set forth in SEQ ID NO: 18, OsSWEET14 comprising the amino acid sequence set forth in SEQ ID NO: 25, and OsSWEET15 comprising the amino acid sequence set forth in SEQ ID NO: 26.

The "nucleic acids encoding a particular transporter protein involved in sugar transportation" that can be used in the present invention are not limited to the nucleic acids encoding the particular transporter protein involved in sugar transportation identified by a specific SEQ ID NO as described above, but any nucleic acid encoding a particular transporter protein involved in sugar transportation having Consensus Sequence 1, 2, 3, or 4 described above can be used.

The nucleic acid encoding a particular transporter protein involved in sugar transportation means that the protein encoded by the nucleic acid has the transporter activity involved in sugar transportation. The transporter activity involved in sugar transportation is an activity measured with a FRET (Forster resonance energy transfer or fluorescence resonance energy transfer) sugar sensor localized in cytoplasm or endoplasmic reticulum (ER) for sugar transport across the ER membrane, for example, those described in Methods in Non Patent Literature 1 and 2.

Whether a certain particular transporter protein involved in sugar transportation has Consensus Sequence 1, 2, 3, or 4 or whether the nucleic acid encoding the protein encodes a protein having Consensus Sequence 1, 2, 3, or 4 can be easily determined by comparing the amino acid sequence of the protein or the amino acid sequence encoded by the nucleic acid with an amino acid sequence set forth in Consensus Sequence 1, 2, 3, or 4.

Examples of the transporter proteins involved in sugar transportation, comprising an amino acid sequence different from any of the amino acid sequences set forth in SEQ ID NOs: 15 to 131, and having Consensus Sequence 1, 2, 3, or 4 may include those encoding proteins that comprise an amino acid sequence in which one or plural amino acid sequences are deleted from, substituted with, added to, or inserted into an amino acid sequence set forth in any of SEQ ID NO: 15 to 131, and that have Consensus Sequence 1, 2, 3, or 4 and transporter activity involved in sugar transportation. As used herein, the plural amino acids mean, for example, 1 to 20, preferably, 1 to 10, more preferably, 1 to 7, further preferably, 1 to 5, and most preferably, 1 to 3 amino acids. The deletion, substitution, or addition of the amino acids can be made by modifying the nucleotide sequence of nucleic acids encoding the aforementioned particular transporter protein involved in sugar transportation by a known technique in the art. A mutation can be introduced into a nucleotide sequence by a known technique such as the Kunkel method or the gapped duplex method or a method similar to those. For example, a mutation is introduced using a kit for introducing mutation using a site-directed mutagenesis method (using, for example, Mutant-K or Mutant-G (both trade names, TAKARA Bio Inc.) or a kit of the LA PCR in vitro Mutagenesis series (trade name, TAKARA Bio Inc.)). The method for introducing mutation may be a method involving use of a chemical mutagen as represented by EMS (ethyl methanesulfonic acid), 5-bromouracil, 2-aminopurine, hydroxylamine, N-methyl-N'-nitro-N-nitrosoguanidine, and other carcinogenic compounds or a method involving treatment with a radiation as represented by X-ray, alpha-, beta-, and gamma-rays, and ion beam, or ultraviolet treatment.

Examples of the transporter proteins involved in sugar transportation, comprising an amino acid sequence different from any of the amino acid sequences of SEQ ID NOs: 15 to 131 and having Consensus Sequence 1, 2, 3, or 4 may include those encoding proteins having amino acid sequences having a similarity or an identity to an amino acid sequence set forth in any of SEQ ID NOs: 15 to 131 of, for example, 70% or more, preferably 80% or more, more preferably 90% or more, or most preferably 95% or more, having Consensus Sequence 1, 2, 3, or 4 and having transporter activity involved in sugar transportation. The values of similarity and identity mean values calculated using a computer program equipped with a Basic Local Alignment Search Tool (BLAST®) program with the default setting and a database storing genetic sequence information.

Furthermore, the nucleic acids encoding the transporter proteins involved in sugar transportation, comprising an amino acid sequence different from any of the amino acid sequences of SEQ ID NOs: 15 to 131, and having Consensus Sequence 1, 2, 3, or 4 can be identified by extracting nucleic acid from the plant of interest and isolating a nucleic acid that hybridizes with a nucleic acid encoding an amino acid sequence set forth in any of SEQ ID NOs: 15 to 131 under stringent conditions, when genome information of the plant is unknown. As used herein, the stringent conditions refer to conditions in which so-called specific hybrids are formed, but nonspecific hybrids are not formed. For example, the stringent conditions can include hybridization in 6×SSC (sodium chloride/sodium citrate) at 45° C. and then washing with 0.2 to 1×SSC, 0.1% SDS at 50 to 65° C.; or such conditions can include hybridization in 1×SSC at 65 to 70° C. and then washing with 0.3×SSC at 65 to 70° C. The hybridization can be carried out by a conventionally known method such as those described in J. Sambrook et al., Molecular Cloning, A Laboratory Manual, 2nd Ed., Cold Spring Harbor Laboratory (1989).

As described in the foregoing, a "particular transporter protein involved in a sugar transportation" that is used in the present invention was defined as a protein having Consensus Sequence 1, 2, 3, or 4. However, the "particular transporter proteins involved in a sugar transportation" that can be used in the present invention are not limited to these proteins having Consensus Sequence 1, 2, 3, or 4.

More specifically, examples of the "particular transporter protein involved in a sugar transportation" may include those encoding proteins that comprise an amino acid sequence in which one or plural amino acid sequences are deleted from, substituted with, added to, or inserted into an amino acid sequence set forth in any of SEQ ID NOs: 15 to 131 and that have transporter activity involved in sugar transportation. As used herein, the plural amino acids mean, for example, 1 to 20, preferably, 1 to 10, more preferably, 1 to 7, further preferably, 1 to 5, and most preferably, 1 to 3 amino acids. The deletion, substitution, or addition of the amino acids can be made by modifying the nucleotide sequence of nucleic acids encoding the particular transporter protein involved in sugar transportation by a known technique in the art. The method of introducing a mutation into a nucleotide sequence can be selected from the methods described above as appropriate.

Examples of the "particular transporter protein involved in a sugar transportation" may include those encoding proteins having amino acid sequences having a similarity or an identity to an amino acid sequence set forth in any of SEQ ID NOs: 15 to 131 of, for example, 70% or more, preferably 80% or more, more preferably 90% or more, or most preferably 95% or more, and having transporter activity involved in sugar transportation. The values of similarity and identity can be calculated by the method described above.

Furthermore, examples of the "particular transporter protein involved in a sugar transportation" may include those encoding proteins that are encoded by nucleic acids that hybridize with a nucleic acid encoding an amino acid sequence of any of SEQ ID NOs: 15 to 131 under stringent conditions and that have transporter activity involved in sugar transportation. The stringent conditions here are the same as those described above.

The plant to which the present invention is applied can produce a high sugar concentration exudate by introducing a nucleic acid encoding a "particular transporter protein involved in sugar transportation" as defined above into a cell, or enhancing the expression of the protein encoded by the nucleic acid. Examples of techniques for introducing the nucleic acid encoding this transporter involved in sugar transportation into a cell can include, for example, a technique for introducing into a cell an expression vector in which a DNA encoding the transporter involved in sugar transportation is placed to allow the expression thereof. Also, examples of a technique for enhancing the expression of the nucleic acid encoding the transporter involved in sugar transportation can include a technique for modifying a transcriptional promoter located in proximate to the DNA encoding the transporter involved in sugar transportation in a plant of interest. In particular, a technique for introducing in a cell in the plant of interest an expression vector in which a DNA encoding the aforementioned transporter involved in sugar transportation is placed under the control of a promoter enabling constant expression to allow the expression thereof is preferred.

Artificial Gene Encoding Transporter Involved in Sugar Transportation

The aforementioned "nucleic acids encoding a particular transporter protein involved in a sugar transportation" are not limited to nucleic acids having a nucleotide sequence same as that of a naturally occurring nucleic acid, as long as they are nucleic acids having Consensus Sequence 1, 2, 3, or 4 and encoding a transporter involved in sugar transportation, and they may be nucleic acids having a nucleotide sequence designed artificially, i.e., artificial genes. As used herein, the artificial gene means a deoxyribonucleic acid (DNA) encoding an amino acid sequence designed artificially, and having a nucleotide sequence that does not occur naturally. The artificial gene may be a gene encoding a protein in which a part of a naturally occurring protein is modified (subjected to deletion, substitution, insertion, or the like of one or more amino acid residues), a gene encoding a chimeric protein in which naturally occurring amino acid sequences are connected, or a gene encoding a protein the whole sequence of which from the N-terminus to the C-terminus is designed uniquely.

The artificial gene may be a DNA having a nucleotide sequence encoding an amino acid sequence comprising Consensus Sequence 1, 2, 3, or 4. When a transporter gene involved in sugar transportation is designed as an artificial gene, the gene is preferably designed particularly to comprise the transmembrane domain. This domain is considered to localize the transporter at a more preferred position and contribute to the transporter activity.

More specific examples of the artificial gene encoding a transporter involved in sugar transportation can include those designed to encode amino acid sequences set forth in SEQ ID NOs: 132 to 137. These amino acid sequences set forth in SEQ ID NOs: 132 to 137 comprise one of the aforementioned consensus sequences in the N-terminal side and the transmembrane domain in the C-terminal side. The protein having the amino acid sequence set forth in SEQ ID NO: 132 is referred to as SWo1, the protein having the amino acid sequence set forth in SEQ ID NO: 133 is referred to as SWo2, the protein having the amino acid sequence set forth in SEQ ID NO: 134 is referred to as SWo3, the protein having the amino acid sequence set forth in SEQ ID NO: 135 is referred to as SWo4, the protein having the amino acid sequence set forth in SEQ ID NO: 136 is referred to as SWo5, and the protein having the amino acid sequence set forth in SEQ ID NO: 137 is referred to as SWo6.

Expression Vector

The expression vector is constructed to comprise a nucleic acid having a promoter nucleotide sequence that allows constitutive expression and a nucleic acid encoding a transporter involved in sugar transportation (including both of a nucleic acid having a naturally occurring nucleotide sequence and an artificial gene, which applies to the following as well). A variety of conventionally known vectors can be used as a base vector from which the expression vector is derived. For example, a plasmid, a bacteriophage, or a cosmid can be used and selected appropriately depending on the plant cell into which the vector is introduced and the method of introduction. Specific examples can include, for example, pBR322, pBR325, pUC19, pUC119, pBluescript, pBluescriptSK, and pBI vectors. In particular, use of a binary pBI vector is preferred when the method for introducing the vector into the plant cell is a method involving use of *Agrobacterium*. Specific examples of the binary pIB vector can include pBIG, pBINI9, pBI101, pBI121, pBI221, etc.

The promoter is not particularly limited, as long as it is a promoter capable of allowing the expression of the nucleic acid encoding the transporter involved in sugar transportation in the plant, and a known promoter can be preferably used. Examples of such a promoter can include, for example, cauliflower mosaic virus 35S promoter (CaMV35S), various actin gene promoters, various ubiquitin gene promoters, the nopaline synthetase gene promoter, the PR1a gene promoter in tobacco, ribulose 1 in tomato, the 5-diphosphate carboxylase/oxidase small subunit gene promoter, the napin gene promoter, the oleosin gene promoter, etc. Among these, use of cauliflower mosaic virus 35S promoter, an actin gene promoter, or a ubiquitin gene promoter can be more preferred. Use of any of the aforementioned promoter allows strong expression of any nucleic acid when introduced in a plant cell.

Promoters that can be used include promoters having the function to express a nucleic acid region specifically in plant. Such a promoter that can be used may be any promoter conventionally known. By using such a promoter and region specifically introducing the aforementioned nucleic acid encoding the transporter involved in sugar transportation, the sugar content can be increased in the exudate produced from the plant organ or tissue composed of the cells into which the nucleic acid has been introduced.

The expression vector may further comprise a nucleic acid having another segment sequence in addition to the promoter and the aforementioned nucleic acid encoding the transporter involved in sugar transportation. The nucleic acid having another segment sequence is not particularly limited and examples can include a nucleic acid having a terminator nucleotide sequence, a nucleic acid having a transformant selection marker nucleotide sequence, a nucleic acid having an enhancer nucleotide sequence, a nucleic acid having a nucleotide sequence for increasing the translation efficiency, etc. Moreover, the aforementioned recombinant expression vector may have a T-DNA region. The T-DNA region can increase the efficiency of introduction of nucleic acid, especially when introducing a nucleic acid having the aforementioned nucleotide sequence in the recombination expression vector into a plant cell using *Agrobacterium*.

The nucleic acid having a terminator nucleotide sequence is not particularly limited as long as it has the function as a transcription termination site, and may be a known one. Specific examples of the nucleic acid that can be used include the terminator region of nopaline synthetase gene (Nos terminator), the terminator region of cauliflower mosaic virus 35S (CaMV35S terminator), etc. In particular, use of the Nos terminator may be more preferred. In the aforementioned recombinant vector, placing a terminator at an appropriate position may prevent the synthesis of needlessly long transcript after the vector is introduced into a plant cell.

Examples of the nucleic acid having a transformant selection marker nucleotide sequence that can be used include a nucleic acid containing a drug-resistance gene. Specific examples of such a drug-resistance gene can include nucleic acids containing drug-resistance genes for hygromycin, bleomycin, kanamycin, gentamicin, chloramphenicol, etc. This allows the facilitated selection of transformed plants by selecting plants growing in media containing the aforementioned antibiotics.

Examples of the nucleic acid having a nucleotide sequence for increasing the efficiency of translation can include a nucleic acid having the omega sequence derived from tobacco mosaic virus. By placing this nucleic acid having the omega sequence in the noncoding region (5' UTR) upstream of the protein coding region, the efficiency of expression of the aforementioned nucleic acid encoding a transporter involved in sugar transportation can be increased. As seen above, nucleic acids having various DNA segment sequences can be included in the aforementioned recombinant expression vector depending on its purpose.

Methods for constructing the recombinant expression vector are not particularly limited and the recombinant expression vector can be constructed by introducing the aforementioned nucleic acid having a promoter nucleotide sequence, the nucleic acid encoding the particular transporter protein involved in sugar transportation, and optionally the aforementioned nucleic acid having another DNA segment sequence into the base vector selected as appropriate in a certain order. For example, the recombinant expression vector can be constructed by ligating the nucleic acid encoding a transporter involved in sugar transportation, the nucleic acid having a promoter nucleotide sequence, and (optionally the nucleic acid having a terminator nucleotide sequence) and introducing this into the vector.

Methods for replicating (methods for producing) the aforementioned expression vector are not particularly limited and conventionally known methods can be used. Generally, *Escherichia coli* may be used as a host and the vector may be replicated in the host. Any preferred strain of *Escherichia coli* may be selected depending on the type of vector.

Transformation

The aforementioned expression vector is introduced into a plant cell of interest by a general transformation method. Methods for introducing the expression vector into (methods for transforming) a plant cell are not particularly limited and conventionally known methods suitable for the plant cell can be used. Specific examples of such methods that can be used include methods involving use of *Agrobacterium* and methods involving direct introduction into plant cells. Examples of the methods involving use of *Agrobacterium* that can be used include the methods described in Bechtold, E., Ellis, J. and Pelletier, G. (1993) In Planta, *Agrobacterium*-mediated gene transfer by infiltration of adult *Arabidopsis* plants. C.R. Acad. Sci. Paris Sci. Vie, 316, 1194-1199. or Zyprian E, Kado Cl, *Agrobacterium*-mediated plant transformation by novel mini-T vectors in conjunction with a high-copy vir region helper plasmid. Plant Molecular Biology, 1990, 15 (2), 245-256.

Examples of the methods for directly introducing the expression vector into a plant cell that can be used include microinjection, electroporation, the polyethyleneglycol method, the particle gun method, protoplast fusion, the calcium phosphate method, etc.

When using one of the aforementioned methods for directly introducing the nucleic acid encoding the transporter involved in sugar transportation into a plant cell, a nucleic acid containing a transcription unit necessary for the expression of the nucleic acid encoding the transporter of interest, for example, a nucleic acid having a promoter nucleotide sequence and/or a nucleic acid having a transcription terminator nucleotide sequence; and the nucleic acid encoding the transporter of interest is sufficient and the vector function is not required. Furthermore, even a nucleic acid containing no transcription unit but only the protein-coding region of the aforementioned nucleic acid encoding the transporter involved in sugar transportation is sufficient, if the nucleic acid can be integrated in a transcription unit in the host genome and express the gene of interest. Also, even when the nucleic acid is not integrated in the host genome, it is sufficient if the aforementioned nucleic acid encoding the transporter involved in sugar transportation is transcribed and/or translated in the cell.

Examples of the plant cell into which the aforementioned expression vector or a nucleic acid containing no expression vector and encoding the transporter involved in sugar transportation of interest is introduced can include cells in tissues in plant organs such as flower, leaf, and root, callus, cells in suspension culture, etc. The expression vector may be an appropriate expression vector constructed for the type of plant to be produced if necessary or a preconstructed general-purpose expression vector may be introduced into a plant cell.

The plant constituted of cells into which the expression vector is introduced is not particularly limited. This means that the concentration of sugar contained in an exudate such as guttation can be increased in any plant by introducing the aforementioned nucleic acid encoding the transporter involved in sugar transportation. Preferred examples of such a plant are phanerogam plants. Among the phanerogam plants, angiosperm plants are more preferred. Examples of such angiosperm plants include, but are not limited to, dicot and monocot plants, for example, Brassicaceae, Gramineae, Solanaceae, Leguminosae, and Salicaceae plants (see below)

Brassicaceae thale cress (*Arabidopsis thaliana*), *Arabiopsis lyrata*, rape (*Brassica rapa, Brassica napus, Brassica campestris*), cabbage (*Brassica oleracea* var. *capitata*), Chinese cabbage (*Brassica rapa* var. *pekinensis*), napa cabbage (*Brassica rapa* var. *chinensis*), turnip (*Brassica rapa* var. *rapa*), nozawana (*Brassica rapa* var. *hakabura*), potherb mustard (*Brassica rapa* var. *lancinifolia*), komatsuna (*Brassica rapa* var. *peruviridis*), bok choy (*Brassica rapa* var. *chinensis*), komatsuna (*Raphanus sativus*), wasabi (*Wasabia japonica*), *Capsella rubella*, etc.

Chenopodiaceae: sugar beet (*Beta vulgaris*).
Aceraceae sugar maple (*Acer saccharum*):
Euphorbiaceae: castorbean (*Ricimis communis*):
Solanaceae: Tobacco (*Nicotiana tabacum*), eggplant (*Solanum melongena*), potato (*Solaneum tuberosum*), tomato (*Solanum lycopersicum*), pepper (*Capsicum annuum*), petunia (*Petunia hybrida*), etc.
Fabaceae: Soybean (*Glycine* mar), pea (*Pisum sativum*), broad beans (*Vicia faba*), Japanese wisteria (*Wisteria floribunda*), peanut (*Arachis hypogaea*), bird's-foot trefoil (*Lotus japonicus*), kidney bean (*Phaseolus vulgaris*), adzuki bean (*Vigna angularis*), acacia (Acacia), snail clover (*Medicago truncatula*), chick-pea (*Cicer arietinum*), etc.
Compositae: *chrysanthemum (Chrysanthemum morifolium)*, sunflower (*Helianthus annuus*), etc.
Arecaceae: oil palm (*Elaeis guineensis, Elaeis oleifera*), coconut palm (*Cocos nucifera*), date palm (*Phoenix dactylifera*), wax palm (*Copernicia*), eyc.
Anacardiaceae: wax tree (*Rhus succedanea*), cashew tree (*Anacardium occidentale*), Chinese lacquer tree (*Toxicodendron vernicifluum*), mango (*Mangifera indica*), pistachio (*Pistacia vera*), etc.
Cucurbitaceae: pumpkin (*Cucurbita marima, Cucurbita moschata, Cucurbita pepo*), cucumber (*Cucumis sativus*), Japanese snake gourd (*Trichosanthes cucumeroides*), calabash (*Lagenaria siceraria* var. *gourda*), etc.
Rosaceae: almond (*Amygdalus communis*), rose (Rosa), strawberry (*Fragaria vesca*), cherry tree (*Prunus*), apple (*Malus pumila* var. *domestica*), peach (*Prunus persica*), etc.
Vitaceae: grape (*Vitis vinifera*)
Caryophyllaceae: carnations (*Dianthus caryophyllus*), etc.
Salicaceae: poplar (*Populus trichocarpa, Populus nigra, Populus tremula*), etc.
Poaceae: corn (*Zea mays*), rice (*Oryza sativa*), barley (*Hordeum vulgare*), wheat (*Triticum aestivum*), red wild einkorn (*Triticum urartu*), Tausch's goatgrass (*Aegilops tauschii*), purple false brome (*Brachypodium distachyon*), bamboo (*Phyllostachys*), sugarcane (*Saccharum officinarum*), napier grass (*Pennisetum pupureum*), Erianthus (*Erianthus ravenae*), susuki grass (*Miscanthus virgatum*), sorghum (*Sorghum bicolor*) switchgrass (*Panicum*), etc.
Liliaceae: tulip (*Tulipa*), lily (*Lilium*), etc.

In particular, plants that produce relatively much exudate and have high productivity of sugar and starch, such as sugarcane, corn, rice, *sorghum*, wheat, sugar beet, and sugar maple, are preferred. This is because exudate collected from these plants can be used as raw materials for biofuel and bioplastics, as described in detail later.

While the nucleic acid encoding the transporter involved in sugar transportation that can be used in the present invention can be isolated from a variety of plants and used, as mentioned above, the nucleic acid can be selected as appropriate depending on the class of the plant and used. Thus, when the plant cell of interest is derived from a monocot plant, the nucleic acid encoding a transporter involved in sugar transportation to be introduced can be that isolated from a monocot plant. When the plant of interest is a plant in the family Poaceae, it is particularly preferred to introduce one of the following nucleic acids encoding a transporter involved in sugar transportation derived from *Oryza sativa*: the nucleic acid encoding OsSWEET13 (Os12g047620001) and the nucleic acid encoding OsSWEET14 (Os11t050860001) and the nucleic acid encoding OsSWEET15 (Os02t051310001). By introducing one of the nucleic acid encoding OsSWEET13 (Os12g047620001) and the nucleic acid encoding OsSWEET14 (Os11t050860001) and the nucleic acid encoding OsSWEET15 (Os02t051310001), the amount of sugar contained in the exudate derived from *Oryza sativa* can be markedly increased.

Even when the plant cell of interest is derived from a monocot plant, a nucleic acid encoding a transporter involved in sugar transportation derived from a dicot plant may be introduced. When the plant cell of interest is derived from a monocot plant, it is preferred to introduce the nucleic acid encoding AtSWEET11 (At3g48740) and the nucleic acid encoding AtSWEET12 (At5g23660), among the nucleic acids encoding a transporter involved in sugar transportation derived from *Arabidopsis thaliana*, a dicot plant. These nucleic acid encoding AtSWEET11 (At3g48740) and nucleic acid encoding AtSWEET12 (At5g23660) can markedly increase the amount of sugar contained in the exudate, even if the plant of interest is a monocot plant such as *Oryza* sativa.

Other Processes, Other Methods

After the aforementioned transformation process, a selection process for selecting an appropriate transformant from plants can be conducted by a conventionally known method. The method of the selection is not particularly limited. The appropriate transformant may be selected, for example, on the basis of drug resistance such as hygromycin resistance or by growing transformants, collecting exudate from the plants, measuring sugar contained in the collected exudate, and selecting the plant whose exudate has a concentration of sugar significantly increased in comparison with the wild type. The measurement of sugar contained in the collected exudate may be conducted by a qualitative method, but not a quantitative method. For example, the measurement may be conducted by a coloration method using a test paper that colors in response to sugar.

Progeny plants can be obtained according to a usual method from transformed plants obtained by the transformation process. By selecting progeny plants maintaining a trait associated with significantly increased expression of the aforementioned nucleic acid encoding a transporter involved in sugar transportation in comparison with the wild type on the basis of the amount of sugar contained in the exudate, stable plant strains whose exudate has an increased amount of sugar due to the trait strains can be created. From such transformed plants or progeny thereof, breeding materials such as plant cells, seeds, fruits, rootstocks, calluses, tubers, cuttings, and masses can be obtained to mass-produce, from such materials, stable plant strains whose exudate has an increased amount of sugar due to the aforementioned trait.

As described in the foregoing, the concentration of sugar contained in exudate can be significantly increased in comparison with the wild type plant by introducing a nucleic acid encoding the transporter involved in the aforementioned particular sugar transportation into a cell or enhancing the expression of the nucleic acid according to the present invention. The sugar components contained in the exudate are meant to include monosaccharide such as glucose, galactose, mannose, and fructose, and disaccharides such as sucrose, lactose, and maltose. Accordingly, by introducing the nucleic acid encoding the particular transporter involved in a sugar transportation into a cell or enhancing the expression of the gene present endogenously, the concentration of one or more of sugar components such as glucose, galactose, mannose, fructose, sucrose, lactose and maltose contained in exudate can be increased. In particular, the concentrations of glucose, fructose, and sucrose in exudate can be greatly increased according to the present invention.

In particular, when collecting guttation produced from the hydathode as exudate, it is preferred to cultivate the plant in which the nucleic acid encoding the particular transporter involved in the sugar transportation is introduced into a cell or the expression of the nucleic acid is enhanced under conditions that prevent transpiration of the produced guttation. Furthermore, it is more preferred to culture the plant under conditions in which the amount of guttation production is increased. For example, the transpiration of guttation can be prevented and the amount of guttation production can be increased by cultivating the plant in a closed space under conditions at a humidity of 80% RH or more or more preferably 90% RH or more.

For example, whereas the concentration of sugar contained in guttation of the wild type Arabidopsis thaliana is about 2.0 µM (the mean, monosaccharide equivalent), the sugar concentration in guttation is increased to about 98.5 to 6057.5 µM in the transformed Arabidopsis thaliana in which the aforementioned particular transporter gene involved in a sugar transportation is introduced into cells. In particular, the transformed Arabidopsis thaliana in which the nucleic acid encoding AtSWEET12 (At5g23660) is introduced into cells can produce guttation containing sugar components at a higher concentration in comparison with other transformed Arabidopsis thaliana.

Moreover, the concentration of sugar in the guttation is increased to about 1074.3 to 185641.2 µM in the transformant Oryza sativa in which the aforementioned nucleic acid encoding a particular transporter involved in a sugar transportation is introduced into cells, whereas the concentration of sugar in the guttation is included to about 1.3 µM (mean, monosaccharide equivalent) in the wild type Oryza sativa. In particular, the transformed Oryza sativa in which the nucleic acid encoding AtSWEET11 (At3g48740) or the nucleic acid encoding OsSWEET13 (Os12g0476200) or the nucleic acid encoding SWo5 is introduced into cells can produce guttation containing sugar components at higher concentrations in comparison with other transformed Oryza sativa plants can do. Furthermore, the transformed Oryza sativa in which the nucleic acid encoding OsSWEET15 (Os02g051310001) is introduced into cells can produce guttation containing sugar components at concentrations higher than the highest concentration of sugar in the guttation in the transformed Oryza sativa in which a nucleic acid encoding another particular transporter involved in a sugar transportation is introduced into cells, and the concentration of sugar in the guttation increases to up to 450340.4 µM.

As described in the foregoing, exudate with a high sugar concentration can be collected according to the present invention. The collected exudate can be used for fermentative production of alcohol and/or organic acid. Furthermore, the collected exudate can be used as a raw material for biorefinery. For example, when guttation is used as an exudate for this, the aforementioned nucleic acid encoding the particular transporter involved in a sugar transportation is introduced into cells and the guttation collected from the plant in which the expression of the nucleic acid is enhanced can be used as it is in the reaction system for alcohol fermentation and organic acid fermentation and can be used as a raw material for biorefinery. Alternatively, the guttation collected from the plant can also be used in reaction systems for alcohol fermentation and organic acid fermentation after a concentration process or a process for adding another carbon or nitrogen source.

Examples

The present invention will be described in more detail with reference to Examples below. The technical scope of the present invention is however not limited to these Examples.

1. Construction of DNA Construct for Arabidopsis thaliana Transformation 1.1. Preparation of DNA Encoding AtSWEET Protein by PCR 1.1.1. Amplification of DNA Encoding AtSWEET Protein The DNAs encoding the AtSWEET1, AtSWEET2, AtSWEET3, AtSWEET4, AtSWEET5, AtSWEET6, AtSWEET7, AtSWEET9, AtSWEET11, AtSWEET12, AtSWEET13, AtSWEET15 and AtSWEET17 proteins for assessment were amplified by PCR using cDNA prepared from Arabidopsis thaliana as a template. To insert the DNAs for assessment into the pRI201AN vector (Takara Bio Inc., #3264), forward primers to which Sal I restriction enzyme recognition sequence is added to the 5' end and reverse primers to which Sac I or Pst I restriction enzyme recognition sequence was added to the 3' end were designed (Table 6).

TABLE 6

| Name of Amplified DNA | Name of Primer | Sequence | SEQ ID NO |
|---|---|---|---|
| SWEET1 | sal I-SWEET1-F26mer | 5'-TAAT<u>GTCGAC</u>ATGAACATCGCTCACACTATCTTCGG-3' | 138 |
|  | sac I-SWEET1-R | 5'-TAT<u>GAGCTC</u>TTAAACTTGAAGGTCTTGCTTTCCATTAAC-3' | 139 |
| SWEET2 | sal I-SWEET2-F27mer | 5'-TAAT<u>GTCGAC</u>ATGGATGTTTTGCTTTCAATGCTTC-3' | 140 |
|  | sac I-SWEET2-R27mer | 5'-TAT<u>GAGCTC</u>TCACACGTAAGAAACAATCAAAGGCTC-3' | 141 |
| SWEET3 | sal I-SWEET3-F27mer | 5'-TAAT<u>GTCGAC</u>ATGGGTGATAAACTTCGATTATCCATC-3' | 142 |
|  | sac I-SWEET3-R28mer | 5'-TAT<u>GAGCTC</u>TTAGATCGATGAGGCATTGTTAGAATTC-3' | 143 |
| SWEET4 | sal I-SWEET4-F31mer | 5'-TAAT<u>GTCGAC</u>ATGGTTAACGCTACAGTTGCGAGAAACATTG-3' | 144 |
|  | sac I-SWEET4-R30mer | 5'-TAT<u>GAGCTC</u>TCAAGCTGAAACTCGTTTAGCTTGTCCAC-3' | 145 |
| SWEET5 | sal I-SWEET5-F30mer | 5'-TAAT<u>GTCGAC</u>ATGACGGACCCCCACACCGCCCGGACGATC-3' | 146 |
|  | sac I-SWEET5-R31mer | 5'-TAT<u>GAGCTC</u>TCAAGCCTGGCCAAGTTCGATTCCAGCATTC-3' | 147 |
| SWEET6 | sal I-SWEET6-F33mer | 5'-TAAT<u>GTCGAC</u>ATGGTGCATGAACAGTTGAATCTTATTCGGAAG-3' | 148 |
|  | sac I-SWEET6-R32mer | 5'-TAT<u>GAGCTC</u>TCAAACGCCGCTAACTCTTTTGTTTAAATATG-3' | 149 |
| SWEET7 | sal I-SWEET7-F28mer | 5'-TAAT<u>GTCGAC</u>ATGGTGTTTGCACATTTGAACCTTCTTC-3' | 150 |
|  | sac I-SWEET7-R31mer | 5'-TAT<u>GAGCTC</u>TTAAACATTGTTAGGTTCTTGGTTGGTATTC-3' | 151 |
| SWEET9 | sal I-SWEET9-F31mer | 5'-TAAT<u>GTCGAC</u>ATGTTCCTCAAGGTTCATGAAATTGCTTTTC-3' | 152 |
|  | sac I-SWEET9-R27mer | 5'-TAT<u>GAGCTC</u>TCACTTCATTGGCCTCACCGATCCTTC-3' | 153 |
| SWEET11 | sal I-SWEET11-F29mer | 5'-TAAT<u>GTCGAC</u>ATGAGTCTCTTCAACACTGAAAACACATG-3' | 154 |
|  | sac I-SWEET11-R27mer | 5'-TAT<u>GAGCTC</u>TCATGTAGCTGCTGCGGAAGAGGACTG-3' | 155 |
| SWEET12 | sal I-SWEET12-F29mer | 5'-TAAT<u>GTCGAC</u>ATGGCTCTCTTCGACACTCATAACACATG-3' | 156 |
|  | sac I-SWEET12-R29mer | 5'-TAT<u>GAGCTC</u>TCAAGTAGTTGCAGCACTGTTTCTAACTC-3' | 157 |
| SWEET13 | Nde I-SWEET13-F30mer | 5'-GGAATTC<u>CATA</u>TGGCTCTAACTAACAATTTATGGGCATTTG-3' | 158 |
|  | sal I-SWEET13-R30mer | 5'-TAAT<u>GTCGAC</u>TTAAACTTGACTTTGTTTCTGGACATCCTTG-3' | 159 |
| SWEET15 | sal I-SWEET15-F30mer | 5'-TAAT<u>GTCGAC</u>ATGGGAGTCATGATCAATCACCATTTCCTC-3' | 160 |
|  | sac I-SWEET15-R27mer | 5'-TAT<u>GAGCTC</u>TCAAACGGTTTCAGGACGAGTAGCCTC-3' | 161 |
| SWEET17 | sal I-SWEET17-F30mer | 5'-TAAT<u>GTCGAC</u>ATGGCAGAGGCAAGTTTCTATATCGGAGT-3' | 162 |
|  | sac I-SWEET17-R29mer | 5'-TAT<u>GAGCTC</u>TTAAGAGAGGAGAGGTTCAACACGTGATG-3' | 163 |

And the PCR amplification was conducted using these primers and PrimeSTAR GXL DNA polymerase (TaKaRa, #R050A). The composition of the reaction solution was shown in Table 7 and the reaction conditions were shown in Table 8.

TABLE 7

| Component | (µl) |
|---|---|
| Template DNA (100 ng/µl) | 1 µl |
| 5 × Prime Star GXL buffer | 4 µl |
| dNTP mixture (25 mM) | 1.6 µl |
| Forward primer (10 ng/µl) | 0.4 µl |
| Reverse primer (10 ng/µl) | 0.4 µl |
| Prime Star GXL (1 u/µl) | 0.8 µl |
| Sterile water | 12.6 µl |
| Total | 20 µl |

TABLE 8

94° C.  5 min
↓
98° C.  10 sec ⎤
50° C.  30 sec ⎥ × 30 cycles
68° C.  1 min ⎦
↓
20° C.

Next, the following process was conducted to add adenine to the 5* and 3* ends in order to insert the DNA fragments obtained by the PCR amplification into the pCR2.1-TOPO® vector DNA (Invitrogen, #K4500-01). The composition of the reaction solution was shown in Table 9. The reaction solution shown in Table 9 was reacted at 70° C. for 15 minutes.

TABLE 9

| Component | |
|---|---|
| PCR reaction solution | 15 µl |
| 10 × ExTaq buffer | 3 µl |
| dNTP mixture (25 mM) | 2 µl |
| Ex Taq (0.5 u/µl) | 0.1 µl |
| Sterile water | 9.9 µl |
| Total | 30 µl |

1.1.2. Cutting Out and Purification of Amplified DNA Fragment

The DNA fragments amplified by PCR were subjected to agarose gel electrophoresis and cut out and purified using MagExtractor-PCR & Gel Clean Up Kit (TOYOBO, #NPK-601). The cutting out and purification was conducted following the manual contained in the kit.

1.1.3. Transformation with Amplified DNA Fragment

The purified amplified DNA fragments were inserted into the pCR2.1-TOPO® vector using TOPO TA Cloning® (Invitrogen, #K4500-01). The composition of the reaction solution was shown in Table 10. The reaction solution shown in Table 10 was reacted at room temperature for 5 minutes.

TABLE 10

| Component | (µl) |
|---|---|
| Cut out purification product (amplified SWEET sequence) | 2 µl |
| Salt solution | 0.5 µl |
| pCR2.1-TOPO vector | 0.5 µl |
| Total | 3 µl |

Next, transformation was performed by adding 2 µl of this reaction solution to *Escherichia coli* DH5α competent cells (TOYOBO, #DNA-903). After leaving the cells in ice bath for 30 minutes, the cells were subjected to heat-treatment at 42° C. for 30 seconds. Subsequently, the cells were rapidly cooled in ice bath. 500 µl of SOC medium (Invitrogen, #15544-034) was added and the cells were cultured in suspension at 37° C., 180 rpm for 1 hour. To a LB agar plate containing kanamycin at a final concentration of 50 µg/ml, 40 mg/ml X-gal and 40 µl of 100 mM IPTG dissolved in 40 µl of DMF (N,N-dimethylformamide) were applied and then 100 to 200 µl of the culture were applied. The plate was incubated at 37° C. overnight and colonies were obtained on the next morning.

1.1.4. Check of Transformation by Colony PCR and Selection for Positive Clone

As a result of the transformation, many colonies were obtained. To confirm the presence or absence of the inserted DNA in the colonies, colony PCR was conducted using M13-F: 5'-GTA AAA CGA CCA GTC TTA AG-3' (SEQ ID NO: 164) and M13-R: 5'-CAG GAA ACA GCT ATG AC-3' (SEQ ID NO: 165). The composition of the reaction solution for the colony PCR was shown in Table 11 and the PCR conditions were shown in Table 12.

TABLE 11

| Component | (µl) |
|---|---|
| Template DNA | Colony |
| Amprltaq Gold 360 Master Mix (ABI, #4398881) | 10 µl |
| Forward primer (M13-F) (10 ng/µl) | 0.4 µl |

TABLE 11-continued

| Component | (µl) |
|---|---|
| Reverse primer (M13-R) (10 ng/µl) | 0.4 µl |
| Sterile water | 9.2 µl |
| Total | 20 µl |

TABLE 12

98° C.  10 min
↓
95° C.  15 sec  ⎤
50° C.  30 sec  ⎬ × 30 cycles
72° C.  1 min   ⎦
↓
72° C.  7 min
↓
20° C.

1.1.5. Purification of Plasmid DNA from Positive Clone

The plasmid DNAs were purified from the clones in which the inserted DNAs were confirmed. The purification of the plasmid DNAs were conducted using QIAprep Spin Miniprep Kit (QIAGEN, #27106) following the protocol contained in the kit.

1.1.6. Sequencing of Positive Clone

PCR amplification was conducted using the plasmid DNAs obtained in 1.1.5 as templates and M13-F and M13-R primers and the nucleotide sequences of the DNA fragments were determined by the dideoxy method (the Sanger method).

1.2. Preparation of DNA Encoding AtSWEET Protein by Chemical Synthesis

The DNA encoding the AtSWEETS, AtSWEET 10, AtSWEET 14, and AtSWEET 16 proteins were chemically synthesized in total with their nucleotide sequences designed so as to add Pst I restriction enzyme recognition sequence to the 5' end and Sal I restriction enzyme recognition sequence to the 3' end. As a result, the DNAs encoding the AtSWEETS and AtSWEET 14 proteins inserted in the pEX-A vector (Operon Biotechnologies, Inc.) and the DNAs encoding the AtSWEET 10 and AtSWEET 16 proteins inserted in the pCR2.1-TOPO® vector were able to be obtained.

1.3. Cutting Out of DNA Encoding AtSWEET Protein by Restriction Enzyme Reaction and Purification In order to cut out the DNA fragments encoding the AtSWEET proteins from the plasmid DNAs obtained in 1.1.5 and 1.2, twice of restriction enzyme treatments were conducted. The combination of restriction enzymes for each DNA is shown in Table 13.

TABLE 13

| Name of DNA | First | Second |
|---|---|---|
| AtSWEET1 | Sac I | Sal I |
| AtSWEET2 | Sac I | Sal I |
| AtSWEET3 | Sac I | Sal I |
| AtSWEET4 | Sac I | Sal I |
| AtSWEET5 | Sac I | Sal I |
| AtSWEET6 | Sac I | Sal I |

TABLE 13-continued

| Name of DNA | First | Second |
|---|---|---|
| AtSWEET7 | Sac I | Sal I |
| AtSWEET8 | Nde I | Sal I |
| AtSWEET9 | Sac I | Sal I |
| AtSWEET10 | Sal I | Sac I |
| AtSWEET11 | Sac I | Sal I |
| AtSWEET12 | Sac I | Sal I |
| AtSWEET13 | Nde I | Sal I |
| AtSWEET14 | Nde I | Sal I |
| AtSWEET15 | Sac I | Sal I |
| AtSWEET16 | Sal I | Xba I |
| AtSWEET17 | Sac I | Sal I |

1.3.1. Sac I, Nde I, or Sal I Restriction Enzyme Reaction of Amplified DNA Fragment (First Round)

The reaction solutions shown in the tables below were prepared with Sac I (TaKaRa, #1078A), Nde I (TaKaRa, #1161A) or Sal I (TaKaRa, #1080A) and reacted at 37° C. overnight to digest the plasmids obtained in 1.1.5 or 1.2. The composition of the reaction solution with Sal I was shown in Table 14, the composition of the reaction solution with Nde I was shown in Table 15, and the composition of the reaction solution with Sac I was shown in Table 16.

TABLE 14

| Component | (μl) |
|---|---|
| Plasmid | 45 μl |
| 10 × L buffer | 10 μl |
| Sac I | 1 μl |
| DW | 44 μl |
| Total | 100 μl |

TABLE 15

| Component | (μl) |
|---|---|
| Plasmid | 45 μl |
| 10 × H buffer | 10 μl |
| Nde I | 1 μl |
| DW | 44 μl |
| Total | 100 μl |

TABLE 16

| Component | (μl) |
|---|---|
| Plasmid | 45 μl |
| 10 × H buffer | 10 μl |
| Sal I | 1 μl |
| DW | 44 μl |
| Total | 100 μl |

1.3.2. Purification of DNA Fragment Digested in Restriction Enzyme Reaction

Next, PCI (Phenol:Chloroform:Isoamyl alcohol=24:24:1) extraction and ethanol precipitation were performed to purify DNA. An equal volume of PCI was added to the reaction solution and the mixture was stirred and centrifuge at 15000 rpm for 5 minutes. The upper layer was collected and an equal volume of chloroform was added thereto. The mixture was similarly centrifuged and the upper layer was collected. To the collected upper layer, two times volume of ethanol was added and ethanol precipitation was conducted with Pellet Paint NF Co-Precipitant (Merck, #70748). The resultant DNA was dried and then dissolved in 44 μl of sterile water.

1.3.3. Sal I, Xba I, and Sac I Restriction Enzyme Reaction of Amplified DNA Fragment (Second Round)

Next, the reaction solutions shown in the tables below were prepared with Sal I (TaKaRa, #1080A), Xba I (TaKaRa, #1093A), or Sac I (TaKaRa, #1078A) and reacted at 37° C. overnight to digest the plasmids obtained in 1.3.2. The composition of the reaction solution with Sal I was shown in Table 17, the composition of the reaction solution with Xba I was shown in Table 18, and the composition of the reaction solution with Sac I was shown in Table 19.

TABLE 17

| Component Pellet | (μl) |
|---|---|
| 10 × H buffer | 5 μl |
| Sal I | 1 μl |
| DW | 44 μl |
| Total | 50 μl |

TABLE 18

| Component Pellet | (μl) |
|---|---|
| 10 × M buffer | 5 μl |
| 100 × BSA | 0.5 μl |
| Xba I | 1 μl |
| DW | 43.5 μl |
| Total | 50 μl |

TABLE 19

| Component Pellet | (μl) |
|---|---|
| 10 × L buffer | 5 μl |
| Sac I | 1 μl |
| DW | 44 μl |
| Total | 50 μl |

1.3.4. Purification of DNA Fragment Digested in Restriction Enzyme Reaction

The reaction solutions obtained in 1.3.3 were subjected to agarose gel electrophoresis in a similar way to the procedure of 1.1.2 and the DNAs were cut out and purified with the MagExtractor-PCR & Gel Clean up kit.

1.4. Cutting Out of pRI201AN Vector in Restriction Enzyme Reaction and Purification To ligate the pRI201AN vector with the DNA fragments encoding the AtSWEET proteins obtained in 1.3, the vector was treated with restriction enzymes in a way similar to the procedure of 1.3.

1.5. Ligation 1.5.1. Ligation Reaction

Ligation reaction was conducted to insert the DNA fragments encoding the AtSWEET proteins obtained in 1.3 into the pRI201AN vector obtained in 1.4. Ligation reaction was conducted with DNA Ligation Kit Ver.2. 1 (Takara Bio, #6022) at 16° C. overnight.

1.5.2. Transformation with Ligation Reaction Product

After the abovementioned ligation reaction, transformation with 2 µl of the ligation reaction solution was conducted in a way similar to 1.1.3.

1.5.3. Check of Ligation Reaction by Colony PCR

Insertion of the DNAs encoding the AtSWEET proteins into the vector was confirmed by examining the length of visualized DNA fragments amplified by colony PCR in agarose gel electrophoresis.

1.5.4. Preparation of DNA Constructs Obtained by Ligation Reaction

From the colonies in which the inserted DNAs were confirmed, the plasmid DNAs were purified to obtain the clones in which the DNA fragments of interest were inserted. The plasmid DNAs were purified with QIAprep Spin Miniprep Kit (QIAGEN, #27106) following the protocol contained in the kit. FIG. 6 illustrates the physical map of the resultant DNA construct (AtSWEET/pRI201AN). In FIG. 6, LB stands for left border, RB stands for right border, TNOS stands for transcription terminator of the nopaline synthetase gene NOS derived from the Ti plasmid in *Agrobacterium tumefaciens*, NPTII stands for neomycin phosphotransferase II gene from *Escherichia coli*, Pnos stands for transcription promoter of the nopaline synthetase gene NOS derived from the Ti plasmid in *Agrobacterium tumefaciens*, THSP stands for transcription terminator of the heat shock protein gene HSP derived from *Arabidopsis thaliana*, AtSWEET stands for DNA encoding a SWEET protein derived from *Arabidopsis thaliana*, P35S stands for Cauliflower mosaic virus 35S transcription promoter, AtADH 5'-UTR stands for translation enhancer of the alcohol dehydrogenase gene ADH derived from *Arabidopsis thaliana*, ColEl ori stands for the reproduction origin of *Escherichia coli*, Ri ori stands for the reproduction origin of *Agrobacterium rhizogenes*, respectively.

1.6.1. Preparation of DNA Encoding OsSWEET Protein by Chemical Synthesis and Construction of Construct The DNAs encoding the OsSWEET5, OsSWEET11, OsSWEET12, OsSWEET13, OsSWEET14, and OsSWEET15 proteins, whose nucleotide sequences were newly designed in reference to the codon usage in *Arabidopsis thaliana* so that there will be no change in the amino acid sequence, were designed to have an Nde I restriction enzyme recognition sequence at the start codon side and a Sac I restriction enzyme recognition sequence at the stop codon side. The designed DNAs were totally chemically synthesized and inserted into the pRI201AN vector to obtain the respective DNA constructs. The DNAs were designed so that the ATG in the Nde I restriction enzyme recognition sequence (5'CATATG3') added to the 5' end coincides with the start codons of the DNAs encoding the SWEET proteins.

1.6.2. Preparation of Artificial Gene Encoding Transporter Involved in Sugar Transportation and Construct by Chemical Synthesis Deoxyribonucleic acids (DNAs) encoding transporters involved in sugar transportation that have Consensus Sequence 1 and that have a nucleotide sequence that does not occur naturally, or 6 artificial genes of transporters involved in sugar transportation that have Consensus Sequence 1 were prepared as follows. First, SEQ ID NOs: 168, 169, 170, 171, 172, and 173 were designed respectively as nucleic acids encoding the transporters SWo1, SWo2, SWo3, SWo4, SWo5, and SWo6 having amino acid sequences set forth in SEQ ID NOs: 132 to 137. DNAs were designed so that each of them has an Nde I restriction enzyme recognition sequence at the start codon side and a Sac I restriction enzyme recognition sequence at the stop codon side of SEQ ID NOs: 168, 169, 170, 171, 172, and 173. The designed DNAs were then totally chemically synthesized and inserted into the pRI201AN vector to obtain the 6 DNA constructs. The DNAs were designed so that the ATG in the Nde I restriction enzyme recognition sequence (5'CATATG3') added to the 5' end coincides with the start codons in SEQ ID NOs: 168, 169, 170, 171, 172, and 173.

1.7. Transformation of *Arabidopsis Thaliana*

The vectors for plant expression prepared in 1.5 and 1.6.1 and 1.6.2 were introduced into *Agrobacterium tumefaciens* strain C58C1 by electroporation (Plant Molecular Biology Mannal, Second Edition, B. G. Stanton and A. S. Robbert, Kluwer Academic Publishers 1994). Then, *Agrobacterium tumefaciens* in which the vectors for plant expression were each introduced was introduced into the wild type *Arabidopsis thaliana* ecotype Col-0 by dipping described by Clough, et al. (Steven J. Clough and Andrew F. Bent, 1998, The Plant Journal 16, 735-743) and T1 (the first generation transformant) seeds were collected. The collected T1 seeds were sown in sterile on MS agar medium (agar concentration 0.8%) containing kanamycin (50 mg/L), carbenicillin (100 mg/L) and Benlate wettable powder (10 mg/L: Sumitomo Chemical Co., Ltd.) and cultured for about 2 weeks to select transformants. The selected transformants were transplanted onto a fresh preparation of the same MS agar medium, further cultivated for about 1 week, and then transplanted in a pot containing the soil which is a 1:1 mixture of vermiculite and Soil-mix (Sakata Seed Co.) to obtain T2 (the second generation transformant) seeds.

1.8. Preparation of *Arabidopsis thaliana* Guttation

T1 or T2 plants of *Arabidopsis thaliana* transformed with the DNAs encoding the AtSWEET, OsSWEET, SWo1, SWo2, SWo3, SWo4, SWo5, and SWo6 proteins were cultivated with 18L/6D (24 hour cycles with 18 hours of light conditions followed by 6 hours of dark conditions) at 22° C. After acclimation, 1/1000 Hyponex was given to plants cultivated for 1 to 2 weeks and the plants were wrapped with a plastic wrap (Saran Wrap®, Asahi Chemical Industry) to increase humidity to 80% or more, or preferably 90% or more so that guttation is secreted (FIG. 7). Mainly, guttation attached to the back of leaves was collected and the sugar concentration in the guttation was analyzed. T1 seeds are defined as seeds harvested after infecting the wild type *Arabidopsis thaliana* with *Agrobacterium* and cultivating the resultant, T1 plants are defined as plants which has been confirmed to have introduction of DNA into cells, for example, by screening of T1 seeds with drug or by PCR, and T2 seeds are defined as seeds harvested after cultivating T1 plants.

2. Construction of DNA Construct for *Oryza sativa* Transformation

2.1. Amplification of DNA Encoding AtSWEET Protein

Using the aforementioned DNA constructs (the DNA encoding the AtSWEET8 protein and the DNA encoding the AtSWEET11 protein and the DNA encoding the AtSWEET12 protein) for *Arabidopsis thaliana* transformation prepared in 1.5.4 as templates, the DNA encoding the AtSWEET8 protein and the DNA encoding the AtSWEET11 protein and the DNA encoding the AtSWEET12 protein were amplified by PCR. The sequence CACC was added to the 5' end of each amplification product for the introduction of the amplification product into the pENTR/D-TOPO vector.

2.2. Transformation with Amplified DNA Fragment

Parts of the resultant reaction solutions were subjected to agarose gel electrophoresis to confirm the presence of expected sizes of amplified products. The amplified products were then introduced into the pENTR/D-TOPO® vector using pENTER Directional TOPO Cloning Kit® (Invitrogen).

Next, *Escherichia coli* DH5α competent cells (Takara Bio) were transformed by adding the total amount of the reaction solutions. The cells were allowed to stand in ice bath for 30 minutes and then subjected to 45 seconds of heat treatment at 42° C. Subsequently, the cells were rapidly cooled in ice bath and 300 μl of SOC medium (Takara Bio) was added thereto. The mixture was cultured at 37° C., with shaking at 180 rpm for 1 hour and this liquid culture was plated onto an LB agar plate containing kanamycin at a final concentration of 50 μg/ml and cultured at 37° C. overnight to obtain colonies on the next morning.

2.3. Check of Transformation by Colony PCR and Selection for Positive Clone

Insertion of the DNAs encoding the AtSWEET proteins into the vector was confirmed by examining the length of visualized DNA fragments amplified by colony PCR in agarose gel electrophoresis.

2.4. Purification of Plasmid DNA from Positive Clone

The plasmid DNAs were purified from the clones in which the inserted DNAs were able to be confirmed. The purification of the plasmid DNAs were conducted using QIAprep Spin Miniprep Kit (QIAGEN, #27106) following the protocol contained in the kit.

2.5. Sequencing of Positive Clone

Using the plasmid DNAs purified in 2.4 as templates and M13-F and M13-R primers, the DNA fragments were sequenced by a DNA sequencer (Beckman Coulter, CEQ8000).

2.6. LR Reaction and Transformation

The pENTR/D-TOPO® plasmid DNAs in which the DNA encoding the AtSWEETS protein, the DNA encoding the AtSWEET11 protein, and the DNA encoding the AtSWEET12 protein were inserted obtained in 2.4 and a vector for *Oryza sativa* transformation (pZH2B_GWOx) were subjected to the Gateway LR reaction to construct the constructs for the overexpression in the plant of *Oryza sativa*, as shown in FIG. 8.

Next, *Escherichia coli* DH5α competent cells (Takara Bio) were transformed by adding the total amount of the reaction solutions. The cells were allowed to stand in ice bath for 30 minutes and then subjected to 45 seconds of heat treatment at 42° C. Subsequently, the cells were rapidly cooled in ice bath and 300 μl of SOC medium (Takara Bio) was added thereto. The mixture was cultured at 37° C., with shaking at 180 rpm for 1 hour. This liquid culture was plated onto an LB agar plate containing spectionmycin at a final concentration of 50 μg/ml and cultured at 37° C. overnight to obtain colonies on the next morning.

2.7. Check of Transformation by Colony PCR and Selection for Positive Clone

Insertion of the DNAs encoding the AtSWEET proteins into the vector was confirmed by examining the length of visualized DNA fragments amplified by colony PCR in agarose gel electrophoresis.

2.8. Purification of Plasmid DNA from Positive Clone

The plasmid DNAs were purified from the clones in which the inserted DNAs were able to be confirmed. The plasmid DNAs were purified with QIAprep Spin Miniprep Kit (QIAGEN, #27106) following the protocol contained in the kit.

2.9. Sequencing of Positive Clone

Using the plasmid DNAs purified in 2.8 as templates and the following primers, the DNA fragments were sequenced by the DNA sequencer (Beckman Coulter, CEQ8000).

Ubi3'F:
(SEQ ID NO: 166)
5'-TGC TGT ACT TGC TTG GTA TTG-3'

UbiTseq3:
(SEQ ID NO: 167)
5'-GGA CCA GAC CAG ACA ACC-3'

2.10.1. Preparation of DNA Encoding OsSWEET by Chemical Synthesis

DNAs encoding the OsSWEET13, OsSWEET14, or OsSWEET15 protein were designed to have the sequence CACC at the 5' end for the introduction into the pENTR/D-TOPO vector. The designed DNAs were totally chemically synthesized and inserted into the pENTR/D-TOPO vector.

2.10.2. Preparation of Artificial Gene Encoding Transporter Involved in Sugar Transportation by Chemical Synthesis Deoxyribonucleic acids (DNAs) encoding transporters involved in sugar transportation that have Consensus Sequence 1 and that have a nucleotide sequence that does not occur naturally, or 2 artificial genes of transporters involved in sugar transportation that have Consensus Sequence 1 were prepared as follows. First, SEQ ID NOs: 174 and 175 were designed as nucleic acids encoding the transporters SWo1 and SWo5 having amino acid sequences set forth in SEQ ID NOs: 132 and 136. DNAs were designed to have the sequence CACC at the 5' end of SEQ ID NOs: 174 and 175 for the introduction into the pENTR/D-TOPO vector. The designed DNAs were totally chemically synthesized and inserted into the pENTR/D-TOPO vector.

2.11. Construction of Construct of DNA or Artificial Gene Encoding OsSWEET Protein Vectors for *Oryza sativa* transformation were constructed using the DNAs synthesized in 2.10.1 and 2.10.2 in a way similar to 2.6 to 2.9 above.

2.12. Transformation of *Oryza sativa*

The DNAs encoding the AtSWEET, OsSWEET, SWo1, and SWo5 proteins were introduced into *Oryza sativa* (c.v. Nipponbare) using the aforementioned vectors for plant expression constructed in 2.9 and 2.11 according to the method described in The Plant Journal (2006) 47, 969-976.

2.13. Preparation of *Oryza sativa* Guttation

T1 transformants of *Oryza sativa* in which DNA encoding the AtSWEET, OsSWEET, SWo1, and SWo5 proteins were introduced were transplanted to a pot with a diameter of 6 cm containing 0.8 times volume of vermiculite and acclimated. *Oryza sativa* was cultivated with 18L (30° C.)/6D (25° C.) (24 hours photocycle conditions with 18 hours light conditions at 30° C. followed by 6 hours of dark conditions at 25° C.). After acclimation, 1/1000 Hyponex was sufficiently given to plants cultivated for 1 to 2 weeks and the plants were wrapped with a plastic wrap (Saran Wrap®, Asahi Chemical Industry) to increase humidity to 80% or more, or preferably 90% or more so that guttation is secreted from the hydathode in *Oryza sativa* (FIG. 9). Guttation attached to leaves was collected and analyzed for the sugar concentration.

3. Analysis for Sugar Concentration in Guttation 3.1. Dilution of Guttation Sample The volumes of guttation from *Arabidopsis thaliana* obtained in 1.8 and guttation from *Oryza sativa* obtained in 2.13 were measured using a pipetter and pure water was added to a fixed volume of 0.35 ml. Next, the guttation was centrifuged at 10000×G for 10 minutes and then 0.3 mL of the supernatant was transferred to an automatic sampler vial and used for an HPLC analysis.

3.2. Analysis for Sugar Concentration by HPLC

The sugar concentration was analyzed using HPLC in the following conditions. In this analysis, a standard solution containing a mixture of glucose, fructose, and sucrose at 50 μM each as standard substances was used.

Analytic column: CarboPac PA1 (Dionex)
Eluent: 100 mM NaOH
Flow rate: 1 ml/min
Amount of injection: 25 μl
Detector: Pulsed amperometric detector (Dionex ED40)

4. Result of Analysis

The results of measurement of sugar concentrations in guttation from *Arabidopsis thaliana* obtained in 1.8 and guttation from *Oryza sativa* obtained in 2.13 are shown in Tables 20 and 21.

TABLE 20

| Clade | Transgene | Host | Glc (μM) Ave | Glc (μM) Max | Glc (μM) Min | Fru (μM) Ave | Fru (μM) Max | Fru (μM) Min | Suc (μM) Ave | Suc (μM) Max | Suc (μM) Min | Total Monosaccharide Equivalent (μM) Ave | Total Monosaccharide Equivalent (μM) Max | Total Monosaccharide Equivalent (μM) Min |
|---|---|---|---|---|---|---|---|---|---|---|---|---|---|---|
| I | AtSW01 | A. thaliana | 1.3 | 14.2 | 0.0 | 1.8 | 11.8 | 0.0 | 0.0 | 0.0 | 0.0 | 3.1 | 22.1 | 0.0 |
| I | AtSW02 | A. thaliana | 5.7 | 33.6 | 0.0 | 0.0 | 0.0 | 0.0 | 0.1 | 1.8 | 0.0 | 5.8 | 33.6 | 0.0 |
| I | AtSW03 | A. thaliana | 4.0 | 14.7 | 0.0 | 0.9 | 6.0 | 0.0 | 0.2 | 3.4 | 0.0 | 5.2 | 19.6 | 0.0 |
| II | AtSW04 | A. thaliana | 3.0 | 9.1 | 0.0 | 8.5 | 20.7 | 0.0 | 0.0 | 0.0 | 0.0 | 11.6 | 23.2 | 0.0 |
| II | AtSW05 | A. thaliana | 5.5 | 15.7 | 0.0 | 3.4 | 20.5 | 0.0 | 0.0 | 0.0 | 0.0 | 8.8 | 30.8 | 0.0 |
| II | AtSW06 | A. thaliana | 3.3 | 10.3 | 0.0 | 0.1 | 2.0 | 0.0 | 0.2 | 5.0 | 0.0 | 3.9 | 10.3 | 0.0 |
| II | AtSW07 | A. thaliana | 4.9 | 15.1 | 0.0 | 8.0 | 19.0 | 0.0 | 1.6 | 4.9 | 0.0 | 16.1 | 36.9 | 0.0 |
| II | AtSW08 | A. thaliana | 419.9 | 838.6 | 50.2 | 610.6 | 1,154.3 | 145.6 | 697.1 | 1,172.5 | 217.6 | 2,424.8 | 4,337.8 | 631.0 |
| II | AtSW08 | O. sativa | 571.4 | 1,205.6 | 152.4 | 419.0 | 845.5 | 153.1 | 41.9 | 47.8 | 33.6 | 1,074.3 | 2,146.7 | 394.3 |
| III | AtSW09 | A. thaliana | 399.5 | 2,708.3 | 36.4 | 552.5 | 2,838.7 | 69.5 | 228.3 | 1,309.4 | 41.2 | 1,408.5 | 7,865.4 | 211.8 |
| III | AtSW10 | A. thaliana | 331.6 | 586.3 | 77.0 | 650.9 | 1,085.9 | 215.8 | 280.9 | 516.6 | 45.2 | 1,544.3 | 2,705.4 | 383.1 |
| III | AtSW11 | A. thaliana | 711.1 | 2,137.9 | 80.1 | 674.6 | 1,384.7 | 117.6 | 290.7 | 470.4 | 97.2 | 1,967.1 | 4,463.5 | 449.6 |
| III | AtSW11 | O. sativa | 31,304.7 | 59,730.0 | 757.3 | 36,772.0 | 74,830.9 | 964.0 | 8,196.6 | 19,339.4 | 110.8 | 84,469.9 | 173,239.6 | 1,942.9 |
| III | AtSW12 | A. thaliana | 1,375.5 | 2,920.7 | 183.4 | 1,720.7 | 3,542.4 | 201.4 | 1,480.7 | 6,099.3 | 214.7 | 6,057.5 | 18,661.6 | 1,185.5 |
| III | AtSW12 | O. sativa | 14,006.2 | 45,976.5 | 1,081.6 | 11,477.3 | 43,830.5 | 1,690.7 | 2,598.2 | 22,209.9 | 56.4 | 30,679.9 | 130,872.6 | 3,247.4 |
| III | AtSW13 | A. thaliana | 230.5 | 941.5 | 51.1 | 304.3 | 1,336.8 | 85.5 | 146.8 | 402.7 | 51.9 | 828.5 | 3,083.7 | 287.3 |
| III | AtSW14 | A. thaliana | 60.4 | 211.6 | 24.9 | 163.2 | 451.8 | 74.8 | 48.8 | 118.7 | 22.2 | 321.2 | 900.7 | 151.6 |
| III | AtSW15 | A. thaliana | 796.6 | 2,064.2 | 143.1 | 1,140.0 | 2,727.5 | 226.1 | 514.2 | 1,217.2 | 70.1 | 2,965.0 | 6,511.9 | 582.7 |
| IV | AtSW16 | A. thaliana | 3.1 | 14.6 | 0.0 | 0.5 | 3.0 | 0.0 | 0.0 | 0.0 | 0.0 | 3.5 | 14.6 | 0.0 |
| IV | AtSW17 | A. thaliana | 2.0 | 3.5 | 0.0 | 1.2 | 3.7 | 0.0 | 0.0 | 0.0 | 0.0 | 3.2 | 7.1 | 0.0 |

TABLE 21

| Clade | Transgene | Host | Glc (μM) Ave | Glc (μM) Max | Glc (μM) Min | Fru (μM) Ave | Fru (μM) Max | Fru (μM) Min |
|---|---|---|---|---|---|---|---|---|
| II | OsSW05 | A. thaliana | 2.7 | 5.3 | 0.0 | 3.8 | 12.8 | 0.0 |
| III | OsSW11 | A. thaliana | 318.0 | 607.1 | 81.5 | 490.8 | 833.1 | 179.7 |
| III | OsSW12 | A. thaliana | 41.7 | 172.9 | 9.7 | 89.5 | 334.1 | 32.4 |
| III | OsSW13 | A. thaliana | 48.5 | 160.9 | 8.0 | 121.0 | 367.7 | 24.8 |
| III | OsSW13 | O. sativa | 62,407.2 | 125,776.4 | 3,917.0 | 77,858.6 | 156,842.0 | 4,650.0 |
| III | OsSW14 | A. thaliana | 37.5 | 128.5 | 10.7 | 115.6 | 460.4 | 45.5 |
| III | OsSW14 | O. sativa | 43,115.4 | 90,201.0 | 543.0 | 58,581.3 | 152,827.3 | 229.1 |
| III | OsSW15 | A. thaliana | 14.9 | 39.7 | 8.2 | 39.3 | 97.3 | 19.6 |

TABLE 21-continued

| | | | | | | | | |
|---|---|---|---|---|---|---|---|---|
| III | OsSW15 | O. sativa | 33,018.8 | 246,007.1 | 197.8 | 31,135.4 | 197,244.2 | 461.9 |
| III | SWo1 | A. thaliana | 182.9 | 337.5 | 28.2 | 125.9 | 219.2 | 32.6 |
| III | SWo1 | O. sativa | 11,181.0 | 33,889.1 | 284.2 | 6,586.0 | 19,670.8 | 351.1 |
| III | SWo2 | A. thaliana | 81.6 | 128.4 | 30.6 | 103.3 | 146.3 | 26.7 |
| III | SWo3 | A. thaliana | 141.1 | 141.1 | 141.1 | 166.9 | 166.9 | 166.9 |
| III | SWo4 | A. thaliana | 41.9 | 96.3 | 12.7 | 35.5 | 88.2 | 3.8 |
| III | SWo5 | A. thaliana | 31.8 | 31.8 | 31.8 | 7.7 | 7.7 | 7.7 |
| III | SWo5 | O. sativa | 12,006.9 | 43,461.2 | 1,371.6 | 7,166.2 | 31,839.2 | 734.7 |
| III | SWo6 | A. thaliana | 179.1 | 455.3 | 33.5 | 121.1 | 155.1 | 64.6 |
| — | none | A. thaliana | 1.6 | 8.1 | 0.0 | 0.3 | 7.3 | 0.0 |
| — | none | O. sativa | 1.0 | 8.3 | 0.0 | 0.0 | 0.2 | 0.0 |

| | Suc (μM) | | | Total Monosacharide Equivalent (μM) | | |
|---|---|---|---|---|---|---|
| Clade | Ave | Max | Min | Ave | Max | Min |
| II | 2.2 | 3.9 | 0.0 | 10.8 | 21.5 | 0.0 |
| III | 221.0 | 723.7 | 14.0 | 1,250.7 | 2,887.6 | 360.7 |
| III | 36.9 | 127.8 | 3.0 | 205.0 | 762.5 | 71.1 |
| III | 41.3 | 93.7 | 19.6 | 252.1 | 716.0 | 71.9 |
| III | 22,687.7 | 74,320.2 | 64.5 | 185,641.2 | 358,704.4 | 8,994.7 |
| III | 51.2 | 118.0 | 19.4 | 255.6 | 824.9 | 95.0 |
| III | 7,104.2 | 21,756.3 | 10.8 | 115,905.1 | 275,262.5 | 793.8 |
| III | 25.5 | 82.0 | 7.2 | 105.3 | 300.9 | 59.8 |
| III | 2,011.4 | 10,537.3 | 85.2 | 68,176.9 | 450,340.4 | 830.2 |
| III | 14.3 | 22.4 | 6.1 | 337.3 | 601.5 | 73.0 |
| III | 221.1 | 795.8 | 18.5 | 18,209.1 | 51,684.6 | 1,019.9 |
| III | 9.9 | 13.8 | 6.3 | 204.7 | 284.5 | 84.9 |
| III | 16.0 | 16.0 | 16.0 | 340.0 | 340.0 | 340.0 |
| III | 10.6 | 13.4 | 6.7 | 98.5 | 210.9 | 51.7 |
| III | 10.1 | 10.1 | 10.1 | 59.6 | 59.6 | 59.6 |
| III | 892.0 | 4,573.9 | 42.4 | 20,957.0 | 84,448.2 | 2,197.3 |
| III | 10.8 | 21.1 | 2.8 | 321.8 | 638.2 | 108.6 |
| — | 0.0 | 2.6 | 0.0 | 2.0 | 11.0 | 0.0 |
| — | 0.1 | 0.8 | 0.0 | 1.3 | 8.3 | 0.0 |

It was found that the concentration of sugar in guttation is greatly increased in all of *Arabidopsis thaliana* and *Oryza sativa* transformed with DNAs encoding AtSWEET9 to 15 and DNAs encoding OsSWEET13 to 15 classified in clade III among nucleic acids encoding SWEET proteins as seen from Tables 20 and 21. In particular, it was found that the sugar concentration in guttation can be more greatly increased when transformed with any of the DNA encoding AtSWEET11, the DNA encoding AtSWEET12, the DNA encoding AtSWEET15, the DNA encoding OsSWEET13, and the DNA encoding OsSWEET14. Moreover, it was found that the concentration of sugar in guttation is more increased in *Oryza saliva* transformed with DNAs encoding SWEET proteins classified in clade III than in *Arabidopsis thaliana* transformed with DNAs encoding SWEET proteins classified in clade III. In particular, it was found that the concentration of sugar in guttation is markedly increased in *Oryza sativa* transformed with any of the DNA encoding OsSWEET13, the DNA encoding OsSWEET14, and the DNA encoding OsSWEET15 than in *Arabidopsis thaliana* transformed with the same DNA.

Moreover, it was found that the concentration of sugar in guttation can be increased also in the plants in which an artificial gene of a transporter involved in sugar transportation that has Consensus Sequence 1 is introduced. The result revealed that the concentration of sugar in guttation can be increased in any plant, without limited by the host plant, by introducing a nucleic acid encoding a transporter involved in sugar transportation that has Consensus Sequence 1 and/or enhancing the expression of the protein.

Even in the wild type plants, sugar concentrations of around 50 μM can be detected in guttation in some individuals. However, it was revealed that the effect of introducing the DNA encoding the SWEET proteins classified in Clade III is much higher than the highest concentration detected in the wild type plants as seen in the Examples.

The invention claimed is:

1. A modified plant, wherein said modified plant has been modified by introducing therein a nucleic acid comprising a nucleic acid sequence encoding a sugar transporter protein operatively linked to a heterologous promoter, and/or by genetically modifying a promoter of an endogenous gene encoding a sugar transporter protein,
wherein said modified plant exhibits increased expression of said sugar transporter protein, and produces guttation with increased sugar concentration, as compared to a wild-type plant,
wherein said sugar transporter protein has a consensus sequence comprising the following amino acid sequence: (L/I/V/M/F)x(G/A)xx(I/L/V/M/F)xxxx(L/I/V/F)(A/S)(P/S) [SEQ ID NO: 1] (1-3aa)(P/S/T/A)T(F/L)xx(I/V)xxxKxxxxxxxxPYxxx(L/I)xxxx(L/I)x(I/L/M/V/F)xY(A/S/G) [SEQ ID NO: 2] (7-13aa)(I/L/V/M)(1-2aa)(I/V)Nxxxxxx(E/Q)xxYxxx(Y/F)xx(Y/F)(A/G/S) [SEQ ID NO: 3] (35-36aa)(R/Q/H)xxxxGx(V/I/L)xxxxx(V/M/L/I/F)xxxx(A/S/T)P(L/M)x(I/V)(I/M/V/L) [SEQ ID NO: 4] (2-7aa)(V/I)(V/I/M)x(T/S)x(S/N)xx(F/Y)(M/L)(P/S)(F/I/V/L)xLSxx(L/I)(T/V)xx(A/G) xxW(F/L)x YGxxxxDxx(V/I)xxPNxxGxx(F/L)(G/S) xxQ(M/I)x(L/M/I/V/F)(Y/H/F) [SEQ ID NO: 5],
and wherein the sugar transporter protein is a protein comprising the amino acid sequence of one of SEQ ID NOs: 24-26,-132 and 137.

2. The modified plant according to claim 1, wherein the plant is a phanerogam.

3. The modified plant according to claim 2, wherein the phanerogam is an angiosperm.

4. The modified plant according to claim 3, wherein the angiosperm is a monocot.

5. The modified plant according to claim 4, wherein the monocot is a plant of the family Poaceae.

6. The modified plant according to claim 5, wherein the plant of the family Poaceae is a plant of the genus *Oryza*.

7. The modified plant according to claim 3, wherein angiosperm is a dicot.

8. The modified plant according to claim 7, wherein the dicot is a plant of the family Brassicaceae.

9. The modified plant according to claim 8, wherein the plant of the family Brassicaceae is a plant of the genus *Arabidopsis*.

* * * * *